United States Patent
Van Der Plas et al.

(10) Patent No.: US 11,564,923 B2
(45) Date of Patent: Jan. 31, 2023

(54) COMPOUNDS AND PHARMACEUTICAL COMPOSITIONS THEREOF FOR THE TREATMENT OF INFLAMMATORY DISORDERS

(71) Applicant: Galapagos NV, Mechelen (BE)

(72) Inventors: Steven Emiel Van Der Plas, Mechelen (BE); Oscar Mammoliti, Mechelen (BE); Sébastien Laurent Xavier Martina, Mechelen (BE); Pieter Isabelle Roger Claes, Gentbrugge (BE); Ghjuvanni Petru Diunisu Coti, Mechelen (BE); Denis Maurice Annoot, Romainville (FR); Miriam López Ramos, Romainville (FR); René Alexandre Galien, Romainville (FR); David Amantini, Romainville (FR); Reginald Christophe Xavier Brys, Mechelen (BE)

(73) Assignee: GALAPAGOS NV, Mechelen (BE)

( * ) Notice: Subject to any disclaimer, the term of this patent is extended or adjusted under 35 U.S.C. 154(b) by 0 days.

(21) Appl. No.: 16/757,189

(22) PCT Filed: Oct. 11, 2018

(86) PCT No.: PCT/EP2018/077677
§ 371 (c)(1),
(2) Date: Apr. 17, 2020

(87) PCT Pub. No.: WO2019/076716
PCT Pub. Date: Apr. 25, 2019

(65) Prior Publication Data
US 2021/0169879 A1 Jun. 10, 2021

(30) Foreign Application Priority Data

Oct. 20, 2017 (GB) .................................... 1717260

(51) Int. Cl.
*A61K 31/506* (2006.01)
*A61P 37/06* (2006.01)
(Continued)

(52) U.S. Cl.
CPC .......... *A61K 31/506* (2013.01); *A61K 31/444* (2013.01); *A61K 31/4545* (2013.01); *A61K 31/496* (2013.01); *A61K 31/501* (2013.01); *A61K 31/5355* (2013.01); *A61P 35/00* (2018.01); *A61P 37/06* (2018.01); *C07D 471/04* (2013.01); *C07D 519/00* (2013.01); *C07B 2200/05* (2013.01)

(58) Field of Classification Search
CPC ............... A61K 31/506; A61K 31/444; A61K 31/4545; A61K 31/496; A61K 31/501; A61K 31/5355; A61K 31/437; A61P 35/00; A61P 37/06; A61P 29/00; C07D 471/04; C07D 519/00; C07B 2200/05
See application file for complete search history.

(56) References Cited

U.S. PATENT DOCUMENTS

| | | |
|---|---|---|
| 9,556,153 B1 | 1/2017 | Clayton |
| 2015/0203455 A1* | 7/2015 | Menet ............... A61P 27/02 544/131 |
| 2018/0134700 A1* | 5/2018 | Greenwood ........... A61P 5/26 |

FOREIGN PATENT DOCUMENTS

| | | |
|---|---|---|
| WO | 2007077949 A1 | 7/2007 |
| WO | 2008135785 A1 | 11/2008 |

(Continued)

OTHER PUBLICATIONS

Babon et al., The Molecular Regulation of Janus Kinase (JAK) Activation, Biochem. J., (2014), vol. 462, No. 1, pp. 1-13.
(Continued)

*Primary Examiner* — Brandon J Fetterolf
*Assistant Examiner* — Lauren Wells
(74) *Attorney, Agent, or Firm* — ArentFox Schiff LLP

(57) ABSTRACT

The present invention discloses compounds according to Formula I:

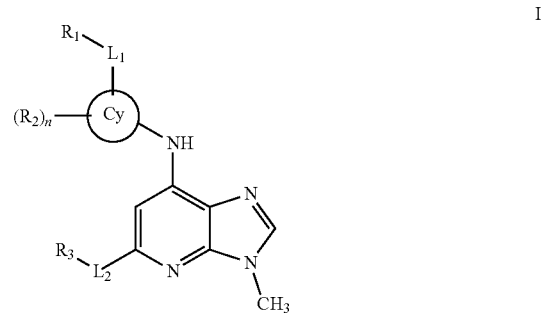

Wherein $R^1$, $L_1$, $R^2$, $L_2$, $R^3$, Cy, and the subscript n are as defined herein.

The present invention relates to compounds, methods for their production, pharmaceutical compositions comprising the same, and methods of treatment using the same, for the prophylaxis and/or treatment of allergic diseases, inflammatory diseases, metabolic diseases, autoinflammatory diseases, autoimmune diseases, proliferative diseases, transplantation rejection, diseases involving impairment of cartilage turnover, congenital cartilage malformations, and/or diseases associated with hypersecretion of IFNα, IL12 and/or IL23 by administering the compound of the invention.

19 Claims, 1 Drawing Sheet

(51) Int. Cl.
    A61P 35/00      (2006.01)
    A61K 31/444     (2006.01)
    A61K 31/4545    (2006.01)
    A61K 31/496     (2006.01)
    A61K 31/501     (2006.01)
    A61K 31/5355    (2006.01)
    C07D 471/04     (2006.01)
    C07D 519/00     (2006.01)

(56) References Cited

FOREIGN PATENT DOCUMENTS

| WO | 2013116291 A1 | 8/2013 |
|---|---|---|
| WO | 2015110378 A1 | 7/2015 |

OTHER PUBLICATIONS

Broekman et al., "Tyrosine Kinase Inhibitors: Multi-Targeted or Single-Targeted?", World Journal of Clinical Oncology, (2011), vol. 2, No. 2, pp. 80-93.
Da et al., "Discovery of Mer Kinase Inhibitors by Virtual Screening Using Structural Protein-Ligand Interaction Fingerprints", Bioorganic & Medical Chemistry, (2015), vol. 23, No. 5, pp. 1096-1101.
Fabian et al., "A Small Molecule-Kinase Interaction Map for Clinical Kinase Inhibitors", Nature Biotechnology, (2005), vol. 23, No. 3, pp. 329-336.
Gillooly et al., "BMS-986165 Is a Highly Potent and Selective Allosteric Inhibitor of Tyk2, Blocks IL-12, IL-23 and Type I Interferon Signaling and Provides for Robust Efficacy in Preclinical Models of Systemic Lupus Erythematosus and Inflammatory Bowel Disease", 2016 ACR/ARHP Annual Meeting, (2016), pp. 1-3.
Neubauer et al., "Jak2 Deficiency Defines an Essential Developmental Checkpoint in Definitive Hematopoiesis", Cell, (1998), vol. 93, pp. 397-409.
O'Shea et al., "JAKs and STATs in Immunoregulation and Immune-Mediated Disease", Immunity Review, (2012), vol. 36, pp. 542-550.
Parganas et al., Jak2 is Essential for Signaling Through a Variety of Cytokine Receptors, Cell, (1998), vol. 93, pp. 385-395.
Schwartz et al., "Type I/II Cytokines, JAKs, and New Strategies for Treating Autoimmune Disease", Nature Reviews—Rheumatology, (2016), vol. 12, pp. 25-36.
Sohn et al., "A Restricted Role for TYK2 Catalytic Activity in Human Cytokine Responses Revealed by Novel TYK2-Selective Inhibitors", The Journal of Immunology, (2013), vol. 191, pp. 2205-2216.
Vainchenker et al., JAKs in Pathology: Role of Janus Kinases in Hematopoietic Malignancies and Immunodeficiencies, Seminars in Cell & Developmental Biology, (2008), vol. 19, pp. 385-393.
International Search Report and Written Opinion for PCT/EP2018/077677 dated Jan. 22, 2019.

* cited by examiner

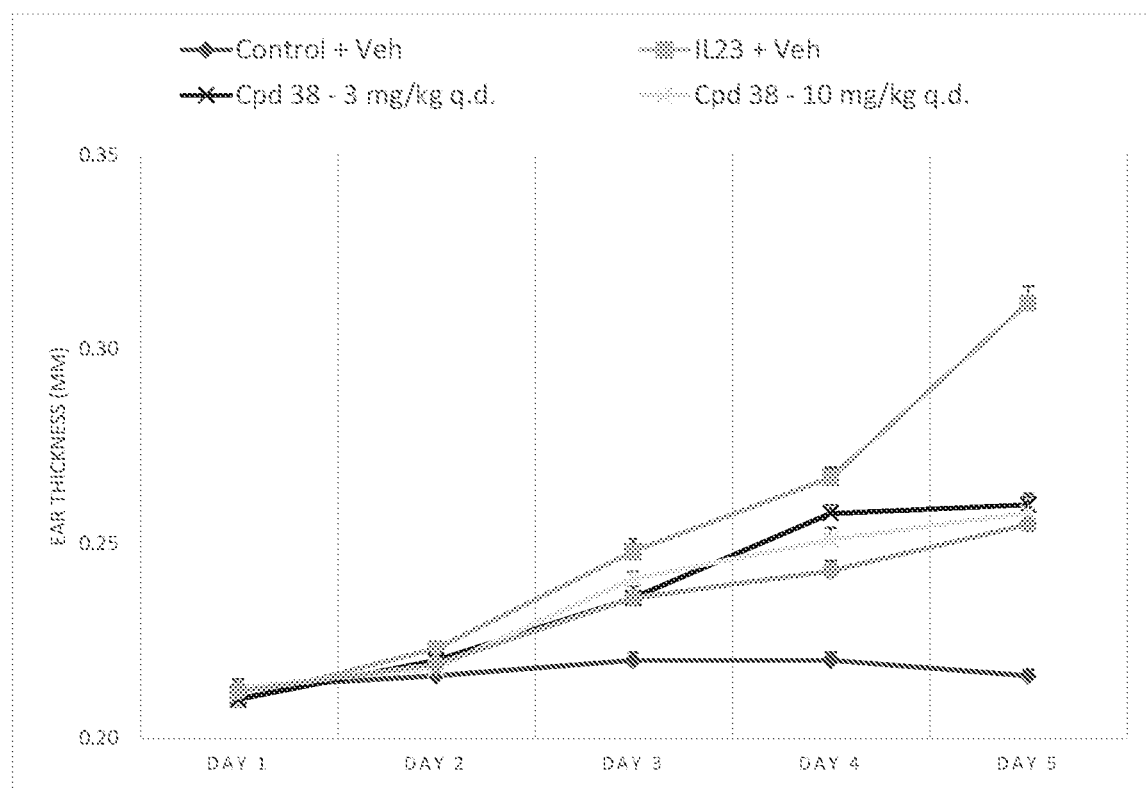

COMPOUNDS AND PHARMACEUTICAL COMPOSITIONS THEREOF FOR THE TREATMENT OF INFLAMMATORY DISORDERS

CROSS-REFERENCE TO RELATED APPLICATIONS

This application is a National Stage Entry of PCT/EP2018/077677, filed Oct. 11, 2018, which claims priority to GB Application No. 1717260.2 filed on Oct. 20, 2017, the disclosure of which is hereby incorporated by reference in its entirety.

FIELD OF THE INVENTION

The present invention relates to compounds which may be useful in the prophylaxis and/or treatment of allergic diseases, inflammatory diseases, metabolic diseases, autoinflammatory diseases, autoimmune diseases, proliferative diseases, transplantation rejection, diseases involving impairment of cartilage turnover, congenital cartilage malformations, and/or diseases associated with hypersecretion of IFNα, IL12 and/or IL23. In particular, the compound of the invention inhibits JAK, a family of tyrosine kinases, and more particularly TYK2. The present invention also provides methods for the production of the compound of the invention, pharmaceutical compositions comprising the compound of the invention, methods for the prophylaxis and/or treatment of allergic diseases, inflammatory diseases, metabolic diseases, autoinflammatory diseases, autoimmune diseases, proliferative diseases, transplantation rejection, diseases involving impairment of cartilage turnover, congenital cartilage malformations, and/or diseases associated with hypersecretion of IFNα, IL12 and/or IL23 by administering the compound of the invention.

BACKGROUND OF THE INVENTION

Janus kinases (JAKs) are cytoplasmic tyrosine kinases that transduce cytokine signalling from membrane receptors to STAT transcription factors. Four JAK family members are described, JAK1, JAK2, JAK3 and TYK2. Upon binding of the cytokine to its receptor, JAK family members auto- and/or transphosphorylate each other, followed by phosphorylation of STATs that then migrate to the nucleus to modulate transcription. JAK-STAT intracellular signal transduction serves the interferons, most interleukins, as well as a variety of cytokines and endocrine factors such as EPO, TPO, GH, OSM, LIF, CNTF, GM-CSF and PRL. (Vainchenker et al., 2008)

The combination of genetic models and small molecule JAK inhibitor research revealed the therapeutic potential of JAK inhibitors (JAKinibs) (Babon et al., 2014). The last decade has seen the development of JAKinibs with various degrees of selectivity profiles versus the JAK family members. In particular, whereas targeting multiple JAK may not be detrimental (Broekman et al., 2011), developing selective JAKinibs would be very desirable to develop treatment course tailored to the needs of the patient despite the challenge it represents (Fabian et al., 2005). For example, whereas JAK2 inhibition has proven useful in the treatment of polycythemia and myelofibrosis, undesirable effect associated with JAK2 inhibition were observed (O'Shea and Plenge, 2012) thus rendering compounds with JAK2 inhibition components unsuitable for the treatment of non-JAK2 mediated diseases.

Using TYK2 knockout mice, it has been shown that IL-6, IL-10, IL-11, IL12, IL-13, IL-19, IL-20, IL-22, IL-23, IL-27, IL-28, IL-29, IL-31, IL-35 and/or type 1 interferons signaling are dependent on TYK2 (Schwartz et al., 2016). However, it has recently been shown that whereas JAK1 is a key driver in IFNα, IL6, IL10 and IL22 signaling, TYK2 is involved in type I interferons (including IFNα, INFβ), IL23 and IL12 signaling (Gillooly et al., 2016; Sohn et al., 2013). Since the activity of IL12 and IL23 is particularly increased in patients with auto-immune diseases (O'Shea and Plenge, 2012) such as psoriasis and/or inflammatory bowel disorders, selective TYK2 inhibition may be particularly advantageous in the treatment of these diseases while avoiding JAK2 dependent erythropoietin (EPO) and thrombopoietin (TPO) signaling (Neubauer et al., 1998; Parganas et al., 1998).

Furthermore, TYK2 has been reported as a target for multiple autoimmune disorders, providing protection against inflammatory diseases as well as type 2 diabetes with a limited impact on the immune system. (Dendrou et al., 2016)

Accordingly, there remains a need for new compounds which would effectively and selectively inhibit JAK enzymes, in particular TYK2, thus allowing the design of specific treatments and dosages tailored to the pathology.

SUMMARY OF THE INVENTION

The present invention relates to compounds useful in the prophylaxis and/or treatment of allergic diseases, inflammatory diseases, metabolic diseases, autoinflammatory diseases, autoimmune diseases, proliferative diseases, transplantation rejection, diseases involving impairment of cartilage turnover, congenital cartilage malformations, and/or diseases associated with hypersecretion of IFNα, IL12 and/or IL23. In particular, the compound of the invention inhibits JAK, a family of tyrosine kinases, and more particularly TYK2. The present invention also provides methods for the production of the compound of the invention, pharmaceutical compositions comprising the compound of the invention, methods for the prophylaxis and/or treatment of allergic diseases, inflammatory diseases, metabolic diseases, autoinflammatory diseases, autoimmune diseases, proliferative diseases, transplantation rejection, diseases involving impairment of cartilage turnover, congenital cartilage malformations, and/or diseases associated with hypersecretion of IFNα, IL12 and/or IL23 by administering the compound of the invention.

Accordingly, in a first aspect of the invention, the compounds of the invention are provided having a Formula (I):

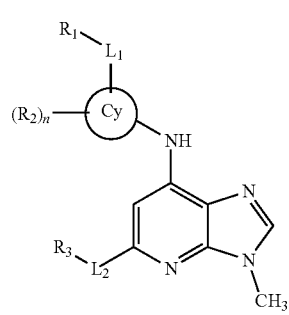

I wherein

Cy is phenyl, or 5-6 membered heteroaryl comprising one, two or three N atoms;

$L_1$ is a single bond, —O—, —C(=O)—, —C(=O)O—, —S(O)$_2$—, —NR$^{6a}$—, —C(=O)NR$^{6b}$—, —S(O)$_2$NR$^{6c}$—, or —C(=O)NR$^{6d}$S(O)$_2$—;

$R^1$ is:
  H,
  $C_{1-6}$ alkyl optionally substituted with one or more independently selected
    OH,
    halo,
    $C_{1-4}$ alkoxy,
    —NR$^{7a}$R$^{7b}$,
    —C(=O)OH—,
    —C(=O)NR$^{7c}$R$^{7d}$,
    —C(=O)OC$_{1-4}$ alkyl, or
    4-8 membered monocyclic heterocycloalkyl comprising one, two, or three heteroatoms independently selected from N, S, and O;
  $C_{3-7}$ cycloalkyl optionally substituted with one or more OH, $C_{1-4}$ alkoxy, or
  4-9 membered monocyclic or spirobicyclic or bridged or fused bicyclic heterocycloalkyl comprising one, two, or three heteroatoms independently selected from N, S, and O; which heterocycloalkyl is optionally substituted with one or more independently selected $R^{11}$ groups;

each $R^{11}$ is independently:
  OH,
  CN,
  halo,
  oxo,
  —NR$^{8a}$R$^{8b}$,
  $C_{3-7}$ cycloalkyl,
  $C_{1-4}$ alkyl optionally substituted with one or more independently selected halo, OH, $C_{1-4}$ alkoxy, —NR$^{9a}$R$^{9b}$,
  $C_{1-4}$ alkoxy optionally substituted with one $C_{1-4}$ alkoxy,
  4-7 membered monocyclic heterocycloalkyl comprising one, two, or three heteroatoms independently selected from N, S, and O,
  —C(=O)OC$_{1-4}$alkyl, or
  —NR$^{8c}$C(=O)OC$_{1-4}$alkyl;

$R^2$ is
  halo,
  CN, or
  $C_{1-4}$ alkyl;

the subscript n is 0, or 1;

$L_2$ is O, or —NR$^4$—, $R^3$ is
  $C_{1-6}$ alkyl optionally substituted with one or more independently selected
    halo, or
    $C_{3-7}$ cycloalkyl,
  Phenyl substituted with one $R^{5a}$ group and one or two independently selected $R^{5b}$ groups,
  6-membered heteroaryl comprising one or two N atoms, substituted with one $R^{5a}$ group and one or two independently selected $R^{5b}$ groups,
  4-10 membered monocyclic or fused, bridged or spiro bicyclic heterocycloalkyl comprising one or two heteroatoms independently selected from N, S, and O, optionally substituted with one, two or three groups independently selected from $R^{5a}$ and $R^{5b}$, or
  4-10 membered monocyclic or fused, bridged or spiro bicyclic cycloalkyl, optionally substituted with one, two or three groups independently selected from $R^{5a}$ and $R^{5b}$;

$R^4$ is
  H,
  $C_{1-4}$ alkyl optionally substituted with one or more independently selected OH or $C_{1-4}$ alkoxy, or
  $C_{3-7}$ cycloalkyl;

$R^{5a}$ is —CN, —SO—C$_{1-4}$ alkyl, or —CF$_3$;

each $R^{5b}$ is independently selected from halo, $C_{1-4}$ alkyl, and $C_{3-7}$ cycloalkyl;

each $R^{7a}$, and $R^{7b}$ is independently selected from
  H, and
  $C_{1-4}$ alkyl optionally substituted with one —NR$^{10a}$R$^{10b}$; and each $R^{6a}$, $R^{6b}$, $R^{6c}$, $R^{6d}$, $R^{7c}$, $R^{7d}$, $R^{8a}$, $R^{8b}$, $R^{8c}$, $R^{9a}$, $R^{9b}$, $R^{10a}$, and $R^{10b}$ is independently selected from H, and $C_{1-4}$ alkyl.

In a particular aspect, the compounds of the invention are provided for use in the prophylaxis and/or treatment of allergic diseases, inflammatory diseases, metabolic diseases, autoinflammatory diseases, autoimmune diseases, proliferative diseases, transplantation rejection, diseases involving impairment of cartilage turnover, congenital cartilage malformations, and/or diseases associated with hypersecretion of IFNα, IL12 and/or IL23.

Furthermore, it has also been unexpectedly demonstrated that the compounds of the invention exhibit improved selectivity towards TYK2 versus other JAK family members, which may be advantageous in the treatment of IFNα, IL12 and/or IL23 associated diseases, particularly auto-immune diseases such as psoriasis and/or inflammatory bowel disorders.

Moreover, the compounds of the invention and their TYK2 selectivity may be advantageous for the design of patient specific treatments and patient tailored dosages.

In a further aspect, the present invention provides pharmaceutical compositions comprising a compound of the invention, and a pharmaceutical carrier, excipient or diluent. In a particular aspect, the pharmaceutical composition may additionally comprise further therapeutically active ingredients suitable for use in combination with the compounds of the invention. In a more particular aspect, the further therapeutically active ingredient is an agent for the prophylaxis and/or treatment of allergic diseases, inflammatory diseases, metabolic diseases, autoinflammatory diseases, autoimmune diseases, proliferative diseases, transplantation rejection, diseases involving impairment of cartilage turnover, congenital cartilage malformations, and/or diseases associated with hypersecretion of IFNα, IL12 and/or IL23.

Moreover, the compounds of the invention, useful in the pharmaceutical compositions and treatment methods disclosed herein, are pharmaceutically acceptable as prepared and used.

In a further aspect of the invention, this invention provides a method of treating a mammal, in particular humans, afflicted with a condition selected from among those listed herein, and particularly allergic diseases, inflammatory diseases, metabolic diseases, autoinflammatory diseases, autoimmune diseases, proliferative diseases, transplantation rejection, diseases involving impairment of cartilage turnover, congenital cartilage malformations, and/or diseases associated with hypersecretion of IFNα, IL12 and/or IL23, which method comprises administering an effective amount of the pharmaceutical composition or compounds of the invention as described herein.

The present invention also provides pharmaceutical compositions comprising a compound of the invention, and a suitable pharmaceutical carrier, excipient or diluent for use in medicine. In a particular aspect, the pharmaceutical composition is for use in the prophylaxis and/or treatment of allergic diseases, inflammatory diseases, metabolic diseases, autoinflammatory diseases, autoimmune diseases, proliferative diseases, transplantation rejection, diseases involving impairment of cartilage turnover, congenital cartilage malformations, and/or diseases associated with hypersecretion of IFNα, IL12 and/or IL23.

In additional aspects, this invention provides methods for synthesizing the compounds of the invention, with representative synthetic protocols and pathways disclosed later on herein.

Other objects and advantages will become apparent to those skilled in the art from a consideration of the ensuing detailed description.

It will be appreciated that compounds of the invention may be metabolized to yield biologically active metabolites.

BRIEF DESCRIPTION OF THE DRAWINGS

FIG. 1 shows the effect of a test compound of the invention on Day 1-5 in the murine psoriatic-like epidermal hyperplasia model, vs the vehicle (filled diamonds) and the control group (filled squares), when dosed q.d. at 3 mg/kg (crosses), 10 mg/kg (asterisks), and 30 mg/kg (filled circles).

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles 'a' and 'an' may be used herein to refer to one or to more than one (i.e. at least one) of the grammatical objects of the article. By way of example 'an analogue' means one analogue or more than one analogue.

'Alkyl' means straight or branched aliphatic hydrocarbon having the specified number of carbon atoms. Particular alkyl groups have 1 to 6 carbon atoms or 1 to 4 carbon atoms. Branched means that one or more alkyl groups such as methyl, ethyl or propyl is attached to a linear alkyl chain. Particular alkyl groups are methyl (—CH$_3$), ethyl (—CH$_2$—CH$_3$), n-propyl (—CH$_2$—CH$_2$—CH$_3$), isopropyl (—CH(CH$_3$)$_2$), n-butyl (—CH$_2$—CH$_2$—CH$_2$—CH$_3$), tert-butyl (—CH$_2$—C(CH$_3$)$_3$), sec-butyl (—CH$_2$—CH(CH$_3$)$_2$), n-pentyl (—CH$_2$—CH$_2$—CH$_2$—CH$_2$—CH$_3$), n-hexyl (—CH$_2$—CH$_2$—CH$_2$—CH$_2$—CH$_2$—CH$_3$), and 1,2-dimethylbutyl (—CHCH$_3$)—C(CH$_3$)H$_2$—CH$_2$—CH$_3$). Particular alkyl groups have between 1 and 4 carbon atoms.

'Alkenyl' refers to monovalent olefinically (unsaturated) hydrocarbon groups with the number of carbon atoms specified. Particular alkenyl has 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═CH$_2$), n-propenyl (—CH$_2$CH═CH$_2$), isopropenyl (—C(CH$_3$)═CH$_2$) and the like.

'Alkylene' refers to divalent alkene radical groups having the number of carbon atoms specified, in particular having 1 to 6 carbon atoms and more particularly 1 to 4 carbon atoms which can be straight-chained or branched. This term is exemplified by groups such as methylene (—CH$_2$—), ethylene (—CH$_2$—CH$_2$—), or —CH(CH$_3$)— and the like.

'Alkynylene' refers to divalent alkyne radical groups having the number of carbon atoms and the number of triple bonds specified, in particular 2 to 6 carbon atoms and more particularly 2 to 4 carbon atoms which can be straight-chained or branched. This term is exemplified by groups such as —C≡C—, —CH$_2$—C≡C—, and —C(CH$_3$)H—C≡CH—.

'Alkoxy' refers to the group O-alkyl, where the alkyl group has the number of carbon atoms specified. In particular the term refers to the group —O—C$_{1-6}$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Amino' refers to the radical —NH$_2$.

'Aryl' refers to a monovalent aromatic hydrocarbon group derived by the removal of one hydrogen atom from a single carbon atom of a parent aromatic ring system. In particular aryl refers to an aromatic ring structure, monocyclic or fused polycyclic, with the number of ring atoms specified. Specifically, the term includes groups that include from 6 to 10 ring members. Particular aryl groups include phenyl, and naphthyl.

'Cycloalkyl' refers to a non-aromatic hydrocarbyl ring structure, monocyclic, fused polycyclic, bridged polycyclic, or spirocyclic, with the number of ring atoms specified. A cycloalkyl may have from 3 to 12 carbon atoms, in particular from 3 to 10, and more particularly from 3 to 7 carbon atoms. Such cycloalkyl groups include, by way of example, single ring structures such as cyclopropyl, cyclobutyl, cyclopentyl, cyclohexyl, and cycloheptyl.

'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, and the like having from 1 to 4, and particularly from 1 to 3 heteroatoms, more typically 1 or 2 heteroatoms, for example a single heteroatom.

'Heteroaryl' means an aromatic ring structure, monocyclic or fused polycyclic, that includes one or more heteroatoms independently selected from O, N and S and the number of ring atoms specified. In particular, the aromatic ring structure may have from 5 to 9 ring members. The heteroaryl group can be, for example, a five membered or six membered monocyclic ring or a fused bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered monocyclic heteroaryl groups include but are not limited to pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered monocyclic heteroaryl groups include but are not limited to pyridinyl, pyrazinyl, pyridazinyl, pyrimidinyl and triazinyl.

Particular examples of bicyclic heteroaryl groups containing a five membered ring fused to another five-membered ring include but are not limited to imidazothiazolyl and imidazoimidazolyl.

Particular examples of bicyclic heteroaryl groups containing a six membered ring fused to a five membered ring include but are not limited to benzofuranyl, benzothiophenyl, benzoimidazolyl, benzoxazolyl, isobenzoxazolyl, benzisoxazolyl, benzothiazolyl, benzoisothiazolyl, isobenzofuranyl, indolyl, isoindolyl, indolizinyl, purinyl (e.g. adenine, guanine), indazolyl, pyrazolopyrimidinyl, triazolopyrimidinyl, and pyrazolopyridinyl groups.

Particular examples of bicyclic heteroaryl groups containing two fused six membered rings include but are not limited to quinolinyl, isoquinolinyl, pyridopyridinyl, quinoxalinyl, quinazolinyl, cinnolinyl, phthalazinyl, naphthyridinyl, and pteridinyl groups. Particular heteroaryl groups are those derived from thiophenyl, pyrrolyl, benzothiophenyl, benzofuranyl, indolyl, pyridinyl, quinolinyl, imidazolyl, oxazolyl and pyrazinyl.

Examples of representative heteroaryls include the following:

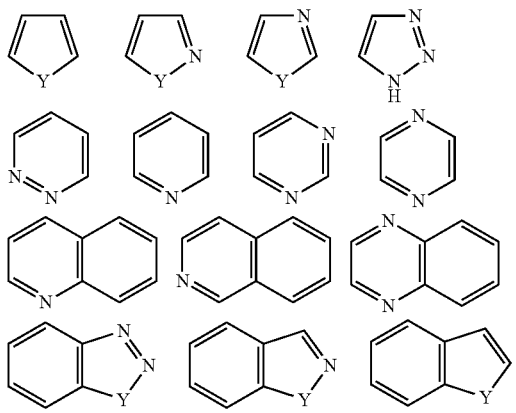

wherein each Y is selected from >C=O, NH, O and S.

'Heterocycloalkyl' means a non-aromatic fully saturated ring structure, monocyclic, fused polycyclic, spirocyclic, or bridged polycyclic, that includes one or more heteroatoms independently selected from O, N and S and the number of ring atoms specified. The heterocycloalkyl ring structure may have from 4 to 12 ring members, in particular from 4 to 10 ring members and more particularly from 4 to 7 ring members. Each ring may contain up to four heteroatoms typically selected from nitrogen, sulphur and oxygen. Typically the heterocycloalkyl ring will contain up to 4 heteroatoms, more typically up to 3 heteroatoms, more usually up to 2, for example a single heteroatom. Examples of heterocyclic rings include, but are not limited to azetidinyl, oxetanyl, thietanyl, pyrrolidinyl (e.g. 1-pyrrolidinyl, 2-pyrrolidinyl and 3-pyrrolidinyl), tetrahydrofuranyl (e.g. 1-tetrahydrofuranyl, 2-tetrahydrofuranyl and 3-tetrahydrofuranyl), tetrahydrothiophenyl (e.g. 1-tetrahydrothiophenyl, 2-tetrahydrothiophenyl and 3-tetrahydrothiophenyl), piperidinyl (e.g. 1-piperidinyl, 2-piperidinyl, 3-piperidinyl and 4-piperidinyl), tetrahydropyranyl (e.g. 4-tetrahydropyranyl), tetrahydrothiopyranyl (e.g. 4-tetrahydrothiopyranyl), morpholinyl, thiomorpholinyl, dioxanyl, or piperazinyl.

As used herein, the term 'heterocycloalkenyl' means a 'heterocycloalkyl', which comprises at least one double bond. Particular examples of heterocycloalkenyl groups are shown in the following illustrative examples:

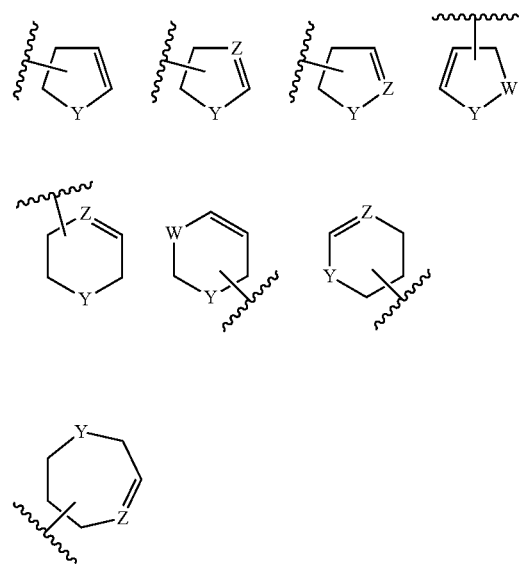

wherein each W is selected from $CH_2$, NH, O and S; each Y is selected from NH, O, C(=O), $SO_2$, and S; and each Z is selected from N and CH.

Particular examples of monocyclic rings are shown in the following illustrative examples:

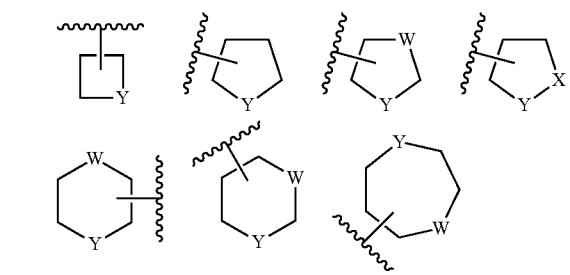

wherein each W and Y is independently selected from —$CH_2$—, —NH—, —O— and —S—.

Particular examples of fused bicyclic rings are shown in the following illustrative examples:

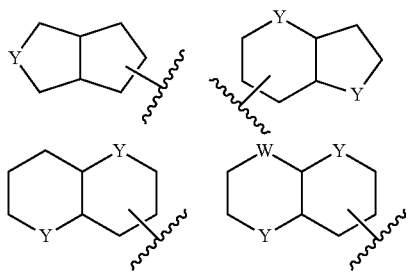

wherein each W and Y is independently selected from —CH₂—, —NH—, —O— and —S—.

Particular examples of bridged bicyclic rings are shown in the following illustrative examples:

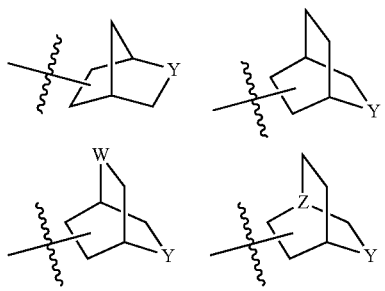

wherein each W and Y is independently selected from —CH₂—, —NH—, —O— and —S— and each Z is selected from N and CH.

Particular examples of spirocyclic rings are shown in the following illustrative examples:

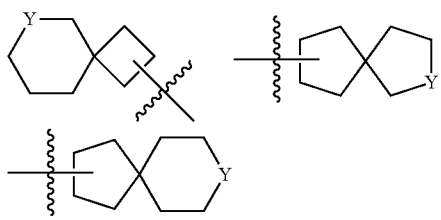

wherein each Y is selected from —CH₂—, —NH—, —O— and —S—.

'Hydroxyl' refers to the radical —OH.

'Oxo' refers to the radical =O.

'Substituted' refers to a group in which one or more hydrogen atoms are each independently replaced with the same or different substituent(s).

'Sulfo' or 'sulfonic acid' refers to a radical such as —SO₃H.

'Thiol' refers to the group —SH.

As used herein, term 'substituted with one or more' refers to one to four substituents. In one embodiment it refers to one to three substituents. In further embodiments it refers to one or two substituents. In a yet further embodiment it refers to one substituent.

'Thioalkoxy' refers to the group —S-alkyl where the alkyl group has the number of carbon atoms specified. In particular the term refers to the group —S—C$_{1-6}$ alkyl. Particular thioalkoxy groups are thiomethoxy, thioethoxy, n-thiopropoxy, isothiopropoxy, n-thiobutoxy, tert-thiobutoxy, sec-thiobutoxy, n-thiopentoxy, n-thiohexoxy, and 1,2-dimethyl-thiobutoxy. Particular thioalkoxy groups are lower thioalkoxy, i.e. with between 1 and 6 carbon atoms. Further particular alkoxy groups have between 1 and 4 carbon atoms.

One having ordinary skill in the art of organic synthesis will recognize that the maximum number of heteroatoms in a stable, chemically feasible heterocyclic ring, whether it is aromatic or non-aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term 'pharmaceutically acceptable cation' refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, EtOH, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Effective amount' means the amount of a compound of the invention that, when administered to a subject for treating a disease, is sufficient to effect such treatment for the disease. The "effective amount" can vary depending on the compound, the disease and its severity, and the age, weight, etc., of the subject to be treated.

'Preventing' or 'prevention' refers to a reduction in risk of acquiring or developing a disease or disorder (i.e. causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e. arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g. stabilization of a discernible symptom), physiologically, (e.g. stabilization of a physical parameter), or both. In a further embodiment, "treating" or "treatment" relates to slowing the progression of the disease.

As used herein the term 'allergic disease(s)' refers to the group of conditions characterized by a hypersensitivity disorder of the immune system including, allergic airway disease (e.g. asthma, rhinitis), sinusitis, eczema and hives, as well as food allergies or allergies to insect venom.

As used herein the term 'asthma' as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate the cause.

As used herein the term 'inflammatory disease(s)' refers to the group of conditions including, rheumatoid arthritis, osteoarthritis, juvenile idiopathic arthritis, psoriasis, psoriatic arthritis, ankylosing spondylitis, allergic airway disease (e.g. asthma, rhinitis), chronic obstructive pulmonary disease (COPD), inflammatory liver diseases (e.g. primary biliary cholangitis (PBC), and/or primary sclerosing cholangitis (PSC)), inflammatory bowel diseases (e.g. Crohn's disease, ulcerative colitis), endotoxin-driven disease states (e.g. complications after bypass surgery or chronic endotoxin states contributing to e.g. chronic cardiac failure), and related diseases involving cartilage, such as that of the joints. Particularly the term refers to rheumatoid arthritis, osteoarthritis, allergic airway disease (e.g. asthma), chronic obstructive pulmonary disease (COPD) and inflammatory bowel diseases. More particularly the term refers to rheumatoid arthritis, chronic obstructive pulmonary disease (COPD), primary biliary cholangitis (PBC), primary sclerosing cholangitis (PSC) and inflammatory bowel diseases. Most particularly the term refers to rheumatoid arthritis, chronic obstructive pulmonary disease (COPD) and inflammatory bowel diseases.

As used herein the term 'metabolic disease(s)' refers to the group of conditions involving the body's ability to process certain nutrients and vitamins. Metabolic disorders include phenylketonuria (PKU), type II diabetes, hyperlipidemia, gout, and rickets. A particular example of metabolic disorders is type II diabetes and/or obesity.

As used herein the term 'autoinflammatory diseases(s)' refers to the group of diseases including Cryopyrin-Associated Periodic Syndromes (CAPS), Familial Mediterranean Fever (FMF) and Tumor necrosis factor receptor-associated periodic syndrome (TRAPS), Behgets, Systemic-Onset Juvenile Idiopathic Arthritis (SJIA) or Still's disease.

As used herein the term 'autoimmune disease(s)' refers to the group of diseases including obstructive airways disease, including conditions such as COPD, asthma (e.g intrinsic asthma, extrinsic asthma, dust asthma, infantile asthma) particularly chronic or inveterate asthma (for example late asthma and airway hyperreponsiveness), bronchitis, including bronchial asthma, systemic lupus erythematosus (SLE), cutaneous lupus erythrematosis, lupus nephritis, dermatomyositis, Sjogren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease and ulcerative colitis), interferonopathy, atherosclerosis and amyotrophic lateral sclerosis. Particularly the term refers to COPD, asthma, systemic lupus erythematosis, type I diabetes mellitus, interferonopathy, and inflammatory bowel disease.

As used herein the term 'proliferative disease(s)' refers to conditions such as cancer (e.g. uterine leiomyosarcoma or prostate cancer), myeloproliferative disorders (e.g. polycythemia vera, essential thrombocytosis and myelofibrosis), leukemia (e.g. acute myeloid leukaemia, acute and chronic lymphoblastic leukemia), multiple myeloma, psoriasis, restenosis, scleroderma or fibrosis. In particular the term refers to cancer, leukemia, multiple myeloma and psoriasis.

As used herein, the term 'cancer' refers to a malignant or benign growth of cells in skin or in body organs, for example but without limitation, breast, prostate, lung, kidney, pancreas, stomach or bowel. A cancer tends to infiltrate into adjacent tissue and spread (metastasise) to distant organs, for example to bone, liver, lung or the brain. As used herein the term cancer includes both metastatic tumour cell types (such as but not limited to, melanoma, lymphoma, leukaemia, fibrosarcoma, rhabdomyosarcoma, and mastocytoma) and types of tissue carcinoma (such as but not limited to, colorectal cancer, prostate cancer, small cell lung cancer and non-small cell lung cancer, breast cancer, pancreatic cancer, bladder cancer, renal cancer, gastric cancer, glioblastoma, primary liver cancer, ovarian cancer, prostate cancer and uterine leiomyosarcoma). In particular, the term 'cancer' refers to acute lymphoblastic leukemia, acute myeloidleukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-celllymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, asopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilms tumor As used herein the term 'leukemia' refers to neoplastic diseases of the blood and blood forming organs. Such diseases can cause bone marrow and immune system dysfunction, which renders the host highly susceptible to infection and bleeding. In particular the term leukemia refers to acute myeloid leukaemia (AML), and acute lymphoblastic leukaemia (ALL) and chronic lymphoblastic leukaemia (CLL).

As used herein the term 'transplantation rejection' refers to the acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or oesophagus, or graft-versus-host diseases.

As used herein the term 'diseases involving impairment of cartilage turnover' includes conditions such as osteoarthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis. In a particular embodiment, the term refers to ankylosing spondylitis.

As used herein the term 'congenital cartilage malformation(s)' includes conditions such as hereditary chondrolysis, chondrodysplasias and pseudochondrodysplasias, in particular, but without limitation, microtia, anotia, metaphyseal chondrodysplasia, and related disorders.

As used herein the term 'disease(s) associated with hypersecretion of IFNα, IL12 and/or IL23 includes conditions such as systemic and cutaneous lupus erythematosis, lupus nephritis, dermatomyositis, Sjogren's syndrome, psoriasis, rheumatoid arthritis, psoriatic arthritis, multiple sclerosis, trisomy 21 and/or Crohn's disease.

'Compound(s) of the invention', and equivalent expressions, are meant to embrace compounds of the Formula(e) as herein described, which expression includes the pharmaceutically acceptable salts, and the solvates, e.g. hydrates, and the solvates of the pharmaceutically acceptable salts where the context so permits. Similarly, reference to intermediates, whether or not they themselves are claimed, is meant to embrace their salts, and solvates, where the context so permits.

When ranges are referred to herein, for example but without limitation, $C_{1-8}$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (Bundgard, H, 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particularly useful prodrugs. In some cases it is desirable to prepare double ester type prodrugs such as (acyloxy)alkyl esters or ((alkoxycarbonyl)oxy)alkylesters. Particular such prodrugs are the $C_{1-8}$ alkyl, $C_{2-8}$ alkenyl, $C_{6-10}$ optionally substituted aryl, and ($C_{6-10}$ aryl)-($C_{1-4}$ alkyl) esters of the compounds of the invention.

The present disclosure includes all isotopic forms of the compounds of the invention provided herein, whether in a form (i) wherein all atoms of a given atomic number have a mass number (or mixture of mass numbers) which predominates in nature (referred to herein as the "natural isotopic form") or (ii) wherein one or more atoms are replaced by atoms having the same atomic number, but a mass number different from the mass number of atoms which predominates in nature (referred to herein as an "unnatural variant isotopic form"). It is understood that an atom may naturally exists as a mixture of mass numbers. The term "unnatural variant isotopic form" also includes embodiments in which the proportion of an atom of given atomic number having a mass number found less commonly in nature (referred to herein as an "uncommon isotope") has been increased relative to that which is naturally occurring e.g. to the level of >20%, >50%, >75%, >90%, >95% or >99% by number of the atoms of that atomic number (the latter embodiment referred to as an "isotopically enriched variant form"). The term "unnatural variant isotopic form" also includes embodiments in which the proportion of an uncommon isotope has been reduced relative to that which is naturally occurring. Isotopic forms may include radioactive forms (i.e. they incorporate radioisotopes) and non-radioactive forms. Radioactive forms will typically be isotopically enriched variant forms.

An unnatural variant isotopic form of a compound may thus contain one or more artificial or uncommon isotopes such as deuterium ($^2$H or D), carbon-11 ($^{11}$C), carbon-13 ($^{13}$C), carbon-14 ($^{14}$C), nitrogen-13 ($^{13}$N), nitrogen-15 ($^{15}$N), oxygen-15 ($^{15}$O), oxygen-17 ($^{17}$O), oxygen-18 ($^{18}$O), phosphorus-32 ($^{32}$P), sulphur-35 ($^{35}$S), chlorine-36 ($^{36}$Cl), chlorine-37 ($^{37}$Cl), fluorine-18 ($^{18}$F) iodine-123 ($^{123}$I), iodine-125 ($^{125}$I) in one or more atoms or may contain an increased proportion of said isotopes as compared with the proportion that predominates in nature in one or more atoms.

Unnatural variant isotopic forms comprising radioisotopes may, for example, be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Unnatural variant isotopic forms which incorporate deuterium i.e. $^2$H or D may afford certain therapeutic advantages resulting from greater metabolic stability, for example, increased in vivo half-life or reduced dosage requirements, and hence may be preferred in some circumstances. Further, unnatural variant isotopic forms may be prepared which incorporate positron emitting isotopes, such as $^{11}$C, $^{18}$F, $^{15}$O and $^{13}$N, and would be useful in Positron Emission Topography (PET) studies for examining substrate receptor occupancy.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e. as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of 7 electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of the invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

It will be appreciated that compounds of the invention may be metabolized to yield biologically active metabolites.

THE INVENTION

The present invention relates to compounds which may be useful in the prophylaxis and/or treatment of allergic diseases, inflammatory diseases, metabolic diseases, autoinflammatory diseases, autoimmune diseases, proliferative diseases, transplantation rejection, diseases involving impairment of cartilage turnover, congenital cartilage malformations, and/or diseases associated with hypersecretion of IFNα, IL12 and/or IL23. In particular, the compound of the invention inhibits JAK, a family of tyrosine kinases, and more particularly TYK2. The present invention also provides methods for the production of the compound of the invention, pharmaceutical compositions comprising the compound of the invention, methods for the prophylaxis and/or treatment of allergic diseases, inflammatory diseases, metabolic diseases, autoinflammatory diseases, autoimmune diseases, proliferative diseases, transplantation rejection, diseases involving impairment of cartilage turnover, congenital cartilage malformations, and/or diseases associated with hypersecretion of IFNα, IL12 and/or IL23 by administering the compound of the invention.

Accordingly, in a first aspect of the invention, the compounds of the invention are provided having a Formula (I):

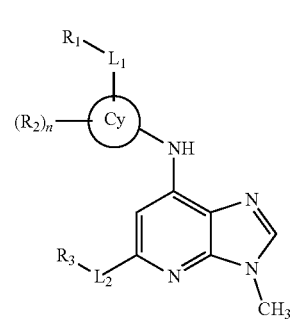

wherein
Cy is phenyl, or 5-6 membered heteroaryl comprising one, two or three N atoms;

$L_1$ is a single bond, —O—, —C(=O)—, —C(=O)O—, —S(O)$_2$—, —NR$^{6a}$—, —C(=O)NR$^{6b}$—, —S(O)$_2$NR$^{6c}$—, or —C(=O)NR$^{6d}$S(O)$_2$—;

$R^1$ is:
H,
$C_{1-6}$ alkyl optionally substituted with one or more independently selected
OH,
halo,
$C_{1-4}$ alkoxy,
—NR$^{7a}$R$^{7b}$,
—C(=O)OH—,
—C(=O)NR$^{7c}$R$^{7d}$,
—C(=O)OC$_{1-4}$ alkyl, or
4-8 membered monocyclic heterocycloalkyl comprising one, two, or three heteroatoms independently selected from N, S, and O;
$C_{3-7}$ cycloalkyl optionally substituted with one or more OH, $C_{1-4}$ alkoxy, or
4-9 membered monocyclic or spirobicyclic or bridged or fused bicyclic heterocycloalkyl comprising one, two, or three heteroatoms independently selected from N, S, and O; which heterocycloalkyl is optionally substituted with one or more independently selected $R^{11}$ groups;
each $R^{11}$ is independently:
OH,
CN,
halo,
oxo,
—NR$^{8a}$R$^{8b}$,
$C_{3-7}$ cycloalkyl,
$C_{1-4}$ alkyl optionally substituted with one or more independently selected halo, OH, $C_{1-4}$ alkoxy, —NR$^{9a}$R$^{9b}$,
$C_{1-4}$ alkoxy optionally substituted with one $C_{1-4}$ alkoxy,
4-7 membered monocyclic heterocycloalkyl comprising one, two, or three heteroatoms independently selected from N, S, and O,
—C(=O)OC$_{1-4}$alkyl, or
—NR$^{8c}$C(=O)OC$_{1-4}$alkyl;

$R^2$ is
halo,
CN, or
$C_{1-4}$ alkyl;
the subscript n is 0, or 1;
$L_2$ is O, or —NR$^4$—,
$R^3$ is
$C_{1-6}$ alkyl optionally substituted with one or more independently selected
halo, or
$C_{3-7}$ cycloalkyl,
Phenyl substituted with one $R^{5a}$ group and one or two independently selected $R^{5b}$ groups,
6-membered heteroaryl comprising one or two N atoms, substituted with one $R^{5a}$ group and one or two independently selected $R^{5b}$ groups,
4-10 membered monocyclic or fused, bridged or spiro bicyclic heterocycloalkyl comprising one or two heteroatoms independently selected from N, S, and O, optionally substituted with one, two or three groups independently selected from $R^{5a}$ and $R^{5b}$, or
4-10 membered monocyclic or fused, bridged or spiro bicyclic cycloalkyl, optionally substituted with one, two or three groups independently selected from $R^{5a}$ and $R^{5b}$;

$R^4$ is
H,
$C_{1-4}$ alkyl optionally substituted with one or more independently selected OH or $C_{1-4}$ alkoxy, or
$C_{3-7}$ cycloalkyl;
$R^{5a}$ is —CN, —SO$_2$—C$_{1-4}$ alkyl, or —CF$_3$;
each $R^{5b}$ is independently selected from halo, $C_{1-4}$ alkyl, and $C_{3-7}$ cycloalkyl;
each $R^{7a}$, and $R^{7b}$ is independently selected from
H, and
$C_{1-4}$ alkyl optionally substituted with one —NR$^{10a}$R$^{10b}$; and
each $R^{6a}$, $R^{6b}$, $R^{6c}$, $R^{6d}$, $R^{7c}$, $R^{7d}$, $R^{8a}$, $R^{8b}$, $R^{8c}$, $R^{9a}$, $R^{9b}$, $R^{10a}$, and $R^{10b}$ is independently selected from H, and $C_{1-4}$ alkyl.

In another embodiment, the compound of the invention is according to Formula I, wherein $L_2$ is —NR$^4$, wherein $R^4$ is as previously described. In a particular embodiment, $R^4$ is H. In another particular embodiment, $R^4$ is —CH$_3$, —CH$_2$—CH$_2$—CH$_2$—OH, —CH$_2$—CHOH—CH$_3$, —CH$_2$—CH$_2$—CH$_2$—OCH$_3$, or cyclopropyl.

In one embodiment, the compound of the invention is according to Formula I, wherein $L_2$ is O.

In one embodiment, the compound of the invention is according to Formula I, wherein $R^3$ is $C_{1-6}$ alkyl. In a particular embodiment, $R^3$ is —CH$_3$, —CH$_2$CH$_3$, —CH(CH$_3$)CH(CH$_3$)$_2$, or —CH(CH$_3$)C(CH$_3$)$_3$.

In one embodiment, the compound of the invention is according to Formula I, wherein $R^3$ is $C_{1-6}$ alkyl substituted with one or more independently selected halo, or $C_{3-7}$ cycloalkyl. In a particular embodiment, $R^3$ is —CH$_3$, —CH$_2$CH$_3$, —CH(CH$_3$)CH(CH$_3$)$_2$, —CH(CH$_3$)C(CH$_3$)$_3$, each of which is optionally substituted with one or more independently selected halo, or $C_{3-7}$ cycloalkyl. In another particular embodiment, $R^3$ is $C_{1-6}$ alkyl optionally substituted with one or more independently F, cyclopropyl, or cyclobutyl. In a more particular embodiment, $R^3$ is selected from:

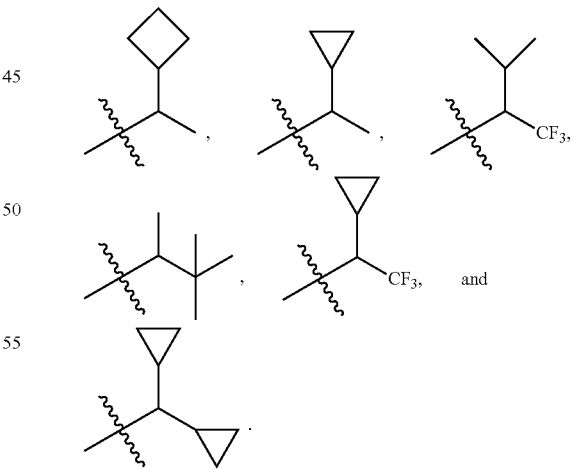

In another embodiment, the compound of the invention is according to Formula I, wherein $R^3$ is phenyl substituted with one $R^{5a}$ group and one or two independently selected $R^{5b}$ groups. In a particular embodiment, $R^3$ is phenyl substituted with one $R^{5a}$ group and two independently selected $R^{5b}$ groups.

In another embodiment, the compound of the invention is according to Formula I, wherein $R^3$ is 6-membered heteroaryl substituted with one $R^{5a}$ group and one or two independently selected $R^{5b}$ groups. In one embodiment, $R^3$ is pyridinyl, or pyridazinyl, each of which is substituted with one $R^{5a}$ group and one $R^{5b}$ group.

In one embodiment, the compound of the invention is according to Formula I, wherein $R^3$ is

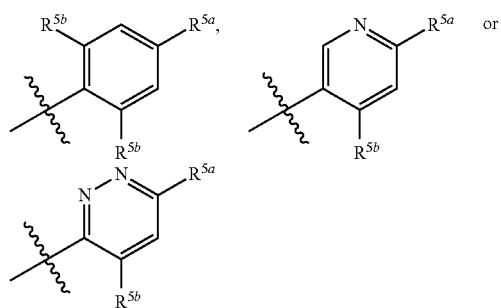

wherein $R^{5a}$ and $R^{5b}$ are as described above.

In one embodiment, the compound of the invention is according to Formula I, wherein $R^3$ is as described above, and $R^{5a}$ is —CN, —SO$_2$—C$_{1-4}$ alkyl, or —CF$_3$. In a particular embodiment, $R^{5a}$ is —CN, —SO$_2$CH$_3$, or —CF$_3$. In a more particular embodiment, $R^{5a}$ is —CN.

In one embodiment, the compound of the invention is according to Formula I, wherein $R^3$ is as described above, and each $R^{5b}$ is independently selected from halo, C$_{1-4}$ alkyl, and C$_{3-7}$ cycloalkyl. In a particular embodiment, each $R^{5b}$ is independently selected from F, —CH$_3$, —CH$_2$CH$_3$, and cyclopropyl.

In one embodiment, the compound of the invention is according to Formula I, wherein $R^3$ is 4-10 membered monocyclic or fused, bridged or spiro bicyclic heterocycloalkyl comprising one or two heteroatoms independently selected from N, S, and O. In a particular embodiment, $R^3$ is tetrahydropyranyl, or oxa-spiro[3.5]nonane.

In one embodiment, the compound of the invention is according to Formula I, wherein $R^3$ is 4-10 membered monocyclic or fused, bridged or spiro bicyclic heterocycloalkyl comprising one or two heteroatoms independently selected from N, S, and O, optionally substituted with one, two or three groups independently selected from $R^{5a}$ and $R^{5b}$. In a particular embodiment, $R^3$ is tetrahydropyranyl, or oxa-spiro[3.5]nonane, each of which is optionally substituted with one, two or three groups independently selected from $R^{5a}$ and $R^{5b}$. In another particular embodiment, $R^3$ is 4-10 membered monocyclic or fused, bridged or spiro bicyclic heterocycloalkyl comprising one or two heteroatoms independently selected from N, S, and O, optionally substituted with one, two or three groups independently selected from $R^{5a}$ and $R^{5b}$ wherein $R^{5a}$ is —CN, —SO$_2$CH$_3$, or —CF$_3$, and $R^{5b}$ is selected from F, —CH$_3$, —CH$_2$CH$_3$, and cyclopropyl.

In one embodiment, the compound of the invention is according to Formula I, wherein $R^3$ is 4-10 membered monocyclic or fused, bridged or spiro bicyclic cycloalkyl. In a particular embodiment, $R^3$ is cyclohexyl, or bicyclo[1.1.1]pentane.

In one embodiment, the compound of the invention is according to Formula I, wherein $R^3$ is 4-10 membered monocyclic or fused, bridged or spiro bicyclic cycloalkyl, optionally substituted with one, two or three groups independently selected from $R^{5a}$ and $R^{5b}$. In a particular embodiment, $R^3$ is cyclohexyl, or bicyclo[1.1.1]pentane, each of which is optionally substituted with one, two or three groups independently selected from $R^{5a}$ and $R^{5b}$. In another particular embodiment, $R^3$ is 4-10 membered monocyclic or fused, bridged or spiro bicyclic heterocycloalkyl comprising one or two heteroatoms independently selected from N, S, and O, optionally substituted with one, two or three groups independently selected from $R^{5a}$ and $R^{5b}$, wherein $R^{5a}$ is —CN, —SO$_2$CH$_3$, or —CF$_3$, and $R^{5b}$ is selected from F, —CH$_3$, —CH$_2$CH$_3$, and cyclopropyl.

In one embodiment, the compound of the invention is according to any one of Formula II:

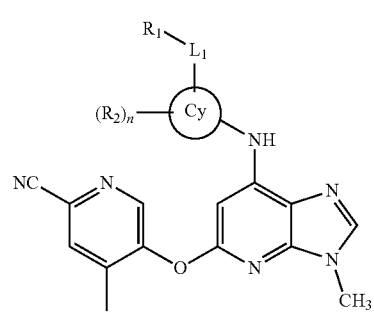

wherein $R^1$, $L_1$, $R^2$, Cy, and the subscript n is as previously described.

In one embodiment, the compound of the invention is according to Formula I, or II, wherein Cy is phenyl.

In one embodiment, the compound of the invention is according to Formula I, or II, wherein Cy is 5-6 membered heteroaryl comprising one, two or three N atoms. In a particular embodiment, Cy is pyrazolyl, pyridinyl, pyrimidinyl, or pyridazinyl. In a more particular embodiment, Cy is pyridinyl, pyrimidinyl, or pyridazinyl. In a most particular embodiment, Cy is pyridazinyl.

In one embodiment, the compound of the invention is according to Formula I, or II, wherein the subscript n is 1, and $R^2$ is as previously described. In a particular embodiment, $R^2$ is F, CN, or —CH$_3$.

In one embodiment, the compound of the invention is according to Formula I, or II, wherein the subscript n is 0.

In one embodiment, the compound of the invention is according to formula IIIa, IIIb, IIIc, or IIId:

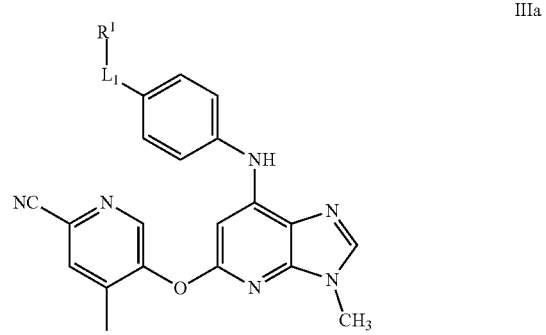

-continued

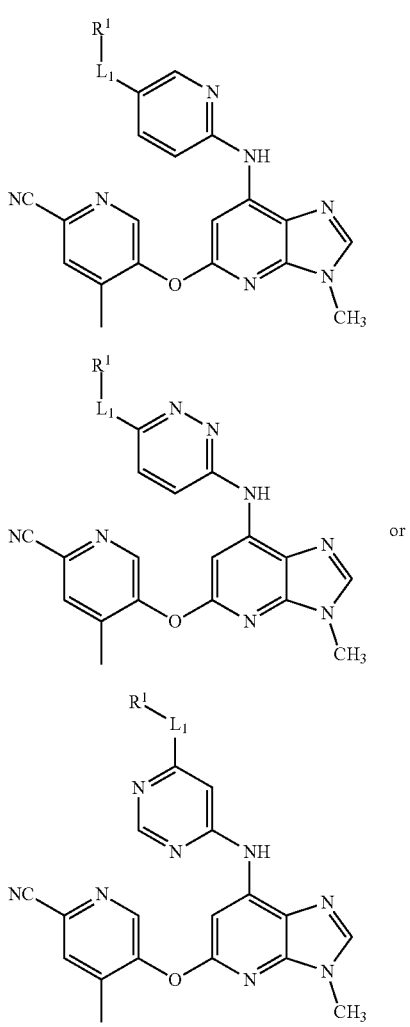

IIIb

IIIc

IIId wherein $L_1$ and $R^1$ are as previously described.

In one embodiment, the compound of the invention is according to any one of Formula I-IIId, wherein $L_1$ is a single bond.

In one embodiment, the compound of the invention is according to any one of Formula I-IIId, wherein $L_1$ is —O—

In one embodiment, the compound of the invention is according to any one of Formula I-IIId, wherein $L_1$ is —C(=O)—.

In one embodiment, the compound of the invention is according to any one of Formula I-IIId, wherein $L_1$ is —S(O)$_2$—.

In one embodiment, the compound of the invention is according to any one of Formula I-IIId, wherein $L_1$ is —NR$^{6a}$—, and R$^{6a}$ is selected from H, and C$_{1-4}$ alkyl. In a particular embodiment, R$^{6a}$ is selected from H, and —CH$_3$.

In one embodiment, the compound of the invention is according to any one of Formula I-IIId, wherein $L_1$ is —C(=O)NR$^{6b}$—, and R$^{6b}$ is selected from H, and C$_{1-4}$ alkyl. In a particular embodiment, R$^{6b}$ is selected from H, and —CH$_3$.

In one embodiment, the compound of the invention is according to any one of Formula I-IIId, wherein $L_1$ is —S(O)$_2$NR$^{6c}$—, and R$^{6c}$ is selected from H, and C$_{1-4}$ alkyl. In a particular embodiment, R$^{6c}$ is selected from H, and —CH$_3$.

In one embodiment, the compound of the invention is according to any one of Formula I-IIId, wherein $L_1$ is —C(=O)NR$^{6d}$S(O)$_2$—, and R$^{6d}$ is selected from H, and C$_{1-4}$ alkyl. In a particular embodiment, R$^{6d}$ is selected from H, and —CH$_3$.

In one embodiment, the compound of the invention is according to any one of Formula I-IIId, wherein $R^1$ is H.

In one embodiment, the compound of the invention is according to any one of Formula I-IIId, wherein $R^1$ is C$_{1-6}$ alkyl. In a particular embodiment, $R^1$ is —CH$_3$, or —CH$_2$CH$_3$.

In one embodiment, the compound of the invention is according to any one of Formula I-IIId, wherein $R^1$ is C$_{1-6}$ alkyl substituted with one or more independently selected OH, halo, C$_{1-4}$ alkoxy, —NR$^{7a}$R$^{7b}$, —C(=O)OH—, —C(=O)NR$^{7c}$R$^{7d}$, —C(=O)OC$_{1-4}$ alkyl, or 4-8 membered monocyclic heterocycloalkyl comprising one, two, or three heteroatoms independently selected from N, S, and O, and wherein each Ra, R$^{7b}$, R$^{7c}$ and R$^{7d}$ are as previously described. In a particular embodiment, $R^1$ is —CH$_3$, —CH$_2$CH$_3$, —CH$_2$CH$_2$CH$_3$, —CH$_2$CH(CH$_3$)$_2$, —CH$_2$CH$_2$CH$_2$CH$_3$, or —CH$_2$CH$_2$CH(CH$_3$)$_2$, each of which is substituted with one or more independently selected OH, halo, C$_{1-4}$ alkoxy, —NR$^{7a}$R$^{7b}$, —C(=O) OH—, —C(=O)NR$^{7c}$R$^{7d}$, —C(=O)OC$_{1-4}$ alkyl, 4-8 membered monocyclic heterocycloalkyl comprising one, two, or three heteroatoms independently selected from N, S, and O, and wherein each R$^{7a}$, R$^{7b}$, R$^{7c}$ and Rd are as previously described. In a particular embodiment, each R$^{7a}$ and R$^{7b}$ is independently H, or C$_{1-4}$ alkyl optionally substituted with one —NR$^{10a}$R$^{10b}$, wherein each R$^{10a}$ and R$^{10b}$ is independently selected H, —CH$_3$, or —CH$_2$CH$_3$. In a more particular embodiment, each R$^{7a}$ and R$^{7b}$ is independently H, or —CH$_3$, or —CH$_2$CH$_3$, each of which is optionally substituted with one —NR$^{10a}$R$^{10b}$. wherein each R$^{10a}$ and R$^{10b}$ is independently selected H, —CH$_3$, or —CH$_2$CH$_3$. In another particular embodiment, each R$^{7c}$ and R$^{7d}$ is independently H, —CH$_3$, or —CH$_2$CH$_3$.

In another particular embodiment, $R^1$ is C$_{1-6}$ alkyl substituted with one or more OH, F, —OCH$_3$, —OCH$_2$CH$_3$, —NH$_2$, —NHCH$_3$, —NHCH$_2$CH$_2$—N(CH$_3$)$_2$, —NHCH$_2$CH$_3$, —C(=O)OH—, —C(=O)NH$_2$, —C(=O) NHCH$_3$, —C(=O)NHCH$_2$CH$_3$, —C(=O)N(CH$_3$)$_2$, —C(=O)OC$_{1-4}$ alkyl, dioxanyl, morpholinyl. In a more particular embodiment, $R^1$ is —CH$_3$, —CH$_2$CH$_3$, —CH$_2$CH$_2$CH$_3$, —CH$_2$CH(CH$_3$)$_2$, —CH$_2$CH$_2$CH$_2$CH$_3$, or —CH$_2$CH$_2$CH(CH$_3$)$_2$, each of which is substituted with one or more OH, F, —OCH$_3$, —OCH$_2$CH$_3$, —NH$_2$, —NHCH$_3$, —NHCH$_2$CH$_2$—N(CH$_3$)$_2$, —NHCH$_2$CH$_3$, —C(=O) OH—, —C(=O)NH$_2$, —C(=O)NHCH$_3$, —C(=O) NHCH$_2$CH$_3$, —C(=O)N(CH$_3$)$_2$, —C(=O)OC$_{1-4}$ alkyl, dioxanyl, morpholinyl.

In a most particular embodiment, $R^1$ is —CH$_3$, —CH$_2$CH$_3$, —CH$_2$NH$_2$, —CH$_2$CH(OH)CH$_3$, —CH$_2$—CH$_2$OCH$_3$, —CH$_2$CH$_2$CH$_2$OH, —CH$_2$CH$_2$CH$_2$OCH$_3$, —CH$_2$CH$_2$CH(CH$_3$)OCH$_3$, —CH$_2$CH$_2$C(CH$_3$)OH, —CH$_2$—C(=O)NHCH$_2$CH$_3$, —CH$_2$-morpholinyl, —CH$_2$-dioxanyl, or —CH$_2$N(CH$_3$)CH$_2$CH$_2$N(CH$_3$)$_2$.

In one embodiment, the compound of the invention is according to any one of Formula I-IIId, wherein $R^1$ is C$_{3-7}$ cycloalkyl. In a particular embodiment, $R^1$ is cyclopropyl, cyclobutyl, cyclopentyl or cyclohexyl.

In one embodiment, the compound of the invention is according to any one of Formula I-IIId, wherein $R^1$ is C$_{3-7}$ cycloalkyl substituted with one or more independently selected OH, or C$_{1-4}$ alkoxy. In a particular embodiment, $R^1$ is C$_{3-7}$ cycloalkyl substituted with one, two or three independently selected OH, $C_{1-4}$ alkoxy. In a more particular embodiment, $R^1$ is cyclopropyl, cyclobutyl, cyclopentyl or cyclohexyl, each of which is substituted with one, two or three independently selected OH, $C_{1-4}$ alkoxy. In another more particular embodiment, $R^1$ is $C_{3-7}$ cycloalkyl substituted with one, two or three independently selected OH, —OCH$_3$, or —OCH$_2$CH$_3$.

In one embodiment, the compound of the invention is according to any one of Formula I-IIId, wherein $R^1$ is 4-9 membered monocyclic or spirobicyclic or bridged or fused bicyclic heterocycloalkyl comprising one, two, or three heteroatoms independently selected from N, S, and O. in a particular embodiment, $R^1$ is azetidinyl, oxetanyl, pyrrolidinyl, morpholinyl, octadeuteriomorpholin-4-yl, tetrahydropyranyl, piperazinyl, dioxanyl, [1,4]Oxazepanyl, 2-Oxa-5-aza-bicyclo[2.2.1]heptanyl, 1-Oxa-6-aza-spiro[3.3]heptanyl, Octahydro-pyrrolo[3,4-b]pyrrolyl, 2-Oxa-6-aza-spiro[3.4]octanyl, 2-Oxa-7-aza-spiro[4.4]nonanyl, 2,6-Diaza-spiro[3.3]heptanyl, or 2,5-Diaza-bicyclo[2.2.1]heptanyl. In a more particular embodiment, $R^1$ is azetidinyl, oxetanyl, pyrrolidinyl, morpholinyl, octadeuteriomorpholin-4-yl, tetrahydropyranyl, piperazinyl, or dioxanyl.

In one embodiment, the compound of the invention is according to any one of Formula I-IIId, wherein $R^1$ is 4-9 membered monocyclic or spirobicyclic or bridged or fused bicyclic heterocycloalkyl comprising one, two, or three heteroatoms independently selected from N, S, and O; which heterocycloalkyl is substituted with one or more independently selected $R^{11}$ groups. In a particular embodiment, $R^1$ is 4-9 membered monocyclic or spirobicyclic or bridged or fused bicyclic heterocycloalkyl comprising one, two, or three heteroatoms independently selected from N, S, and O; which heterocycloalkyl is substituted with one, two or three independently selected $R^{11}$ groups. In a more particular embodiment, $R^1$ is azetidinyl, oxetanyl, pyrrolidinyl, morpholinyl, octadeuteriomorpholin-4-yl, piperidinyl, tetrahydropyranyl, piperazinyl, dioxanyl, [1,4]oxazepanyl, 2-oxa-5-aza-bicyclo[2.2.1]heptanyl, 1-oxa-6-aza-spiro[3.3]heptanyl, octahydro-pyrrolo[3,4-b]pyrrolyl, 2-oxa-6-aza-spiro[3.4]octanyl, 2-oxa-7-aza-spiro[4.4]nonanyl, 2,6-diaza-spiro[3.3]heptanyl, or 2,5-diaza-bicyclo[2.2.1]heptanyl, each of which is substituted with one, two or three independently selected $R^{11}$ groups. In a most particular embodiment, $R^1$ is azetidinyl, oxetanyl, pyrrolidinyl, morpholinyl, octadeuteriomorpholin-4-yl, tetrahydropyranyl, piperazinyl, or dioxanyl, each of which is substituted with one, two or three independently selected $R^{11}$ groups.

In one embodiment, the compound of the invention is according to any one of Formula I-IIId, wherein $R^1$ is 4-9 membered monocyclic or spirobicyclic or bridged or fused bicyclic heterocycloalkyl comprising one, two, or three heteroatoms independently selected from N, S, and O; which heterocycloalkyl is substituted with one or more independently selected $R^{11}$ groups, wherein one or more of the $R^{11}$ groups is OH.

In one embodiment, the compound of the invention is according to any one of Formula I-IIId, wherein $R^1$ is 4-9 membered monocyclic or spirobicyclic or bridged or fused bicyclic heterocycloalkyl comprising one, two, or three heteroatoms independently selected from N, S, and O; which heterocycloalkyl is substituted with one or more independently selected $R^{11}$ groups, wherein one or more of the $R^{11}$ groups is —CN.

In one embodiment, the compound of the invention is according to any one of Formula I-IIId, wherein $R^1$ is 4-9 membered monocyclic or spirobicyclic or bridged or fused bicyclic heterocycloalkyl comprising one, two, or three heteroatoms independently selected from N, S, and O; which heterocycloalkyl is substituted with one or more independently selected $R^{11}$ groups, wherein one or more of the $R^{11}$ groups is halo. In a particular embodiment, $R^{11}$ is F, or.Cl , In one embodiment, the compound of the invention is according to any one of Formula I-IIId, wherein $R^1$ is 4-9 membered monocyclic or spirobicyclic or bridged or fused bicyclic heterocycloalkyl comprising one, two, or three heteroatoms independently selected from N, S, and O; which heterocycloalkyl is substituted with one or more independently selected $R^{11}$ groups, wherein one or more of the $R^{11}$ groups is oxo.

, In one embodiment, the compound of the invention is according to any one of Formula I-IIId, wherein $R^1$ is 4-9 membered monocyclic or spirobicyclic or bridged or fused bicyclic heterocycloalkyl comprising one, two, or three heteroatoms independently selected from N, S, and O; which heterocycloalkyl is substituted with one or more independently selected $R^{11}$ groups, wherein one or more of the $R^{11}$ groups is —NR$^{8a}$R$^{8b}$, and each R$^{8a}$ and R$^{8b}$ is as previously defined. In a particular embodiment, each R$^{8a}$ and R$^{8b}$ is independently H, or $C_{1-4}$ alkyl. In a more particular embodiment, each R$^{8a}$ and R$^{8b}$ is independently H, —CH$_3$, or —CH$_2$CH$_3$.

In one embodiment, the compound of the invention is according to any one of Formula I-IIId, wherein $R^1$ is 4-9 membered monocyclic or spirobicyclic or bridged or fused bicyclic heterocycloalkyl comprising one, two, or three heteroatoms independently selected from N, S, and O; which heterocycloalkyl is substituted with one or more independently selected $R^{11}$ groups, wherein one or more of the $R^{11}$ groups is $C_{3-7}$ cycloalkyl. In a particular embodiment, $R^{11}$ is cyclopropyl, cyclobutyl, cyclopentyl, or cyclohexyl.

In one embodiment, the compound of the invention is according to any one of Formula I-IIId, wherein $R^1$ is 4-9 membered monocyclic or spirobicyclic or bridged or fused bicyclic heterocycloalkyl comprising one, two, or three heteroatoms independently selected from N, S, and O; which heterocycloalkyl is substituted with one or more independently selected $R^{11}$ groups. wherein one or more of the $R^{11}$ groups is $C_{1-4}$ alkyl optionally substituted with one or more independently selected halo, OH, $C_{1-4}$ alkoxy, —NR$^{9a}$R$^{9b}$, wherein each R$^{9a}$ and R$^{9b}$ is as previously defined. In a particular embodiment, $R^{11}$ is —CH$_3$, —CH$_2$CH$_3$, or —CH$_2$CH$_2$CH$_3$, each of which is optionally substituted with one or more independently selected halo, OH, $C_{1-4}$ alkoxy, —NR$^{9a}$R$^{9b}$, wherein each R$^{9a}$ and R$^{9b}$ is as previously defined. In another particular embodiment, $R^{11}$ is $C_{1-4}$ alkyl, optionally substituted with one or more independently selected F, —OCH$_3$, —OCH$_2$CH$_3$, —NH$_2$, —NHCH$_3$, or —N(CH$_3$)$_2$. In a more particular embodiment, $R^{11}$ is —CH$_3$, —CH$_2$CH$_3$, —CH(CH$_3$)$_2$ or —CH$_2$CH$_2$CH$_3$, each of which is optionally substituted with one or more more independently selected F, —OCH$_3$, —OCH$_2$CH$_3$, —NH$_2$, —NHCH$_3$, or —N(CH$_3$)$_2$.

In one embodiment, the compound of the invention is according to any one of Formula I-IIId, wherein $R^1$ is 4-9 membered monocyclic or spirobicyclic or bridged or fused bicyclic heterocycloalkyl comprising one, two, or three heteroatoms independently selected from N, S, and O; which heterocycloalkyl is substituted with one or more independently selected $R^{11}$ groups, wherein one or more of the $R^{11}$ groups is $C_{1-4}$ alkoxy optionally substituted with one $C_{1-4}$ alkoxy. In a particular embodiment, $R^{11}$ is —OCH$_3$, —OCH$_2$CH$_3$, or —OCH$_2$CH$_2$CH$_3$, each of which is optionally substituted with one or more independently selected $C_{1-4}$ alkoxy. In another particular embodiment, $R^{11}$ is $C_{1-4}$ alkoxy, optionally substituted with one or more independently selected —OCH$_3$, —OCH$_2$CH$_3$, or —OCH$_2$CH$_2$CH$_3$. In a more particular embodiment, R$^{11}$ is —OCH$_3$, —OCH$_2$CH$_3$, or —OCH$_2$CH$_2$CH$_3$, each of which is optionally substituted with one or more independently selected —OCH$_3$, —OCH$_2$CH$_3$, or —OCH$_2$CH$_2$CH$_3$.

In one embodiment, the compound of the invention is according to any one of Formula I-IIId, wherein R$^1$ is 4-9 membered monocyclic or spirobicyclic or bridged or fused bicyclic heterocycloalkyl comprising one, two, or three heteroatoms independently selected from N, S, and O; which heterocycloalkyl is substituted with one or more independently selected R$^{11}$ groups. wherein one or more of the R$^{11}$ groups is 4-7 membered monocyclic heterocycloalkyl comprising one, two, or three heteroatoms independently selected from N, S, and O. in a particular embodiment, R$^{11}$ is azetidinyl, oxetanyl, pyrolidinyl, tetrahydrofuranyl, piperidinyl, piperazinyl, tetrahydropyranyl, dioxanyl, or morpholinyl.

In one embodiment, the compound of the invention is according to any one of Formula I-IIId, wherein R$^1$ is 4-9 membered monocyclic or spirobicyclic or bridged or fused bicyclic heterocycloalkyl comprising one, two, or three heteroatoms independently selected from N, S, and O; which heterocycloalkyl is substituted with one or more independently selected R$^{11}$ groups, wherein one or more of the R$^{11}$ groups is —C(=O)OC$_{1-4}$alkyl. In a particular embodiment, R$^{11}$ is —C(=O)OCH$_3$.

In one embodiment, the compound of the invention is according to any one of Formula I-IIId, wherein R$^1$ is 4-9 membered monocyclic or spirobicyclic or bridged or fused bicyclic heterocycloalkyl comprising one, two, or three heteroatoms independently selected from N, S, and O; which heterocycloalkyl is substituted with one or more independently selected R$^{11}$ group, wherein one or more of the R$^{11}$ groups is —NR$^{8c}$C(=O)OC$_{1-4}$alkyl, wherein R$^{8c}$ is as previously defined. In a particular embodiment, R$^{11}$ is —NHC(=O)OCH$_3$, —NCH$_3$C(=O)OCH$_3$, or —NHC(=O)OCH$_2$CH$_3$.

In one embodiment, the compound of the invention is selected from:
4-{[7-(6-Amino-pyrimidin-4-ylamino)-3-methyl-3H-imidazo[4,5-b]pyridin-5-yl]-methyl-amino}-3-ethyl-5-fluoro-benzonitrile,
5-{[7-(6-Amino-pyrimidin-4-ylamino)-3-methyl-3H-imidazo[4,5-b]pyridin-5-yl]-methyl-amino}-4-methyl-pyridine-2-carbonitrile
4-{[7-(6-Amino-pyrimidin-4-ylamino)-3-methyl-3H-imidazo[4,5-b]pyridin-5-yl]-methyl-amino}-cyclohexanecarbonitrile,
N7-(6-Amino-pyrimidin-4-yl)-N5-(3,3-dimethyl-tetrahydro-pyran-4-yl)-3,N5-dimethyl-3H-imidazo[4,5-b]pyridine-5,7-diamine,
N7-(6-aminopyrimidin-4-yl)-N5,3-dimethyl-N5-[(1S)-1,2,2-trimethylpropyl]imidazo[4,5-b]pyridine-5,7-diamine,
(±)-(1R,3R)-3-{[7-(6-Amino-pyrimidin-4-ylamino)-3-methyl-3H-imidazo[4,5-b]pyridin-5-yl]-methyl-amino}-cyclohexanecarbonitrile,
4-{[7-(6-Amino-pyrimidin-4-ylamino)-3-methyl-3H-imidazo[4,5-b]pyridin-5-yl]-methyl-amino}-3-cyclopropyl-5-fluoro-benzonitrile,
5-{[7-(6-Amino-pyrimidin-4-ylamino)-3-methyl-3H-imidazo[4,5-b]pyridin-5-yl]-methyl-amino}-4-ethyl-pyridine-2-carbonitrile,
N7-(6-aminopyrimidin-4-yl)-N5-[(1R)-1-cyclopropylethyl]-N5,3-dimethyl-imidazo[4,5-b]pyridine-5,7-diamine,
N7-(6-Amino-pyrimidin-4-yl)-3,N5-dimethyl-N5-((3R,4S)-3-methyl-tetrahydro-pyran-4-yl)-3H-imidazo[4,5-b]pyridine-5,7-diamine,
N7-(6-Amino-pyrimidin-4-yl)-N5-bicyclo[1.1.1]pent-1-yl-3,N5-dimethyl-3H-imidazo[4,5-b]pyridine-5,7-diamine,
N7-(6-Amino-pyrimidin-4-yl)-3,N5-dimethyl-N5-(3-methyl-tetrahydro-pyran-4-yl)-3H-imidazo[4,5-b]pyridine-5,7-diamine,
N7-(6-Amino-pyrimidin-4-yl)-N5-(1-cyclopropyl-2,2,2-trifluoro-ethyl)-3,N5-dimethyl-3H-imidazo[4,5-b]pyridine-5,7-diamine,
N7-(6-Amino-pyrimidin-4-yl)-3,N5-dimethyl-N5-(5-oxaspiro[3.5]non-8-yl)-3H-imidazo[4,5-b]pyridine-5,7-diamine,
5-(1-cyclopropyl-2,2,2-trifluoro-ethoxy)-3-methyl-N-(5-methylsulfonyl-2-pyridyl)imidazo[4,5-b]pyridin-7-amine,
6-[5-(6-Cyano-4-methyl-pyridin-3-yloxy)-3-methyl-3H-imidazo[4,5-b]pyridin-7-ylamino]-pyridazine-3-carboxylic acid ethylamide,
6-[5-(6-Cyano-4-methyl-pyridin-3-yloxy)-3-methyl-3H-imidazo[4,5-b]pyridin-7-ylamino]-N-(2-hydroxy-propyl)-nicotinamide,
6-[5-(6-Cyano-4-methyl-pyridin-3-yloxy)-3-methyl-3H-imidazo[4,5-b]pyridin-7-ylamino]-pyridazine-3-carboxylic acid (2-hydroxy-propyl)-amide,
5-[5-(6-Cyano-4-methyl-pyridin-3-yloxy)-3-methyl-3H-imidazo[4,5-b]pyridin-7-ylamino]-pyridine-2-carboxylic acid ethylamide,
2-{4-[5-(6-Cyano-4-methyl-pyridin-3-yloxy)-3-methyl-3H-imidazo[4,5-b]pyridin-7-ylamino]-phenyl}-N-ethyl-acetamide,
4-Methyl-5-{3-methyl-7-[6-(morpholine-4-carbonyl)-pyridin-3-ylamino]-3H-imidazo[4,5-b]pyridin-5-yloxy}-pyridine-2-carbonitrile,
5-[5-(6-Cyano-4-methyl-pyridin-3-yloxy)-3-methyl-3H-imidazo[4,5-b]pyridin-7-ylamino]-pyridine-2-carboxylic acid methylamide,
5-[5-(6-Cyano-4-methyl-pyridin-3-yloxy)-3-methyl-3H-imidazo[4,5-b]pyridin-7-ylamino]-pyridine-2-carboxylic acid (2-hydroxy-propyl)-amide,
5-{7-[6-(2-Methoxy-ethylamino)-pyrimidin-4-ylamino]-3-methyl-3H-imidazo[4,5-b]pyridin-5-yloxy}-4-methyl-pyridine-2-carbonitrile,
5-{7-[6-(3-Methoxy-propylamino)-pyrimidin-4-ylamino]-3-methyl-3H-imidazo[4,5-b]pyridin-5-yloxy}-4-methyl-pyridine-2-carbonitrile,
5-{7-[6-(3-Hydroxy-3-methyl-butylamino)-pyrimidin-4-ylamino]-3-methyl-3H-imidazo[4,5-b]pyridin-5-yloxy}-4-methyl-pyridine-2-carbonitrile,
5-{7-[6-(3-Hydroxy-propylamino)-pyrimidin-4-ylamino]-3-methyl-3H-imidazo[4,5-b]pyridin-5-yloxy}-4-methyl-pyridine-2-carbonitrile,
5-(7-{6-[([1,4]Dioxan-2-ylmethyl)-amino]-pyrimidin-4-ylamino}-3-methyl-3H-imidazo[4,5-b]pyridin-5-yloxy)-4-methyl-pyridine-2-carbonitrile,
5-{7-[6-(3-Methoxy-cyclobutylamino)-pyrimidin-4-ylamino]-3-methyl-3H-imidazo[4,5-b]pyridin-5-yloxy}-4-methyl-pyridine-2-carbonitrile,
5-{7-[6-(3-Methoxy-butylamino)-pyrimidin-4-ylamino]-3-methyl-3H-imidazo[4,5-b]pyridin-5-yloxy}-4-methyl-pyridine-2-carbonitrile,
4-Methyl-5-[3-methyl-7-(6-morpholin-4-yl-pyridazin-3-ylamino)-3H-imidazo[4,5-b]pyridin-5-yloxy]-pyridine-2-carbonitrile, 4-Methyl-5-{3-methyl-7-[6-(4-methyl-piperazin-1-yl)-pyridazin-3-ylamino]-3H-imidazo[4,5-b]pyridin-5-yloxy}-pyridine-2-carbonitrile, 5-{7-[6-(3-Dimethylaminomethyl-azetidin-1-yl)-pyridazin-3-ylamino]-3-methyl-3H-imidazo[4,5-b]pyridin-5-yloxy}-4-methyl-pyridine-2-carbonitrile, (±)-4-Methyl-5-{3-methyl-7-[6-((3R,5S)-3,4,5-trimethyl-piperazin-1-yl)-pyridazin-3-ylamino]-3H-imidazo[4,5-b]pyridin-5-yloxy}-pyridine-2-carbonitrile, 4-Methyl-5-(3-methyl-7-{6-[4-(2,2,2-trifluoro-ethyl)-piperazin-1-yl]-pyridazin-3-ylamino}-3H-imidazo[4,5-b]pyridin-5-yloxy)-pyridine-2-carbonitrile, (±)-5-{7-[6-((2R,6S)-2,6-Dimethyl-morpholin-4-yl)-pyridazin-3-ylamino]-3-methyl-3H-imidazo[4,5-b]pyridin-5-yloxy}-4-methyl-pyridine-2-carbonitrile, 4-Methyl-5-{3-methyl-7-[6-((S)-2-methyl-morpholin-4-yl)-pyridazin-3-ylamino]-3H-imidazo[4,5-b]pyridin-5-yloxy}-pyridine-2-carbonitrile, 5-{7-[6-(4-Cyano-piperidin-1-yl)-pyridazin-3-ylamino]-3-methyl-3H-imidazo[4,5-b]pyridin-5-yloxy}-4-methyl-pyridine-2-carbonitrile, 4-methyl-5-[3-methyl-7-[[5-(4-propan-2-ylpiperazine-1-carbonyl)pyridin-2-yl]amino]imidazo[4,5-b]pyridin-5-yl]oxypyridine-2-carbonitrile, 5-[7-[[5-(4-cyclobutylpiperazine-1-carbonyl)pyridin-2-yl]amino]-3-methylimidazo[4,5-b]pyridin-5-yl]oxy-4-methylpyridine-2-carbonitrile, 5-[7-[[5-(4-cyclopropylpiperazine-1-carbonyl)pyridin-2-yl]amino]-3-methylimidazo[4,5-b]pyridin-5-yl]oxy-4-methylpyridine-2-carbonitrile, 4-methyl-5-[3-methyl-7-[(5-morpholin-4-ylpyridin-2-yl)amino]imidazo[4,5-b]pyridin-5-yl]oxypyridine-2-carbonitrile, 4-methyl-5-[3-methyl-7-[[5-(4-methylpiperazin-1-yl)pyridin-2-yl]amino]imidazo[4,5-b]pyridin-5-yl]oxypyridine-2-carbonitrile, 4-methyl-5-[7-[[5-(4-methylpiperazine-1-carbonyl)pyridin-2-yl]amino]-3-(trideuteriomethyl)imidazo[4,5-b]pyridin-5-yl]oxypyridine-2-carbonitrile, 5-[7-[(6-aminopyrimidin-4-yl)amino]-3-methyl-imidazo[4,5-b]pyridin-5-yl]oxy-4-methyl-pyridine-2-carbonitrile, 4-[[5-[(6-cyano-4-methyl-3-pyridyl)oxy]-3-methyl-imidazo[4,5-b]pyridin-7-yl]amino]-N-ethyl-benzenesulfonamide, N4-[5-(1-cyclopropyl-2,2,2-trifluoro-ethoxy)-3-methyl-imidazo[4,5-b]pyridin-7-yl]pyrimidine-4,6-diamine, 5-[[7-[(6-aminopyrimidin-4-yl)amino]-3-methyl-imidazo[4,5-b]pyridin-5-yl]amino]-4-methyl-pyridine-2-carbonitrile, 5-[7-[4-(aminomethyl)anilino]-3-methyl-imidazo[4,5-b]pyridin-5-yl]oxy-4-methyl-pyridine-2-carbonitrile formate salt, 4-methyl-5-[3-methyl-7-[(5-methylsulfonyl-2-pyridyl)amino]imidazo[4,5-b]pyridin-5-yl]oxy-pyridine-2-carbonitrile, 4-methyl-5-[3-methyl-7-[[5-(trifluoromethyl)-2-pyridyl]amino]imidazo[4,5-b]pyridin-5-yl]oxy-pyridine-2-carbonitrile, 4-methyl-5-[3-methyl-7-(4-methylsulfonylanilino)imidazo[4,5-b]pyridin-5-yl]oxy-pyridine-2-carbonitrile, 4-methyl-5-[3-methyl-7-[(1-methylpyrazol-4-yl)amino]imidazo[4,5-b]pyridin-5-yl]oxy-pyridine-2-carbonitrile, 4-[[5-[(6-cyano-4-methyl-3-pyridyl)oxy]-3-methyl-imidazo[4,5-b]pyridin-7-yl]amino]-N,N-dimethyl-benzamide, 4-methyl-5-[3-methyl-7-(4-morpholinosulfonylanilino)imidazo[4,5-b]pyridin-5-yl]oxy-pyridine-2-carbonitrile, 6-[[5-[(6-cyano-4-methyl-3-pyridyl)oxy]-3-methyl-imidazo[4,5-b]pyridin-7-yl]amino]-N-ethyl-4-methyl-pyridine-3-carboxamide, 3-methyl-N7-(5-methylsulfonyl-2-pyridyl)-N5-[2-methyl-1-(trifluoromethyl)propyl]imidazo[4,5-b]pyridine-5,7-diamine, 4-[[5-[(6-cyano-4-methyl-3-pyridyl)amino]-3-methyl-imidazo[4,5-b]pyridin-7-yl]amino]-N,N-dimethyl-benzamide, 6-[[5-[(6-cyano-4-methyl-3-pyridyl)amino]-3-methyl-imidazo[4,5-b]pyridin-7-yl]amino]-N,N-dimethyl-pyridine-3-carboxamide, 5-[7-[4-(difluoromethylsulfonyl)anilino]-3-methyl-imidazo[4,5-b]pyridin-5-yl]oxy-4-methyl-pyridine-2-carbonitrile, 5-[7-(4-cyclopropylsulfonylanilino)-3-methyl-imidazo[4,5-b]pyridin-5-yl]oxy-4-methyl-pyridine-2-carbonitrile, 5-[7-[(1,1-dimethyl-3-oxo-isoindolin-5-yl)amino]-3-methyl-imidazo[4,5-b]pyridin-5-yl]oxy-4-methyl-pyridine-2-carbonitrile, 5-[7-[4-(3-methoxypropylsulfonyl)anilino]-3-methyl-imidazo[4,5-b]pyridin-5-yl]oxy-4-methyl-pyridine-2-carbonitrile, N4-[5-(1-cyclopropylethoxy)-3-methyl-imidazo[4,5-b]pyridin-7-yl]pyrimidine-4,6-diamine, 6-[[5-[(6-cyano-4-methyl-3-pyridyl)oxy]-3-methyl-imidazo[4,5-b]pyridin-7-yl]amino]-N,N-dimethyl-pyridazine-3-carboxamide, 6-[[5-[(6-cyano-4-methyl-3-pyridyl)oxy]-3-methyl-imidazo[4,5-b]pyridin-7-yl]amino]-N,N-dimethyl-pyridine-3-carboxamide, 4-methyl-5-[3-methyl-7-[[5-(morpholine-4-carbonyl)-2-pyridyl]amino]imidazo[4,5-b]pyridin-5-yl]oxy-pyridine-2-carbonitrile, 6-[[5-[(6-cyano-4-methyl-3-pyridyl)amino]-3-methyl-imidazo[4,5-b]pyridin-7-yl]amino]-N,N-dimethyl-pyridazine-3-carboxamide, 6-[[5-[(6-cyano-4-methyl-3-pyridyl)oxy]-3-methyl-imidazo[4,5-b]pyridin-7-yl]amino]-N,N,2-trimethyl-pyridine-3-carboxamide, 6-[[5-[(6-cyano-4-methyl-3-pyridyl)oxy]-3-methyl-imidazo[4,5-b]pyridin-7-yl]amino]-N-ethyl-2-methyl-pyridine-3-carboxamide, 5-[7-[[5-[(dimethylamino)methyl]pyridin-2-yl]amino]-3-methylimidazo[4,5-b]pyridin-5-yl]oxy-4-methylpyridine-2-carbonitrile formate salt, 4-methyl-5-[3-methyl-7-[[5-(morpholin-4-ylmethyl)pyridin-2-yl]amino]imidazo[4,5-b]pyridin-5-yl]oxypyridine-2-carbonitrile formate salt, 5-[7-[[5-[[2-(dimethylamino)ethyl-methylamino]methyl]pyridin-2-yl]amino]-3-methylimidazo[4,5-b]pyridin-5-yl]oxy-4-methylpyridine-2-carbonitrile formate salt, 5-[7-[(5-methoxypyridin-2-yl)amino]-3-methylimidazo[4,5-b]pyridin-5-yl]oxy-4-methylpyridine-2-carbonitrile, 4-methyl-5-[3-methyl-7-[[5-[(3S)-3-methylmorpholin-4-yl]pyridin-2-yl]amino]imidazo[4,5-b]pyridin-5-yl]oxypyridine-2-carbonitrile, 4-methyl-5-[3-methyl-7-[[5-(1-methylpiperidin-4-yl)oxypyridin-2-yl]amino]imidazo[4,5-b]pyridin-5-yl]oxypyridine-2-carbonitrile, 4-methyl-5-[3-methyl-7-[[5-(oxan-4-yl)pyridin-2-yl]amino]imidazo[4,5-b]pyridin-5-yl]oxypyridine-2-carbonitrile, 5-[[7-[(6-aminopyrimidin-4-yl)amino]-3-methyl-imidazo[4,5-b]pyridin-5-yl]-cyclopropyl-amino]-4-methyl-pyridine-2-carbonitrile, 5-[7-[4-(3-hydroxyoxetan-3-yl)anilino]-3-methylimidazo[4,5-b]pyridin-5-yl]oxy-4-methylpyridine-2-carbonitrile, 4-methyl-5-[3-methyl-7-[[6-(1-methylazetidin-3-yl)oxy-pyridazin-3-yl]amino]imidazo[4,5-b]pyridin-5-yl]oxy-pyridine-2-carbonitrile, 5-[[5-[(1-cyclopropyl-2,2,2-trifluoro-ethyl)amino]-3-methyl-imidazo[4,5-b]pyridin-7-yl]amino]-N-ethyl-pyridine-2-carboxamide, N5-(1-cyclopropyl-2,2,2-trifluoro-ethyl)-3-methyl-N7-(5-methylsulfonyl-2-pyridyl)imidazo[4,5-b]pyridine-5,7-diamine, N7-(6-aminopyrimidin-4-yl)-3-methyl-N5-[2-methyl-1-(trifluoromethyl)propyl]imidazo[4,5-b]pyridine-5,7-diamine, N7-(6-aminopyrimidin-4-yl)-N5-(1-cyclobutylethyl)-3-methyl-imidazo[4,5-b]pyridine-5,7-diamine, N7-(6-aminopyrimidin-4-yl)-N5-(dicyclopropylmethyl)-3-methyl-imidazo[4,5-b]pyridine-5,7-diamine, 5-[7-[[5-(3-hydroxyazetidine-1-carbonyl)-2-pyridyl]amino]-3-methyl-imidazo[4,5-b]pyridin-5-yl]oxy-4-methyl-pyridine-2-carbonitrile, N,N-dimethyl-6-[[3-methyl-5-[[(1R)-2-methyl-1-(trifluoromethyl)propyl]amino]imidazo[4,5-b]pyridin-7-yl]amino]pyridine-3-carboxamide, N7-(6-aminopyrimidin-4-yl)-3-methyl-N5-[(1R)-2-methyl-1-(trifluoromethyl)propyl]imidazo[4,5-b]pyridine-5,7-diamine, 6-[[5-[(6-cyano-4-methyl-3-pyridyl)oxy]-3-methyl-imidazo[4,5-b]pyridin-7-yl]amino]-N-(2-dimethylaminoethyl)pyridine-3-carboxamide, 6-[[5-[(6-cyano-4-methyl-3-pyridyl)oxy]-3-methyl-imidazo[4,5-b]pyridin-7-yl]amino]-N-(3-methoxypropyl)pyridine-3-carboxamide, 6-[[5-[(6-cyano-4-methyl-3-pyridyl)oxy]-3-methyl-imidazo[4,5-b]pyridin-7-yl]amino]-N-(3-hydroxypropyl)pyridine-3-carboxamide, 5-[7-[[5-[3-(1-hydroxy-1-methyl-ethyl)azetidine-1-carbonyl]-2-pyridyl]amino]-3-methyl-imidazo[4,5-b]pyridin-5-yl]oxy-4-methyl-pyridine-2-carbonitrile, 5-[7-[[5-(3-methoxyazetidine-1-carbonyl)-2-pyridyl]amino]-3-methyl-imidazo[4,5-b]pyridin-5-yl]oxy-4-methyl-pyridine-2-carbonitrile, 5-[7-[[5-[3-(methoxymethyl)azetidine-1-carbonyl]-2-pyridyl]amino]-3-methyl-imidazo[4,5-b]pyridin-5-yl]oxy-4-methyl-pyridine-2-carbonitrile, 4-methyl-5-[3-methyl-7-[[5-(4-methylpiperazine-1-carbonyl)-2-pyridyl]amino]imidazo[4,5-b]pyridin-5-yl]oxy-pyridine-2-carbonitrile, 5-[7-[[5-[3-(dimethylamino)azetidine-1-carbonyl]-2-pyridyl]amino]-3-methyl-imidazo[4,5-b]pyridin-5-yl]oxy-4-methyl-pyridine-2-carbonitrile, 5-[7-[[5-[(3R)-3-(dimethylamino)pyrrolidine-1-carbonyl]pyridin-2-yl]amino]-3-methylimidazo[4,5-b]pyridin-5-yl]oxy-4-methylpyridine-2-carbonitrile, 4-methyl-5-[3-methyl-7-[[6-(morpholine-4-carbonyl)pyridazin-3-yl]amino]imidazo[4,5-b]pyridin-5-yl]oxy-pyridine-2-carbonitrile, 4-methyl-5-[3-methyl-7-(4-morpholinoanilino)imidazo[4,5-b]pyridin-5-yl]oxy-pyridine-2-carbonitrile, 4-methyl-5-[3-methyl-7-[4-(4-methylpiperazin-1-yl)anilino]imidazo[4,5-b]pyridin-5-yl]oxy-pyridine-2-carbonitrile, 5-[7-[[6-[3-(1-hydroxy-1-methyl-ethyl)azetidine-1-carbonyl]pyridazin-3-yl]amino]-3-methyl-imidazo[4,5-b]pyridin-5-yl]oxy-4-methyl-pyridine-2-carbonitrile, 5-[7-[[5-[(3S)-3-hydroxypyrrolidine-1-carbonyl]-2-pyridyl]amino]-3-methyl-imidazo[4,5-b]pyridin-5-yl]oxy-4-methyl-pyridine-2-carbonitrile, 5-[7-[[5-(3-cyclopropyl-3-hydroxy-azetidine-1-carbonyl)-2-pyridyl]amino]-3-methyl-imidazo[4,5-b]pyridin-5-yl]oxy-4-methyl-pyridine-2-carbonitrile, 4-methyl-5-[3-methyl-7-[[5-(8-oxa-3-azaspiro[4.4]nonane-3-carbonyl)-2-pyridyl]amino]imidazo[4,5-b]pyridin-5-yl]oxy-pyridine-2-carbonitrile, 5-[7-[[6-(3-hydroxyazetidine-1-carbonyl)pyridazin-3-yl]amino]-3-methyl-imidazo[4,5-b]pyridin-5-yl]oxy-4-methyl-pyridine-2-carbonitrile, 5-[7-[[6-(3-methoxyazetidine-1-carbonyl)pyridazin-3-yl]amino]-3-methyl-imidazo[4,5-b]pyridin-5-yl]oxy-4-methyl-pyridine-2-carbonitrile, 5-[7-[[6-[3-(methoxymethyl)azetidine-1-carbonyl]pyridazin-3-yl]amino]-3-methyl-imidazo[4,5-b]pyridin-5-yl]oxy-4-methyl-pyridine-2-carbonitrile, 5-[7-[[5-[3-(hydroxymethyl)azetidine-1-carbonyl]-2-pyridyl]amino]-3-methyl-imidazo[4,5-b]pyridin-5-yl]oxy-4-methyl-pyridine-2-carbonitrile, 5-[7-[[5-(3-hydroxy-3-methyl-azetidine-1-carbonyl)-2-pyridyl]amino]-3-methyl-imidazo[4,5-b]pyridin-5-yl]oxy-4-methyl-pyridine-2-carbonitrile, 4-methyl-5-[3-methyl-7-[[5-(3-oxa-6-azaspiro[3.3]heptane-6-carbonyl)-2-pyridyl]amino]imidazo[4,5-b]pyridin-5-yl]oxy-pyridine-2-carbonitrile, 5-[7-[[5-(3-methoxy-3-methyl-azetidine-1-carbonyl)-2-pyridyl]amino]-3-methyl-imidazo[4,5-b]pyridin-5-yl]oxy-4-methyl-pyridine-2-carbonitrile, tert-butyl 1-[6-[[5-[(6-cyano-4-methyl-3-pyridyl)oxy]-3-methyl-imidazo[4,5-b]pyridin-7-yl]amino]pyridine-3-carbonyl]azetidine-3-carboxylate, 4-methyl-5-[3-methyl-7-[[5-(6-methyl-2,6-diazaspiro[3.3]heptane-2-carbonyl)-2-pyridyl]amino]imidazo[4,5-b]pyridin-5-yl]oxy-pyridine-2-carbonitrile, 5-[7-[[5-(4-hydroxypiperidine-1-carbonyl)pyridin-2-yl]amino]-3-methylimidazo[4,5-b]pyridin-5-yl]oxy-4-methylpyridine-2-carbonitrile, 5-[7-[[5-(4-methoxypiperidine-1-carbonyl)pyridin-2-yl]amino]-3-methylimidazo[4,5-b]pyridin-5-yl]oxy-4-methylpyridine-2-carbonitrile, 5-[7-[[5-[4-(dimethylamino)piperidine-1-carbonyl]pyridin-2-yl]amino]-3-methylimidazo[4,5-b]pyridin-5-yl]oxy-4-methylpyridine-2-carbonitrile, 5-[7-[[5-[(3R)-3-hydroxypyrrolidine-1-carbonyl]pyridin-2-yl]amino]-3-methylimidazo[4,5-b]pyridin-5-yl]oxy-4-methylpyridine-2-carbonitrile, 4-{6-[5-(6-Cyano-4-methyl-pyridin-3-yloxy)-3-methyl-3H-imidazo[4,5-b]pyridin-7-ylamino]-pyridine-3-carbonyl}-piperazine-1-carboxylic acid tert-butyl ester, 5-[7-[[5-[(3R)-3-(2-methoxyethoxy)pyrrolidine-1-carbonyl]pyridin-2-yl]amino]-3-methylimidazo[4,5-b]pyridin-5-yl]oxy-4-methylpyridine-2-carbonitrile, (1-{6-[5-(6-Cyano-4-methyl-pyridin-3-yloxy)-3-methyl-3H-imidazo[4,5-b]pyridin-7-ylamino]-pyridine-3-carbonyl}-pyrrolidin-3-yl)-methyl-carbamic acid tert-butyl ester, 4-methyl-5-[3-methyl-7-[[5-(2-oxa-7-azaspiro[3.4]octane-7-carbonyl)pyridin-2-yl]amino]imidazo[4,5-b]pyridin-5-yl]oxypyridine-2-carbonitrile, 5-[7-[[5-[3-[(dimethylamino)methyl]azetidine-1-carbonyl]pyridin-2-yl]amino]-3-methylimidazo[4,5-b]pyridin-5-yl]oxy-4-methylpyridine-2-carbonitrile, 5-[7-[[5-[(3S)-3-(dimethylamino)pyrrolidine-1-carbonyl]pyridin-2-yl]amino]-3-methylimidazo[4,5-b]pyridin-5-yl]oxy-4-methylpyridine-2-carbonitrile, 4-methyl-5-[3-methyl-7-[[5-(2-oxa-6-azaspiro[3.3]heptane-6-carbonyl)pyridin-2-yl]amino]imidazo[4,5-b]pyridin-5-yl]oxypyridine-2-carbonitrile, 5-[7-[[5-[3,3-bis(hydroxymethyl)azetidine-1-carbonyl]pyridin-2-yl]amino]-3-methylimidazo[4,5-b]pyridin-5-yl]oxy-4-methylpyridine-2-carbonitrile, 6-[[5-(6-cyano-4-methylpyridin-3-yl)oxy-3-methylimidazo[4,5-b]pyridin-7-yl]amino]-N-(2-hydroxyethyl)-N-methylpyridine-3-carboxamide, 4-methyl-5-[3-methyl-7-[[5-(3-propan-2-yloxyazetidine-1-carbonyl)pyridin-2-yl]amino]imidazo[4,5-b]pyridin-5-yl]oxypyridine-2-carbonitrile, 5-[7-[[5-(4-hydroxy-4-methylpiperidine-1-carbonyl)pyridin-2-yl]amino]-3-methylimidazo[4,5-b]pyridin-5-yl]oxy-4-methylpyridine-2-carbonitrile, 6-[[5-(6-cyano-4-methylpyridin-3-yl)oxy-3-methylimidazo[4,5-b]pyridin-7-yl]amino]-N-[rac-(1R,3R)-3-hydroxycyclopentyl]pyridine-3-carboxamide, 4-methyl-5-[3-methyl-7-[[5-[rac-(3R,4R)-3-fluoro-4-hydroxypyrrolidine-1-carbonyl]pyridin-2-yl]amino]imidazo[4,5-b]pyridin-5-yl]oxypyridine-2-carbonitrile, 4-methyl-5-[3-methyl-7-[[5-[rac-(3R,4R)-3,4-dihydroxypiperidine-1-carbonyl]pyridin-2-yl]amino]imidazo[4,5-b]pyridin-5-yl]oxypyridine-2-carbonitrile, 4-methyl-5-[3-methyl-7-[[5-[rac-(3R,4R)-3-fluoro-4-methoxypyrrolidine-1-carbonyl]pyridin-2-yl]amino]imidazo[4,5-b]pyridin-5-yl]oxypyridine-2-carbonitrile, 5-[7-[[6-[3-(dimethylamino)azetidin-1-yl]pyridazin-3-yl]amino]-3-methylimidazo[4,5-b]pyridin-5-yl]oxy-4-methylpyridine-2-carbonitrile, 4-methyl-5-[3-methyl-7-[[5-[(2S)-2-methylmorpholine-4-carbonyl]pyridin-2-yl]amino]imidazo[4,5-b]pyridin-5-yl]oxypyridine-2-carbonitrile, 4-methyl-5-[3-methyl-7-[[5-[(2R)-2-methylmorpholine-4-carbonyl]pyridin-2-yl]amino]imidazo[4,5-b]pyridin-5-yl]oxypyridine-2-carbonitrile, 4-methyl-5-[3-methyl-7-[[5-[(3R)-3-methylmorpholine-4-carbonyl]pyridin-2-yl]amino]imidazo[4,5-b]pyridin-5-yl]oxypyridine-2-carbonitrile, 4-methyl-5-[3-methyl-7-[[5-[(3S)-3-methylmorpholine-4-carbonyl]pyridin-2-yl]amino]imidazo[4,5-b]pyridin-5-yl]oxypyridine-2-carbonitrile, 4-methyl-5-[3-methyl-7-[[5-[rac-(2R,6S)-2,6-dimethylmorpholine-4-carbonyl]pyridin-2-yl]amino]imidazo[4,5-b]pyridin-5-yl]oxypyridine-2-carbonitrile, 4-methyl-5-[3-methyl-7-[[5-[rac-(2R,6R)-2,6-dimethylmorpholine-4-carbonyl]pyridin-2-yl]amino]imidazo[4,5-b]pyridin-5-yl]oxypyridine-2-carbonitrile, 4-methyl-5-[3-methyl-7-[[6-(4-methylpiperazine-1-carbonyl)pyridazin-3-yl]amino]imidazo[4,5-b]pyridin-5-yl]oxypyridine-2-carbonitrile, 3,5-difluoro-4-[3-methyl-7-[[5-(4-methylpiperazine-1-carbonyl)pyridin-2-yl]amino]imidazo[4,5-b]pyridin-5-yl]oxybenzonitrile, 4-methyl-5-[3-methyl-7-[[6-[(1R,4R)-5-methyl-2,5-diazabicyclo[2.2.1]heptan-2-yl]pyridazin-3-yl]amino]imidazo[4,5-b]pyridin-5-yl]oxypyridine-2-carbonitrile, 5-{7-[5-((3R,4R)-3-Dimethylamino-4-hydroxy-pyrrolidine-1-carbonyl)-pyridin-2-ylamino]-3-methyl-3H-imidazo[4,5-b]pyridin-5-yloxy}-4-methyl-pyridine-2-carbonitrile, 5-{7-[5-((3S,4S)-3-Hydroxy-4-morpholin-4-yl-pyrrolidine-1-carbonyl)-pyridin-2-ylamino]-3-methyl-3H-imidazo[4,5-b]pyridin-5-yloxy}-4-methyl-pyridine-2-carbonitrile, 4-methyl-5-[3-methyl-7-[[5-[2-(trifluoromethyl)morpholine-4-carbonyl]pyridin-2-yl]amino]imidazo[4,5-b]pyridin-5-yl]oxypyridine-2-carbonitrile, 5-[7-[[5-(2-cyclopropylmorpholine-4-carbonyl)pyridin-2-yl]amino]-3-methylimidazo[4,5-b]pyridin-5-yl]oxy-4-methylpyridine-2-carbonitrile, 4-methyl-5-[3-methyl-7-[[5-[(3R)-3-propan-2-ylmorpholine-4-carbonyl]pyridin-2-yl]amino]imidazo[4,5-b]pyridin-5-yl]oxypyridine-2-carbonitrile, 4-methyl-5-[3-methyl-7-[[5-(2-oxa-5-azabicyclo[2.2.1]heptane-5-carbonyl)pyridin-2-yl]amino]imidazo[4,5-b]pyridin-5-yl]oxypyridine-2-carbonitrile, 5-[7-[[5-(3-cyclopropylmorpholine-4-carbonyl)pyridin-2-yl]amino]-3-methylimidazo[4,5-b]pyridin-5-yl]oxy-4-methylpyridine-2-carbonitrile, 4-[6-[[5-(6-cyano-4-methylpyridin-3-yl)oxy-3-methylimidazo[4,5-b]pyridin-7-yl]amino]pyridine-3-carbonyl]morpholine-2-carbonitrile, 4-Methyl-5-{3-methyl-7-[5-((3aS,6aS)-1-methyl-hexahydro-pyrrolo[3,4-b]pyrrole-5-carbonyl)-pyridin-2-ylamino]-3H-imidazo[4,5-b]pyridin-5-yloxy}-pyridine-2-carbonitrile, 4-[6-[[5-(6-cyano-4-methylpyridin-3-yl)oxy-3-methylimidazo[4,5-b]pyridin-7-yl]amino]pyridine-3-carbonyl]morpholine-3-carbonitrile, 5-[7-[[6-[(2R)-2-(hydroxymethyl)morpholin-4-yl]pyridazin-3-yl]amino]-3-methylimidazo[4,5-b]pyridin-5-yl]oxy-4-methylpyridine-2-carbonitrile, 4-methyl-5-[3-methyl-7-[[6-(2,2,3,3,5,5,6,6-octadeuteriomorpholin-4-yl)pyridazin-3-yl]amino]imidazo[4,5-b]pyridin-5-yl]oxy-pyridine-2-carbonitrile, 5-[7-[[6-[(2S)-2-(hydroxymethyl)morpholin-4-yl]pyridazin-3-yl]amino]-3-methylimidazo[4,5-b]pyridin-5-yl]oxy-4-methylpyridine-2-carbonitrile, 5-[7-[[6-[(2S,6S)-2,6-dimethylmorpholin-4-yl]pyridazin-3-yl]amino]-3-methylimidazo[4,5-b]pyridin-5-yl]oxy-4-methylpyridine-2-carbonitrile, 4-methyl-5-[3-methyl-7-[[6-(1,4-oxazepan-4-yl)pyridazin-3-yl]amino]imidazo[4,5-b]pyridin-5-yl]oxypyridine-2-carbonitrile, 5-[7-[[6-[(2R,6R)-2,6-dimethylmorpholin-4-yl]pyridazin-3-yl]amino]-3-methylimidazo[4,5-b]pyridin-5-yl]oxy-4-methylpyridine-2-carbonitrile, 5-[7-[[6-[2-(hydroxymethyl)morpholin-4-yl]pyridazin-3-yl]amino]-3-methylimidazo[4,5-b]pyridin-5-yl]oxy-4-methylpyridine-2-carbonitrile, 4-methyl-5-[3-methyl-7-[[6-(8-oxa-3-azabicyclo[3.2.1]octan-3-yl)pyridazin-3-yl]amino]imidazo[4,5-b]pyridin-5-yl]oxypyridine-2-carbonitrile, 4-[6-[[5-(6-cyano-4-methylpyridin-3-yl)oxy-3-methylimidazo[4,5-b]pyridin-7-yl]amino]pyridazin-3-yl]morpholine-2-carbonitrile, 4-methyl-5-[3-methyl-7-[[6-[(2R)-2-methylmorpholin-4-yl]pyridazin-3-yl]amino]imidazo[4,5-b]pyridin-5-yl]oxypyridine-2-carbonitrile, 4-methyl-5-[3-methyl-7-[[6-[(2R)-2-propan-2-ylmorpholin-4-yl]pyridazin-3-yl]amino]imidazo[4,5-b]pyridin-5-yl]oxypyridine-2-carbonitrile, 4-methyl-5-[3-methyl-7-[[6-[(1S,4S)-2-oxa-5-azabicyclo[2.2.1]heptan-5-yl]pyridazin-3-yl]amino]imidazo[4,5-b]pyridin-5-yl]oxypyridine-2-carbonitrile, 5-[7-[[6-(2,2-dimethylmorpholin-4-yl)pyridazin-3-yl]amino]-3-methylimidazo[4,5-b]pyridin-5-yl]oxy-4-methylpyridine-2-carbonitrile, 4-methyl-5-[3-methyl-7-[[6-[rac-(2R,6R)-2,6-dimethylmorpholin-4-yl]pyridazin-3-yl]amino]imidazo[4,5-b]pyridin-5-yl]oxypyridine-2-carbonitrile, 4-methyl-5-[3-methyl-7-[[6-[(2S)-2-propan-2-ylmorpholin-4-yl]pyridazin-3-yl]amino]imidazo[4,5-b]pyridin-5-yl]oxypyridine-2-carbonitrile, 4-methyl-5-[3-methyl-7-[[5-(piperazine-1-carbonyl)pyridin-2-yl]amino]imidazo[4,5-b]pyridin-5-yl]oxypyridine-2-carbonitrile, N7-(6-aminopyrimidin-4-yl)-N5-(1-cyclopropyl-2,2,2-trifluoro-ethyl)-3-methyl-imidazo[4,5-b]pyridine-5,7-diamine,
4-methyl-5-[3-methyl-7-[(5-piperazin-1-yl-2-pyridyl)amino]imidazo[4,5-b]pyridin-5-yl]oxy-pyridine-2-carbonitrile,
5-[7-[[5-[4-(dimethylamino)-1-piperidyl]-2-pyridyl]amino]-3-methyl-imidazo[4,5-b]pyridin-5-yl]oxy-4-methyl-pyridine-2-carbonitrile,
5-[7-[[5-[3-(dimethylamino)pyrrolidin-1-yl]-2-pyridyl]amino]-3-methyl-imidazo[4,5-b]pyridin-5-yl]oxy-4-methyl-pyridine-2-carbonitrile,
5-[7-[[5-[2-methoxyethyl(methyl)amino]-2-pyridyl]amino]-3-methyl-imidazo[4,5-b]pyridin-5-yl]oxy-4-methyl-pyridine-2-carbonitrile,
5-[7-[[5-[4-(hydroxymethyl)-1-piperidyl]-2-pyridyl]amino]-3-methyl-imidazo[4,5-b]pyridin-5-yl]oxy-4-methyl-pyridine-2-carbonitrile,
5-[7-[[5-(dimethylamino)-2-pyridyl]amino]-3-methyl-imidazo[4,5-b]pyridin-5-yl]oxy-4-methyl-pyridine-2-carbonitrile,
4-methyl-5-[3-methyl-7-[[1-(2-morpholinoethyl)pyrazol-4-yl]amino]imidazo[4,5-b]pyridin-5-yl]oxy-pyridine-2-carbonitrile,
5-[[7-[(6-aminopyrimidin-4-yl)amino]-3-methyl-imidazo[4,5-b]pyridin-5-yl]-(2-hydroxypropyl)amino]-4-methyl-pyridine-2-carbonitrile,
4-methyl-5-[3-methyl-7-[[5-(2,2,3,3,5,5,6,6-octadeuterio-4-methyl-piperazine-1-carbonyl)-2-pyridyl]amino]imidazo[4,5-b]pyridin-5-yl]oxy-pyridine-2-carbonitrile,
4-methyl-5-[3-methyl-7-[[5-(2,2,6,6-tetradeuterio-4-methyl-piperazine-1-carbonyl)-2-fpyridyl]amino]imidazo[4,5-b]pyridin-5-yl]oxy-pyridine-2-carbonitrile, and
4-methyl-5-[3-methyl-7-[[5-[2,2,3,3,5,5,6,6-octadeuterio-4-(trideuteriomethyl)piperazine-1-carbonyl]-2-pyridyl]amino]imidazo[4,5-b]pyridin-5-yl]oxy-pyridine-2-carbonitrile.

In one embodiment, the compound of the invention is 4-Ethyl-5-{3-methyl-7-[5-(morpholine-4-carbonyl)-pyridin-2-ylamino]-3H-imidazo[4,5-b]pyridin-5-yloxy}-pyridine-2-carbonitrile.

In another embodiment, the compound of the invention is not 4-Ethyl-5-{3-methyl-7-[5-(morpholine-4-carbonyl)-pyridin-2-ylamino]-3H-imidazo[4,5-b]pyridin-5-yloxy}-pyridine-2-carbonitrile.

In one embodiment, the compound of the invention is 4-Methyl-5-[3-methyl-7-(6-morpholin-4-yl-pyridazin-3-ylamino)-3H-imidazo[4,5-b]pyridin-5-yloxy]-pyridine-2-carbonitrile.

In another embodiment, the compound of the invention is not 4-Methyl-5-[3-methyl-7-(6-morpholin-4-yl-pyridazin-3-ylamino)-3H-imidazo[4,5-b]pyridin-5-yloxy]-pyridine-2-carbonitrile.

In one embodiment, the present invention provides a compound for the preparation of the compounds of the invention according to Formula A:

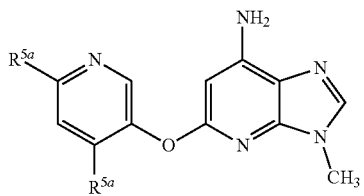

A wherein
$R^{5a}$ is —CN, —SO$_2$C$_{1-4}$ alkyl, or —CF$_3$;
$R^{5b}$ is selected from halo, C$_{1-4}$ alkyl, and C$_{3-7}$ cycloalkyl.

In a further embodiment, the present invention provides a compound for the preparation of the compounds of the invention according to Formula A, wherein $R^{5a}$ is —CN, —SO$_2$CH$_3$, or —CF$_3$. In a particular embodiment, $R^{5a}$ is —CN.

In a further embodiment, the present invention provides a compound for the preparation of the compounds of the invention according to Formula A, wherein $R^{5b}$ is selected from halo, C$_{1-4}$ alkyl, and C$_{3-7}$ cycloalkyl. In a particular embodiment, $R^{5b}$ is F, —CH$_3$, —CH$_2$CH$_3$, or cyclopropyl. In a more particular embodiment, $R^{5b}$ is —CH$_3$.

In one embodiment, the present invention provides a compound for the preparation of the compounds of the invention according to Formula A wherein $R^{5a}$ is —CN and $R^{5b}$ is —CH$_3$.

In one embodiment, the compounds of the invention are provided in a natural isotopic form.

In one embodiment, the compounds of the invention are provided in an unnatural variant isotopic form. In a specific embodiment, the unnatural variant isotopic form is a form in which deuterium (i.e. $^2$H or D) is incorporated where hydrogen is specified in the chemical structure in one or more atoms of a compound of the invention. In one embodiment, the atoms of the compounds of the invention are in an isotopic form which is not radioactive. In one embodiment, one or more atoms of the compounds of the invention are in an isotopic form which is radioactive. Suitably radioactive isotopes are stable isotopes. Suitably the unnatural variant isotopic form is a pharmaceutically acceptable form.

In one embodiment, a compound of the invention is provided whereby a single atom of the compound exists in an unnatural variant isotopic form. In another embodiment, a compound of the invention is provided whereby two or more atoms exist in an unnatural variant isotopic form.

Unnatural isotopic variant forms can generally be prepared by conventional techniques known to those skilled in the art or by processes described herein e.g. processes analogous to those described in the accompanying Examples for preparing natural isotopic forms. Thus, unnatural isotopic variant forms could be prepared by using appropriate isotopically variant (or labelled) reagents in place of the normal reagents employed in the Examples.

In one embodiment a compound of the invention is not an isotopic variant.

In one aspect a compound of the invention according to any one of the embodiments herein described is present as the free base.

In one aspect a compound of the invention according to any one of the embodiments herein described is a pharmaceutically acceptable salt.

In one aspect a compound of the invention according to any one of the embodiments herein described is a solvate of the compound.

In one aspect a compound of the invention according to any one of the embodiments herein described is a solvate of a pharmaceutically acceptable salt of a compound.

While specified groups for each embodiment have generally been listed above separately, a compound of the invention includes one in which several or each embodiment in the above Formula, as well as other formulae presented herein, is selected from one or more of particular members or groups designated respectively, for each variable. Therefore, this invention is intended to include all combinations of such embodiments within its scope.

While specified groups for each embodiment have generally been listed above separately, a compound of the invention may be one for which one or more variables (for example, R groups) is selected from one or more embodiments according to any of the Formula(e) listed above. Therefore, the present invention is intended to include all combinations of variables from any of the disclosed embodiments within its scope.

Alternatively, the exclusion of one or more of the specified variables from a group or an embodiment, or combinations thereof is also contemplated by the present invention.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (Bundgard, H, 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Particularly useful are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

CLAUSES

1). A compound according to Formula (I):

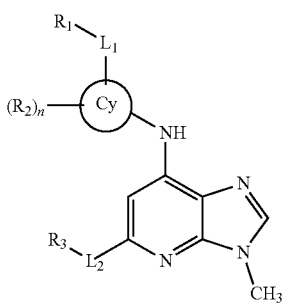

I wherein
Cy is phenyl, or 5-6 membered heteroaryl comprising one, two or three N atoms;
$L_1$ is a single bond, —O—, —C(=O)—, —C(=O)O—, —S(O)$_2$—, —NR$^{6a}$—, —C(=O)NR$^{6b}$—, —S(O)$_2$NR$^{6c}$—, or —C(=O)NR$^{6d}$S(O)$_2$—;

$R^1$ is:
H,
$C_{1-6}$ alkyl optionally substituted with one or more independently selected
OH,
halo,
$C_{1-4}$ alkoxy,
—NR$^{7a}$R$^{7b}$,
—C(=O)OH—,
—C(=O)NR$^{7c}$R$^{7d}$,
—C(=O)OC$_{1-4}$ alkyl, or
4-8 membered monocyclic heterocycloalkyl comprising one, two, or three heteroatoms independently selected from N, S, and O;
$C_{3-7}$ cycloalkyl optionally substituted with one or more OH, $C_{1-4}$ alkoxy, or
4-9 membered monocyclic or spirobicyclic or bridged or fused bicyclic heterocycloalkyl comprising one, two, or three heteroatoms independently selected from N, S, and O; which heterocycloalkyl is optionally substituted with one or more independently selected $R^{11}$ groups;
each $R^{11}$ is independently:
OH,
CN,
halo,
oxo,
—NR$^{8a}$R$^{8b}$,
$C_{3-7}$ cycloalkyl,
$C_{1-4}$ alkyl optionally substituted with one or more independently selected halo, OH, $C_{1-4}$ alkoxy, —NR$^{9a}$R$^{9b}$,
$C_{1-4}$ alkoxy optionally substituted with one $C_{1-4}$ alkoxy,
4-7 membered monocyclic heterocycloalkyl comprising one, two, or three heteroatoms independently selected from N, S, and O,
—C(=O)OC$_{1-4}$alkyl, or
—NR$^{8c}$C(=O)OC$_{1-4}$alkyl;
$R^2$ is
halo,
CN, or
$C_{1-4}$ alkyl;
the subscript n is 0, or 1;
$L_2$ is O, or —NR$^4$—,
$R^3$ is
$C_{1-6}$ alkyl optionally substituted with one or more independently selected
halo, or
$C_{3-7}$ cycloalkyl,
Phenyl substituted with one $R^{5a}$ group and one or two independently selected $R^{5b}$ groups,
6-membered heteroaryl comprising one or two N atoms, substituted with one $R^{5a}$ group and one or two independently selected $R^{5b}$ groups,
4-10 membered monocyclic or fused, bridged or spiro bicyclic heterocycloalkyl comprising one or two heteroatoms independently selected from N, S, and O, optionally substituted with one, two or three groups independently selected from $R^{5a}$ and $R^{5b}$, or
4-10 membered monocyclic or fused, bridged or spiro bicyclic cycloalkyl, optionally substituted with one, two or three groups independently selected from $R^{5a}$ and $R^{5b}$;
$R^4$ is
H,
$C_{1-4}$ alkyl optionally substituted with one or more independently selected OH or $C_{1-4}$ alkoxy, or
$C_{3-7}$ cycloalkyl;
$R^{5a}$ is —CN, —SO$_2$—C$_{1-4}$ alkyl, or —CF$_3$;
each $R^{5b}$ is independently selected from halo, $C_{1-4}$ alkyl, and $C_{3-7}$ cycloalkyl;

each $R^{7a}$, and $R^{7b}$ is independently selected from
H, and
$C_{1-4}$ alkyl optionally substituted with one —$NR^{10a}R^{10b}$; and
each $R^{6a}$, $R^{6b}$, $R^{6c}$, $R^{6d}$, $R^{7c}$, $R^{7d}$, $R^{8a}$, $R^{8b}$, $R^{8c}$, $R^{9a}$, $R^{9b}$, $R^{10a}$, and $R^{10b}$ is independently selected from H, and $C_{1-4}$ alkyl;
or a pharmaceutically acceptable salt thereof, or a solvate or the solvate of a pharmaceutically acceptable salt thereof.

2). The compound or pharmaceutically acceptable salt thereof according to clause 1, wherein $L_2$ is —$NR^4$.

3). The compound or pharmaceutically acceptable salt thereof according to clause 2, wherein $R^4$ is H.

4). The compound or pharmaceutically acceptable salt thereof according to clause 2, wherein $R^4$ is —$CH_3$, —$CH_2$—$CH_2$—$CH_2$—OH, —$CH_2$—CHOH—$CH_3$, —$CH_2$—$CH_2$—$CH_2$—$OCH_3$, or cyclopropyl.

5). The compound or pharmaceutically acceptable salt thereof according to clause 1, wherein $L_2$ is O.

6). The compound or pharmaceutically acceptable salt thereof according to clause 1, wherein $R^3$ is $C_{1-6}$ alkyl optionally substituted with one or more independently selected halo, or $C_{3-7}$ cycloalkyl.

7). The compound or pharmaceutically acceptable salt thereof according to clause 1, wherein $R^3$ is —$CH_3$, —$CH_2CH_3$, —$CH(CH_3)CH(CH_3)_2$, —$CH(CH_3)C(CH_3)_3$, each of which is optionally substituted with one or more independently selected halo, or $C_{3-7}$ cycloalkyl.

8). The compound or pharmaceutically acceptable salt thereof according to clause 1, wherein $R^3$ is $C_{1-6}$ alkyl optionally substituted with one or more independently F, cyclopropyl, or cyclobutyl.

9). The compound or pharmaceutically acceptable salt thereof according to clause 1, wherein $R^3$ is selected from:

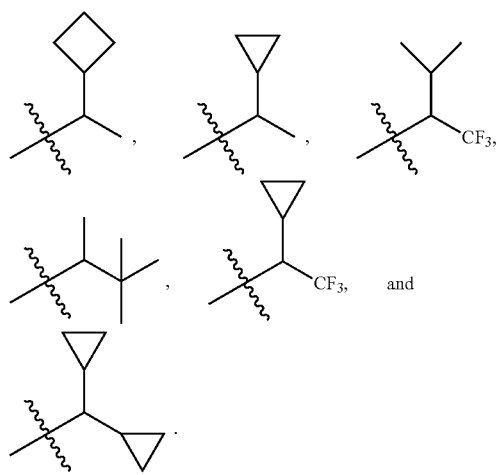

10). The compound or pharmaceutically acceptable salt thereof according to clause 1, wherein $R^3$ is phenyl substituted with one $R^{5a}$ group and one or two independently selected $R^{5b}$ groups.

11). The compound or pharmaceutically acceptable salt thereof according to clause 1, wherein $R^3$ is phenyl substituted with one $R^{5a}$ group and two independently selected $R^{5b}$ groups.

12). The compound or pharmaceutically acceptable salt thereof according to clause 1, wherein $R^3$ is 6-membered heteroaryl substituted with one $R^{5a}$ group and one or two independently selected $R^{5b}$ groups.

13). The compound or pharmaceutically acceptable salt thereof according to clause 1, wherein $R^3$ is pyridinyl, or pyridazinyl, each of which is substituted with one $R^{5a}$ group and one $R^{5b}$ group.

14). The compound or pharmaceutically acceptable salt thereof according to clause 1, wherein $R^3$ is

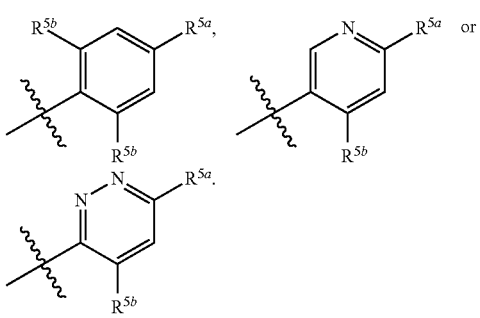

15). The compound or pharmaceutically acceptable salt thereof according to any one of clauses 1-14, wherein $R^{5a}$ is —CN, —$SO_2$—$C_{1-4}$ alkyl, or —$CF_3$.

16). The compound or pharmaceutically acceptable salt thereof according to any one of clauses 1-14, wherein $R^{5a}$ is —CN, —$SO_2CH_3$, or —$CF_3$.

17). The compound or pharmaceutically acceptable salt thereof according to any one of clauses 1-14, wherein $R^{5a}$ is —CN.

18). The compound or pharmaceutically acceptable salt thereof according to any one of clauses 1-17, wherein $R^{5b}$ is independently selected from halo, $C_{1-4}$ alkyl, and $C_{3-7}$ cycloalkyl.

19). The compound or pharmaceutically acceptable salt thereof according to any one of clauses 1-17, wherein $R^{5b}$ is independently selected from F, —$CH_3$, —$CH_2CH_3$, and cyclopropyl.

20). The compound or pharmaceutically acceptable salt thereof according to clause 1, wherein $R^3$ is 4-10 membered monocyclic or fused, bridged or spiro bicyclic heterocycloalkyl comprising one or two heteroatoms independently selected from N, S, and O, optionally substituted with one, two or three groups independently selected from $R^{5a}$ and $R^{5b}$.

21). The compound or pharmaceutically acceptable salt thereof according to clause 1, wherein $R^3$ is tetrahydropyranyl, or oxa-spiro[3.5]nonane, each of which is optionally substituted with one, two or three groups independently selected from $R^{5a}$ and $R^{5b}$.

22). The compound or pharmaceutically acceptable salt thereof according to clause 1-9, 20 or 21, wherein $R^{5a}$ is —CN, —$SO_2CH_3$, or —$CF_3$.

23). The compound or pharmaceutically acceptable salt thereof according to clause 1-9, 20, 21 or 22, wherein $R^{5b}$ is selected from F, —$CH_3$, —$CH_2CH_3$, and cyclopropyl.

24). The compound or pharmaceutically acceptable salt thereof according to clause 20, wherein $R^3$ is 4-10 membered monocyclic or fused, bridged or spiro bicyclic cycloalkyl, optionally substituted with one, two or three groups independently selected from $R^{5a}$ and $R^{5b}$.

25). The compound or pharmaceutically acceptable salt thereof according to clause 24, wherein $R^3$ is cyclohexyl, or bicyclo[1.1.1]pentane, each of which is optionally substituted with one, two or three groups independently selected from $R^{5a}$ and $R^{5b}$.

26). The compound or pharmaceutically acceptable salt thereof according to clause 1-9, 24 or 25, wherein $R^{5a}$ is —CN, —SO$_2$CH$_3$, or —CF$_3$.

27). The compound or pharmaceutically acceptable salt thereof according to clause 1-9, or 24-26, wherein $R^{5b}$ is selected from F, —CH$_3$, —CH$_2$CH$_3$, and cyclopropyl.

28). The compound or pharmaceutically acceptable salt thereof according to clause 1, wherein the compound is according to Formula II:

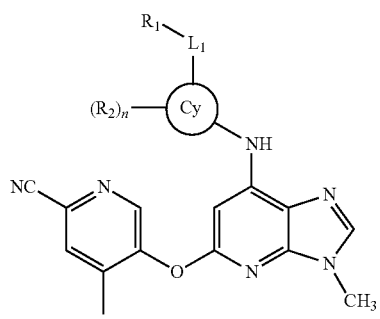

II

29). The compound or pharmaceutically acceptable salt thereof according to any one of clause 1-28, wherein Cy is phenyl.

30). The compound or pharmaceutically acceptable salt thereof according to any one of clause 1-28, wherein Cy is 5-6 membered heteroaryl comprising one, two or three N atoms.

31). The compound or pharmaceutically acceptable salt thereof according to any one of clause 1-28, wherein Cy is pyrazolyl, pyridinyl, pyrimidinyl, or pyridazinyl.

32). The compound or pharmaceutically acceptable salt thereof according to any one of clause 1-28, wherein Cy is pyridinyl, pyrimidinyl, or pyridazinyl.

33). The compound or pharmaceutically acceptable salt thereof according to any one of clause 1-28, wherein Cy is pyridazinyl.

34). The compound or pharmaceutically acceptable salt thereof according to any one of clause 1-33, wherein the subscript n is 1.

35). The compound or pharmaceutically acceptable salt thereof according to any one of clause 1-34, wherein $R^2$ is F, CN, or —CH$_3$.

36). The compound or pharmaceutically acceptable salt thereof according to any one of clause 1-33, wherein the subscript n is 0.

37). The compound or pharmaceutically acceptable salt thereof according to clause 1, wherein the compound is according to formula IIIa, IIIb, IIIc, or IIId:

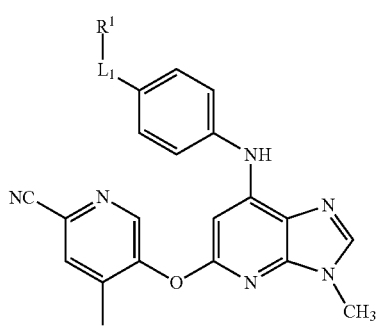

IIIa

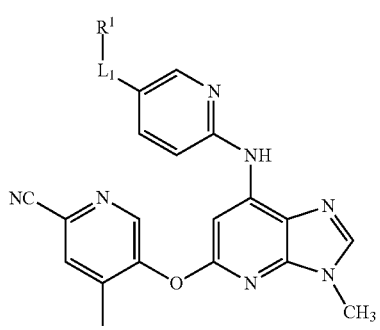

IIIb

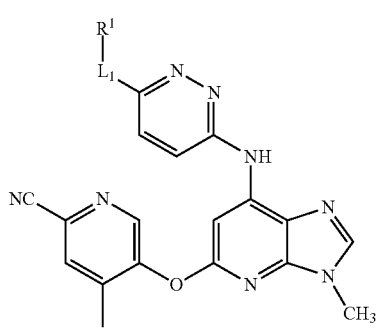

IIIc

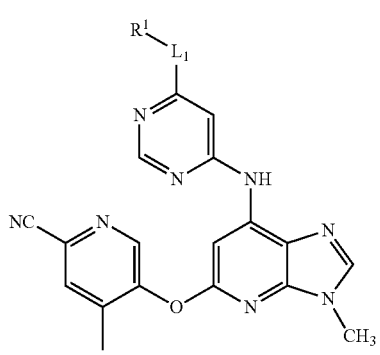

IIId

38). The compound or pharmaceutically acceptable salt thereof according to any one of clause 1-37, wherein L$_1$ is a single bond.

39). The compound or pharmaceutically acceptable salt thereof according to clause to any one of clause 1-37, wherein L$_1$ is —O—

40). The compound or pharmaceutically acceptable salt thereof according to any one of clause 1-37, wherein L$_1$ is —C(=O)—.

41). The compound or pharmaceutically acceptable salt thereof according to any one of clause 1-37, wherein L$_1$ is —S(O)$_2$—.

42). The compound or pharmaceutically acceptable salt thereof according to any one of clause 1-37, wherein $L_1$ is —$NR^{6a}$—.

43). The compound or pharmaceutically acceptable salt thereof according to clause 42, wherein $R^{6a}$ is H, or $C_{1-4}$ alkyl.

44). The compound or pharmaceutically acceptable salt thereof according to clause 42, wherein $R^{6a}$ is H, or —$CH_3$.

45). The compound or pharmaceutically acceptable salt thereof according to any one of clause 1-37, wherein $L_1$ is —$C(=O)NR^{6b}$—.

46). The compound or pharmaceutically acceptable salt thereof according to clause 45, wherein $R^{6b}$ is H, or $C_{1-4}$ alkyl.

47). The compound or pharmaceutically acceptable salt thereof according to clause 45, wherein $R^{6b}$ is H, or —$CH_3$.

48). The compound or pharmaceutically acceptable salt thereof according to any one of clause 1-37, wherein $L_1$ is —$S(O)_2NR^{6c}$—.

49). The compound or pharmaceutically acceptable salt thereof according to clause 48, wherein $R^{6c}$ is H, or $C_{1-4}$ alkyl.

50). The compound or pharmaceutically acceptable salt thereof according to clause 48, wherein $R^{6c}$ is H, or —$CH_3$.

51). The compound or pharmaceutically acceptable salt thereof according to any one of clause 1-37, wherein $L_1$ is —$C(=O)NR^{6d}S(O)_2$—.

52). The compound or pharmaceutically acceptable salt thereof according to clause 51, wherein $R^{6d}$ is H, or $C_{1-4}$ alkyl.

53). The compound or pharmaceutically acceptable salt thereof according to clause 51, wherein Rd is H, or —$CH_3$.

54). The compound or pharmaceutically acceptable salt thereof according to any one of clause 1-53, wherein $R^1$ is H.

55). The compound or pharmaceutically acceptable salt thereof according to any one of clause 1-37, wherein $R^1$ is $C_{1-6}$ alkyl.

56). The compound or pharmaceutically acceptable salt thereof according to clause 55, wherein $R^1$ is —$CH_3$, or —$CH_2CH_3$.

57). The compound or pharmaceutically acceptable salt thereof according to any one of clause 1-37, wherein $R^1$ is $C_{1-6}$ alkyl substituted with one or more independently selected OH, halo, $C_{1-4}$ alkoxy, —$NR^{7a}R^{7b}$, —$C(=O)OH$—, —$C(=O)NR^{7c}R^{7d}$, —$C(=O)OC_{1-4}$ alkyl, or 4-8 membered monocyclic heterocycloalkyl comprising one, two, or three heteroatoms independently selected from N, S, and O, 58). The compound or pharmaceutically acceptable salt thereof according to clause 57, wherein $R^1$ is —$CH_3$, —$CH_2CH_3$, —$CH_2CH_2CH_3$, —$CH_2CH(CH_3)_2$, —$CH_2CH_2CH_2CH_3$, or —$CH_2CH_2CH(CH_3)_2$, each of which is substituted with one or more independently selected OH, halo, $C_{1-4}$ alkoxy, —$NR^{7a}R^{7b}$, —$C(=O)OH$—, —$C(=O)NR^{7c}R^{7d}$, —$C(=O)OC_{1-4}$ alkyl, 4-8 membered monocyclic heterocycloalkyl comprising one, two, or three heteroatoms independently selected from N, S, and O.

59). The compound or pharmaceutically acceptable salt thereof according to clause 57, or 58, wherein $R^{7a}$ is H, or $C_{1-4}$ alkyl optionally substituted with one —$NR^{10a}R^{10b}$.

60). The compound or pharmaceutically acceptable salt thereof according to clause 57, or 58, wherein $R^{7a}$ is H.

61). The compound or pharmaceutically acceptable salt thereof according to clause 59, wherein $R^{7a}$ is —$CH_3$, or —$CH_2CH_3$, each of which is optionally substituted with one —$NR^{10a}R^{10b}$.

62). The compound or pharmaceutically acceptable salt thereof according to clause 61, wherein each $R^{10a}$ and $R^{10b}$ is independently selected H, —$CH_3$, or —$CH_2CH_3$.

63). The compound or pharmaceutically acceptable salt thereof according to clause 57, or 58, wherein $R^{7b}$ is H, or $C_{1-4}$ alkyl optionally substituted with one —$NR^{10a}R^{10b}$.

64). The compound or pharmaceutically acceptable salt thereof according to clause 57, or 58, wherein $R^{7b}$ is H.

65). The compound or pharmaceutically acceptable salt thereof according to clause 63, wherein $R^{7b}$ is —$CH_3$, or —$CH_2CH_3$, each of which is optionally substituted with one —$NR^{10a}R^{10b}$.

66). The compound or pharmaceutically acceptable salt thereof according to clause 65, wherein each $R^{10a}$ and $R^{10b}$ is independently selected H, —$CH_3$, or —$CH_2CH_3$.

67). The compound or pharmaceutically acceptable salt thereof according to clause 57, or 58, wherein $R^{7c}$ is H.

68). The compound or pharmaceutically acceptable salt thereof according to clause 57, or 58, wherein $R^{7c}$ is —$CH_3$, or —$CH_2CH_3$.

69). The compound or pharmaceutically acceptable salt thereof according to clause 57, or 58, wherein $R^{7d}$ is H.

70). The compound or pharmaceutically acceptable salt thereof according to clause 57, or 58, wherein $R^{7d}$ is —$CH_3$, or —$CH_2CH_3$.

71). The compound or pharmaceutically acceptable salt thereof according to any one of clause 1-37, wherein $R^1$ is $C_{1-6}$ alkyl substituted with one or more OH, F, —$OCH_3$, —$OCH_2CH_3$, —$NH_2$, —$NHCH_3$, —$NHCH_2CH_2$—$N(CH_3)_2$, —$NHCH_2CH_3$, —$C(=O)OH$—, —$C(=O)NH_2$, —$C(=O)NHCH_3$, —$C(=O)NHCH_2CH_3$, —$C(=O)N(CH_3)_2$, —$C(=O)OC_{1-4}$ alkyl, dioxanyl, or morpholinyl.

72). The compound or pharmaceutically acceptable salt thereof according to any one of clause 1-37, wherein $R^1$ is —$CH_3$, —$CH_2CH_3$, —$CH_2CH_2CH_3$, —$CH_2CH(CH_3)_2$, —$CH_2CH_2CH_2CH_3$, or —$CH_2CH_2CH(CH_3)_2$, each of which is substituted with one or more OH, F, —$OCH_3$, —$OCH_2CH_3$, —$NH_2$, —$NHCH_3$, —$NHCH_2CH_2$—$N(CH_3)_2$, —$NHCH_2CH_3$, —$C(=O)OH$—, —$C(=O)NH_2$, —$C(=O)NHCH_3$, —$C(=O)NHCH_2CH_3$, —$C(=O)N(CH_3)_2$, —$C(=O)OC_{1-4}$ alkyl, dioxanyl, or morpholinyl.

73). The compound or pharmaceutically acceptable salt thereof according to any one of clause 1-37, wherein $R^1$ is $C_{3-7}$ cycloalkyl.

74). The compound or pharmaceutically acceptable salt thereof according to any one of clause 1-37, wherein $R_1$ is cyclopropyl, cyclobutyl, cyclopentyl or cyclohexyl.

75). The compound or pharmaceutically acceptable salt thereof according to any one of clause 1-37, wherein $R^1$ is $C_{3-7}$ cycloalkyl substituted with one or more independently selected OH, or $C_{1-4}$ alkoxy.

76). The compound or pharmaceutically acceptable salt thereof according to any one of clause 1-37, wherein $R^1$ is $C_{3-7}$ cycloalkyl substituted with one, two or three independently selected OH, or $C_{1-4}$ alkoxy.

77). The compound or pharmaceutically acceptable salt thereof according to any one of clause 1-37, wherein $R^1$ is cyclopropyl, cyclobutyl, cyclopentyl or cyclohexyl, each of which is substituted with one, two or three independently selected OH, or $C_{1-4}$ alkoxy.

78). The compound or pharmaceutically acceptable salt thereof according to any one of clause 1-37, wherein $R^1$ is $C_{3-7}$ cycloalkyl substituted with one, two or three independently selected OH, —$OCH_3$, or —$OCH_2CH_3$.

79). The compound or pharmaceutically acceptable salt thereof according to any one of clause 1-37, wherein $R^1$ is 4-9 membered monocyclic or spirobicyclic or bridged or fused bicyclic heterocycloalkyl comprising one, two, or three heteroatoms independently selected from N, S, and O.

80). The compound or pharmaceutically acceptable salt thereof according to any one of clause 1-37, wherein $R^1$ is azetidinyl, oxetanyl, pyrrolidinyl, morpholinyl, octadeuteriomorpholin-4-yl, piperidinyl, tetrahydropyranyl, piperazinyl, dioxanyl, [1,4]oxazepanyl, 2-oxa-5-aza-bicyclo[2.2.1]heptanyl, 1-oxa-6-aza-spiro[3.3]heptanyl, octahydropyrrolo[3,4-b]pyrrolyl, 2-oxa-6-aza-spiro[3.4]octanyl, 2-oxa-7-aza-spiro[4.4]nonanyl, 2,6-diaza-spiro[3.3]heptanyl, or 2,5-diaza-bicyclo[2.2.1]heptanyl.

81). The compound or pharmaceutically acceptable salt thereof according to any one of clause 1-37, wherein $R^1$ is 4-9 membered monocyclic or spirobicyclic or bridged or fused bicyclic heterocycloalkyl comprising one, two, or three heteroatoms independently selected from N, S, and O; which heterocycloalkyl is substituted with one or more independently selected $R^{11}$ groups.

82). The compound or pharmaceutically acceptable salt thereof according to any one of clause 1-37, wherein $R^1$ is 4-9 membered monocyclic or spirobicyclic or bridged or fused bicyclic heterocycloalkyl comprising one, two, or three heteroatoms independently selected from N, S, and O; which heterocycloalkyl is substituted with one, two or three independently selected $R^{11}$ groups.

83). The compound or pharmaceutically acceptable salt thereof according to any one of clause 1-37, wherein $R^1$ is azetidinyl, oxetanyl, pyrrolidinyl, morpholinyl, octadeuteriomorpholin-4-yl, piperidinyl, tetrahydropyranyl, piperazinyl, dioxanyl, [1,4]oxazepanyl, 2-oxa-5-aza-bicyclo[2.2.1]heptanyl, 1-oxa-6-aza-spiro[3.3]heptanyl, octahydropyrrolo[3,4-b]pyrrolyl, 2-oxa-6-aza-spiro[3.4]octanyl, 2-oxa-7-aza-spiro[4.4]nonanyl, 2,6-diaza-spiro[3.3]heptanyl, or 2,5-diaza-bicyclo[2.2.1]heptanyl, each of which is substituted with one, two or three independently selected $R^{11}$ groups.

84). The compound, according to clause 81, 82, or 83, wherein $R^{11}$ is OH.

85). The compound, according to clause 81, 82, or 83, wherein $R^{11}$ is CN.

86). The compound, according to clause 81, 82, or 83, wherein $R^{11}$ is halo.

87). The compound, according to clause 81, 82, or 83, wherein $R^{11}$ is F, or Cl 88). The compound, according to clause 81, 82, or 83, wherein $R^{11}$ is oxo.

89). The compound, according to clause 81, 82, or 83, wherein $R^{11}$ is —$NR^{8a}R^{8b}$, and each $R^{8a}$ and $R^{8b}$ is independently H, or $C_{1-4}$ alkyl.

90). The compound, according to clause 81, 82, or 83, wherein $R^{11}$ is —$NR^{8a}R^{8b}$, and each $R^{8a}$ and $R^{8b}$ H, —$CH_3$, or —$CH_2CH_3$.

91). The compound, according to clause 81, 82, or 83, wherein $R^{11}$ is $C_{3-7}$ cycloalkyl.

92). The compound, according to clause 81, 82, or 83, wherein $R^{11}$ is cyclopropyl, cyclobutyl, cyclopentyl, or cyclohexyl.

93). The compound, according to clause 81, 82, or 83, wherein $R^{11}$ is $C_{1-4}$ alkyl optionally substituted with one or more independently selected halo, OH, $C_{1-4}$ alkoxy, or —$NR^{9a}R^{9b}$, wherein each $R^{9a}$ and $R^{9b}$ is independently H, or $C_{1-4}$ alkyl.

94). The compound, according to clause 81, 82, or 83, wherein $R^{11}$ is —$CH_3$, —$CH_2CH_3$, —$CH(CH_3)_2$, or —$CH_2CH_2CH_3$, each of which is optionally substituted with one or more independently selected halo, OH, $C_{1-4}$ alkoxy, —$NR^{9a}R^{9b}$, wherein each $R^{9a}$ and $R^{9b}$ is independently H, or $C_{1-4}$ alkyl.

95). The compound, according to clause 81, 82, or 83, wherein $R^{11}$ is $C_{1-4}$ alkyl, optionally substituted with one or more independently selected F, —$OCH_3$, $OCH_2CH_3$, —$NH_2$, —$NHCH_3$, or —$N(CH_3)_2$.

96). The compound, according to clause 81, 82, or 83, wherein $R^{11}$ is —$CH_3$, —$CH_2CH_3$, —$CH(CH_3)_2$ or —$CH_2CH_2CH_3$, each of which is optionally substituted with one or more independently F, —$OCH_3$, —$OCH_2CH_3$, —$NH_2$, —$NHCH_3$, or —$N(CH_3)_2$.

97). The compound, according to clause 81, 82, or 83, wherein $R^{11}$ is $C_{1-4}$ alkoxy optionally substituted with one $C_{1-4}$ alkoxy.

98). The compound, according to clause 81, 82, or 83, wherein $R^{11}$ is —$OCH_3$, —$OCH_2CH_3$, or —$OCH_2CH_2CH_3$, optionally substituted with one $C_{1-4}$ alkoxy.

99). The compound, according to clause 81, 82, or 83, wherein $R^{11}$ is $C_{1-4}$ alkoxy optionally substituted with one —$OCH_3$, —$OCH_2CH_3$, or —$OCH_2CH_2CH_3$.

100). The compound, according to clause 81, 82, or 83, wherein $R^{11}$ is —$OCH_3$, —$OCH_2CH_3$, or —$OCH_2CH_2CH_3$, optionally substituted with one —$OCH_3$, —$OCH_2CH_3$, or —$OCH_2CH_2CH_3$.

101). The compound, according to clause 81, 82, or 83, wherein $R^{11}$ is —$OCH_3$, or —$OCH_2CH_2OCH_3$.

102). The compound, according to clause 81, 82, or 83, wherein $R^{11}$ is 4-7 membered monocyclic heterocycloalkyl comprising one, two, or three heteroatoms independently selected from N, S, and O.

103). The compound, according to clause 81, 82, or 83, wherein $R^{11}$ is azetidinyl, oxetanyl, pyrolidinyl, tetrahydrofuranyl, piperidinyl, piperazinyl, tetrahydropyranyl, dioxanyl, or morpholinyl.

104). The compound, according to clause 81, 82, or 83, wherein $R^{11}$ is —C(=O)O$C_{1-4}$alkyl.

105). The compound, according to clause 81, 82, or 83, wherein $R^{11}$ is —C(=O)OCH$_3$.

106). The compound, according to clause 81, 82, or 83, wherein $R^{11}$ is —NRC(=O)O$C_{1-4}$alkyl.

107). The compound, according to clause 81, 82, or 83, wherein $R^{11}$ is —NHC(=O)OCH$_3$, —NCH$_3$C(=O)OCH$_3$, or —NHC(=O)OCH$_2$CH$_3$.

108). A pharmaceutical composition comprising a pharmaceutically acceptable carrier and a pharmaceutically effective amount of a compound according to any one of clauses 1-107.

109). The pharmaceutical composition according to clause 108 comprising a further therapeutic agent.

110). The compound or pharmaceutically acceptable salt thereof, according to any one of clauses 1-107, or the pharmaceutical composition according any one of clauses 108-109, for use in medicine.

111). A compound according to any one of clauses 1-107, or the pharmaceutical composition according any one of clauses 108-109, for use in the treatment, or prophylaxis of allergic diseases, inflammatory diseases, metabolic diseases, autoinflammatory diseases, autoimmune diseases, proliferative diseases, transplantation rejection, diseases involving impairment of cartilage turnover, congenital cartilage malformations, and/or diseases associated with hypersecretion of IFNα, IL12 and/or IL23.

112). The compound or pharmaceutically acceptable salt thereof according to any one of clauses 1-107, or the pharmaceutical composition according any one of clauses 108-109, is administered in combination with a further therapeutic agent.

113). The pharmaceutical composition according to clause 109, or the method according to clause 112, wherein the further therapeutic agent is an agent for the treatment, or prophylaxis of allergic diseases, inflammatory diseases, metabolic diseases, autoinflammatory diseases, autoimmune diseases, proliferative diseases, transplantation rejection, diseases involving impairment of cartilage turnover, congenital cartilage malformations, and/or diseases associated with hypersecretion of IFNα, IL12 and/or IL23.

114). The compound for the preparation of the compound or pharmaceutically acceptable salt thereof according to clause 1, wherein the compound for the preparation is according to Formula A:

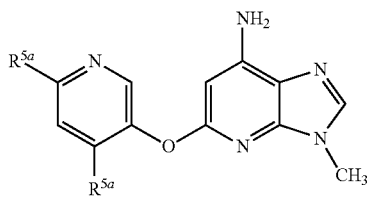

wherein
$R^{5a}$ is —CN, —SO$_2$C$_{1-4}$ alkyl, or —CF$_3$;
$R^{5b}$ is selected from halo, C$_{1-4}$ alkyl, and C$_{3-7}$ cycloalkyl.

115). The compound for the preparation according to clause 114, wherein $R^{5a}$ is —CN, —SO$_2$CH$_3$, or —CF$_3$.

116). The compound for the preparation according to clause 114, wherein $R^{5a}$ is —CN.

117). The compound for the preparation according to any one of clauses 114-116, wherein $R^{5b}$ is F, —CH$_3$, —CH$_2$CH$_3$, or cyclopropyl.

118). The compound for the preparation according to any one of clauses 114-116, wherein $R^{5b}$ is —CH$_3$.

PHARMACEUTICAL COMPOSITIONS

Formulation 1—Tablets

A compound of the invention according to Formula I may be admixed as a dry powder with a dry gelatin binder in an approximate 1:2 weight ratio. A minor amount of magnesium stearate may be added as a lubricant. The mixture may be formed into 240-270 mg tablets (80-90 mg of active compound of the invention according to Formula I per tablet) in a tablet press.

Formulation 2—Capsules

A compound of the invention according to Formula I may be admixed as a dry powder with a starch diluent in an approximate 1:1 weight ratio. The mixture may be filled into 250 mg capsules (125 mg of active compound of the invention according to Formula I per capsule).

Formulation 3—Liquid

A compound of the invention according to Formula I (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color may be diluted with water and added with stirring. Sufficient water may then be added with stirring. Further sufficient water may be then added to produce a total volume of 5 mL.

Formulation 4—Tablets

A compound of the invention according to Formula I may be admixed as a dry powder with a dry gelatin binder in an approximate 1:2 weight ratio. A minor amount of magnesium stearate may be added as a lubricant. The mixture may be formed into 450-900 mg tablets (150-300 mg of active compound of the invention according to Formula I) in a tablet press.

Formulation 5—Injection

A compound of the invention according to Formula I may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of A compound of the invention according to Formula I (50 g) methylparaben (0.25 g), propylparaben (0.15 g), sodium lauryl sulfate (10 g), and propylene glycol (120 g) dissolved in water (about 370 g) may be added and the resulting mixture may be stirred until it congeals.

Methods of Treatment

In one embodiment, the present invention provides compounds of the invention, or pharmaceutical compositions comprising a compound of the invention, for use in medicine. In a particular embodiment, the present invention provides compounds of the invention or pharmaceutical compositions comprising a compound of the invention, for use in the prophylaxis and/or treatment of allergic diseases, inflammatory diseases, metabolic diseases, autoinflammatory diseases, autoimmune diseases, proliferative diseases, transplantation rejection, diseases involving impairment of cartilage turnover, congenital cartilage malformations, and/or diseases associated with hypersecretion of IFNα, IL12 and/or IL23.

In another embodiment, the present invention provides compounds of the invention, or pharmaceutical compositions comprising a compound of the invention for use in the manufacture of a medicament for use in the prophylaxis and/or treatment of allergic diseases, inflammatory diseases, metabolic diseases, autoinflammatory diseases, autoimmune diseases, proliferative diseases, transplantation rejection, diseases involving impairment of cartilage turnover, congenital cartilage malformations, and/or diseases associated with hypersecretion of IFNα, IL12 and/or IL23.

In additional method of treatment aspects, this invention provides methods of prophylaxis and/or treatment of a mammal afflicted with allergic diseases, inflammatory diseases, metabolic diseases, autoinflammatory diseases, autoimmune diseases, proliferative diseases, transplantation rejection, diseases involving impairment of cartilage turnover, congenital cartilage malformations, and/or diseases associated with hypersecretion of IFNα, IL12 and/or IL23, which methods comprise the administration of an effective amount of a compound of the invention or one or more of the pharmaceutical compositions herein described for the treatment or prophylaxis of said condition.

In one embodiment, the present invention provides pharmaceutical compositions comprising a compound of the invention, and another therapeutic agent. In a particular embodiment, the other therapeutic agent is a allergic diseases, inflammatory diseases, metabolic diseases, autoinflammatory diseases, autoimmune diseases, proliferative diseases, transplantation rejection, diseases involving impairment of cartilage turnover, congenital cartilage malformations, and/or diseases associated with hypersecretion of IFNα, IL12 and/or IL23 treatment agent.

In one embodiment, the present invention provides compounds of the invention, or pharmaceutical compositions comprising a compound of the invention, for use in medicine. In a particular embodiment, the present invention provides compounds of the invention or pharmaceutical compositions comprising a compound of the invention, for use in the prophylaxis and/or treatment of allergic diseases. In a particular embodiment, the allergic disease is asthma.

In another embodiment, the present invention provides compounds of the invention, or pharmaceutical compositions comprising a compound of the invention for use in the manufacture of a medicament for use in the prophylaxis and/or treatment of allergic diseases. In a particular embodiment, the allergic disease is asthma.

In additional method of treatment aspects, this invention provides methods of prophylaxis and/or treatment of a mammal afflicted with allergic diseases, which methods comprise the administration of an effective amount of a compound of the invention or one or more of the pharmaceutical compositions herein described for the treatment or prophylaxis of said condition. In a particular embodiment, the allergic disease is asthma.

In one embodiment, the present invention provides pharmaceutical compositions comprising a compound of the invention, and another therapeutic agent. In a particular embodiment, the other therapeutic agent is an allergic diseases treatment agent. In a particular embodiment, the allergic disease is asthma.

In one embodiment, the present invention provides compounds of the invention, or pharmaceutical compositions comprising a compound of the invention, for use in medicine. In a particular embodiment, the present invention provides compounds of the invention or pharmaceutical compositions comprising a compound of the invention, for use in the prophylaxis and/or treatment of inflammatory diseases. In a particular embodiment, the inflammatory disease is rheumatoid arthritis, chronic obstructive pulmonary disease (COPD), primary biliary cholangitis (PBC), primary sclerosing cholangitis (PSC) and inflammatory bowel diseases. In a more particular embodiment, the inflammatory disease is rheumatoid arthritis, chronic obstructive pulmonary disease (COPD) and inflammatory bowel diseases.

In another embodiment, the present invention provides compounds of the invention, or pharmaceutical compositions comprising a compound of the invention for use in the manufacture of a medicament for use in the prophylaxis and/or treatment of inflammatory diseases. In a particular embodiment, the inflammatory disease is rheumatoid arthritis, chronic obstructive pulmonary disease (COPD), primary biliary cholangitis (PBC), primary sclerosing cholangitis (PSC) and inflammatory bowel diseases. In a more particular embodiment, the inflammatory disease is rheumatoid arthritis, chronic obstructive pulmonary disease (COPD) and inflammatory bowel diseases.

In additional method of treatment aspects, this invention provides methods of prophylaxis and/or treatment of a mammal afflicted with inflammatory diseases, which methods comprise the administration of an effective amount of a compound of the invention or one or more of the pharmaceutical compositions herein described for the treatment or prophylaxis of said condition. In a particular embodiment, the inflammatory disease is rheumatoid arthritis, chronic obstructive pulmonary disease (COPD), primary biliary cholangitis (PBC), primary sclerosing cholangitis (PSC) and inflammatory bowel diseases. In a more particular embodiment, the inflammatory disease is rheumatoid arthritis, chronic obstructive pulmonary disease (COPD) and inflammatory bowel diseases.

In one embodiment, the present invention provides pharmaceutical compositions comprising a compound of the invention, and another therapeutic agent. In a particular embodiment, the other therapeutic agent is inflammatory diseases treatment agent. In a particular embodiment, the inflammatory disease is rheumatoid arthritis, chronic obstructive pulmonary disease (COPD), primary biliary cholangitis (PBC), primary sclerosing cholangitis (PSC) and inflammatory bowel diseases. In a more particular embodiment, the inflammatory disease is rheumatoid arthritis, chronic obstructive pulmonary disease (COPD) and inflammatory bowel diseases.

In one embodiment, the present invention provides compounds of the invention, or pharmaceutical compositions comprising a compound of the invention, for use in medicine. In a particular embodiment, the present invention provides compounds of the invention or pharmaceutical compositions comprising a compound of the invention, for use in the prophylaxis and/or treatment of metabolic diseases. In a particular embodiment, the metabolic disease is type II diabetes and/or obesity.

In another embodiment, the present invention provides compounds of the invention, or pharmaceutical compositions comprising a compound of the invention for use in the manufacture of a medicament for use in the prophylaxis and/or treatment of metabolic diseases. In a particular embodiment, the metabolic disease is type II diabetes and/or obesity.

In additional method of treatment aspects, this invention provides methods of prophylaxis and/or treatment of a mammal afflicted with metabolic diseases, which methods comprise the administration of an effective amount of a compound of the invention or one or more of the pharmaceutical compositions herein described for the treatment or prophylaxis of said condition. In a particular embodiment, the metabolic disease is type II diabetes and/or obesity.

In one embodiment, the present invention provides pharmaceutical compositions comprising a compound of the invention, and another therapeutic agent. In a particular embodiment, the other therapeutic agent is metabolic diseases treatment agent. In a particular embodiment, the metabolic disease is type II diabetes and/or obesity.

In one embodiment, the present invention provides compounds of the invention, or pharmaceutical compositions comprising a compound of the invention, for use in medicine. In a particular embodiment, the present invention provides compounds of the invention or pharmaceutical compositions comprising a compound of the invention, for use in the prophylaxis and/or treatment of autoimmune diseases. In a particular embodiment, the autoimmune disease is COPD, asthma, systemic lupus erythematosis, type I diabetes mellitus, interferonopathy, and inflammatory bowel disease.

In another embodiment, the present invention provides compounds of the invention, or pharmaceutical compositions comprising a compound of the invention for use in the manufacture of a medicament for use in the prophylaxis and/or treatment of autoimmune diseases. In a particular embodiment, the autoimmune disease is COPD, asthma, systemic lupus erythematosis, type I diabetes mellitus, interferonopathy, and inflammatory bowel disease.

In additional method of treatment aspects, this invention provides methods of prophylaxis and/or treatment of a mammal afflicted with autoimmune diseases, which methods comprise the administration of an effective amount of a compound of the invention or one or more of the pharmaceutical compositions herein described for the treatment or prophylaxis of said condition. In a particular embodiment, the autoimmune disease is COPD, asthma, systemic lupus erythematosis, type I diabetes mellitus, interferonopathy, and inflammatory bowel disease.

In one embodiment, the present invention provides pharmaceutical compositions comprising a compound of the invention, and another therapeutic agent. In a particular embodiment, the other therapeutic agent is an autoimmune diseases treatment agent. In a particular embodiment, the autoimmune disease is COPD, asthma, systemic lupus erythematosis, type I diabetes mellitus, interferonopathy, and inflammatory bowel disease.

In one embodiment, the present invention provides compounds of the invention, or pharmaceutical compositions comprising a compound of the invention, for use in medicine. In a particular embodiment, the present invention provides compounds of the invention or pharmaceutical compositions comprising a compound of the invention, for use in the prophylaxis and/or treatment of autoinflammatory diseases. In a particular embodiment, the autoimmune disease is Cryopyrin-Associated Periodic Syndromes (CAPS), Familial Mediterranean Fever (FMF) and Tumor necrosis factor receptor-associated periodic syndrome (TRAPS), Behgets, Systemic-Onset Juvenile Idiopathic Arthritis (SJIA) or Still's disease.

In another embodiment, the present invention provides compounds of the invention, or pharmaceutical compositions comprising a compound of the invention for use in the manufacture of a medicament for use in the prophylaxis and/or treatment of autoinflammatory diseases. In a particular embodiment, the autoimmune disease is Cryopyrin-Associated Periodic Syndromes (CAPS), Familial Mediterranean Fever (FMF) and Tumor necrosis factor receptor-associated periodic syndrome (TRAPS), Behgets, Systemic-Onset Juvenile Idiopathic Arthritis (SJIA) or Still's disease.

In additional method of treatment aspects, this invention provides methods of prophylaxis and/or treatment of a mammal afflicted with autoinflammatory diseases, which methods comprise the administration of an effective amount of a compound of the invention or one or more of the pharmaceutical compositions herein described for the treatment or prophylaxis of said condition. In a particular embodiment, the autoimmune disease is Cryopyrin-Associated Periodic Syndromes (CAPS), Familial Mediterranean Fever (FMF) and Tumor necrosis factor receptor-associated periodic syndrome (TRAPS), Behgets, Systemic-Onset Juvenile Idiopathic Arthritis (SJIA) or Still's disease.

In one embodiment, the present invention provides pharmaceutical compositions comprising a compound of the invention, and another therapeutic agent. In a particular embodiment, the other therapeutic agent is an autoinflammatory diseases treatment agent. In a particular embodiment, the autoimmune disease is Cryopyrin-Associated Periodic Syndromes (CAPS), Familial Mediterranean Fever (FMF) and Tumor necrosis factor receptor-associated periodic syndrome (TRAPS), Behgets, Systemic-Onset Juvenile Idiopathic Arthritis (SJIA) or Still's disease.

In one embodiment, the present invention provides compounds of the invention, or pharmaceutical compositions comprising a compound of the invention, for use in medicine. In a particular embodiment, the present invention provides compounds of the invention or pharmaceutical compositions comprising a compound of the invention, for use in the prophylaxis and/or treatment of proliferative diseases. In a particular embodiment, the proliferative disease is cancer, leukemia, multiple myeloma and psoriasis.

In another embodiment, the present invention provides compounds of the invention, or pharmaceutical compositions comprising a compound of the invention for use in the manufacture of a medicament for use in the prophylaxis and/or treatment of proliferative diseases. In a particular embodiment, the proliferative disease is cancer, leukemia, multiple myeloma and psoriasis.

In additional method of treatment aspects, this invention provides methods of prophylaxis and/or treatment of a mammal afflicted with proliferative diseases, which methods comprise the administration of an effective amount of a compound of the invention or one or more of the pharmaceutical compositions herein described for the treatment or prophylaxis of said condition. In a particular embodiment, the proliferative disease is cancer, leukemia, multiple myeloma and psoriasis.

In one embodiment, the present invention provides pharmaceutical compositions comprising a compound of the invention, and another therapeutic agent. In a particular embodiment, the other therapeutic agent is a proliferative diseases treatment agent. In a particular embodiment, the proliferative disease is cancer, leukemia, multiple myeloma and psoriasis.

In one embodiment, the present invention provides compounds of the invention, or pharmaceutical compositions comprising a compound of the invention, for use in medicine. In a particular embodiment, the present invention provides compounds of the invention or pharmaceutical compositions comprising a compound of the invention, for use in the prophylaxis and/or treatment of transplantation rejection. In a particular embodiment, the transplantation rejection is graft versus host disease.

In another embodiment, the present invention provides compounds of the invention, or pharmaceutical compositions comprising a compound of the invention for use in the manufacture of a medicament for use in the prophylaxis and/or treatment of transplantation rejection. In a particular embodiment, the transplantation rejection is graft versus host disease.

In additional method of treatment aspects, this invention provides methods of prophylaxis and/or treatment of a mammal afflicted with transplantation rejection, which methods comprise the administration of an effective amount of a compound of the invention or one or more of the pharmaceutical compositions herein described for the treatment or prophylaxis of said condition. In a particular embodiment, the transplantation rejection is graft versus host disease.

In one embodiment, the present invention provides pharmaceutical compositions comprising a compound of the invention, and another therapeutic agent. In a particular embodiment, the other therapeutic agent is a transplantation rejection treatment agent. In a particular embodiment, the transplantation rejection is graft versus host disease.

In one embodiment, the present invention provides compounds of the invention, or pharmaceutical compositions comprising a compound of the invention, for use in medicine. In a particular embodiment, the present invention provides compounds of the invention or pharmaceutical compositions comprising a compound of the invention, for use in the prophylaxis and/or treatment of diseases involving impairment of cartilage turnover. In a particular embodiment, the disease involving impairment of cartilage turnover is ankylosing spondylitis.

In another embodiment, the present invention provides compounds of the invention, or pharmaceutical compositions comprising a compound of the invention for use in the manufacture of a medicament for use in the prophylaxis and/or treatment of diseases involving impairment of cartilage turnover. In a particular embodiment, the disease involving impairment of cartilage turnover is ankylosing spondylitis.

In additional method of treatment aspects, this invention provides methods of prophylaxis and/or treatment of a mammal afflicted with a disease involving impairment of cartilage turnover, which methods comprise the administration of an effective amount of a compound of the invention or one or more of the pharmaceutical compositions herein described for the treatment or prophylaxis of said condition. In a particular embodiment, the disease involving impairment of cartilage turnover is ankylosing spondylitis.

In one embodiment, the present invention provides pharmaceutical compositions comprising a compound of the invention, and another therapeutic agent. In a particular embodiment, the other therapeutic agent is a disease involving impairment of cartilage turnover treatment agent. In a particular embodiment, the disease involving impairment of cartilage turnover is ankylosing spondylitis.

In one embodiment, the present invention provides compounds of the invention, or pharmaceutical compositions comprising a compound of the invention, for use in medicine. In a particular embodiment, the present invention provides compounds of the invention or pharmaceutical compositions comprising a compound of the invention, for use in the prophylaxis and/or treatment of congenital cartilage malformations. In a particular embodiment, the congenital cartilage malformations is selected from microtia, anotia, and/or metaphyseal chondrodysplasia.

In another embodiment, the present invention provides compounds of the invention, or pharmaceutical compositions comprising a compound of the invention for use in the manufacture of a medicament for use in the prophylaxis and/or treatment of congenital cartilage malformations. In a particular embodiment, the congenital cartilage malformations is selected from microtia, anotia, and/or metaphyseal chondrodysplasia.

In additional method of treatment aspects, this invention provides methods of prophylaxis and/or treatment of a mammal afflicted with congenital cartilage malformations, which methods comprise the administration of an effective amount of a compound of the invention or one or more of the pharmaceutical compositions herein described for the treatment or prophylaxis of said condition. In a particular embodiment, the congenital cartilage malformations is selected from microtia, anotia, and/or metaphyseal chondrodysplasia.

In one embodiment, the present invention provides pharmaceutical compositions comprising a compound of the invention, and another therapeutic agent. In a particular embodiment, the other therapeutic agent is a congenital cartilage malformations treatment agent. In a particular embodiment, the congenital cartilage malformations is selected from microtia, anotia, and/or metaphyseal chondrodysplasia.

In one embodiment, the present invention provides compounds of the invention, or pharmaceutical compositions comprising a compound of the invention, for use in medicine. In a particular embodiment, the present invention provides compounds of the invention or pharmaceutical compositions comprising a compound of the invention, for use in the prophylaxis and/or treatment of diseases associated with hypersecretion of IFNα, IL12 and/or IL23. In a particular embodiment, the disease associated with hypersecretion of IFNα, IL12 and/or IL23 is systemic and cutaneous lupus erythematosis, lupus nephritis, dermatomyositis, Sjogren's syndrome, psoriasis, rheumatoid arthritis, psoriatic arthritis, trisomy 21 and/or Crohn's disease.

In another embodiment, the present invention provides compounds of the invention, or pharmaceutical compositions comprising a compound of the invention for use in the manufacture of a medicament for use in the prophylaxis and/or treatment of diseases associated with hypersecretion of IFNα, IL12 and/or IL23. In a particular embodiment, the disease associated with hypersecretion of IFNα, IL12 and/or IL23 is systemic and cutaneous lupus erythematosis, lupus nephritis, dermatomyositis, Sjogren's syndrome, psoriasis, rheumatoid arthritis, psoriatic arthritis, trisomy 21 and/or Crohn's disease.

In additional method of treatment aspects, this invention provides methods of prophylaxis and/or treatment of a mammal afflicted with diseases associated with hypersecretion of IFNα, IL12 and/or IL23, which methods comprise the administration of an effective amount of a compound of the invention or one or more of the pharmaceutical compositions herein described for the treatment or prophylaxis of said condition. In a particular embodiment, the disease associated with hypersecretion of IFNα, IL12 and/or IL23 is systemic and cutaneous lupus erythematosis, lupus nephritis, dermatomyositis, Sjogren's syndrome, psoriasis, rheumatoid arthritis, psoriatic arthritis, trisomy 21 and/or Crohn's disease.

In one embodiment, the present invention provides pharmaceutical compositions comprising a compound of the invention, and another therapeutic agent. In a particular embodiment, the other therapeutic agent is a diseases associated with hypersecretion of IFNα, IL12 and/or IL23 treatment agent. In a particular embodiment, the disease associated with hypersecretion of IFNα, IL12 and/or IL23 is systemic and cutaneous lupus erythematosis, lupus nephritis, dermatomyositis, Sjogren's syndrome, psoriasis, rheumatoid arthritis, psoriatic arthritis, trisomy 21 and/or Crohn's disease.

Injection dose levels range from about 0.1 mg/kg/h to at least 10 mg/kg/h, all for from about 1 to about 120 h and especially 24 to 96 h. A preloading bolus of from about 0.1 mg/kg to about 10 mg/kg or more may also be administered to achieve adequate steady state levels. The maximum total dose is not expected to exceed about 1 g/day for a 40 to 80 kg human patient.

For the prophylaxis and/or treatment of long-term conditions, such as degenerative conditions, the regimen for treatment usually stretches over many months or years so oral dosing is preferred for patient convenience and tolerance. With oral dosing, one to four (1-4) regular doses daily, especially one to three (1-3) regular doses daily, typically one to two (1-2) regular doses daily, and most typically one (1) regular dose daily are representative regimens. Alternatively for long lasting effect drugs, with oral dosing, once every other week, once weekly, and once a day are representative regimens. In particular, dosage regimen can be every 1-14 days, more particularly 1-10 days, even more particularly 1-7 days, and most particularly 1-3 days.

Using these dosing patterns, each dose provides from about 1 to about 1000 mg of a compound of the invention, with particular doses each providing from about 10 to about 500 mg and especially about 30 to about 250 mg.

Transdermal doses are generally selected to provide similar or lower blood levels than are achieved using injection doses.

When used to prevent the onset of a condition, a compound of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

A compound of the invention can be administered as the sole active agent or it can be administered in combination with other therapeutic agents, including other compound of the inventions that demonstrate the same or a similar therapeutic activity and that are determined to be safe and efficacious for such combined administration. In a specific embodiment, co-administration of two (or more) agents allows for significantly lower doses of each to be used, thereby reducing the side effects seen.

In one embodiment, a compound of the invention or a pharmaceutical composition comprising a compound of the invention is administered as a medicament. In a specific embodiment, said pharmaceutical composition additionally comprises a further active ingredient.

In one embodiment, a compound of the invention is co-administered with another therapeutic agent for the treatment and/or prophylaxis of a disease involving inflammation, particular agents include, but are not limited to, immunoregulatory agents e.g. azathioprine, corticosteroids (e.g. prednisolone or dexamethasone), cyclophosphamide, cyclosporin A, tacrolimus, mycophenolate, mofetil, muromonab-CD3 (OKT3, e.g. Orthocolone®), ATG, aspirin, acetaminophen, ibuprofen, naproxen, and piroxicam.

In one embodiment, a compound of the invention is co-administered with another therapeutic agent for the treatment and/or prophylaxis of arthritis (e.g. rheumatoid arthritis), particular agents include but are not limited to analgesics, non-steroidal anti-inflammatory drugs (NSAIDS), steroids, synthetic DMARDS (for example but without limitation methotrexate, leflunomide, sulfasalazine, auranofin, sodium aurothiomalate, penicillamine, chloroquine, hydroxychloroquine, azathioprine, tofacitinib, baricitinib, fostamatinib, and cyclosporin), and biological DMARDS (for example but without limitation infliximab, etanercept, adalimumab, rituximab, and abatacept).

In one embodiment, a compound of the invention is co-administered with another therapeutic agent for the treatment and/or prophylaxis of proliferative disorders, particular agents include but are not limited to: methotrexate, leukovorin, adriamycin, prednisone, bleomycin, cyclophosphamide, 5-fluorouracil, paclitaxel, docetaxel, vincristine, vinblastine, vinorelbine, doxorubicin, tamoxifen, toremifene, megestrol acetate, anastrozole, goserelin, anti-HER2 monoclonal antibody (e.g. Herceptin™), capecitabine, raloxifene hydrochloride, EGFR inhibitors (e.g. lressa, Tarceva™, Erbitux™), VEGF inhibitors (e.g. Avastin™), proteasome inhibitors (e.g. Velcade™), Glivec® and hsp90 inhibitors (e.g. 17-AAG). Additionally, the compound of the invention according to Formula I may be administered in combination with other therapies including, but not limited to, radiotherapy or surgery. In a specific embodiment the proliferative disorder is selected from cancer, myeloproliferative disease or leukaemia.

In one embodiment, a compound of the invention is co-administered with another therapeutic agent for the treatment and/or prophylaxis of autoimmune diseases, particular agents include but are not limited to: glucocorticoids, cytostatic agents (e.g. purine analogs), alkylating agents, (e.g nitrogen mustards (cyclophosphamide), nitrosoureas, platinum compound of the inventions, and others), antimetabolites (e.g. methotrexate, azathioprine and mercaptopurine), cytotoxic antibiotics (e.g. dactinomycin anthracyclines, mitomycin C, bleomycin, and mithramycin), antibodies (e.g. anti-CD20, anti-CD25 or anti-CD3 (OTK3) monoclonal antibodies, Atgam® and Thymoglobuline®), cyclosporin, tacrolimus, rapamycin (sirolimus), interferons (e.g. IFN-β), TNF binding proteins (e.g. infliximab, etanercept, or adalimumab), mycophenolate, fingolimod and myriocin.

In one embodiment, a compound of the invention is co-administered with another therapeutic agent for the treatment and/or prophylaxis of transplant rejection, particular agents include but are not limited to: calcineurin inhibitors (e.g. cyclosporin or tacrolimus (FK506)), mTOR inhibitors (e.g. sirolimus, everolimus), anti-proliferatives (e.g. azathioprine, mycophenolic acid), corticosteroids (e.g. prednisolone, hydrocortisone), antibodies (e.g. monoclonal anti-IL-2Rα receptor antibodies, basiliximab, daclizumab), polyclonal anti-T-cell antibodies (e.g. anti-thymocyte globulin (ATG), anti-lymphocyte globulin (ALG)).

In one embodiment, a compound of the invention is co-administered with another therapeutic agent for the treatment and/or prophylaxis of asthma and/or rhinitis and/or COPD, particular agents include but are not limited to: beta2-adrenoceptor agonists (e.g. salbutamol, levalbuterol, terbutaline and bitolterol), epinephrine (inhaled or tablets), anticholinergics (e.g. ipratropium bromide), glucocorticoids (oral or inhaled). Long-acting $2-agonists (e.g. salmeterol, formoterol, bambuterol, and sustained-release oral albuterol), combinations of inhaled steroids and long-acting bronchodilators (e.g. fluticasone/salmeterol, budesonide/formoterol), leukotriene antagonists and synthesis inhibitors (e.g. montelukast, zafirlukast and zileuton), inhibitors of mediator release (e.g. cromoglycate and ketotifen), biological regulators of IgE response (e.g. omalizumab), antihistamines (e.g. ceterizine, cinnarizine, fexofenadine) and vasoconstrictors (e.g. oxymethazoline, xylomethazoline, nafazoline and tramazoline).

Additionally, a compound of the invention may be administered in combination with emergency therapies for asthma and/or COPD, such therapies include oxygen or heliox administration, nebulized salbutamol or terbutaline (optionally combined with an anticholinergic (e.g. ipratropium), systemic steroids (oral or intravenous, e.g. prednisone, prednisolone, methylprednisolone, dexamethasone, or hydrocortisone), intravenous salbutamol, non-specific beta-agonists, injected or inhaled (e.g. epinephrine, isoetharine, isoproterenol, metaproterenol), anticholinergics (IV or nebulized, e.g. glycopyrrolate, atropine, ipratropium), methylxanthines (theophylline, aminophylline, bamiphylline), inhalation anesthetics that have a bronchodilatory effect (e.g. isoflurane, halothane, enflurane), ketamine and intravenous magnesium sulfate.

In one embodiment, a compound of the invention is co-administered with another therapeutic agent for the treatment and/or prophylaxis of inflammatory bowel disease (IBD), particular agents include but are not limited to: glucocorticoids (e.g. prednisone, budesonide) synthetic disease modifying, immunomodulatory agents (e.g. methotrexate, leflunomide, sulfasalazine, mesalazine, azathioprine, 6-mercaptopurine and cyclosporin) and biological disease modifying, immunomodulatory agents (infliximab, adalimumab, rituximab, and abatacept).

In one embodiment, a compound of the invention is co-administered with another therapeutic agent for the treatment and/or prophylaxis of SLE, particular agents include but are not limited to: human monoclonal antibodies (belimumab (Benlysta)), Disease-modifying antirheumatic drugs (DMARDs) such as antimalarials (e.g. plaquenil, hydroxychloroquine), immunosuppressants (e.g. methotrexate and azathioprine), cyclophosphamide and mycophenolic acid, immunosuppressive drugs and analgesics, such as nonsteroidal anti-inflammatory drugs, opiates (e.g. dextropropoxyphene and co-codamol), opioids (e.g. hydrocodone, oxycodone, MS Contin, or methadone) and the fentanyl duragesic transdermal patch.

In one embodiment, a compound of the invention is co-administered with another therapeutic agent for the treatment and/or prophylaxis of psoriasis, particular agents include but are not limited to: topical treatments such as bath solutions, moisturizers, medicated creams and ointments containing coal tar, dithranol (anthralin), corticosteroids like desoximetasone (Topicort™), fluocinonide, vitamin D3 analogues (for example, calcipotriol), argan oil and retinoids (etretinate, acitretin, tazarotene), systemic treatments such as methotrexate, cyclosporine, retinoids, tioguanine, hydroxyurea, sulfasalazine, mycophenolate mofetil, azathioprine, tacrolimus, fumaric acid esters or biologics such as Amevive™, Enbrel™, Humira™, Remicade™, Raptiva™ and ustekinumab (a IL-12 and IL-23 blocker). Additionally, a compound of the invention may be administered in combination with other therapies including, but not limited to phototherapy, or photochemotherapy (e.g. psoralen and ultraviolet A phototherapy (PUVA)).

In one embodiment, a compound of the invention is co-administered with another therapeutic agent for the treatment and/or prophylaxis of allergic reaction, particular agents include but are not limited to: antihistamines (e.g. cetirizine, diphenhydramine, fexofenadine, levocetirizine), glucocorticoids (e.g. prednisone, betamethasone, beclomethasone, dexamethasone), epinephrine, theophylline or anti-leukotrienes (e.g. montelukast or zafirlukast), anti-cholinergics and decongestants.

By co-administration is included any means of delivering two or more therapeutic agents to the patient as part of the same treatment regime, as will be apparent to the skilled person. Whilst the two or more agents may be administered simultaneously in a single formulation, i.e. as a single pharmaceutical composition, this is not essential. The agents may be administered in different formulations and at different times.

Chemical Synthetic Procedures

General

The compounds of the invention can be prepared from readily available starting materials using the following general methods and procedures. It will be appreciated that where typical or preferred process conditions (i.e. reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art (Greene, T W; Wuts, P G M; 1991).

The following methods are presented with details as to the preparation of a compound of the invention as defined hereinabove and the comparative examples. A compound of the invention may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography is performed on silica gel 60 (35-70 μm). Thin layer chromatography is carried out using pre-coated silica gel F-254 plates (thickness 0.25 mm). H NMR spectra were recorded on a Bruker Advance 300 NMR spectrometer (300 MHz). Chemical shifts ($\delta$) for H NMR spectra are reported in parts per million (ppm) relative to tetramethylsilane ($\delta$ 0.00) or the appropriate residual solvent peak, i.e. $CHCl_3$ ($\delta$ 7.27), as internal reference. Multiplicities are given as singlet (s), doublet (d), triplet (t), quartet (q), quintuplet (quin), multiplet (m) and broad (br). Electrospray MS spectra were obtained on a Waters platform LC/MS spectrometer or with Waters Acquity H-Class UPLC coupled to a Waters Mass detector 3100 spectrometer. Columns used: Waters Acquity UPLC BEH C18 1.7 μm, 2.1 mm ID×50 mm L, Waters Acquity UPLC BEH C18 1.7 μm, 2.1 mm ID×30 mm L, or Waters Xterra MS 5 μm C18, 100×4.6 mm. The methods are using either MeCN/$H_2O$ gradients ($H_2O$ contains either 0.1% TFA or 0.1% $NH_3$) or MeOH/$H_2O$ gradients ($H_2O$ contains 0.05% TFA). Microwave heating is performed with a Biotage Initiator.

Racemic mixtures were separated on a Agilent HP1100 system with UV detection. Column used: Chiralpak 1A (10×250 mm, 5 μm). Solvents used: iPrOH and tBME. Enantiomeric purity is determined on a Agilent HP1100 system with UV detection. Column used: Chiralpak IA (4.6×250 mm, 5 μm). Solvents used: iPrOH and tBME.

TABLE I

| List of abbreviations used in the experimental section: | |
|---|---|
| Abbreviation | Definition |
| DCM | Dichloromethane |
| MeCN | Acetonitrile |
| DMF | N,N-dimethylformamide |
| Cat. | Catalytic amount |
| TFA | Trifluoroacetic acid |
| THF | Tetrahydrofuran |
| APCI | atmospheric pressure chemical ionization |

TABLE I-continued

List of abbreviations used in the experimental section:

| Abbreviation | Definition |
|---|---|
| Rt | retention time |
| s | singlet |
| br s | broad singlet |
| d | duplet |
| dd | double duplet |
| m | multiplet |
| min | minute |
| mL | milliliter |
| μL | microliter |
| g | gram |
| mg | milligram |
| TEA | Triethylamine |
| mmol | millimoles |
| HPLC | High pressure liquid chromatography |
| NMP | N-Methylpyrrolidone |
| AcCl | Acetyl Chloride |
| ppm | parts per million |
| $Pd_2(dba)_3$ | Tris(dibenzylideneacetone)dipalladium(0) |
| $Pd(OAc)_2$ | Palladium(II) acetate |
| XPhos | 2-Dicyclohexylphosphino-2',4',6'-triisopropylbiphenyl |
| Cpd | Compound |
| Mtd | Method |
| Int | Intermediate |
| MW | Molecular weight |
| Mes | Molecular weight measured |
| NA | Not active |
| $Pd(dppf)CL_2$. DCM | 1,1'-Bis(diphenylphosphino)-ferrocene-palladium(II)-dichloride dichloromethane |
| μm | micrometer |
| tBME | tert-Butylmethylether |
| iPrOH | iso-Propanol |
| DMA | dimethylacetamide |
| TFA | Trifluoroacetic acid |
| DBU | 1,8-Diazabicycloundec-7-ene |
| DiPPF | 1,1'-Bis(di-isopropylphosphino)ferrocene |
| NMR | Nuclear Magnetic Resonnance |
| DMSO | Dimethylsulfoxide |
| LC-MS | Liquid Chromatography-Mass Spectrometry |
| EtOAc | ethyl acetate |
| HATU | 1-[Bis(dimethylamino)methylene]-1H-1,2,3triazolo[4,5-b]pyridinium 3-oxid hexafluorophosphate |
| NIS | N-Iodosuccinimide |
| XantPhos | 4,5-Bis(diphenylphosphino)-9,9-dimethylxanthene |
| XantPhos Pd G3 | [(4,5-Bis(diphenylphosphino)-9,9-dimethyl xanthene)-2-(2'-amino-1,1'-biphenyl)]palladium(II) methanesulfonate |
| MorDALPhos | Di(1-adamantyl)-2-morpholinophenylphosphine |
| MorDALPhos Pd G3 | (2-(Di-1-adamantylphosphino)-morpholinobenzene)[2-(2'-amino-1,1'-biphenyl)]palladium(II) methanesulfonate |
| BrettPhos | 2-(Dicyclohexylphosphino)3,6-dimethoxy-2',4',6'-triisopropyl-1,1'-biphenyl |
| BrettPhos Pd G3 | [(2-Di-cyclohexylphosphino-3,6-dimethoxy-2',4',6'-triisopropyl-1,1'-biphenyl)-2-(2'-amino-1,1'-biphenyl)]palladium(II) methanesulfonate methanesulfonate |

TABLE I-continued

List of abbreviations used in the experimental section:

| Abbreviation | Definition |
|---|---|
| SPhos | 2-Dicyclohexylphosphino-2',6'-dimethoxybiphenyl |
| SPhos Pd G2 | Chloro(2-dicyclohexylphosphino-2',6'-dimethoxy-1,1'-biphenyl)[2-(2'-amino-1,1'-biphenyl)palladium(II) |
| RuPhos | 2-Dicyclohexylphosphino-2',6'-diisopropoxybiphenyl |
| RuPhos Pd G3 | (2-Dicyclohexylphosphino-2',6'-diisopropoxy-1,1'-biphenyl)[2-(2'-amino-1,1'-biphenyl)]palladium(II) methanesulfonate |
| tBuBrettPhos Pd G3 | [(2-Di-tert-butylphosphino-3,6-dimethoxy-2',4',6'-triisopropyl-1,1'-biphenyl)-2-(2'-amino-1,1'-biphenyl)palladium(II) methanesulfonate |
| TMHD | 2,2,6,6-Tetramethyl heptanedione |
| T3P | Propylphosphonic anhydride |

Synthetic Preparation of the Compound of the Invention

General Synthetic Methods

The compounds of the invention and the comparative examples can be produced according to the following schemes.

Scheme 1

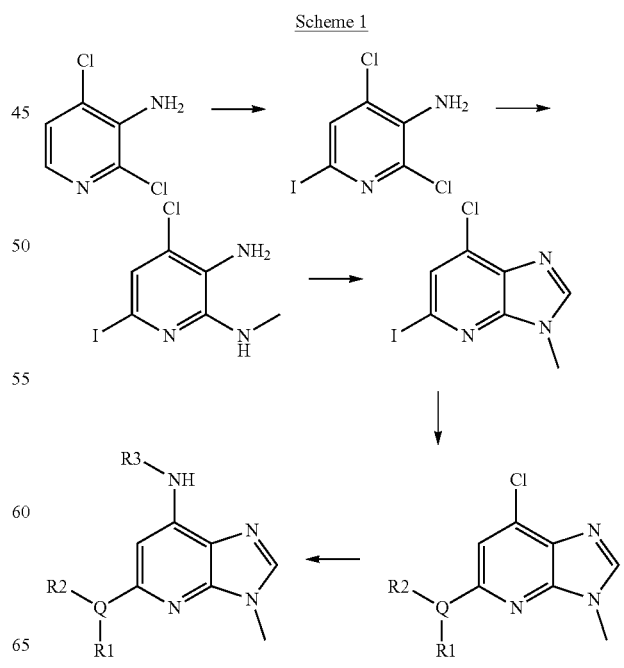

Scheme 2
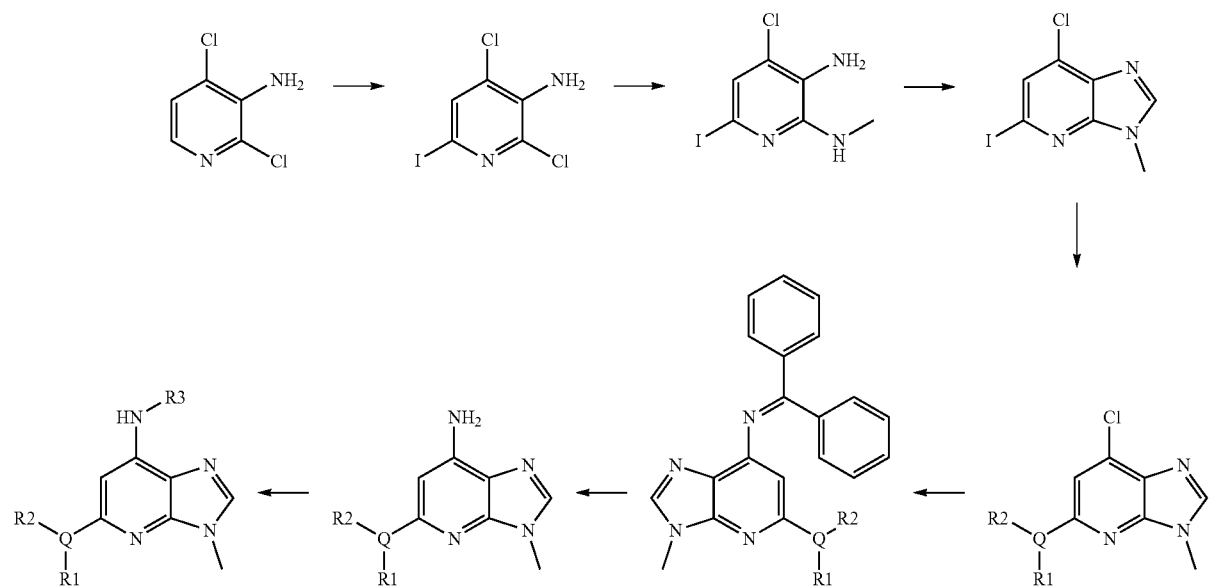
Scheme 3
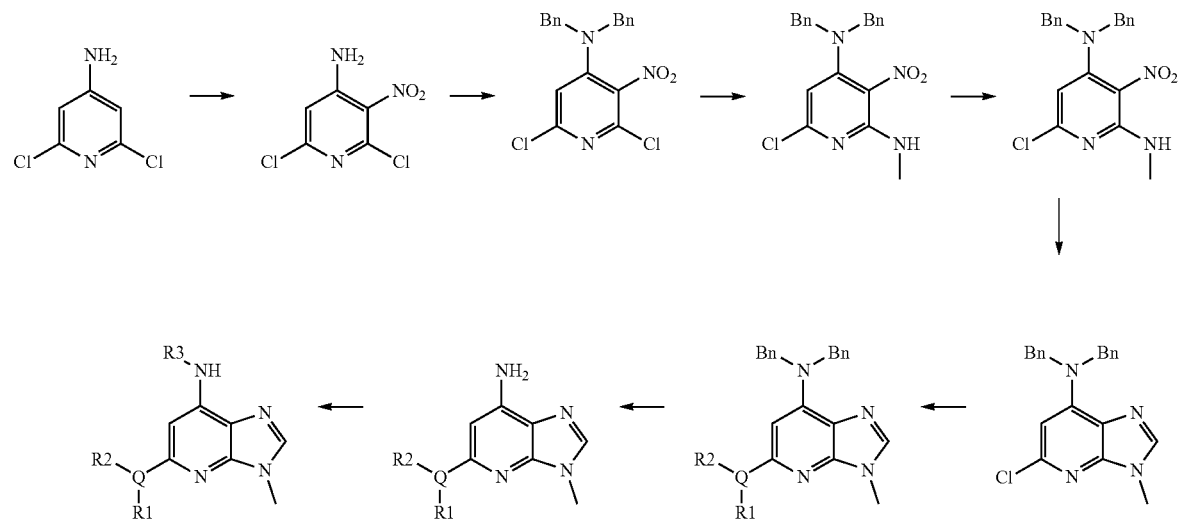
Scheme 4
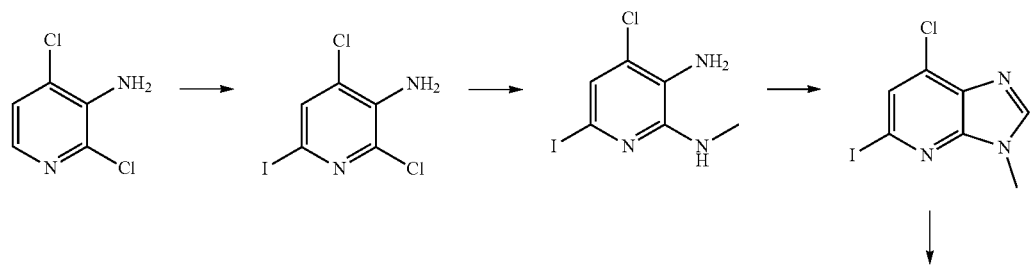

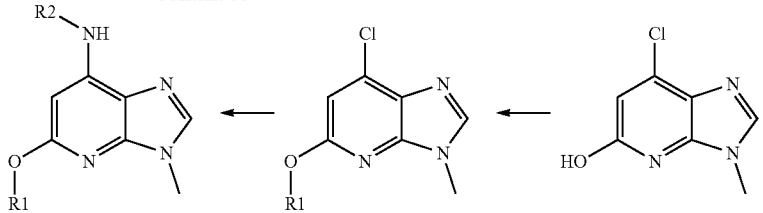

General Methods Used for the Synthesis of Compounds and Intermediates

Method A1-a

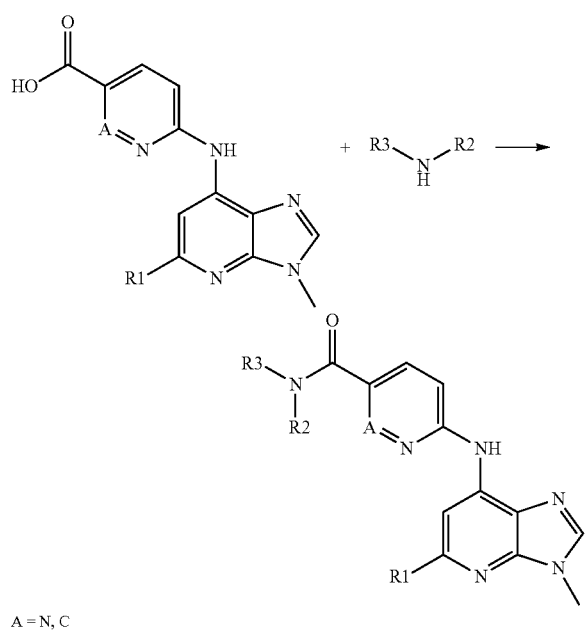

A = N, C

A solution of the acid (1 eq), HATU (1.3 eq) and Et₃N (2.5 eq) in NMP is stirred for 1 min, after which the amine (1 eq) is added. After completion, the mixture is filtered and the filtrate is purified by preparative chromatography to yield the desired product.

Method A1-b

To a suspension of the acid (1 eq), Et₃N (5 eq) and the amine (1 to 3 eq) in DMF is added slowly at room temperature a 50% solution of T3P in AcOEt (2 eq). The reaction mixture is stirred at room temperature until completion. The reaction mixture is poured into ice/water and extracted with DCM. The organic layer is concentrated to dryness to afford the desired product.

Method A2:

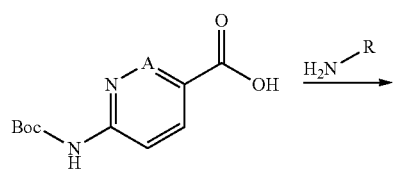

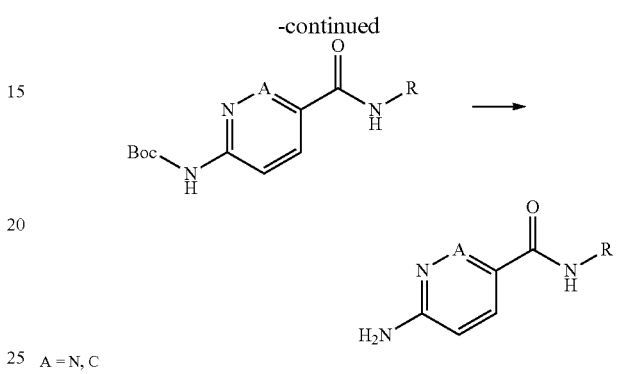

A = N, C

Step 1: To a solution of the acid (1 eq) and EDC.HCl (1.5 eq) in dry DCM at room temperature is added the amine (1.1 eq) followed by DIPEA (2.0 eq). The mixture is stirred at room temperature for 18 h. It is then quenched with aqueous NaHCO₃ followed by extraction with DCM. Organic layer is concentrated to dryness and crude material is either used as such, or purified by column chromatography using EtOAc/DCM or MeOH/DCM as eluent to afford desired amide.

Step 2: A solution of Boc-protected amide (1.0 eq) in DCM/TFA (1:1) is heated at 45° C. for 18 h. It is then concentrated to dryness to remove excess of TFA. Compound is purified via SCX column using MeOH then 2N NH₃ in MeOH as eluent to afford desired product as free base.

Method A3:

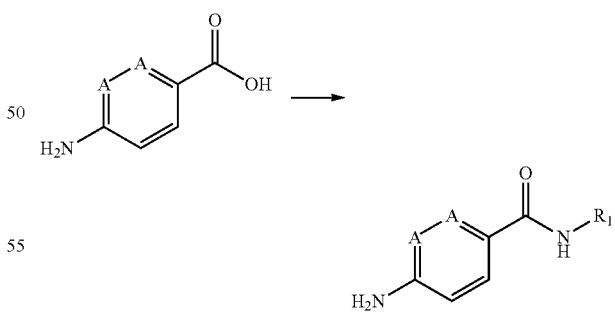

Step 1: To a solution of the acid (1 eq) and HATU (1.1 eq) in dry DMF at room temperature is added the amine (1.5 eq) followed by DIPEA (1.5 eq). The mixture is stirred at room temperature for 18 h. It is then diluted with water followed by extraction EtAOc. The organic layer is concentrated to dryness and crude material is either used as such, or purified by column chromatography using EtOAc/DCM or MeOH/DCM as eluent to afford desired amide.

Method B1

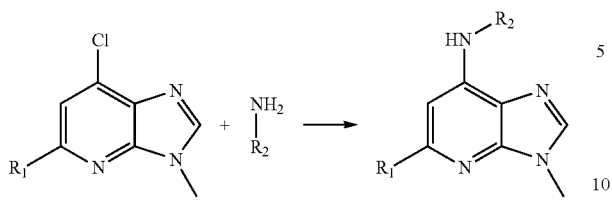

The aryl halide (1.0 eq), amine or aniline (1.0 eq), Pd$_2$Cl$_2$(allyl)$_2$ (0.02 eq), MorDALPhos (0.04 eq) and Cs$_2$CO$_3$ (1.2 eq) are mixed under N$_2$ at room temperature after which 1,4-dioxane is added. The resulting mixture is stirred at 110° C. Next, the mixture is allowed to cool down to room temperature, subsequently diluted in DMSO and filtered. The filtrate is purified by preparative HPLC to yield the desired product.

Method B2-a

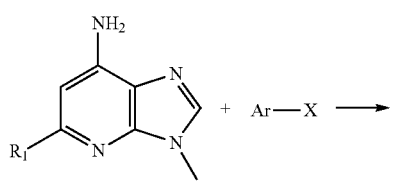

The aniline (1.0 eq), arylhalide (1.2 eq), XantPhos Pd G3 (0.04 eq) and Cs$_2$CO$_3$ (1.2 eq) are mixed under N2 at room temperature after which 1,4-dioxane is added. The resulting mixture is stirred at 80° C. Next, the mixture is allowed to cool down to room temperature, subsequently diluted in DMSO and filtered. The filtrate is purified by preparative HPLC to yield the desired product. Alternatively, the mixture is poured into water and subsequently filtered. The resulting solid is washed with water and dried to afford the desired product.

Method B2-b

A suspension of aniline (1.0 eq), arylhalide (1.1 eq) and K$_3$PO$_4$ (3.0 eq) in degazed dioxane was heated at reflux. To this solution was added dropwise (over 7 hours) a solution of Pd(OAc)$_2$ (0.14 eq) and Xantphos (0.28 eq) in degazed dioxane. After completion, the reaction mixture was filtered hot on a Pad of Dicalite (Carlo Erba, ref P8880014), and the filtering agent was rinsed with THF and CHCl$_3$. The solvent were evaporated and the solid was triturated in acetonitrile. The solid was filtered, washed with acetonitrile. The crude was purified by column chromatography using CHCl$_3$/MeOH: 98/2 as eluent to afford the desired product.

Method B3

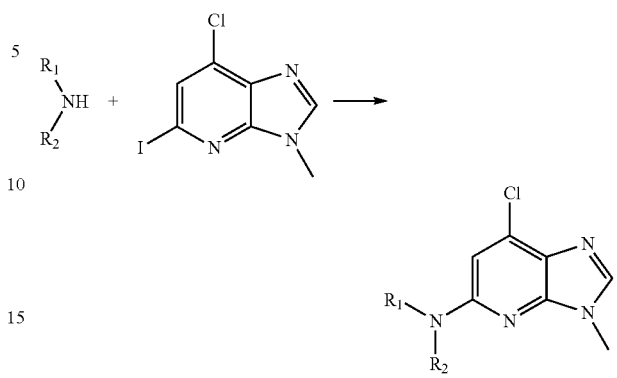

Intermediate 1 (1.0 eq), aniline or amine (2.0 eq), XantPhos Pd G3 (0.03 eq), XantPhos (0.03 eq) and Cs$_2$CO$_3$ (1.3 eq) are mixed under N$_2$ at room temperature after which 1,4-dioxane is added. The resulting mixture is stirred at 110° C. Upon completion, the mixture is cooled down to room temperature and coated on silica. Crude material is purified by column chromatography using EtOAc/petroleum ether or MeOH/DCM as eluent.

Method C1

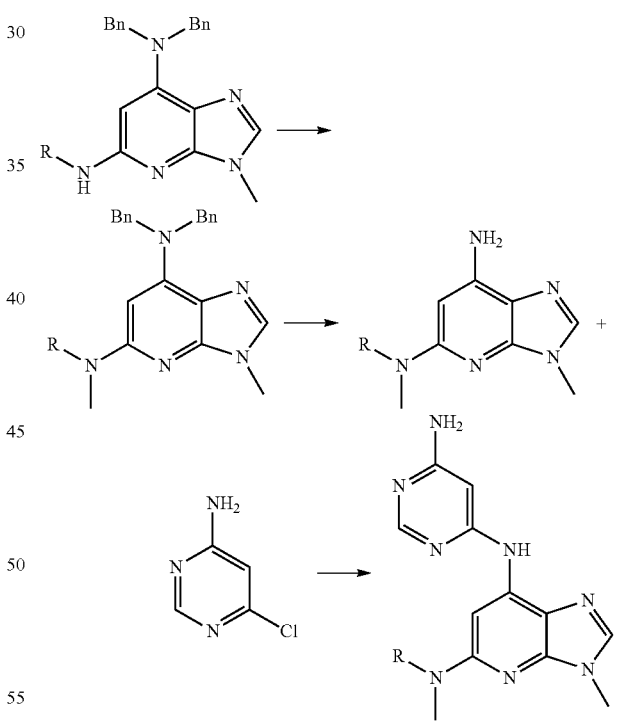

Step 1: To a solution of dry THF containing the aniline (1 eq) is added NaH (60% dispersion in mineral oil, 2.2 eq) under N$_2$. The mixture is stirred for 5 min at room temperature before iodomethane (2 eq) is added. The reaction mixture is then stirred at room temperature overnight. Conversion of the reaction is monitored by LCMS. Reaction is quenched with MeOH then concentrated to dryness. Crude residue is purified by column chromatography using MeOH/DCM, 7N NH$_3$ in MeOH/DCM or EtOAc/petroleum ether as eluent.

Step 2: To a solution of the dibenyl-protected amine (1 eq) in dry DCM (0.25M) at 0° C. is added Tf$_2$O (8 eq) dropwise. Mixture is then stirred at room temperature for 18 h. Conversion of the reaction is monitored by LCMS. Reaction is quenched with NaHCO$_3$ and the mixture is extracted with DCM. Organic layer is concentrated to dryness to afford desired crude material which is used as such or purified by chromatography.

Step 3: Aniline (1 eq), 2-Chloro-4-amino-pyrimidine (2.0 eq), BrettPhos Pd G3 (0.1 eq), BrettPhos (0.1 eq), Cs$_2$CO$_3$ (2.0 eq) are mixed together under inert atmosphere. Solvent, generally 1,4-dioxane, is added and the mixture is stirred at 110° C. for 18 h. Reaction is then cooled down to room temperature, quenched with H$_2$O and compound is extracted with DCM. Organic layer is dried over Na$_2$SO$_4$, filtered and concentrated to dryness. Residue is purified by chromatography to yield the desired compound.

Method C2

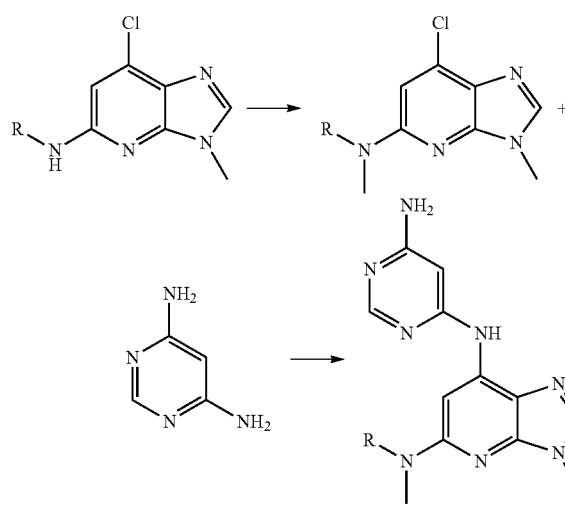

Step 1: To a solution of the aniline (1.0 eq) in dry THF under N$_2$ at 0° C. is added NaH (60% dispersion in mineral oil, 1.5 eq). After 10 min, iodomethane (2.0 eq) is added and the mixture is stirred at 40° C. Upon completion of the reaction (monitored by LCMS), the mixture is allowed cooled down at room temperature and quenched with a saturated aqueous NaHCO$_3$ solution. Next, the mixture is extracted with DCM, dried over MgSO$_4$, filtered and concentrated to dryness. Crude material is purified by column chromatography using EtOAc/petroleum ether or MeOH/DCM as eluent to afford desired product.

Step 2: Aryl chloride (1.0 eq), aniline (2.0 eq), MorDAL-Phos Pd G3 (0.03 eq), MorDALPhos (0.03 eq) and Cs$_2$CO$_3$ (1.3 eq) are mixed under N$_2$ at room temperature after which 1,4-dioxane is added and the mixture was stirred at 110° C. Upon completion, the mixture is cooled down to room temperature and diluted in DMSO. After filtration, the filtrate is purified by preparative HPLC to give the desired product.

Method D1

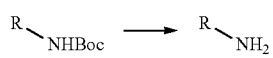

The Boc-protected amine (1.0 equiv.) is dissolved in anhydrous 1,4-dioxane under N$_2$. HCl (4.0 M in dioxane, 10 eq) is added dropwise and the reaction mixture is stirred at room temperature. After 2 h, all volatiles are evaporated in vacuo. The crude is taken up in DCM, washed with saturated aqueous. NaHCO$_3$ solution, dried and evaporated in vacuo. The crude product is either used as such or purified by chromatography to give the desired product.

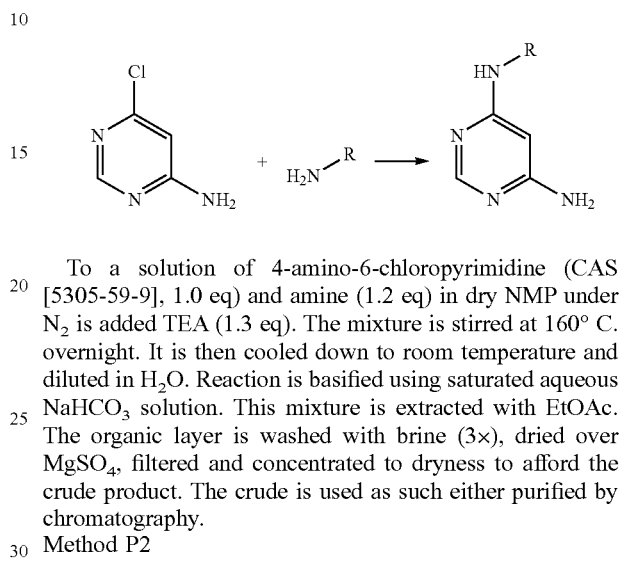

To a solution of 4-amino-6-chloropyrimidine (CAS [5305-59-9], 1.0 eq) and amine (1.2 eq) in dry NMP under N$_2$ is added TEA (1.3 eq). The mixture is stirred at 160° C. overnight. It is then cooled down to room temperature and diluted in H$_2$O. Reaction is basified using saturated aqueous NaHCO$_3$ solution. This mixture is extracted with EtOAc. The organic layer is washed with brine (3×), dried over MgSO$_4$, filtered and concentrated to dryness to afford the crude product. The crude is used as such either purified by chromatography.

Method P2

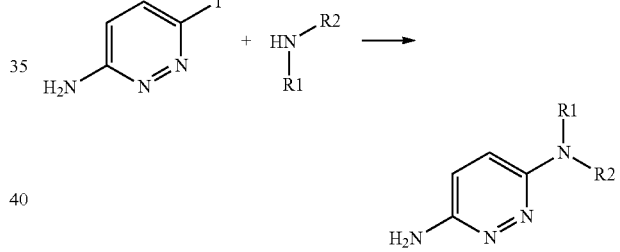

6-iodopyridazin-3-amine (CAS [187973-60-0], 1.0 eq), amine (2.0 eq), CuI (0.1 eq), L-hydroxyproline (CAS [51-35-4], 0.2 eq) and K$_3$PO$_4$ (3.0 eq) are mixed together under N2. DMSO is added and the mixture is stirred at 60° C. After two nights, mixture is cooled down to room temperature and DMSO is removed under reduced pressure. Residue is diluted in MeOH and filtered. Filtrate is purified by column chromatography using 7N NH3 in MeOH/DCM as eluent to afford the desired product.

Method P3

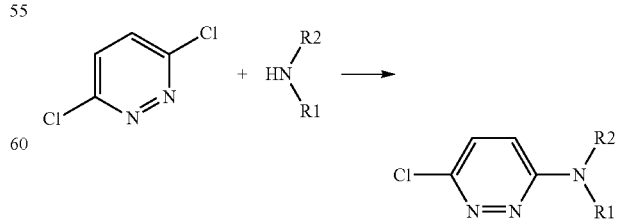

To a solution of the amine (1 eq) in anhydrous dioxane (10 mL) is added DIPEA (4 eq) and 3,6-dichloropyridazine (CAS [141-30-0], 1.0 eq) and the mixture is stirred for 24 h at 100° C. Next, the mixture is diluted with DCM and washed with brine. Reaction mixture is extracted with DCM. Combined organic extracts are dried and evaporated in vacuo to afford a crude which is used as such or purified by chromatography.

Synthesis of Intermediates

Intermediate 1: 7-Chloro-5-iodo-3-methyl-3H-imidazo[4,5-b]pyridine

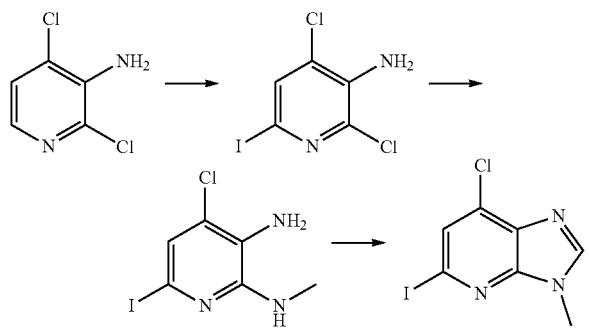

Step 1: 2,4-Dichloro-6-iodo-pyridin-3-ylamine: To a solution of 2,4-dichloro-3-aminopyridine (250 g, 1.54 mmol, 1 eq) in dry MeCN (1.2 L) under $N_2$ atmosphere at room temperature was added NIS (382 g, 1.70 mmol, 1.1 eq) and TFA (35.45 mL, 0.46 mmol, 0.3 eq). The mixture was stirred at 40° C. for 18 hours in 3 L round-bottom flask. Reaction mixture was then quenched with saturated $Na_2S_2O_3$ (500 mL) and $NaHCO_3$ (700 mL). Organic layer was washed with saturated $NaHCO_3$ and aqueous layers were washed twice with EtOAc (2×700 mL). Combined organic layers were dried over $MgSO_4$, filtered and concentrated to dryness to obtain crude product. It was purified by column chromatography using cyclohexane and EtOAc (10%) to give the desired product LCMS: m/z=289 [M+H].

Step 2: 4-Chloro-6-iodo-N2-methyl-pyridine-2,3-diamine 2,4-dichloro-6-iodo-pyridin-3-amine (20 g, 0.07 mmol, 1 eq) was dissolved in n-butanol (300 mL) at autoclave (600 mL). Methylamine (33% in EtOH, 28.72 mL, 0.28 mmol, 4 eq) was added under $N_2$ are room temperature. The mixture was stirred at 180° C. for 18 hours and then cooled to room temperature. This step was repeated twice and in the end, all the reaction mixtures were combined and concentrated to give 60 g of title compound that was used in next step as such. LCMS: m/z=284 [M+H].

Step 3: 7-Chloro-5-iodo-3-methyl-3H-imidazo[4,5-b]pyridine To a solution of 4-chloro-6-iodo-N-2-methyl-pyridine-2,3-diamine (60 g, 021 mmol, 1 eq) in formic acid (30 mL) was added trimethyl orthoformate (69.5 mL, 0.64 mmol, 3 eq). The mixture was stirred at 60° C. for 1 h. Reaction was concentrated to dryness after which the residue was diluted with DCM and quenched with saturated aqueous $NaHCO_3$ solution. After extraction with DCM, organic layer was dried over $Na_2SO4$, filtered and concentrated to dryness to afford crude material. It was purified by column chromatography using eluent cyclohexane/EtOAc from 10 to 60% of EtOAc to give the desired product. LCMS: m/z=294 [M+H]. $^1$H NMR (300 MHz, DMSO-$d_6$) δ ppm: 8.46 (s, 1H), 7.83 (s, 1H), 3.81 (s, 3H).

Intermediate 2: 5-(7-Chloro-3-methyl-3H-imidazo[4,5-b]pyridin-5-yloxy)-4-methyl-pyridine-2-carbonitrile

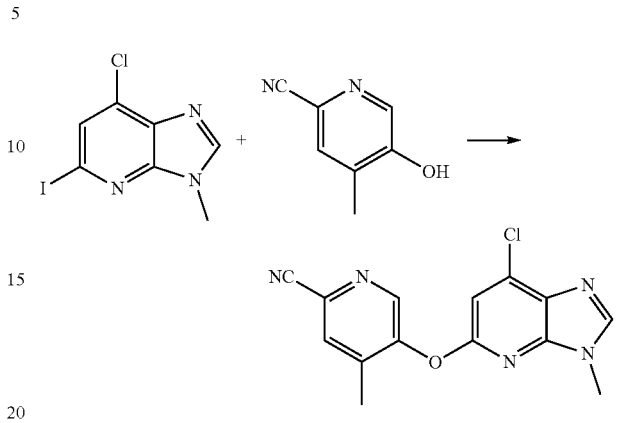

Intermediate 1 (68.51 g, 233.83 mmol, 1.0 eq), Intermediate 21 (47.00 g, 350.75 mmol, 1.5 eq), CuI (8.89 g, 46.77 mmol, 0.2 eq), TMHD (97.45 mL, 467.66 mmol, 2 eq) and $Cs_2CO_3$ (152 g, 467.66 mmol, 2 eq) were mixed together under air, DMF (234 mL) was added and the mixture was stirred at 85° C. for 2 nights. If full conversion was not reached, additional CuI (0.1 eq) and TMHD (1 eq) were added after which the mixture was stirred further at 85° C. for another night. Next, the mixture was cooled to 0° C. The resulting thick paste was then filtered and the cake was washed with ice cooled DMF (2×20 mL). It was then washed with ice cooled MTBE (3×150 mL). After drying the cake, it was suspended in 500 mL of 10% aqueous TMEDA solution. It was stirred for 2 h, filtered and the cake was washed with $H_2O$ to afford the desired product. LCMS: m/z=300 [M+H]$^+$.

Intermediate 3: 5-(7-Amino-3-methyl-3H-imidazo[4,5-b]pyridin-5-yloxy)-4-methyl-pyridine-2-carbonitrile

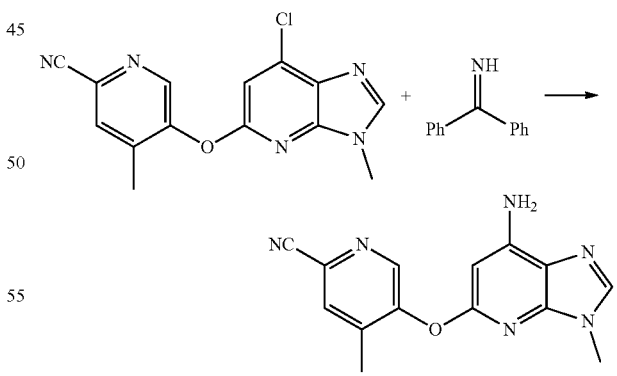

To a mixture of intermediate 2 (5.0 g, 16.72 mmol, 1.0 eq), benzophenone imine (CAS [1013-88-3], 2.81 mL, 16.72 mmol, 1.0 eq), $Pd_2CL_2(allyl)_2$ (122 mg, 0.33 mmol, 0.02 eq), XantPhos (387 mg, 0.67 mmol, 0.04 eq) and $Cs_2CO_3$ (6.54 g, 20.07 mmol, 1.2 eq) under $N_2$ atmosphere, 1,4-dioxane (100 mL) was added and the mixture was stirred at 110° C. for 24 h. After letting it cool down till room temperature, the mixture was diluted with EtOAc and filtered over celite. The cake was washed with EtOAc (100 mL) and the filtrate was poured in 2N aqueous HCl solution (200 mL), stirring it for 10 min. After extraction with EtOAc, the aqueous phase was neutralized to pH=7 using NaHCO$_3$. This was followed by an extraction with EtOAc (5×100 mL) after which the combined organic layers were dried over MgSO$_4$, filtered and concentrated to dryness to afford the crude material which was triturated with DCM to afford the desired product. LCMS: m/z=281 [M+H]$^+$.

Alternative synthesis of Intermediate 3: 5-(7-Amino-3-methyl-3H-imidazo[4,5-b]pyridin-5-yloxy)-4-methyl-pyridine-2-carbonitrile

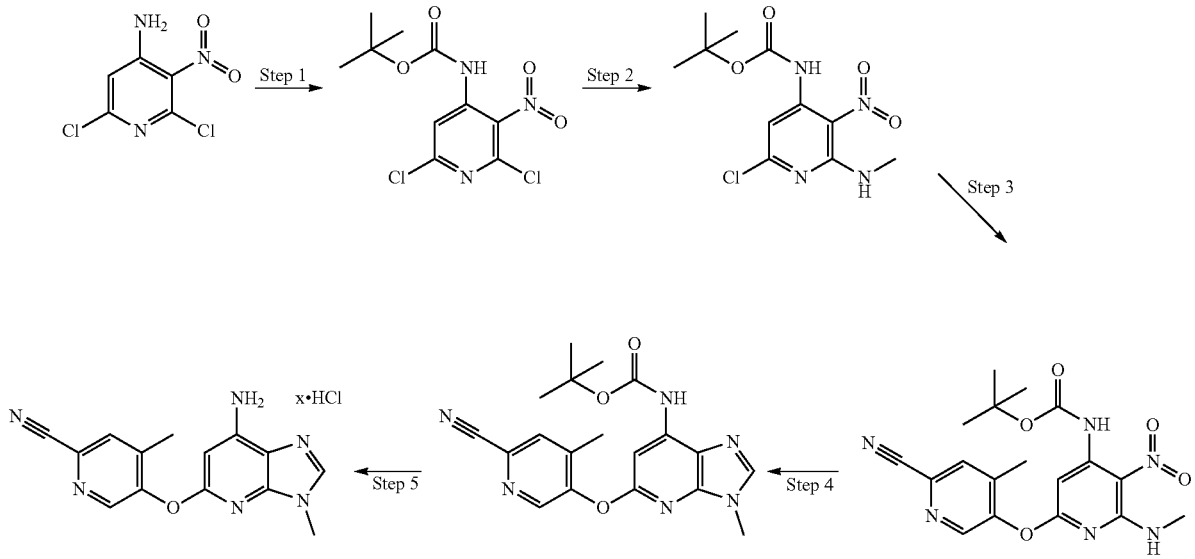

Step 1: 2,6-Dichloro-4-amino-5-nitropyridine (520 g, 2.5 mol, 1.0 eq), was added to acetonitrile (5.2 L) at room temperature. To the mixture were added, under stirring at room temperature, Boc$_2$O (710 g, 3.25 mol, 1.3 eq) and K$_3$PO$_4$ (1000 g, 4.71 mol, 1.9 eq). The reaction mixture was heated at reflux for 1-2 hours. Then a solution of Boc$_2$O (110 g, 0.5 mol, 0.2 eq) in acetonitrile (100 mL) was added and the reaction mixture was heated at reflux for one additional hour. The reaction mixture was cooled down to room temperature and filtered on a pad Na$_2$SO$_4$. The Na$_2$SO$_4$ was washed with acetonitrile (2 L). The filtrate was evaporated under reduced pressure and redissolved in DCM (5 L). The DCM layer was washed with water. The organic layer was extracted with DCM (5 L) and the combined organic layers were dried over Na$_2$SO$_4$, filtered and evaporated to afford the desired product. LCMS: m/z=306/308 [M+H].

Step 2: 2,6-Dichloro-4 Boc-amino-5-nitropyridine (770 g, 2.5 mol, 1.0 eq) was added to isopropanol (11 L) at room temperature. To the mixture were added, under stirring at room temperature, methylamine 33% in EtOH (800 mL, 3.0 eq) over 1 h 30. The reaction mixture was stirred at room temperature for 1 h 30. The suspension was filtered, washed with isopropanol (1 L) then water (4 L). Following drying the desired product was obtained. LCMS: m/z=302.9/304.8 [M+H].

Step 3: tert-butyl N-[6-chloro-2-(methylamino)-3-nitro-4-pyridyl]carbamate (788 g, 2.6 mol, 1.0 eq), was added to acetonitrile (5.5 L) at room temperature. To the mixture were added, under stirring at room temperature, 5-hydroxy-4-methyl-pyridine-2-carbonitrile (384 g, 2.86 mol 1.1 eq) and Na$_2$CO$_3$ (414 g, 3.9 mol, 1.5 eq). The reaction mixture was heated at reflux for 48 hours. The reaction mixture was cooled down to room temperature and the insoluble were filtered and washed with acetonitrile (2 L). The combined organic layers were evaporated. The crude was washed with water (5 L), collected and dried to afford the desired product. LCMS: m/z=401.1 [M+H]; m/z=399.2 [M−H]. $^1$H NMR (400 MHz, DMSO-d$_6$) δ 10.70 (s, 1H), 9.05 (q, 1H), 8.62 (s, 1H), 8.13 (s, 1H), 7.23 (s, 1H), 2.59 (d, 3H), 2.24 (s, 3H), 1.50 (s, 9H).

Step 4: tert-butyl N-[6-[(6-cyano-4-methyl-3-pyridyl)oxy]-2-(methylamino)-3-nitro-4-pyridyl]carbamate (150 g, 375 mmol, 1.0 eq) was added to a mixture of acetic acid (750 mL, 35 eq) and trimethyl orthoformate (750 mL, 18 eq) at room temperature. To the mixture were added by portions, under vigorous stirring at 20-21° C., Zn dust <10 μm (total of 120 g, 4.9 eq, added by portions of 15 g). Each addition was performed after the reaction mixture had cooled down to 20-21° C. The reaction mixture was stirred during one hour after the last addition. The suspension was filtered on Dicalite 4158 (Carlo Erba, ref P8880014), washed with THF (1 L) and the combined organic layers were evaporated. The residue was slowly poured into a cold mixture of 20% ammoniac solution (100 mL) and water (2 L). The resulting solid was filtered, washed with water (2 L) and dried to afford the desired product. LCMS: m/z=381.0 [M+H]; m/z=379.2 [M−H]. H NMR (400 MHz, DMSO-d$_6$) δ 9.32 (bs, 1H), 8.55 (s, 1H), 8.22 (s, 1H), 8.10 (s, 1H), 7.54 (s, 1H), 3.60 (s, 3H), 2.27 (s, 3H), 1.49 (s, 9H).

Step 5: tert-buty N-[6-[(6-cyano-4-methyl-3-pyridyl)oxy]-2-(methylamino)-3-nitro-4-pyridyl]carbamate (197 g, 0.518 mol, 1.0 eq) was suspended in a mixture of Hydrochloric acid, 4N solution in water (1 L) and THF (1 L). The reaction mixture was heated at 60° C. during 5 hours. The reaction mixture was cooled down to room temperature and the solid was filtered, washed with THF (1 L) and dried to afford the desired product as hydrochloric salt. LCMS: m/z=281.4 [M+H]. $^1$H NMR (400 MHz, DMSO-d$_6$) δ ppm: 9.28 (s, 1H), 8.54 (s, 1H), 8.12 (s, 1H), 7.57 (bs, 2-3H), 6.33 (s, 1H), 3.67 (s, 3H), 2.25 (s, 3H).

Intermediate 4: 5-(7-Chloro-3-methyl-3H-imidazo[4,5-b]pyridin-5-ylamino)-4-methyl-pyridine-2-carbonitrile

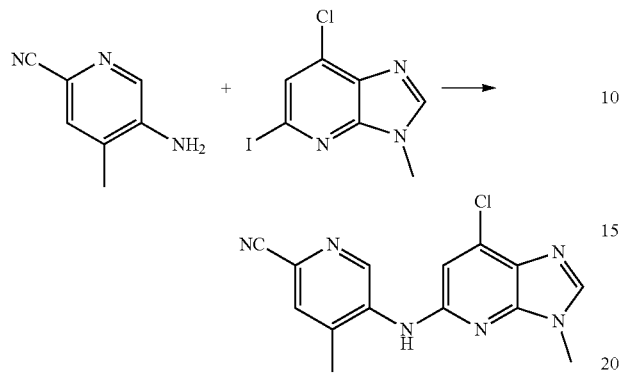

7-Chloro-5-iodo-3-methyl-3H-imidazo[4,5-b]pyridine (Int 1, 50 mg, 0.171 mmol, 1.0 eq), 5-amino-4-methylpyridine-2-carbonitrile (Int 17, 24 mg, 0.205 mmol, 1.2 eq), XantPhos Pd G3 (5 mg, 0.005 mmol, 0.03 eq), XantPhos (3 mg, 0.005 mmol, 0.03 eq) and K₃PO₄ (72 mg, 0.342 mmol, 2.0 eq) were mixed under N₂ at room temperature. Diglyme (1 mL) was added and the mixture was stirred at 80° C. After one night, it was cooled down to room temperature, quenched with water and the mixture was extracted with DCM. Organic layer was washed with brine, dried over Na₂SO₄, filtered and concentrated to dryness. Crude material was purified by column chromatography (EtOAc/petroleum ether, 7:3 to 1:0) to afford the desired product. LCMS: m/z=299 [M+H]⁺.

Intermediate 5: 5-[(7-Chloro-3-methyl-3H-imidazo[4,5-b]pyridin-5-yl)-methyl-amino]-4-methyl-pyridine-2-carbonitrile

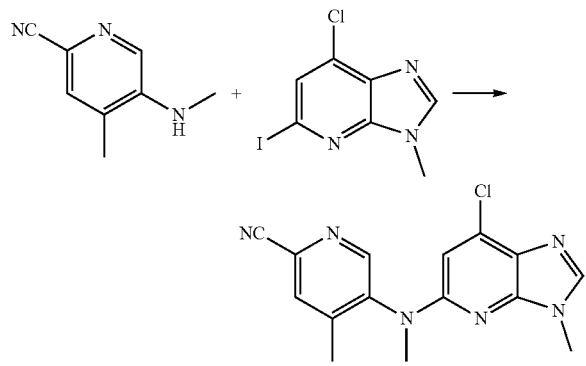

7-Chloro-5-iodo-3-methyl-3H-imidazo[4,5-b]pyridine (Int 1, 50 mg, 0.171 mmol, 1.0 eq), 5-amino-4-methylpyridine-2-carbonitrile (Int 18, 30 mg, 0.205 mmol, 1.2 eq), RuPhos Pd G3 (4 mg, 0.005 mmol, 0.03 eq), RuPhos (2 mg, 0.005 mmol, 0.03 eq) and K₃PO₄ (72 mg, 0.342, 2.0 eq) were mixed under N₂ at room temperature. Diglyme (1 mL) was added and the mixture was stirred at 80° C. After one night, it was cooled down to room temperature, quenched with water and compound was extracted with DCM. Organic layer was washed with brine, dried over Na₂SO₄, filtered and concentrated to dryness. Crude material was purified by column chromatography (EtOAc/petroleum ether, 1:1 to 1:0) to afford the desired product. LCMS: m/z=313 [M+H]⁺.

Intermediate 8: (7-Chloro-3-methyl-3H-imidazo[4,5-b]pyridin-5-yl)-methyl-((S)-1,2,2-trimethyl-propyl)-amine

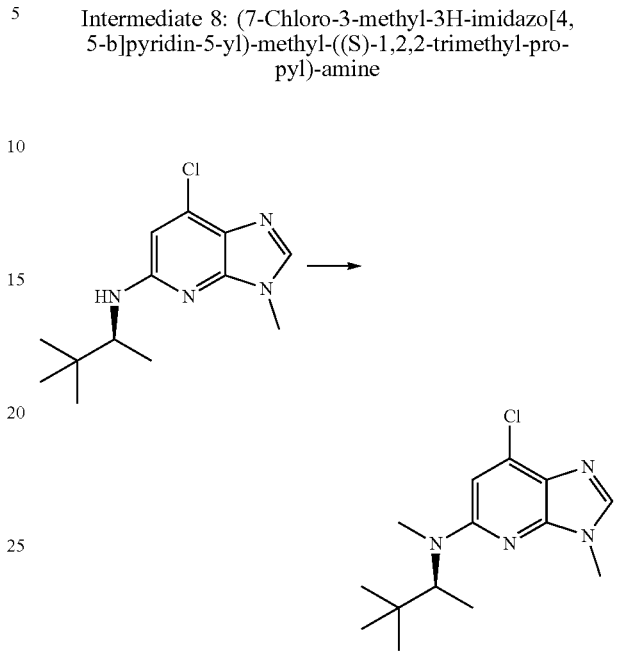

To a solution of Int 67 (130 mg, 0.49 mmol, 1 eq) in dry THF (2 mL) was added sodium hydride (60% in oil, 39 mg, 0.98 mmol, 2.0 eq) under a N₂ atmosphere. After 5 minutes, methyl iodide (46 µL, 0.73 mmol, 1.5 eq) was added. Reaction was heated at 40° C. for 18 hours. Next, the reaction was diluted with EtOAc and washed with brine. Combined organic extracts were dried and evaporated in vacuo. The resulting crude was purified by column chromatography (PE/EtOAc gradient elution from 20% till 80% EtOAc) to yield the desired product. LCMS: m/z=281 [M+H]⁺.

Intermediate 12: (7-Chloro-3-methyl-3H-imidazo[4,5-b]pyridin-5-yl)-((R)-1-cyclopropyl-ethyl)-methyl-amine

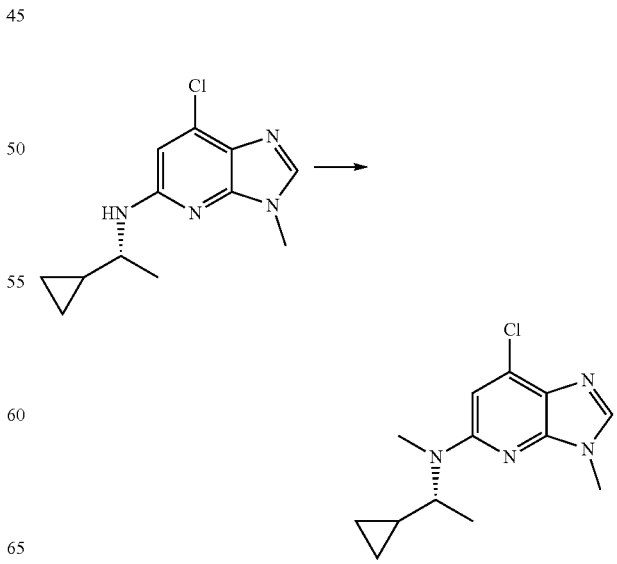

To a solution of Intermediate 65 (220 mg, 0.88 mmol, 1 eq) in dry THF (2 mL) was added sodium hydride (60% in oil, 71 mg, 1.76 mmol, 2 eq) under $N_2$ atmosphere. After 5 minutes, methyl iodide (82 µL, 1.32 mmol, 1.5 eq) was added. Reaction was heated at 40° C. for 18 h. Next, the reaction was diluted with EtOAc and washed with brine. Combined organic extracts dried and evaporated in vacuo. The resulting crude was purified by column chromatography (PE/EtOAc gradient elution from 20% till 80% EtOAc) to yield the desired product. LCMS: m/z=265 [M+H]$^+$.

Intermediate 14: Dibenzyl-(5-chloro-3-methyl-3H-imidazo[4,5-b]pyridin-7-yl)-amine

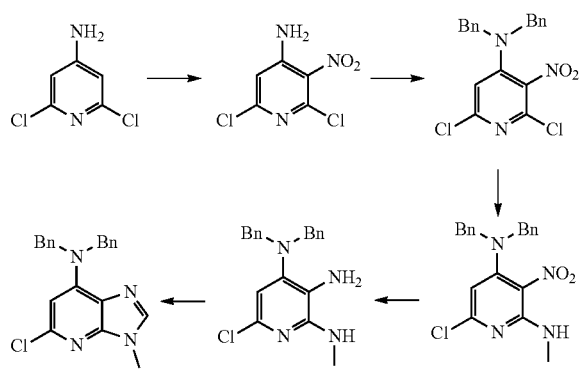

Step 1: 2,6-Dichloro-3-nitro-pyridin-4-ylamine

To 25 mL of conc $H_2SO4$ in a round-bottom flask at −5° C. was added 2,6-dichloro-pyridin-4-ylamine (3.0 g, 18.5 mmol). The mixture was stirred at −5° C. until a homogenous solution was obtained. 1.4 mL (22.5 mmol, 1.2 equivalents) of nitric acid in 5 mL of $H_2SO_4$ was slowly added keeping the internal T below 10° C. the mixture was stirred at 0-10° C. for 30 min. the mixture was then heated to 80° C. for 30 min. The mixture was cooled to room temperature and the mixture was poured into ice. The resulting yellow suspension was neutralized by slow addition of aqueous $NH_3$ to pH 4. The product was filtered and washed with ice cold water to obtain the desired product. LCMS: m/z=209 [M+H]$^+$.

Step 2: Dibenzyl-(2,6-dichloro-3-nitro-pyridin-4-yl)-amine

To a solution of 2,6-dichloro-3-nitro-pyridin-4-ylamine (5.0 g, 24.1 mmol) in dry DMF (200 mL) was added benzylbromide (8.6 mL, 72.5 mmol, 3.0 eq) and $K_2CO_3$ (16.6 g, 120.5 mmol, 5.0 eq) and the mixture was stirred at 80° C. After 1 h, full conversion was observed by LCMS. The mixture was diluted with EtOAc and quenched with water. Compound was extracted with EtOAc. The combined organic layers were washed with sat $NaHCO_3$, dried over $Na_2SO_4$, filtered and concentrated under reduced pressure. Crude material was purified by silica chromatography (petroleum ether/EtOAc: 100/0 to 80/20) to afford the desired product. LCMS: m/z=388 [M+H]$^+$.

Step 3: N4,N4-Dibenzyl-6-chloro-N2-methyl-3-nitro-pyridine-2,4-diamine

To a mixture of dibenzyl-(2,6-dichloro-3-nitro-pyridin-4-yl)-amine (6.9 g, 17.8 mmol) and $Cs_2CO_3$ (5.8 g, 17.8 mmol, 1.0 eq) in THF (100 mL) was added $MeNH_2$ (2N in THF, 8.9 mL, 17.8 mmol, 1 eq) at 0° C. and the mixture was stirred at rt for 24 h. Full conversion was observed by LCMS. The volatiles were removed in vacuum. The residue was dissolved in DCM and washed twice with water, and brine. The organic layer was dried over $Na_2SO_4$, filtered and concentrated under reduced pressure to afford the desired product which was used as such in the next step. LCMS: m/z=383 [M+H]$^+$ Step 4: N4,N4-Dibenzyl-6-chloro-N2-methyl-pyridine-2,3,4-triamine To a solution of N4,N4-Dibenzyl-6-chloro-N2-methyl-3-nitro-pyridine-2,4-diamine (crude mixture, 15.5 mmol) in MeOH/THF (1:1) (100 mL) was added zinc (5.0 g, 77.5 mmol 5 eq) and $NH_4Cl$ (170 mg, 3.0 mmol, 0.2 eq). The resulting mixture was stirred at rt. After one night, reaction was heated to 50° C. until competition of the reaction was observed by LCMS. The reaction was then cooled down to room temperature then filtered over celite. The filtrate was evaporated. The residue was dissolved in DCM and washed with sat $NaHCO_3$. The organic layer was dried over $Na_2SO_4$, filtered and concentrated to obtain the desired product which was used as such in the next step. LCMS: m/z=353[M+H]$^+$.

Step 5: Dibenzyl-(5-chloro-3-methyl-3H-imidazo[4,5-b]pyridin-7-yl)-amine (Intermediate 14)

To a suspension of N4,N4-Dibenzyl-6-chloro-N2-methyl-pyridine-2,3,4-triamine (crude material, 15.5 mmol) in acetonitrile (100 mL) was added triethylorthoformate (5.1 mL, 31 mmol, 2 eq) and the mixture was stirred at 80° C. After 18 h, LCMS showed full conversion toward desired product. Acetonitrile was removed in vacuo. The residue was dissolved in DCM and washed with sat $NaHCO_3$, dried over $Na_2SO_4$, filtered and concentrated. Crude material was purified by silica chromatography (petroleum ether/EtOAc: 100/0 to 70/30) to obtain the desired product. LCMS: m/z=363 [M+H]$^+$.

Intermediate 15: 4-amino-3-ethyl-5-fluorobenzonitrile

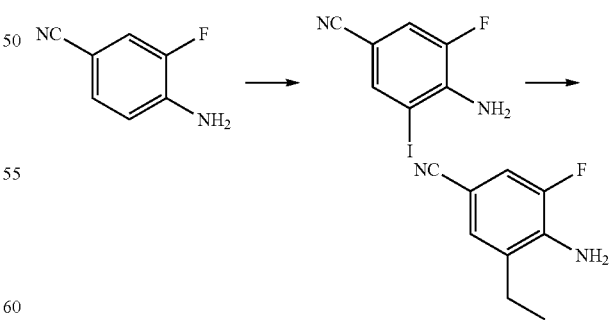

Starting from the commercial available 4-amino3-fluorobenzonitrile [63069-50-1], 4-amino-3-ethyl-5-fluorobenzonitrile was prepared in 2 steps according to WO2017012647 (intermediate 13, page 61). LCMS: m/z=165 [M+H]$^+$.

Intermediate 16: 4-(7-Dibenzylamino-3-methyl-3H-imidazo[4,5-b]pyridin-5-ylamino)-3-ethyl-5-fluoro-benzonitrile

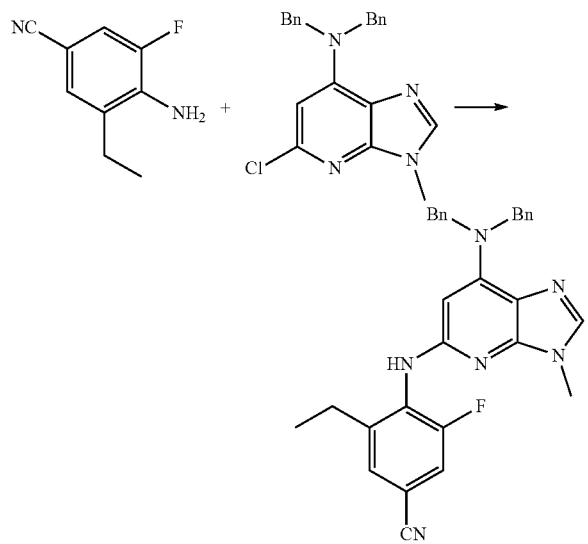

Step 3: 4-(7-Dibenzylamino-3-methyl-3H-imidazo[4,5-b]pyridin-5-ylamino)-3-ethyl-5-fluoro-benzonitrile Dibenzyl-(5-chloro-3-methyl-3H-imidazo[4,5-b]pyridin-7-yl)-amine (Int 14, 200 mg, 0.552 mmol, 1.0 eq), 4-amino-3-ethyl-5-fluorobenzonitrile (Int 15, 181 mg, 1.104 mmol, 2.0 eq), XantPhos Pd G3 (52 mg, 0.055 mmol, 0.1 eq), XantPhos (30 mg, 0.055 mmol, 0.1 eq), Cs$_2$CO$_3$ (360 mg, 1.104 mmol, 2.0 eq), were mixed together under N$_2$. Dry 1,4-dioxane (3 mL) was added and the mixture was stirred at 110° C. for 18 h. Reaction mixture was cooled down to room temperature and quenched with H$_2$O. Extraction was performed with DCM. Organic layer was dried over Na$_2$SO$_4$, filtered and concentrated to dryness to afford the desired product which was used as such in the next step. LCMS: m/z=491 [M+H]$^+$.

Intermediate 17: 5-amino-4-methylpyridine-2-carbonitrile

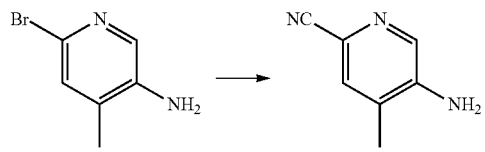

5-amino-2-bromo-4-methy-pyridine (1.0 g, 5 mmol, 1 eq), Zn(CN)$_2$ (640 mg, 5.5 mmol, 1.1 eq) and Pd(PPh$_3$)$_4$ (580 mg, 0.5 mmol, 0.1 eq) were mixed in dry DMF (10 mL) under N$_2$ and heated in a closed microwave tube at 150° C. for 5 min under microwave irradiations. The reaction mixture was cooled down to room temperature and poured in aqueous sat. NaHCO$_3$. Extraction was performed with EtOAc. The combined organic layers were dried over Na$_2$SO$_4$, filtered and concentrated to dryness. The obtained crude residue was triturated with Et$_2$O to afford the desired product. LCMS: m/z=134 [M+H]$^+$.

Intermediate 18: 3-Methyl-4-methylamino-benzonitrile

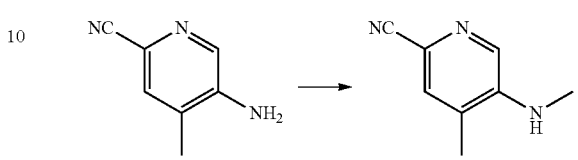

A solution of 5-amino-4-methylpyridine-2-carbonitrile (Int 17, 1.0 g, 7.52 mmol, 1.0 eq) in dry THF (25 mL) under N$_2$ was cooled till −78° C. Next, LiHMDS (1M in THF, 7.52 mL, 7.52 mmol, 1.0 eq) was slowly added. The resulting mixture was stirred at room temperature for 3 h after which iodomethane (940 µL, 15.04 mmol, 2.0 eq) was added dropwise. The mixture was stirred at room temperature for 18 h. It was then quenched with 1 mL of water and concentrated to dryness. The obtained crude material was purified by column chromatography (acetone/petroleum ether, 1:3) to afford the desired product. LCMS: m/z=148 [M+H]$^+$.

Intermediate 19: 4-Amino-3-cyclopropyl-5-fluoro-benzonitrile

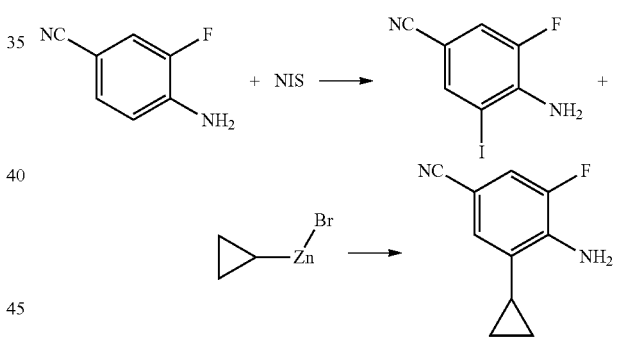

Step 1: 4-Amino-3-fluoro-5-iodo-benzonitrile

To a solution of 4-Amino-3-fluoro-benzonitrile (4.00 g, 29.4 mmol, 1.0 eq) and NIS (6.64 g, 29.4 mmol, 1.0 eq) in dry THF (90 mL) was added TFA (680 µL, 8.84 mmol, 0.3 eq). Reaction mixture was stirred at room temperature for 24 h. It was then quenched with saturated NaHCO$_3$ solution followed by extraction with DCM. Resulting organic layer washed with brine, dried over Na$_2$SO$_4$ and concentrated to dryness to afford the desired product. This was used as such in the next step. LCMS: m/z=263 [M+H]$^+$.

Step 2: 4-Amino-3-cyclopropyl-5-fluoro-benzonitrile

4-Amino-3-fluoro-5-iodo-benzonitrile (2.00 g, 7.64 mmol, 1.0 eq) and SPhos Pd G2 (165 mg, 0.24 mmol, 0.03 eq) were dissolved in dry THF (30 mL) under N$_2$ at room temperature and cyclopropyl zinc bromide (0.5M in THF, 24.45 mL, 12.23 mmol, 1.6 eq) was slowly added. The mixture was stirred at room temperature for 2 h then it was quenched with MeOH, concentrated to dryness, taken up in DCM, coated on silica and purified by column chromatography (EtOAc/petroleum ether, gradient elution from 15% EtOAc till 30% EtOAC) to afford the desired product LCMS: m/z=177 [M+H]+.

Intermediate 20:
5-Amino-4-ethyl-pyridine-2-carbonitrile

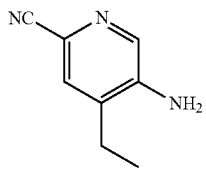

5-amino-4-methylpyridine-2-carbonitrile was prepared from 6-Bromo-4-ethyl-pyridin-3-ylamine (CAS [929617-29-8]) as described in patent WO2017012647 (page 55). LCMS: m/z=148 [M+H]+.

Intermediate 21:
5-hydroxy-4-methylpyridine-2-carbonitrile

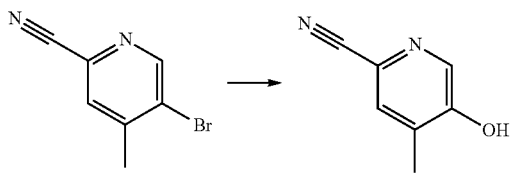

A mixture of 5-bromo-2-cyano-4-methylpyridine (CAS [886364-86-9], 26.8 g mg, 136 mmol, 1 eq), 4,4,4',4',5,5,5',5'-octamethyl-2,2'-bi(1,3,2-dioxaborolane) (CAS [73183-34-3], 48.4 g, 190 mmol, 1.4 eq), Pd(dppf)CL$_2$.CH$_2$CL$_2$ (5.55 g, 6.80 mmol, 0.05 eq), potassium acetate (40 g, 408 mmol, 3 eq) were stirred under N$_2$ in 1,4-dioxane (500 mL) for 2 hours at 110° C. Then, the reaction mixture was cooled to 0° C. prior to the addition dropwise of hydrogen peroxide (30% water solution, 83 mL, 816 mmol, 6.0 eq). After 2 hours, the reaction mixture was diluted with DCM and washed with water. The aqueous phase was acidified to pH 4-5 and extracted 3 times with DCM. Combined organic extracts dried and evaporated in vacuo. The resulting crude was purified by column chromatography (PE/EtOAc gradient elution 30% till 50% EtOAc). Obtained material was triturated with pentane and diethylether to afford the desired product.

Intermediate 22: 5-Amino-pyridine-2-carboxylic acid (2-hydroxy-propyl)-amide

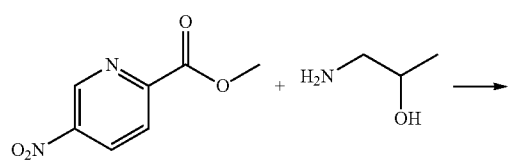

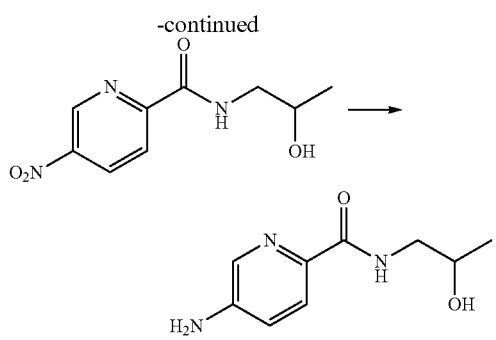

Step 1: 5-Nitro-pyridine-2-carboxylic acid (2-hydroxy-propyl)-amide

A solution of 5-Nitro-pyridine-2-carboxylic acid methyl ester (CAS [29682-14-2], 1.0 g, 5.49 mmol, 1.0 eq) and 1-Amino-propan-2-ol (CAS [78-96-6], 472 µL, 6.04 mmol, 1.1 eq) in dry EtOH (15 mL) under N$_2$ was stirred at 110° C. in a sealed tube. After one night, it was cooled down to room temperature and concentrated to dryness and crude residue was purified by column chromatography (EtOAc/petroleum ether, gradient from 50% till 80% EtOAc) to afford the desired product. LCMS: m/z=226 [M+H]+.

Step 2: 5-Amino-pyridine-2-carboxylic acid (2-hydroxy-propyl)-amide

A suspension of 5-Nitro-pyridine-2-carboxylic acid (2-hydroxy-propyl)-amide and Pd/C in MeOH under N$_2$ was put under H$_2$ atmosphere. It was then stirred at room temperature. After 3 h, reaction was stopped and filtered over thick Pall-Seitz filter paper. The resulting cake was washed with MeOH and filtrate was concentrated to dryness to afford 1.08 g of colorless oil. It was suspended in H$_2$O and freeze dried to afford the desired product. LCMS: m/z=196 [M+H]+.

Intermediate 23:
2-fluoro-6-methyl-4-methylsulfonyl-phenol

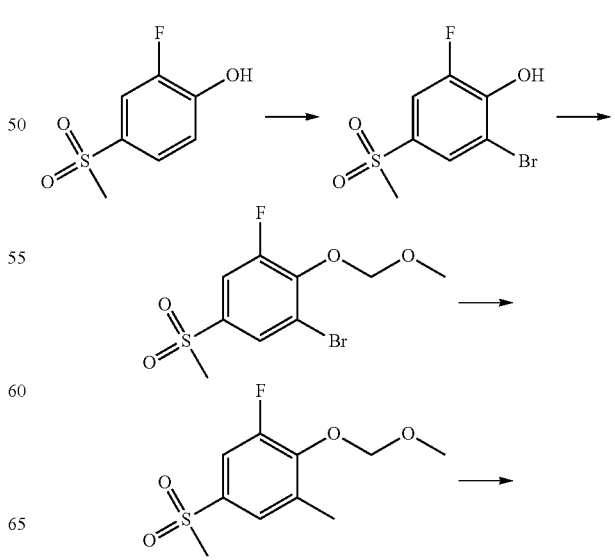

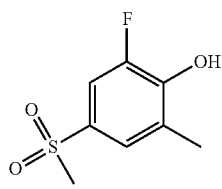

Step 1: 2-bromo-6-fluoro-4-methylsulfonyl-phenol

A mixture of 2-fluoro-4-methylsulfonyl-phenol (CAS [398456-87-6], 3 g, 15.7 mmol, 1 eq) and KOAc (1.55 g, 15.7 mmol, 1 eq) in AcOH (40 mL) was stirred at room temperature. The mixture was cooled to 0° C. and BR$^2$ (0.812 mL, 15.7 mmol, 1 eq) was added dropwise. The mixture was stirred for 30 min at 0° C., then concentrated and precipitate was filtered off to give the desired product. LCMS: m/z=269.18 [M+H].

Step 2: 1-fluoro-2-(methoxymethoxy)-3-bromo-5-methylsulfonyl-benzene

Chloromethyl methyl ether (107-30-2, 0.87 mL, 11.45 mmol, 1.1 eq) was dropwise added to the solution of 2-bromo-6-fluoro-4-methylsulfonyl-phenol (2.8 g, 10.41 mmol, 1 eq) and DIPEA in DCM (20 mL) at 0° C. The reaction was stirred at room temperature overnight. Next, the reaction mixture was washed with water and the isolated organic layer was dried and evaporated to obtain crude product. Crude product was purified by column chromatography using a gradient elution ranging from 0% till 100% EtOac in cyclohexane. Solvent evaporation gave the desired product. $^1$H NMR (300 MHz, DMSO-d$_6$) δ ppm 8.02-7.98 (m, 1H), 7.91 (dd, J$_1$=10.7 Hz, J$_2$=2.1 Hz, 1H), 5.31 (s, 2H), 3.52 (s, 3H), 3.30 (s, 3H).

Step 3: 1-fluoro-2-(methoxymethoxy)-3-methyl-5-methylsulfonyl-benzene

The reaction was performed in 2×1.4 g scale in microwave vials in parallel. 1-fluoro-2-(methoxymethoxy)-3-bromo-5-methylsulfonyl-benzene (2.8 g, 8.9 mmol, 1 eq) and Cs$_2$CO$_3$ (8.74 g, 26.8 mmol, 3 eq) were suspended in dioxane (34 mL) and the reaction mixture was purged with argon for 10 minutes in a microwave vial. The catalyst Pd(dppf)CL$_2$.DCM (1.638 g, 1.8 mmol, 0.2 eq) and methylboronic acid (CAS [13061-96-6], 803 mg, 13.4 mmol, 1.5 eq) were added to the reaction mixture and the reaction was sealed. The reaction is stirred at 100° C. for 2 hours. After 2 hours the reaction mixture was diluted with EtOAc (50 mL) and filtered. Filtrate was evaporated to obtain 5.8 g of crude product. Crude product was purified by column chromatography using a gradient of MeOH in DCM (0% till 5% MeOOH) giving the desired product. LC-MS: m/z=249 [M+H].

Step 4: 2-fluoro-6-methyl-4-methylsulfonyl-phenol 1-fluoro-2-(methoxymethoxy)-3-methyl-5-methylsulfonyl-benzene (1.9 g, 7.65 mmol, 1 eq) was dissolved in DCM (12 mL) and TFA (12 mL) and water (2 mL) were added. The reaction was stirred at room temperature for 2 h. Next, the reaction mixture was evaporated till dryness to obtain a crude product. Crude product was dissolved in EtOAc and precipitated with cyclohexane. Precipitate was filtered and dried to obtain the desired product. LCMS: m/z=205.33 [M+H]. $^1$H NMR (300 MHz, CDCl$_3$) δ ppm 7.55-7.50 (m, 2H), 5.74 (d, J=5.4 Hz, 1H), 3.01 (s, 3H), 2.33 (s, 3H).

Intermediate 28: (7-Chloro-3-methyl-3H-imidazo[4,5-b]pyridin-5-yl)-(1-cyclopropyl-2,2,2-trifluoroethyl)-amine

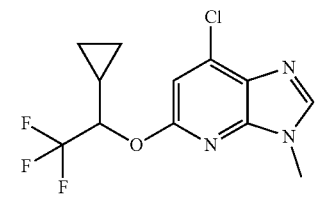

Int 1 (450 mg, 1.53 mmol, 1.0 equiv.), CuI (29 mg, 0.15 mmol, 0.1 eq), 3,4,7,8-tetramethyl-1,10-phenanthroline (72 mg, 0.3 mmol, 0.2 eq), cesium carbonate (72 mg, 0.3 mmol, 0.2 eq) were mixed together in dimethylformamide (2 mL), then 1-cyclopropyl-2,2,2-trifluoroethan-1-ol (CAS [1993-77-7], 858 mg, 6.13 mmol, 4.0 eq) was added and the mixture was heated at 80° C. Reaction was diluted with EtOAc and washed with brine. Combined organic extracts dried and evaporated in vacuo. The resulting crude was purified by column chromatography (PE/EtOAc gradient elution from 20% till 80% EtOAc) to afford the desired product. LCMS: m/z=306 [M+H]$^+$.

Intermediate 32: Amino-pyridine-2-carboxylic acid ethylamide

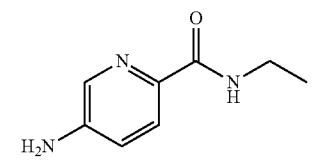

A suspension of 5-Nitro-pyridine-2-carboxylic acid ethylamide (CAS [1437794-42-7], 3.0 g, 15.38 mmol, 1.0 eq) and Pd/C (10% loading, 163 mg, 1.54 mmol, 0.1 eq) was stirred in MeOH (15 mL) under N$_2$. The mixture was put under H$_2$ atmosphere. It was then stirred at room temperature. After 3 h, the mixture was filtered. The resulting cake was washed with MeOH and filtrate was concentrated to dryness to afford the desired product. LCMS: m/z=166 [M+H]$^+$.

Intermediate 48: 7-Chloro-5-(1-cyclopropyl-ethoxy)-3-methyl-3H-imidazo[4,5-b]pyridine

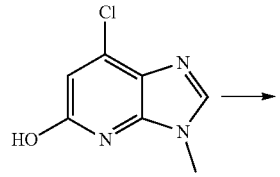

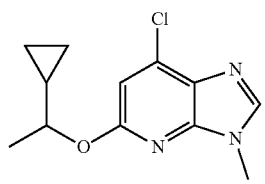

An ice cooled solution of Intermediate 57 (225 mg, 1.23 mmol, 1.0 equiv.), tri-n-butylphosphine (460 μL, 1.84 mmol, 1.5 eq) and 1-cyclopropylethanol (CAS [765-42-4], 225 mg, 1.23 mmol, 1.0 eq) in THF (10 mL) was for 10 minutes. Then, azodicarboxylic dimorpholide (CAS [10465-82-4], 472 mg, 1.84 mmol, 1.5 eq) was added at 0° C. Reaction was let to warm up to room temperature and stirred for 18 h. Mixture diluted with EtOAC and washed with brine. Combined organic extracts dried and evaporated in vacuo. The resulting crude was purified by column chromatography (PE/EtOAc gradient elution from 20% till 80% EtOAc) to afford the desired product. LCMS: m/z=252 [M+H]$^+$.

Intermediate 50: N-ethyl-4-methyl-pyridine-3-carboxamide

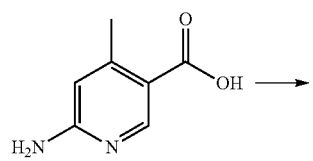

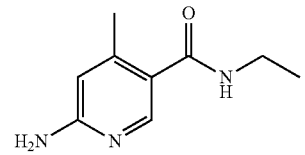

2-Amino-4-methyl-5-pyridinecarboxylic acid (CAS 179555-11-4, 250 mg, 1.64 mmol, 1.0 equiv.) was mixed with HATU (686 mg, 1.80 mmol, 1.1 eq), DIPEA (857 μL, 4.92 mmol, 3.0 eq) and DMF (1.0 M). The mixture was stirred for 5 minutes at room temperature, EtNH$_3$Cl (201 mg, 2.5 mmol, 1.5 eq) was added and stirring was continued overnight. Next, the reaction mixture was diluted with water (10 mL) and extracted with EtOAc (3×10 mL). The combined organic extracts were washed with brine (10 mL), saturated aqueous NaHCO$_3$ solution (10 mL) and brine again (10 mL). Next, the organic layer was dried and evaporated in vacuo to afford the desired product which was used as such in the next step. LCMS: m/z=180 [M+H]$^+$.

Intermediate 52: 6-[[5-[(6-cyano-4-methyl-3-pyridyl)oxy]-3-methyl-imidazo[4,5-b]pyridin-7-yl]amino]-2-methyl-pyridine-3-carboxylic acid

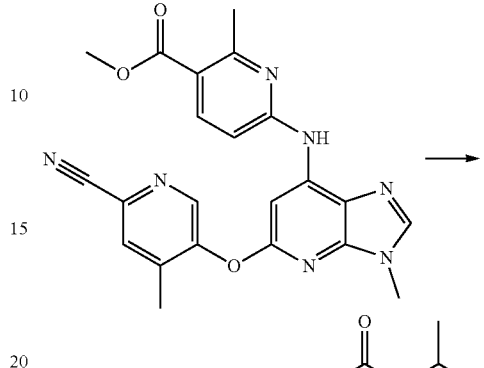

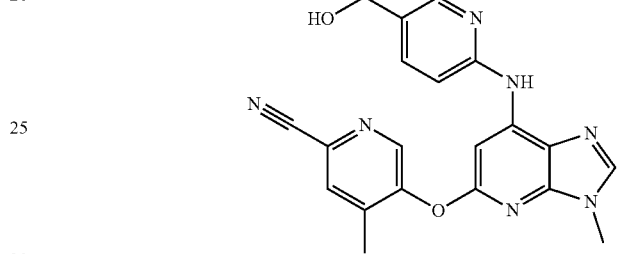

Int 51 (550 mg, 1.1 mmol, 1.0 eq) and LiI (573 mg, 4.3 mmol, 4.0 eq) were suspended in anhydrous pyridine (5 mL) under a N$_2$ atmosphere and heated to 115° C. for 48 h. Next, the reaction mixture was evaporated in vacuo and the residue was suspended in saturated aqueous Na$_2$CO$_3$ solution and EtOAc. The EtOAc phase was discarded and the pH of the aqueous phase was adjusted to 5-6. The resulting precipitate was filtered and dried overnight in vacuo at 50° C. to afford the desired product. LCMS: m/z=416 [M+H]$^+$.

Intermediate 53: 5-((S)-3-methyl-4-morpholinyl)-2-pyridinamine

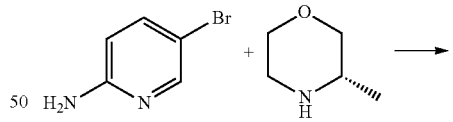

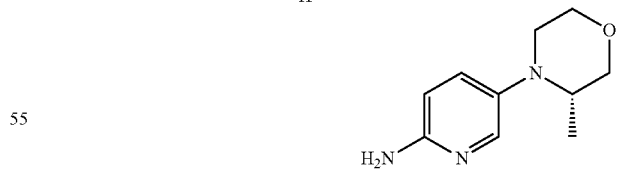

A reaction vial was loaded with 2-amino-5-bromopyridine (CAS [1072-97-5], 250 mg, 1.45 mmol, 1.0 eq), (S)-3-methylmorpholine (CAS [350595-57-2], 246 μL, 2.17 mmol, 1.5 eq) and RuPhos Pd G3 (61 mg, 0.073 mmol, 0.05 eq). The mixture flushed with N$_2$ and LiHMDS (3.5 mL, 3.48 mmol, 2.4 eq, 1.0 M in THF) was added dropwise. After stirring for 20 min at 60° C. the mixture was allowed to cool to room temperature and quenched with a few drops of MeOH. Next, the crude was purified by chromatography (DCM/MeOH 95/5 isocratic elution) to afford the desired product. LCMS: m/z=194 [M+H]$^+$.

Intermediate 54: 5-((S)-3-methyl-4-morpholinyl)-2-pyridinamine

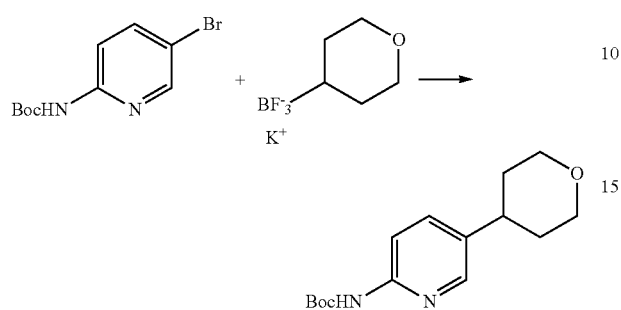

NiCL$_2$.dme (21 mg, 0.09 mmol, 0.12 eq) and dtbbpy (24 mg, 0.09 mmol, 0.12 eq) were mixed in DMA (3 mL) at room temperature under nitrogen and stirred for 5 minutes. Next, 2-(Boc-amino)-5-bromopyridine (CAS [159451-66-8], 204 mg, 0.75 mmol, 1.0 eq), potassium (tetrahydro-2H-pyran-4-yl)trifluoroborane (CAS [1279123-50-0], 152 mg, 0.79 mmol, 1.05 eq), 2,6-lutidine (140 µL, 1.2 mmol, 1.6 eq) and [Ir{dFCF$_3$ppy}$_2$(bpy)]PF$_6$ (24 mg, 0.023 mmol, 0.03 eq) were added in succession. The mixture was stirred until all solids dissolved after which anhydrous 1,4-dioxane (12 mL) was added and stirred overnight at room temperature under blue light irradiation (Kessil KSH150B LED Grow Light 150, Blue, 34W). Notes: the vial was placed in a crystallizing dish containing water. Air flow was applied to keep the reaction below 20° C. The distance between the vial and the lamp was approx. 5 cm. The distance between the funnel (air flow) and the vial was approx. 5 cm. The mixture was concentrated and partitioned between DCM and water. Aqueous layer was discarded. The organic phase dried and evaporated in vacuo. The resulting crude was purified by column chromatography (Petroleum ether/EtOAc 8/2 to 1/1) to afford the desired product. LCMS: m/z=279 [M+H]$^+$.

Intermediate 56: 3-chloro-6-(1-methylazetidin-3-yl)oxypyridazine

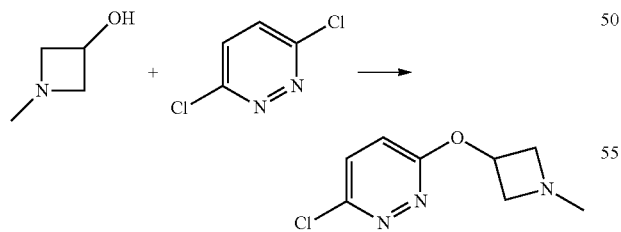

To a solution of 1-methylazetidin-3-ol (CAS [111043-48-2], 250 mg, 1.68 mmol, 1.0 eq) in anhydrous THF (4 mL) was added NaH (101 mg, 2.52 mmol, 4.5 eq, 60% in mineral oil). The mixture was stirred at room temperature for 10 min and subsequently heated to 50° C. for another 10 min. It was then cooled to rt after which 3,6-dichloropyridazine (CAS [141-30-0], 161 mg, 1.85 mmol, 1.1 eq) was added and the mixture was stirred for 2 h at room temperature. Next, the mixture was added dropwise to a stirred solution of NaHCO$_3$ (10 mL of saturated solution+10 mL of water) and extracted with DCM (3×10 mL). Combined organic extracts dried and evaporated in vacuo to afford the desired product. LCMS: m/z=200 [M+H]$^+$.

Intermediate 57: 7-Chloro-3-methyl-3H-imidazo[4,5-b]pyridin-5-ol

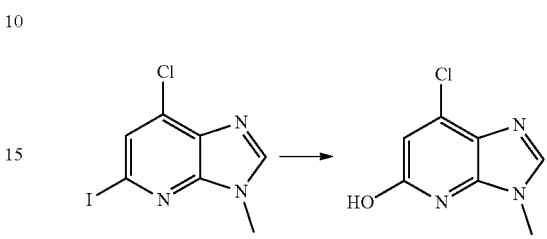

Intermediate 1 (6.0 g, 20.48 mmol, 1 eq), tBuBrettPhos Pd G3 (348 mg, 0.410 mmol, 0.02 eq) and CsOH monohydrate (10.08 g, 61.44 mmol, 3 eq) were mixed in 1,4-dioxane (40 mL) after which H$_2$O (3.68 mL, 204.80 mmol, 10 eq) was added. The mixture was stirred at room temperature. After one night, reaction mixture was quenched with H$_2$O and impurities were extracted with EtOAc. Aqueous layer was acidified to pH=5 and compound was extracted with EtOAc. Organic layer was dried over MgSO$_4$, filtered and concentrated to dryness to afford the desired product. LCMS: m/z=184 [M+H]$^+$.

Intermediate 61: 6-[5-(6-Cyano-4-methyl-pyridin-3-yloxy)-3-methyl-3H-imidazo[4,5-b]pyridin-7-ylamino]-nicotinic acid

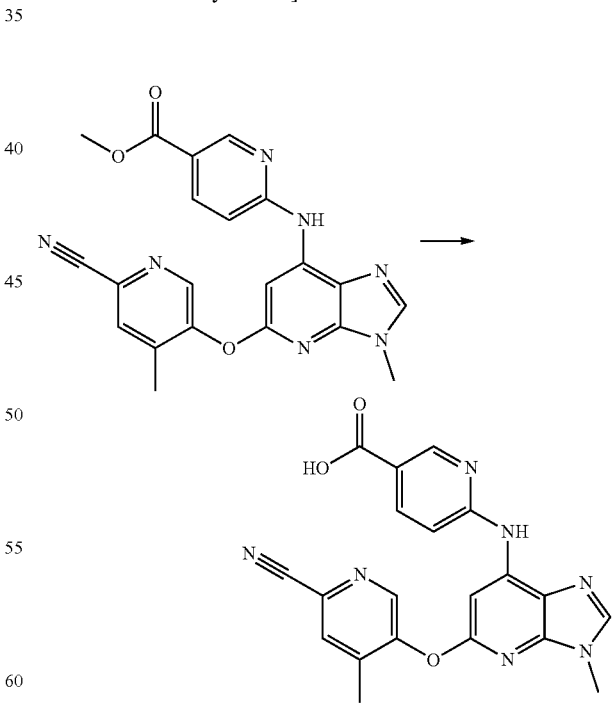

Intermediate 60 (1.24 g, 3.0 mmol, 1.0 eq) and LiI (1.20 g, 9.0 mmol, 3.0 eq) were suspended in anhydrous pyridine (10 mL, 0.3 M) under N$_2$ atmosphere and heated to 115° C. for 2 days. Next, the reaction mixture was evaporated in vacuo and the residue was suspended in saturated aqueous Na₂CO₃ solution and EtOAc. The EtOAc phase was discarded and the pH of the aqueous phase was adjusted to 5-6. The resulting precipitate was filtered and dried overnight in vacuo at 50° C. to afford the desired product. LCMS: m/z=402 [M+H]⁺.

Intermediate 63: 6-[5-(6-Cyano-4-methyl-pyridin-3-yloxy)-3-methyl-3H-imidazo[4,5-b]pyridin-7-ylamino]-pyridazine-3-carboxylicacid

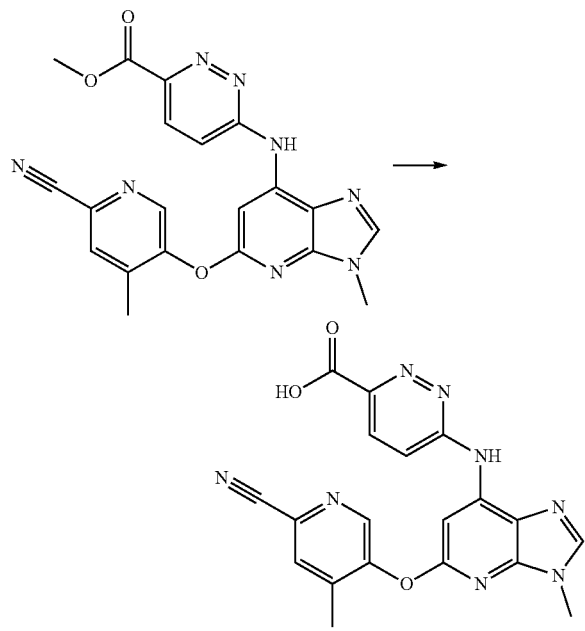

Intermediate 62 (1.24 g, 3.0 mmol, 1.0 eq) and LiI (1.20 g, 9.0 mmol, 3.0 eq) were suspended in anhydrous pyridine (10 mL) under N₂ atmosphere and heated to 115° C. for 48 h. Next, the reaction mixture was evaporated in vacuo and the residue was suspended in saturated aqueous Na₂CO₃ solution and EtOAc. The EtOAc phase was discarded and the pH of the aqueous phase was adjusted to a pH between 5 and 6. The resulting precipitate was filtered and dried overnight in vacuo at 50° C. to afford the desired product. LCMS: m/z=403 [M+H]⁺.

Intermediate 83:
2-(4-Amino-phenyl)-N-ethyl-acetamide

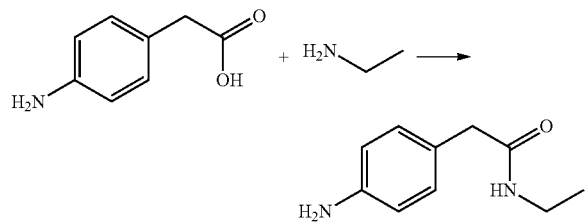

To a solution of 4-Aminophenylacetic acid (CAS [1197-55-3], 1.0 g, 6.61 mmol, 1.0 eq), EDCI (1.52 g, 7.94 mmol, 1.2 eq) and HOBt (1.21 g, 7.94 mmol, 1.2 eq) in dichloromethane (30 mL) was added ethyl amine (CAS [75-04-7], 3.63 mL, 7.27 mmol, 1.0 eq) and DIPEA (2.30 mL, 13.2 mmol, 2.0 eq) The mixture was stirred at room temperature for 18 h. Next, the reaction was diluted with EtOAc and washed with brine. Combined organic extracts dried and evaporated in vacuo to afford the desired product. LCMS: m/z=179 [M+H]⁺.

Intermediate 84: 6-amino-pyridin-3-yl)-(4-methyl-piperazin-1-yl)-methanone

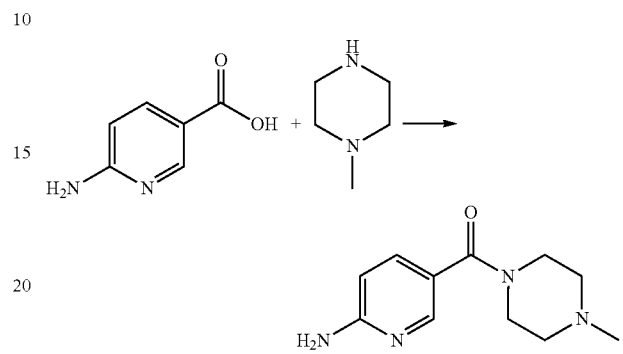

6-Amino-nicotinic acid (CAS [3167-49-5], 19.6 g, 142 mmol, 1.0 eq), N-methyl-piperazine (CAS [109-01-3], 19 mL, 170 mmol, 1.2 eq) and DIPEA (54 mL, 313 mmol, 2.2 eq) were stirred in dry EtOH (250 mL) before addition of HATU (81 g, 213 mmol, 1.5 eq). The mixture was stirred at room temperature for 18 h then concentrated. A solid appeared which was filtered and discarded. Filtrate was purified by column chromatography using DCM/EtOH/25% aqueous NH₃ (in a ratio 7/1/0.1) as eluent to afford the desired product. LCMS: m/z=221 [M+H]⁺.

Intermediate 85: 7-chloro-5-iodo-3-(trideuteriomethyl)imidazo[4,5-b]pyridine

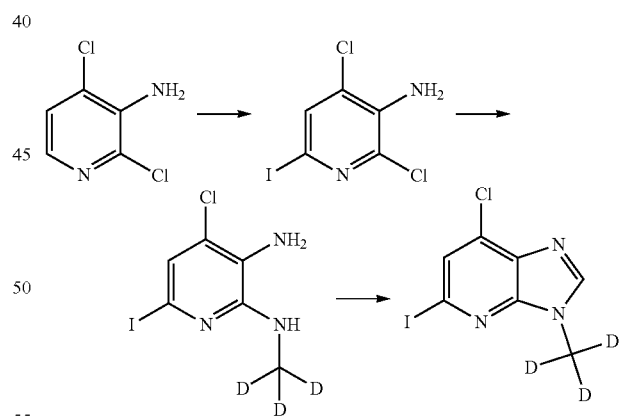

Step 1 and Step 2 were similar as for intermediate 1.

Step 3: 4-chloro-6-iodo-N2-(trideuteriomethyl)pyridine-2,3-diamine 2,4-dichloro-6-iodo-pyridin-3-amine (10 g, 0.03 mmol, 1 eq) was dissolved in n-butanol (150 mL) at autoclave (300 mL). Methyl-d3-amine hydrochloride (CAS [74326-22-8], 5 g, 0.07 mmol, 2.3 eq) and TEA (9.69 mL, 0.07 mmol, 1 eq) were added under N₂ at room temperature. The mixture was stirred at 180° C. for 48 h and then cooled to room temperature. Reaction mixture was concentrated to give the desired product that was used in next step as such. LCMS: m/z=287 [M+H].

Step 4: 7-chloro-5-iodo-3-(trideuteriomethyl)imidazo[4,5-b]pyridine

To a solution of 4-chloro-6-iodo-N2-(trideuteriomethyl) pyridine-2,3-diamine (10 g, 0.03 mmol, 1 eq) in formic acid (5 mL) was added trimethyl orthoformate (10 mL, 0.09 mmol, 3 eq). The mixture was stirred at 60° C. for 1 h. Reaction was concentrated to dryness, residue was diluted with DCM and quenched with saturated aqueous NaHCO₃ solution. After extraction with DCM, organic layer was dried over Na₂SO₄, filtered and concentrated to dryness to afford crude material. It was purified by column chromatography using eluent cyclohexane/EtOAc, gradient from 0 to 70% of EtOAc to give the desired product. LCMS: m/z=297 [M+H].

Intermediate 86: 5-[(7-chloro-3-methyl-imidazo[4,5-b]pyridin-5-yl)-cyclopropyl-amino]-4-methyl-pyridine-2-carbonitrile

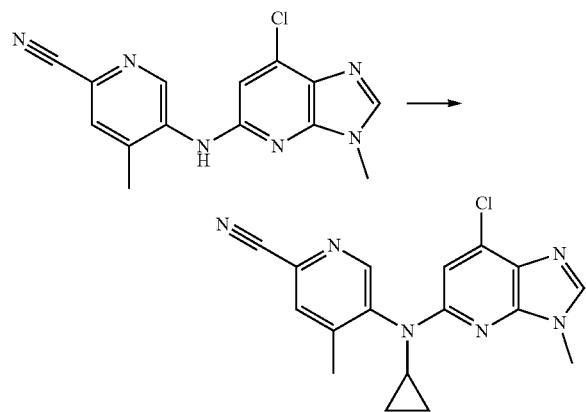

Intermediate 4 (150 mg, 0.50 mmol, 1 eq), cyclopropyl-boronic acid (CAS [411235-57-9], 86.26 mg mL, 1.0 mmol, 2 eq) and Cs₂CO₃ (106.44 mg, 1.0 mmol, 2 eq) was suspended in DMF (5 mL) in round bottom flask equipped with drying tube and molecular sieves 4A. The resulting suspension was stirred at room temperature. In separate flask, 2,2'-bipyridine (78.42 mg, 0.05 mmol, 0.1 eq) and copper(II)-acetate (91.20 mg, 1.00 mmol, 2 eq) were suspended in acetonitrile (2.5 mL) and the mixture was heated at 80° C. for 10 minutes. After 10 minutes, the warm solution was added to the suspension of compounds in DMF. The reaction mixture was stirred overnight at room temperature. After overnight stirring at room temperature, reaction temperature was raised at 55° C., The reaction was stirred overnight at 55° C. The reaction was cooled, water is added and the obtained suspension was extracted with DCM. Organic layers were combined, dried over Na₂SO₄, filtered and evaporated to obtain crude product. Crude product was purified chromatographic separation using 0-25% (10% MeOH/DCM) in DCM system to give the desired product. LCMS: m/z=340 [M+H].

Intermediate 87: 4-ethyl-5-hydroxy-pyridine-2-carbonitrile

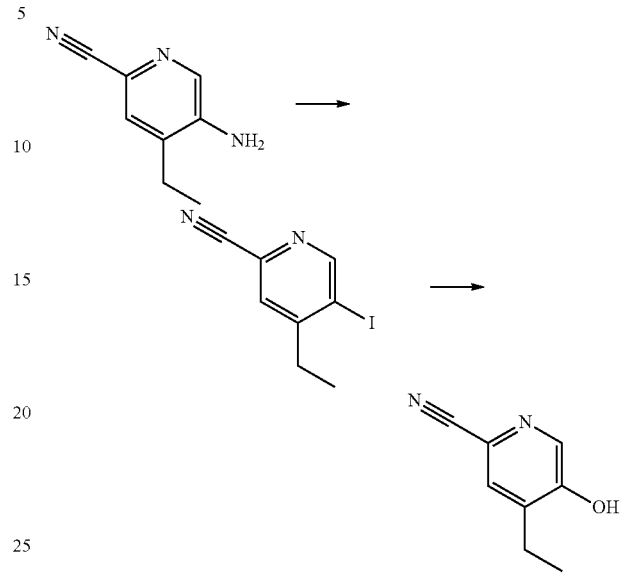

Step 1: 4-ethyl-5-iodo-pyridine-2-carbonitrile

To an ice cooled suspension of intermediate 20 (1 g, 6.8 mmol, 1 eq) in water (20 mL) was added hydrochloric acid (3.5 mL, 7.5 mmol, 1.1 eq) and an aqueous solution (3 mL) of sodium nitrite (0.518 g, 7.5 mmol, 1.1 eq). The reaction mixture was left to stir at 0° C. for 15 min upon which an aqueous solution (5 mL) of potassium iodide (1.24 g, 7.5 mmol, 1.1 eq) was added. The reaction mixture was continued to stir at ambient temperature for 1 h. Next, the reaction mixture was diluted with EtOAc (100 mL). The organic phase was isolated and the remaining aqueous phase was extracted with ethyl acetate (100 mL). The combined organic phases were concentrated under reduced pressure and the obtained crude was purified by column chromatography (cyclohexane as solvent A and cyclohexane:ethyl acetate=5:1 as solvent B gradient from 0-100% solvent B). The fractions containing product were combined and evaporated to afford the desired product. LCMS: m/z=259 [M+H].

Step 2: 4-ethyl-5-hydroxy-pyridine-2-carbonitrile

The reaction was carried out in 2 microwave vessels. To a solution of 4-ethyl-5-iodo-pyridine-2-carbonitrile (1.38 g, 5.35 mmol, 1 eq) in 1,4-dioxane (20 mL) were added bis(pinacolato)diboron (1.9 g, 7.49 mmol, 1.4 eq) and [1,1'-bis(diphenylphosphino)ferrocene] dichloropalladium (II), complex with dichloromethane (0.441 g, 0.54 mmol, 0.1 eq) and potassium acetate (1.58 g, 16.1 mmol, 3 eq). The reaction mixture was purged with argon and then heated in microwave reactor for 30 min at 150° C. The reaction mixtures were cooled to 0° C. after which hydrogen peroxide solution (30% w/wn 3.28 mL, 32.1 mmol, 6 eq) was slowly added. The reaction mixture was continued to stir at ambient temperature for 18 h. The combined mixtures were filtered and the residue was washed with ethyl acetate (100 mL). The mother liquor was washed with water (50 mL) and evaporated under reduced pressure affording crude. The purification is done by column chromatography using cyclohexane as solvent A and cyclohexane:ethyl acetate=1:1 as solvent B (gradient from 0-100% of solvent B) to afford the desired product. LCMS: m/z=149.05 [M+H].

Intermediate 89: 5-[7-chloro-3-(trideuteriomethyl)imidazo[4,5-b]pyridin-5-yl]oxy-4-methyl-pyridine-2-carbonitrile

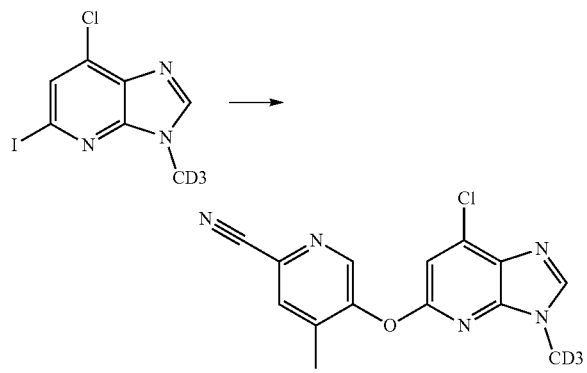

Intermediate 85 (2.1 g, 7.1 mmol, 1.0 eq), Intermediate 21 (1.43 g, 10.6 mmol, 1.5 eq), CuI (270 mg, 1.42 mmol, 0.2 eq), TMHD (3.0 mL, 14.2 mmol, 2 eq) and Cs$_2$CO$_3$ (4.61 g, 14.2 mmol, 2 eq) were mixed together under air, DMF (12 mL) was added and the mixture was stirred at 85° C. for 72 h. Next, the mixture was cooled to 0° C. The resulting thick paste was then filtered and the cake was washed with ice cooled DMF. It was then washed with ice cooled MTBE. After drying the cake, it was suspended in 25 mL of 10% aqueous TMEDA solution. It was stirred for 2 h, filtered and the cake was washed with water to afford the desired product. LCMS: m/z=303 [M+H]$^+$.

Intermediate 92: 4-(7-Chloro-3-methyl-3H-imidazo[4,5-b]pyridin-5-yloxy)-3,5-difluoro-benzonitrile

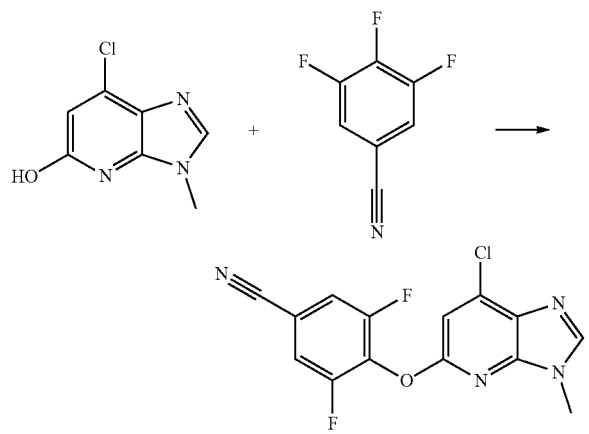

A mixture of Int 57 (300 mg, 1.63 mmol, 1 eq), 3,4,5-trifluorobenzonitrile ([134227-45-5], 300 mg, 1.63 mmol, 1 eq), K$_2$CO$_3$ (452 mg, 3.26 mmol, 2 eq) in NMP (3 mL) was heated for 18 h at 100° C. Next, the reaction was diluted with EtOAc and washed with brine. Combined organic extracts dried and evaporated in vacuo. The resulting crude was purified by column chromatography (PE/EtOAc 50/50 to 0/100) to afford the desired product. LCMS: m/z=321 [M+H]$^+$.

Intermediate 93: (6-bromo-3-pyridyl)-[2,2,3,3,5,5,6,6-octadeuterio-4-(trideuteriomethyl)piperazin-1-yl]methanone

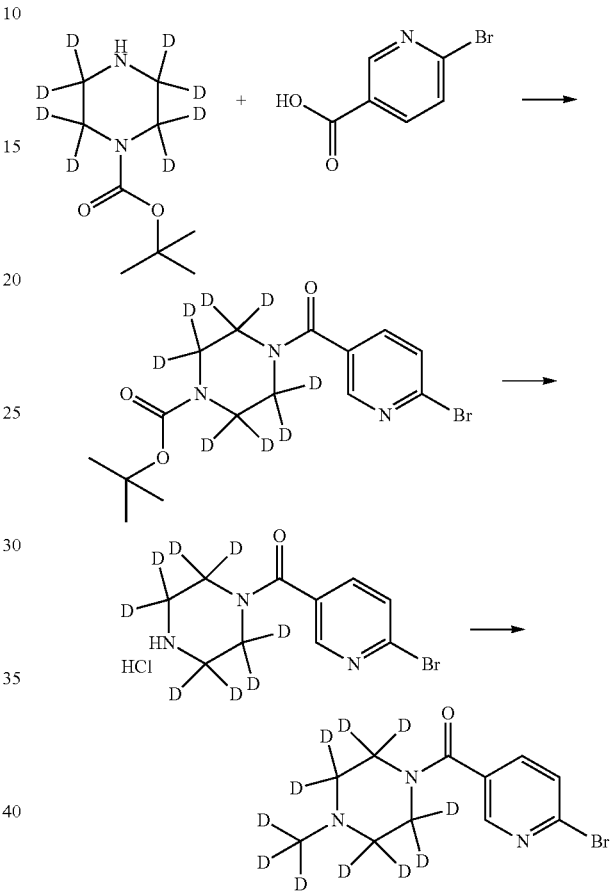

Step 1: tert-butyl-4-(6-bromopyridine-3-carbonyl)-2,2,3,3,5,5,6,6-octadeuterio-piperazine-1-carboxylate A mixture of 6-bromonicotinic acid ([6311-35-9], 745 mg, 3.69 mmol, 1.1 eq), piperazine-d8-N-T-Boc ([1126621-86-0], 650 mg, 3.35 mmol, 1 eq), HATU (1.4 g, 3.69 mmol, 1.1 mmol) and Et$_3$N (0.93 mL, 6.7 mmol, 2 eq) in DCM (15 mL) was stirred overnight at room temperature. Next, the mixture was diluted with DCM and extracted twice with a saturated aqueous solution of NH$_4$Cl. The resulting organic layer was evaporated to give an oil. The resulting oil was purified by column chromatography (DCM/MeOH 100/0 till 98/2) to afford the desired product.

Step 2: (6-bromo-3-pyridyl)-(2,2,3,3,5,5,6,6-octadeuteriopiperazin-1-yl)methanone Tert-butyl-4-(6-bromopyridine-3-carbonyl)-2,2,3,3,5,5,6,6-octadeuterio-piperazine-1-carboxylate (1.1 g, 2.9 mmol, 1 eq) was mixed with a 4 M HCl in dioxane solution (7 mL, 29 mmol, 10 eq) in dioxane (20 mL). A small amount of water was added to improve the overall solubility. After completion of the reaction, the mixture was concentrated to dryness to afford the HCl salt of the desired product.

Step 3: (6-bromo-3-pyridyl)-[2,2,3,3,5,5,6,6-octadeuterio-4-(trideuteriomethyl)piperazin-1-yl]methanone The HCl salt of (6-bromo-3-pyridyl)-(2,2,3,3,5,5,6,6-octadeuteriopiperazin-1-yl)methanone (300 mg, 0.96 mmol, 1 eq) was mixed with NaH (115 mg, 2.88 mmol, 3 eq) in THF (6 mL). The resulting mixture was stirred at rT for 30 min. Next, idomethane-d$_3$ (60 µL, 0.96 mmol, 1 eq) was added dropwise to the mixture. The mixture was stirred at 40° C. After cooling till 0° C., the mixture was diluted with water and extracted with DCM. The organic layer was concentrated to give the crude desired product which was used as such.

TABLE II

Intermediates towards illustrative compounds of the invention

| Int | Structure | Name | SM | Method | MW | Mes |
|---|---|---|---|---|---|---|
| 1 | 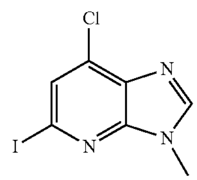 | 7-Chloro-5-iodo-3-methyl-3H-imidazo[4,5-b]pyridine | CAS [2587-02-2] | Exemplified | 293 | 294 |
| 2 | 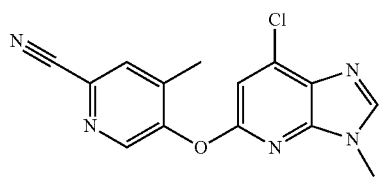 [SMILES: Cc1cc(C#N)ncc1Oc1cc(Cl)c2ncn(C)c2n1] | 5-(7-Chloro-3-methyl-3H-imidazo[4,5-b]pyridin-5-yloxy)-4-methyl-pyridine-2-carbonitrile | Int 1 | Exemplified | 300 | 300 |
| 3 | 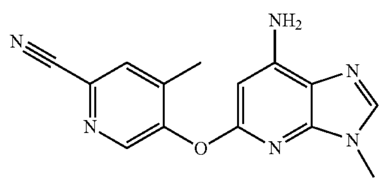 [SMILES: Cc1cc(C#N)ncc1Oc1cc(N)c2ncn(C)c2n1] | 5-(7-Amino-3-methyl-3H-imidazo[4,5-b]pyridin-5-yloxy)-4-methyl-pyridine-2-carbonitrile | Int 2 | Exemplified | 280 | 281 |
| 4 | 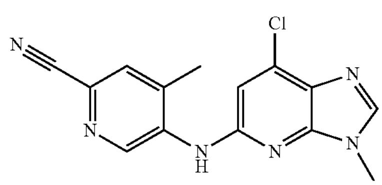 [SMILES: Cc1cc(C#N)ncc1Nc1cc(Cl)c2ncn(C)c2n1] | 5-(7-Chloro-3-methyl-3H-imidazo[4,5-b]pyridin-5-ylamino)-4-methyl-pyridine-2-carbonitrile | Int 1, Int 17 | Exemplified | 299 | 299 |
| 5 | 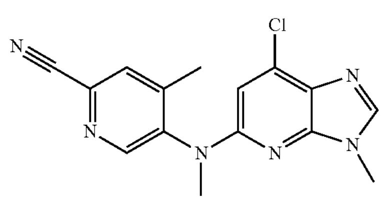 [SMILES: Cc1cc(C#N)ncc1N(C)c1cc(Cl)c2ncn(C)c2n1] | 5-[(7-Chloro-3-methyl-3H-imidazo[4,5-b]pyridin-5-yl)-methyl-amino]-4-methyl-pyridine-2-carbonitrile | Int 1, Int 18 | Exemplified | 313 | 313 |
| 6 | 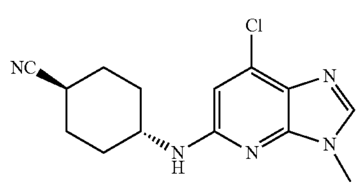 [SMILES: Cn1cnc2c(Cl)cc(N[C@H]3CC[C@H](C#N)CC3)nc21] | (±)-4-[(7-chloro-3-methyl-imidazo[4,5-b]pyridin-5-yl)amino]cyclohexanecarbonitrile | Int 1, [873537-33-8] | B3 | 290 | 290 |
| 7 | 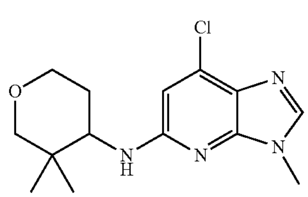 [SMILES: Cn1cnc2c(Cl)cc(NC3CCOCC3(C)C)nc21] | 7-chloro-N-(3,3-dimethyltetrahydropyran-4-yl)-3-methyl-imidazo[4,5-b]pyridin-5-amine | Int 1, [1400580-54-2] | B3 | 295 | 295 |

TABLE II-continued

Intermediates towards illustrative compounds of the invention

| Int | Structure | Name | SM | Method | MW | Mes |
|---|---|---|---|---|---|---|
| 8 | 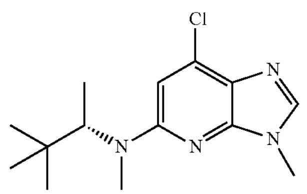 [SMILES: C[C@H](N(C)c1cc(Cl)c2ncn(C)c2n1)C(C)(C)C] | (7-Chloro-3-methyl-3H-imidazo[4,5-b]pyridin-5-yl)-methyl-((S)-1,2,2-trimethyl-propyl)-amine | Int 67 | Exemplified | 280 | 281 |
| 9 | 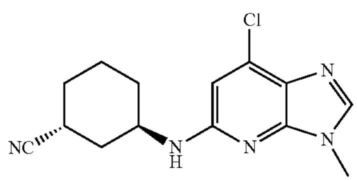 [SMILES: Cn1cnc2c(Cl)cc(N[C@@H]3CCC[C@@H](C#N)C3)nc21] | (±)-(1R,3R)-3-[(7-chloro-3-methyl-imidazo[4,5-b]pyridin-5-yl)amino]cyclohexanecarbonitrile | Int 1, [920966-30-9] | B3 | 290 | 290 |
| 10 | 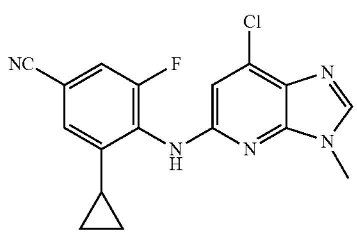 [SMILES: Cn1cnc2c(Cl)cc(Nc3c(F)cc(C#N)cc3C3CC3)nc21] | 4-[(7-chloro-3-methyl-imidazo[4,5-b]pyridin-5-yl)amino]-3-cyclopropyl-5-fluoro-benzonitrile | Int 1, Int 19 | B3 | 342 | 342 |
| 11 | 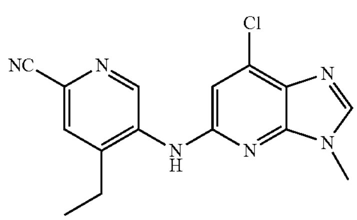 [SMILES: CCc1cc(C#N)ncc1Nc1cc(Cl)c2ncn(C)c2n1] | 5-[(7-chloro-3-methyl-imidazo[4,5-b]pyridin-5-yl)amino]-4-ethyl-pyridine-2-carbonitrile | Int 1, Int 20 | B3 | 313 | 313 |
| 12 | 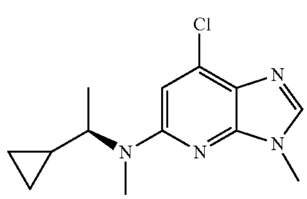 [SMILES: C[C@H](C1CC1)N(C)c1cc(Cl)c2ncn(C)c2n1] | (7-Chloro-3-methyl-3H-imidazo[4,5-b]pyridin-5-yl)-((R)-1-cyclopropyl-ethyl)-methyl-amine | Int 65, [6240-96-6] | Exemplified | 264 | 265 |
| 13 | 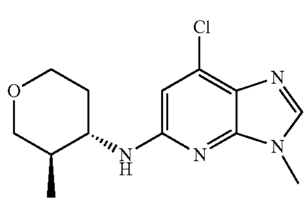 [SMILES: C[C@H]1COCC[C@@H]1Nc1cc(Cl)c2ncn(C)c2n1] | (±)-7-chloro-3-methyl-N-[(3R,4S)-3-methyltetrahydropyran-4-yl]imidazo[4,5-b]pyridin-5-amine | Int 1, [1682655-57-5] | B3 | 281 | 281 |
| 14 | 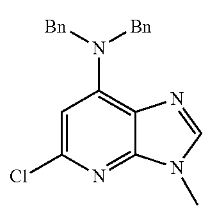 [SMILES: Cn1cnc2c(N(Cc3ccccc3)Cc3ccccc3)cc(Cl)nc21] | Dibenzyl-(5-chloro-3-methyl-3H-imidazo[4,5-b]pyridin-7-yl)-amine | [2587-02-2] | Exemplified | 362 | 363 |

TABLE II-continued

Intermediates towards illustrative compounds of the invention

| Int | Structure | Name | SM | Method | MW | Mes |
|---|---|---|---|---|---|---|
| 15 | 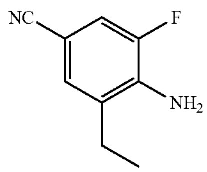 | 4-amino-3-ethyl-5-fluorobenzonitrile | [63069-50-1] | Exemplified | 164 | 165 |
| 16 | 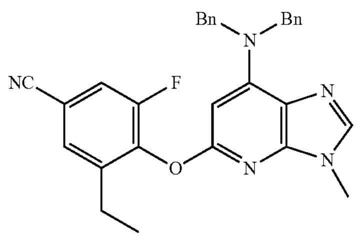 [SMILES: CCc1cc(C#N)cc(F)c1Oc1cc(N(Cc2ccccc2)Cc2ccccc2)c2ncn(C)c2n1] | 4-(7-Dibenzylamino-3-methyl-3H-imidazo[4,5-b]pyridin-5-ylamino)-3-ethyl-5-fluoro-benzonitrile | Int 15, Int. 16 | Exemplified | 490 | 491 |
| 17 | 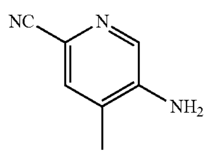 | 5-amino-4-methylpyridine-2-carbonitrile | [156118-16-0] | Exemplified | 133 | 134 |
| 18 | 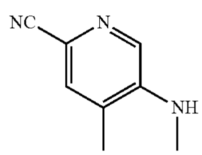 | 3-Methyl-4-methylamino-benzonitrile | Int 17 | Exemplified | 147 | 148 |
| 19 | 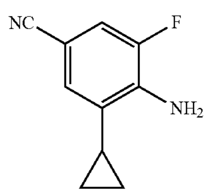 [SMILES: N#Cc1cc(F)c(N)c(C2CC2)c1] | 4-Amino-3-cyclopropyl-5-fluoro-benzonitrile | [63069-50-1] | Exemplified | 176 | 177 |
| 20 | 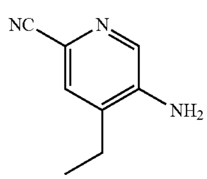 | 5-Amino-4-ethyl-pyridine-2-carbonitrile | [929617-29-8] | Exemplified | 147 | 148 |
| 21 | 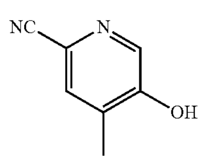 | 5-hydroxy-4-methyl-pyridine-2-carbonitrile | [886364-86-9] | Exemplified | 134 | 135 |
| 22 | 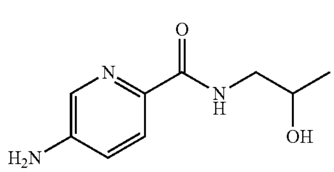 | 5-Amino-pyridin-2-carboxylic acid (2-hydroxy-propyl)-amide | [29682-14-2], [78-96-6] | Exemplified | 195 | 226 |

TABLE II-continued

| Int | Structure | Name | SM | Method | MW | Mes |
|---|---|---|---|---|---|---|
| 23 | 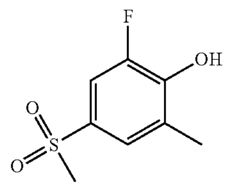 | 2-fluoro-6-methyl-4-methylsulfonyl-phenol | [398456-87-6] | Exemplified | 204 | 205 |
| 24 | 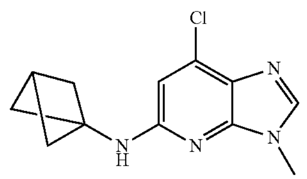 [SMILES: Cn1cnc2c(Cl)cc(NC34CC(C3)C4)nc21] | N-(3-bicyclo[1.1.1]pentanyl)-7-chloro-3-methyl-imidazo[4,5-b]pyridin-5-amine | Int 1, [2287-35-0] | B3 | 249 | 249 |
| 25 | 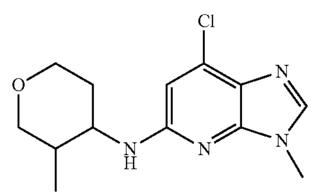 [SMILES: CC1COCCC1Nc1cc(Cl)c2ncn(C)c2n1] | 7-chloro-3-methyl-N-(3-methyltetrahydropyran-4-yl)imidazo[4,5-b]pyridin-5-amine | Int 1, [1787906-12-0] | B3 | 281 | 281 |
| 26 | 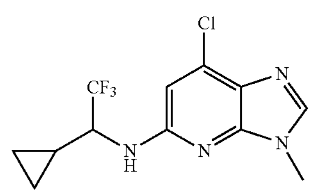 [SMILES: Cn1cnc2c(Cl)cc(NC(C3CC3)C(F)(F)F)nc21] | 7-chloro-N-(1-cyclopropyl-2,2,2-trifluoro-ethyl)-3-methyl-imidazo[4,5-b]pyridin-5-amine | Int 1, [75702-99-7] | B3 | 305 | 305 |
| 27 | 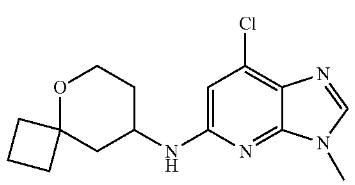 [SMILES: Cn1cnc2c(Cl)cc(NC3CCOC4(CCC4)C3)nc21] | 7-chloro-3-methyl-N-(5-oxaspiro[3.5]nonan-8-yl)imidazo[4,5-b]pyridin-5-amine | Int 1, [1309434-30-7] | B3 | 307 | 307 |
| 28 | 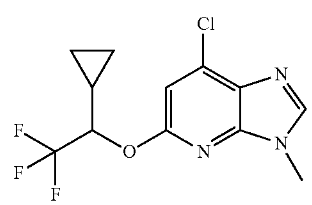 [SMILES: Cn1cnc2c(Cl)cc(OC(C3CC3)C(F)(F)F)nc21] | 7-Chloro-5-(1-cyclopropyl-2,2,2-trifluoro-ethoxy)-3-methyl-3H-imidazo[4,5-b]pyridine | Int 1, [1993-77-7] | Exemplified | 305 | 306 |
| 29 | 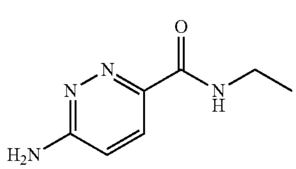 | 6-Amino-pyridazine-3-carboxylic acid ethylamide | [301548-08-3] and [75-04-7] | A2 | 166 | 167 |
| 30 | 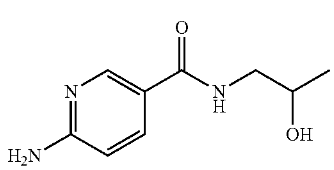 | 6-Amino-N-(2-hydroxy-propyl)-nicotinamide | [231958-14-8] and [78-96-6] | A2 | 195 | 196 |

TABLE II-continued

Intermediates towards illustrative compounds of the invention

| Int | Structure | Name | SM | Method | MW | Mes |
|---|---|---|---|---|---|---|
| 31 | 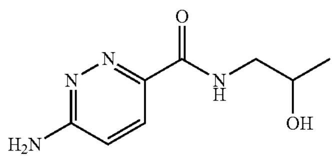 | 6-Amino-pyridazine-3-carboxylic acid (2-hydroxy-propyl)-amide | [301548-08-3] and [78-96-6] | A2 | 167 | 168 |
| 32 | 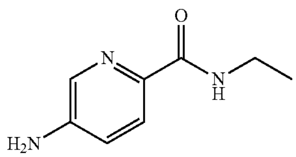 | 5-Amino-pyridine-2-carboxylic acid ethylamide | [1437794-42-7] | Exemplified | 165 | 166 |
| 33 | 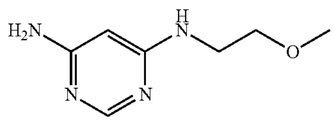 | N-(2-Methoxy-ethyl)-pyrimidine-4,6-diamine | [5305-59-9] and [109-85-3] | P1 | 168 | 169 |
| 34 | 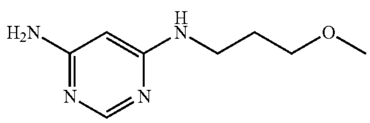 | N-(3-Methoxy-propyl)-pyrimidine-4,6-diamine | [5305-59-9] and [5332-73-0] | P1 | 182 | 183 |
| 35 | 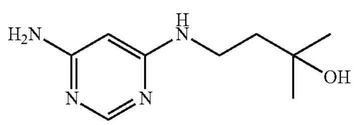 | 4-(6-Amino-pyrimidin-4-ylamino)-2-methyl-butan-2-ol | [5305-59-9] and [26734-08-7] | P1 | 196 | 197 |
| 36 | 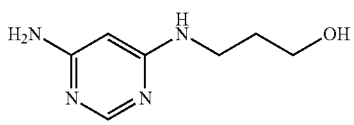 [SMILES: Nc1cc(NCCCO)ncn1] | 3-(6-Amino-pyrimidin-4-ylamino)-propan-1-ol | [5305-59-9] and [156-87-6] | P1 | 168 | 169 |
| 37 | 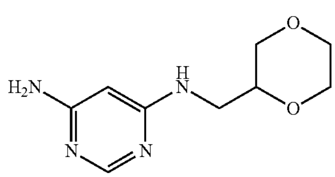 [SMILES: Nc1cc(NCC2COCCO2)ncn1] | N-[1,4]Dioxan-2-ylmethyl-pyrimidine-4,6-diamine | [5305-59-9] and [88277-83-2] | P1 | 210 | 211 |
| 38 | 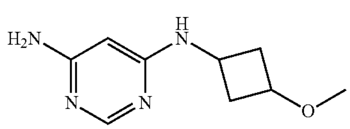 | N-(3-Methoxy-cyclobutyl)-pyrimidine-4,6-diamine | [5305-59-9] and [1234615-98-5] | P1 | 194 | 195 |
| 39 | 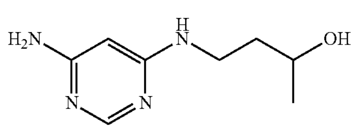 | 4-(6-Amino-pyrimidin-4-ylamino)-butan-2-ol | [5305-59-9] and [39884-48-5] | P1 | 182 | 183 |
| 40 | 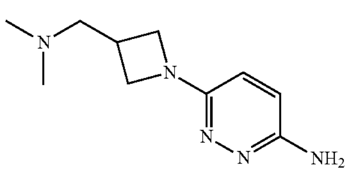 | 6-(3-Dimethylaminomethyl-azetidin-1-yl)-pyridazin-3-ylamine | [187973-60-0] and [321890-22-6] | P2 | 207 | 208 |

TABLE II-continued

Intermediates towards illustrative compounds of the invention

| Int | Structure | Name | SM | Method | MW | Mes |
|---|---|---|---|---|---|---|
| 41 | 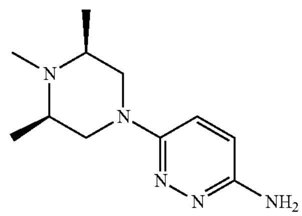 [SMILES: C[C@@H]1CN(c2ccc(N)nn2)C[C@H](C)N1C] | (±)-6-((3R,5S)-3,4,5-Trimethyl-piperazin-1-yl)-pyridazin-3-ylamine | [187973-60-0] and [147539-61-5] | P2 | 221 | 222 |
| 42 | 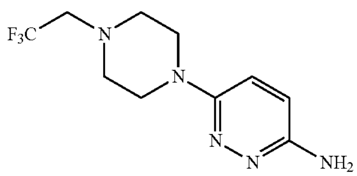 [SMILES: Nc1ccc(N2CCN(CC(F)(F)F)CC2)nn1] | 6-[4-(2,2,2-Trifluroo-ethyl)-piperazin-1-yl]-pyridazin-3-ylamine | [187973-60-0] and [13349-90-1] | P2 | 261 | 262 |
| 43 | 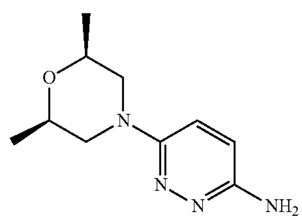 | (±)-6-((2R,6S)-2,6-Dimethyl-morpholin-4-yl)-pyridazin-3-ylamine | [187973-60-0] and [6485-55-8] | P2 | 208 | 209 |
| 44 | 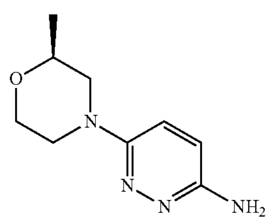 | 6-((S)-2-Methyl-morpholin-4-yl)-pyridazin-3-ylamine | [187973-60-0] and [74572-13-7] | P2 | 194 | 195 |
| 45 | 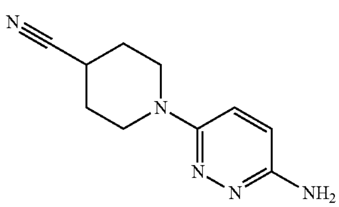 [SMILES: N#CC1CCN(c2ccc(N)nn2)CC1] | 1-(6-Amino-pyridazin-3-yl)-piperidine-4-carbonitrile | [187973-60-0] and [4395-98-6] | P2 | 203 | 204 |
| 46 | 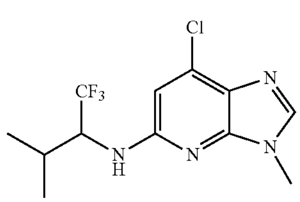 | (7-Chloro-3-methyl-3H-imidazo[4,5-b]pyridin-5-yl)-(2-methyl-1-trifluoromethyl-propyl)-amine | Int 1, [1582-18-9] | B3 | 307 | 307 |
| 47 | 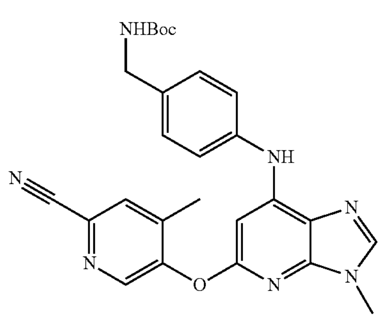 [SMILES: Cc1cc(C#N)ncc1Oc1cc(Nc2ccc(CNC(=O)OC(C)(C)C)cc2)c2ncn(C)c2n1] | 5-[7-[4-(N-Boc-aminomethyl)anilino]-3-methyl-imidazo[4,5-b]pyridin-5-yl]oxy-4-methyl-pyridine-2-carbonitrile | Int 1, [94838-55-8] | B1 | 485 | 486 |

TABLE II-continued

Intermediates towards illustrative compounds of the invention

| Int | Structure | Name | SM | Method | MW | Mes |
|---|---|---|---|---|---|---|
| 48 | 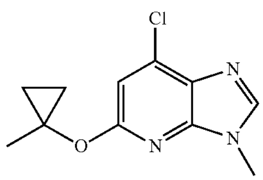 [SMILES: Cn1cnc2c(Cl)cc(OC3(C)CC3)nc21] | 7-Chloro-5-(1-cyclopropyl-ethoxy)-3-methyl-3H-imidazo[4,5-b]pyridine | Int 57 | Exemplified | 251 | 252 |
| 49 | 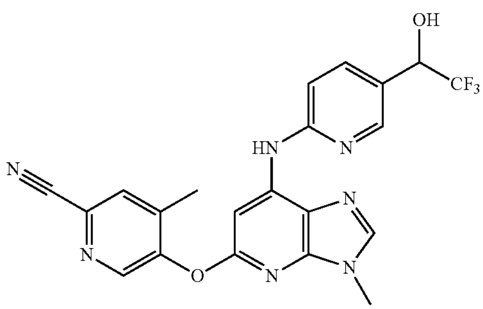 [SMILES: Cc1cc(C#N)ncc1Oc1cc(Nc2ccc(C(O)C(F)(F)F)cn2)c2ncn(C)c2n1] | 4-Methyl-5-[3-methyl-7-[[5-(2,2,2-trifluoro-1-hydroxy-ethyl)-2-pyridyl]amino]imidazo[4,5-b]pyridin-5-yl]oxy-pyridine-2-carbonitrile | Int 3, [1188477-81-7] | B3 | 455 | 456 |
| 50 | 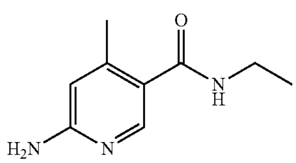 | N-ethyl-4-methyl-pyridine-3-carboxamide | [179555-11-4] | Exemplified | 179 | 180 |
| 51 | 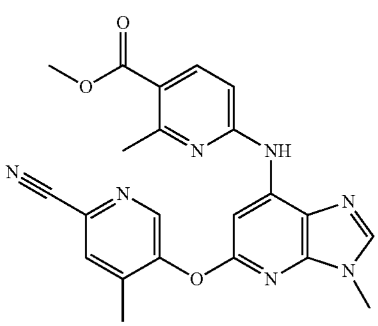 [SMILES: COC(=O)c1ccc(Nc2cc(Oc3cnc(C#N)cc3C)nc3c2ncn3C)nc1C] | Methyl 6-[[5-[(6-cyano-4-methyl-3-pyridyl)oxy]-3-methyl-imidazo[4,5-b]pyridin-7-yl]amino]-2-methyl-pyridine-3-carboxylate | Int 2, [872355-52-7] | B1 | 429 | 430 |
| 52 | 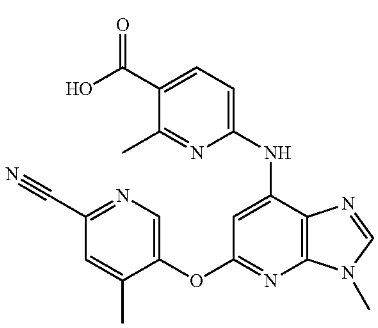 [SMILES: Cc1cc(C#N)ncc1Oc1cc(Nc2ccc(C(=O)O)c(C)n2)c2ncn(C)c2n1] | 6-[[5-[(6-cyano-4-methyl-3-pyridyl)oxy]-3-methyl-imidazo[4,5-b]pyridin-7-yl]amino]-2-methyl-pyridine-3-carboxylic acid | Int 51 | Exemplified | 415 | 416 |
| 53 | 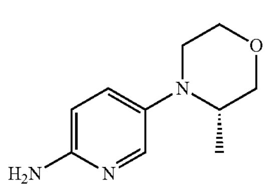 | 5-((S)-3-methyl-4-morpholinyl)-2-pyridinamine | [1072-97-5], [350595-57-2] | Exemplified | 193 | 194 |

TABLE II-continued

Intermediates towards illustrative compounds of the invention

| Int | Structure | Name | SM | Method | MW | Mes |
|-----|-----------|------|-----|--------|-----|-----|
| 54 | 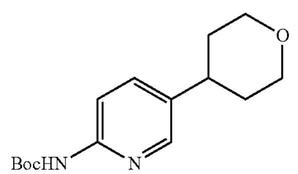 [SMILES: CC(C)(C)OC(=O)Nc1ccc(C2CCOCC2)cn1] | N-Boc-5-(tetrahydro-2H-pyran-4-yl)pyridin-2-amine | [159451-66-8], [1279123-50-0] | Exemplified | 278 | 279 |
| 55 | 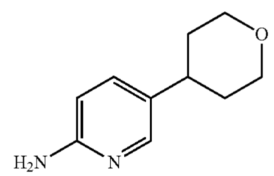 | 5-(tetrahydro-2H-pyran-4-yl)pyridin-2-amine | Int 54 | D1 | 178 | 179 |
| 56 | 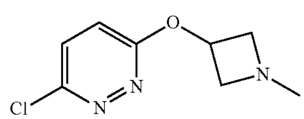 | 3-chloro-6-(1-methylazetidin-3-yl)oxypyridazine | [111043-48-2], [141-30-0] | Exemplified | 200 | 200 |
| 57 | 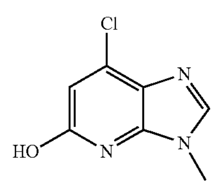 | 7-Chloro-3-methyl-3H-imidazo[4,5-b]pyridin-5-ol | Int 1 | Exemplified | 184 | 184 |
| 58 | 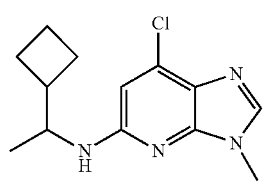 [SMILES: CC(Nc1cc(Cl)c2ncn(C)c2n1)C1CCC1] | (7-Chloro-3-methyl-3H-imidazo[4,5-b]pyridin-5-yl)-(1-cyclobutyl-ethyl)-amine | Int 1, [60637-96-9] | B3 | 264 | 265 |
| 59 | 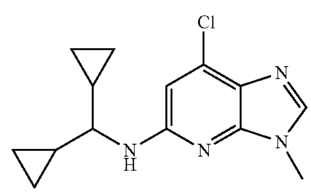 [SMILES: Cn1cnc2c(Cl)cc(NC(C3CC3)C3CC3)nc21] | (7-Chloro-3-methyl-3H-imidazo[4,5-b]pyridin-5-yl)-dicyclopropylmethyl-amine | Int 1, [13375-29-6] | B3 | 276 | 277 |
| 60 | 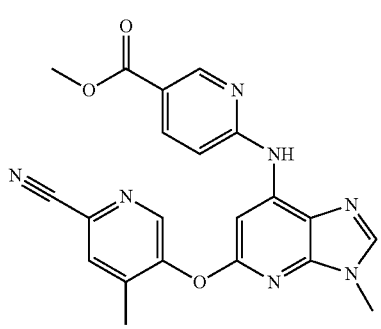 [SMILES: COC(=O)c1ccc(Nc2cc(Oc3cnc(C#N)cc3C)nc3c2ncn3C)nc1] | 6-[5-(6-Cyano-4-methyl-pyridin-3-yloxy)-3-methyl-3H-imidazo[4,5-b]pyridin-7-ylamino]-nicotinic acid methyl ester | Int 2, [36052-24-1] | B1 | 415 | 416 |

TABLE II-continued

Intermediates towards illustrative compounds of the invention

| Int | Structure | Name | SM | Method | MW | Mes |
|---|---|---|---|---|---|---|
| 61 | 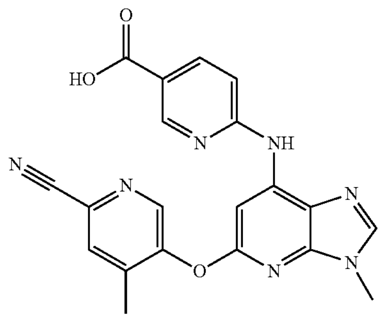 [SMILES: Cc1cc(C#N)ncc1Oc1cc(Nc2ccc(C(=O)O)cn2)c2ncn(C)c2n1] | 6-[5-(6-Cyano-4-methyl-pyridin-3-yloxy)-3-methyl-3H-imidazo[4,5-b]pyridin-7-ylamino]-nicotinic acid | Int 60 | Exemplified | 401 | 402 |
| 62 | 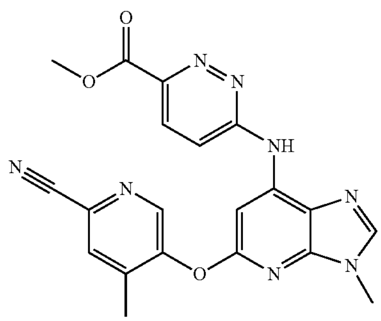 [SMILES: COC(=O)c1ccc(Nc2cc(Oc3cnc(C#N)cc3C)nc3c2ncn3C)nn1] | 6-[5-(6-Cyano-4-methyl-pyridin-3-yloxy)-3-methyl-3H-imidazo[4,5-b]pyridin-7-ylamino]-pyridazine-3-carboxylic acid methyl ester | Int 2, [98140-96-6] | B1 | 416 | 417 |
| 63 | 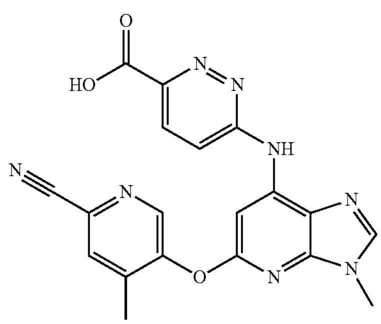 [SMILES: Cc1cc(C#N)ncc1Oc1cc(Nc2ccc(C(=O)O)nn2)c2ncn(C)c2n1] | 6-[5-(6-Cyano-4-methyl-pyridin-3-yloxy)-3-methyl-3H-imidazo[4,5-b]pyridin-7-ylamino]-pyridazine-3-carboxylic acid | Int 62 | Exemplified | 402 | 403 |
| 64 | 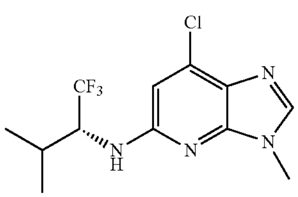 [SMILES: CC(C)[C@@H](Nc1cc(Cl)c2ncn(C)c2n1)C(F)(F)F] | (7-Chloro-3-methyl-3H-imidazo[4,5-b]pyridin-5-yl)-((R)-2-methyl-1-trifluoromethyl-propyl)-amine | Int 1, [1032181-63-7] | B3 | 306 | 307 |
| 65 | 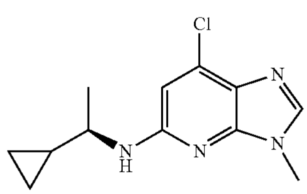 [SMILES: C[C@@H](Nc1cc(Cl)c2ncn(C)c2n1)C1CC1] | (7-Chloro-3-methyl-3H-imidazo[4,5-b]pyridin-5-yl)-((R)-1-cyclopropyl-ethyl)-amine | Int 1, [6240-96-6] | B3 | 251 | 251 |
| 66 | 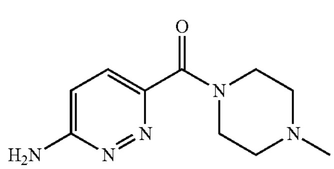 | (6-aminopyridazin-3-yl)-(4-methylpiperazin-1-yl)methanone | [301548-08-3] and [109-01-3] | A3 | 221 | 222 |

TABLE II-continued

Intermediates towards illustrative compounds of the invention

| Int | Structure | Name | SM | Method | MW | Mes |
|---|---|---|---|---|---|---|
| 67 | 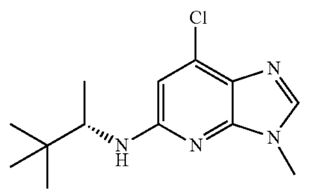 [SMILES: C[C@H](Nc1cc(Cl)c2ncn(C)c2n1)C(C)(C)C] | (7-Chloro-3-methyl-3H-imidazo[4,5-b]pyridin-5-yl)-((S)-1,2,2-trimethyl-propyl)-amine | Int 1, [22526-47-2] | B1 | 267 | 267 |
| 68 | 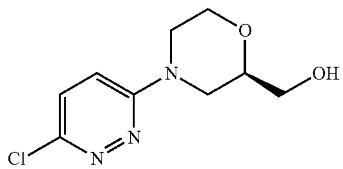 [SMILES: OC[C@H]1CN(c2ccc(Cl)nn2)CCO1] | [(R)-4-(6-Chloro-pyridazin-3-yl)-morpholin-2-yl]-methanol | [141-30-0], [1436436-17-7] | P3 | 229 | 230 |
| 69 | 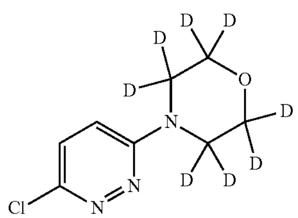 [SMILES: [2H]C1([2H])OC([2H])([2H])C([2H])([2H])N(c2ccc(Cl)nn2)C1([2H])[2H]] | 4-(6-chloropyridazin-3-yl)-2,2,3,3,5,5,6,6-octadeuterio-morpholine | [141-30-0], [342611-02-3] | P3 | 207 | 208 |
| 70 | 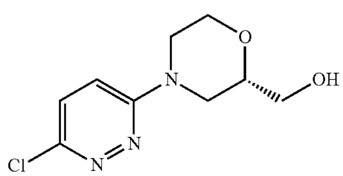 [SMILES: OC[C@@H]1CN(c2ccc(Cl)nn2)CCO1] | [(S)-4-(6-Chloro-pyridazin-3-yl)-morpholin-2-yl]-methanol | [141-30-0], [1313584-92-7] | P3 | 229 | 230 |
| 71 | 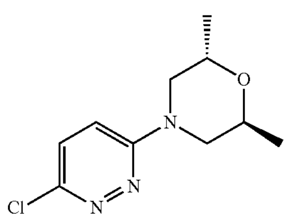 | (2S,6S)-4-(6-Chloro-pyridazin-3-yl)-2,6-dimethyl-morpholine | [141-30-0], [276252-76-4] | P3 | 227 | 228 |
| 72 | 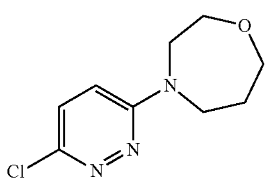 [SMILES: Clc1ccc(N2CCCOCC2)nn1] | 4-(6-Chloro-pyridazin-3-yl)-[1,4]oxazepane | [141-30-0], [5638-60-8] | P3 | 213 | 214 |
| 73 | 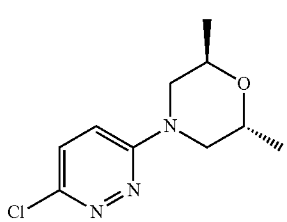 | (2R,6R)-4-(6-Chloro-pyridazin-3-yl)-2,6-dimethyl-morpholine | [141-30-0], [171753-74-5] | P3 | 227 | 228 |

TABLE II-continued

Intermediates towards illustrative compounds of the invention

| Int | Structure | Name | SM | Method | MW | Mes |
|---|---|---|---|---|---|---|
| 74 | 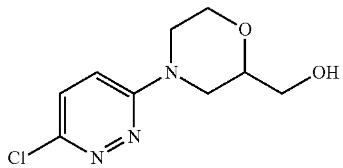 [SMILES: OCC1CN(c2ccc(Cl)nn2)CCO1] | [4-(6-Chloro-pyridazin-3-yl)-morpholin-2-yl]-methanol | [141-30-0], [103003-01-6] | P3 | 229 | 230 |
| 75 | 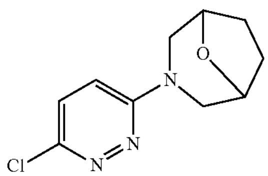 [SMILES: Clc1ccc(N2CC3CCC(C2)O3)nn1] | 3-(6-Chloro-pyridazin-3-yl)-8-oxa-3-aza-bicyclo[3.2.1]octane | [141-30-0], [54745-74-3] | P3 | 225 | 226 |
| 76 | 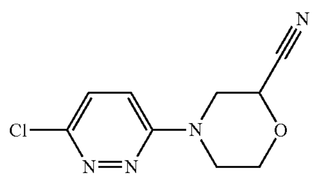 [SMILES: N#CC1CN(c2ccc(Cl)nn2)CCO1] | 4-(6-Chloro-pyridazin-3-yl)-morpholine-2-carbonitrile | [141-30-0], [1205751-07-0] | P3 | 224 | 225 |
| 77 | 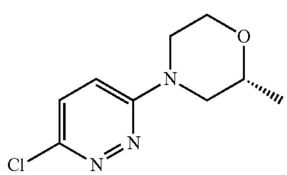 | (R)-4-(6-Chloro-pyridazin-3-yl)-2-methyl-morpholine | [141-30-0], [168038-14-0] | P3 | 213 | 214 |
| 78 | 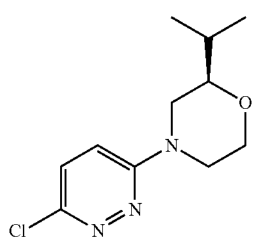 [SMILES: CC(C)[C@@H]1CN(c2ccc(Cl)nn2)CCO1] | (R)-4-(6-Chloro-pyridazin-3-yl)-2-isopropyl-morpholine | [141-30-0], [792886-64-7] | P3 | 241 | 242 |
| 79 | 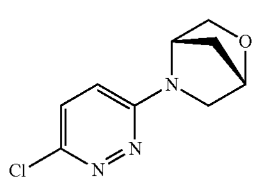 [SMILES: Clc1ccc(N2C[C@@H]3C[C@H]2CO3)nn1] | (1S,4S)-5-(6-Chloro-pyridazin-3-yl)-2-oxa-5-aza-bicyclo[2.2.1]heptane | [141-30-0], [547716-11-0] | P3 | 211 | 212 |
| 80 | 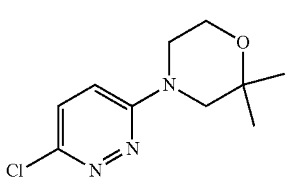 | 4-(6-Chloro-pyridazin-3-yl)-2,2-dimethyl-morpholine | [141-30-0], [147688-58-2] | P3 | 227 | 228 |
| 81 | 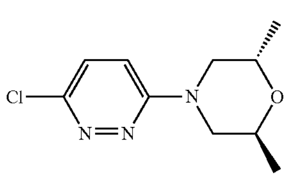 | (rel)-(2S,6S)-4-(6-Chloro-pyridazin-3-yl)-2,6-dimethyl-morpholine | [141-30-0], [6485-45-6] | P3 | 227 | 228 |

TABLE II-continued

Intermediates towards illustrative compounds of the invention

| Int | Structure | Name | SM | Method | MW | Mes |
|---|---|---|---|---|---|---|
| 82 | 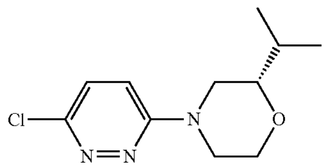 [SMILES: CC(C)[C@H]1CN(c2ccc(Cl)nn2)CCO1] | (S)-4-(6-Chloro-pyridazin-3-yl)-2-isopropyl-morpholine | [141-30-0], [1286768-31-7] | P3 | 241 | 242 |
| 83 | 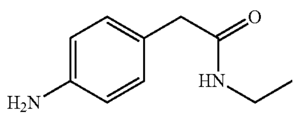 | 2-(4-Amino-phenyl)-N-ethyl-acetamide | [1197-55-3], [75-04-7] | Exemplified | 178 | 179 |
| 84 | 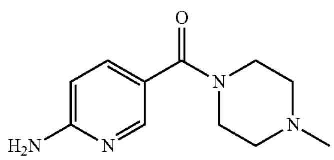 [SMILES: CN1CCN(C(=O)c2ccc(N)nc2)CC1] | 6-amino-pyridin-3-yl)-(4-methyl-piperazin-1-yl)-methanone | [3167-49-5], [109-01-3] | Exemplified | 220 | 221 |
| 85 | 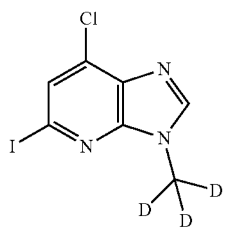 [SMILES: [2H]C([2H])([2H])n1cnc2c(Cl)cc(I)nc21] | 7-chloro-5-iodo-3-(trideuteriomethyl)imidazo[4,5-b]pyridine | [2587-02-2] | Exemplified | 297 | 297 |
| 86 | 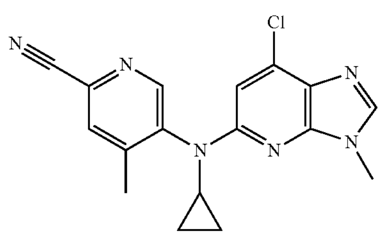 [SMILES: Cc1cc(C#N)ncc1N(c1cc(Cl)c2ncn(C)c2n1)C1CC1] | 5-[(7-chloro-3-methyl-imidazo[4,5-b]pyridin-5-yl)-cyclopropyl-amino]-4-methyl-pyridine-2-carbonitrile | Int 4, [411235-57-9] | Exemplified | 339 | 340 |
| 87 | 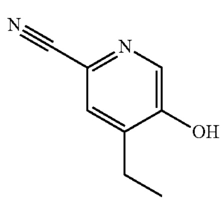 | 4-ethyl-5-hydroxy-pyridine-2-carbonitrile | Int 20 | Exemplified | 148 | 149 |
| 88 | 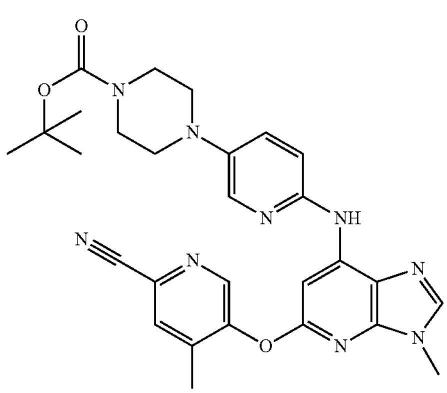 [SMILES: Cc1cc(C#N)ncc1Oc1cc(Nc2ccc(N3CCN(C(=O)OC(C)(C)C)CC3)cn2)c2ncn(C)c2n1] | Tert-butyl4-[6-[[5-[(6-cyano-4-methyl-3-pyridyl)oxy]-3-methyl-imidazo[4,5-b]pyridin-7-yl]amino]-3-pyridyl]piperazine-1-carboxylate | Int 2, [571188-59-5] | B1 | 542 | 543 |

TABLE II-continued

Intermediates towards illustrative compounds of the invention

| Int | Structure | Name | SM | Method | MW | Mes |
|---|---|---|---|---|---|---|
| 89 | 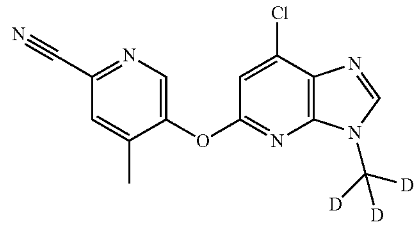 [SMILES: [2H]C([2H])([2H])n1cnc2c(Cl)cc(Oc3cnc(C#N)cc3C)nc21] | 5-[7-chloro-3-(trideuteriomethyl)imidazo[4,5-b]pyridin-5-yl]oxy-4-methyl-pyridine-2-carbonitrile | Int 85, Int 21 | Exemplified | 303 | 303 |
| 90 | 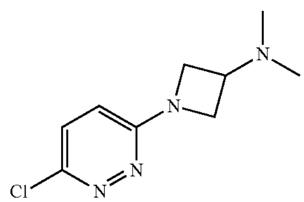 | 1-(6-chloropyridazin-3-yl)-N,N-dimethyl-azetidin-3-amine | [141-30-0], [935670-07-8] | P3 | 213 | 213 |
| 91 | 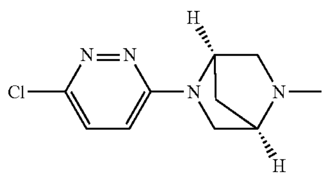 | (1R,4R)-2-(6-Chloro-pyridazin-3-yl)-5-methyl-2,5-diaza-bicyclo[2.2.1]heptane | [141-30-0], [125224-64-8] | P3 | 224 | 225 |
| 92 | 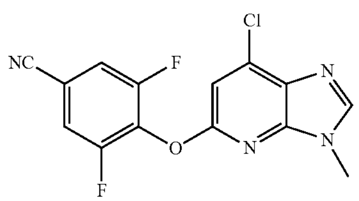 [SMILES: Cn1cnc2c(Cl)cc(Oc3c(F)cc(C#N)cc3F)nc21] | 4-(7-Chloro-3-methyl-3H-imidazo[4,5-b]pyridin-5-yloxy)-3,5-difluoro-benzonitrile | Int 57, [134227-45-5] | Exemplified | 321 | 321 |
| 93 | 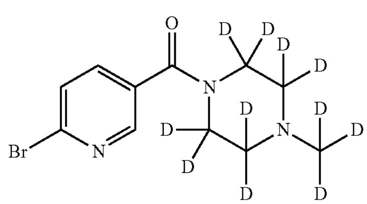 | (6-bromo-3-pyridyl)-[2,2,3,3,5,5,6,6-octadeuterio-4-(trideuteriomethyl)piperazin-1-yl]methanone | [1126621-86-0], [6311-35-9] and [865-50-9] | Exemplified | 295 | 295-297 |

Illustrative Examples

Compound 1: N-[3-Methyl-5-(4-methyl-6-trifluoromethyl-pyridin-3-yloxy)-3H-imidazo[4,5-b]pyridin-7-yl]-pyrimidine-4,6-diamine

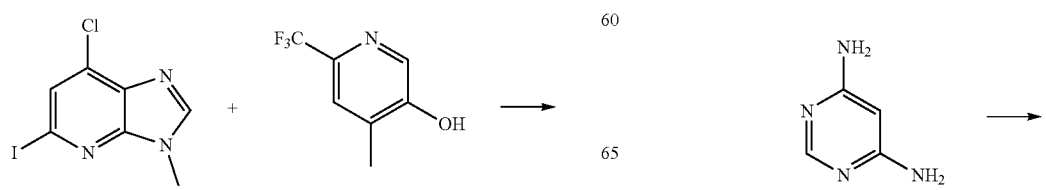

-continued

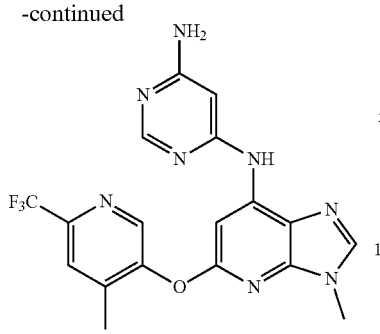

Step 1: 7-Chloro-3-methyl-5-(4-methyl-6-trifluoromethyl-pyridin-3-yloxy)-3H-imidazo[4,5-b]pyridine Intermediate 1 (110 mg, 0.377 mmol, 1.0 eq), 4-Methyl-6-trifluoromethyl-pyridin-3-ol (CAS [1253790-72-5], 100 mg, 0.565 mmol, 1.5 eq), CuI (7 mg, 0.038 mmol, 0.1 eq), TMHD [1118-71-4] (78 µL, 0.377, 1.0 eq) and Cs$_2$CO$_3$ (246 mg, 0.754 mmol, 2.0 eq) were mixed together under air, dry DMF (1 mL) was added and the mixture was stirred at 85° C. overnight. After cooling down to room temperature, the mixture was filtered over pall-seitz thick filter paper. The resulting cake was washed with EtOAc. The obtained filtrate was washed with H$_2$O. Aqueous layer was extracted with EtOAc. Combined organic layers were washed with brine, dried over MgSO$_4$, filtered and concentrated to dryness. Crude material was purified by column chromatography (EtOAc/DCM, gradient of 20% till 60% EtOAc) to afford the desired product. LCMS: m/z=343 [M+H]$^+$.

Step 2: N-[3-Methyl-5-(4-methyl-6-trifluoromethyl-pyridin-3-yloxy)-3H-imidazo[4,5-b]pyridin-7-yl]-pyrimidine-4,6-diamine 7-Chloro-3-methyl-5-(4-methyl-6-trifluoromethyl-pyridin-3-yloxy)-3H-imidazo[4,5-b]pyridine (40 mg, 0.117 mmol, 1.0 eq), Pyrimidine-4,6-diamine (CAS [79364-63-9], 26 mg, 0.234 mmol, 2.0 eq), MorDALPhos Pd G3 (2 mg, 0.002 mmol, 0.02 eq), MorDALPhos (1 mg, 0.002 mmol, 0.02 eq), Cs$_2$CO$_3$ (46 mg, 0.140 mmol, 1.2 eq) were mixed together under N$_2$ after which 1,4-dioxane (1 mL) was added. The resulting mixture was stirred at 110° C. After one night, it was cooled down to room temperature. The mixture was diluted with 2 mL of DMSO and purified preparative-HPLC to afford the desired product.
LCMS: m/z=417 [M+H]$^+$.

Compound 2: N-[5-(2-Fluoro-4-methanesulfonyl-6-methyl-phenoxy)-3-methyl-3H-imidazo[4,5-b]pyridin-7-yl]-pyrimidine-4,6-diamine

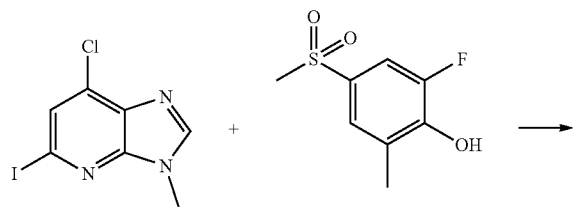

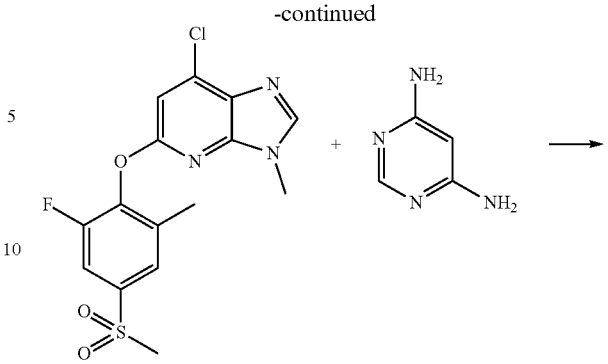

Step 1: 7-Chloro-5-(2-fluoro-4-methanesulfonyl-6-methyl-phenoxy)-3-methyl-3H-imidazo[4,5-b]pyridine Intermediate 1 (957 mg, 3.27 mmol, 1.0 eq), intermediate 23 (1.0 g, 4.90 mmol, 1.5 eq), CuI (62 mg, 0.327 mmol, 0.1 eq), TMHD (CAS [1118-71-4], 681 µL, 3.27,1.0 eq) and Cs$_2$CO$_3$ (2.13 g, 6.54 mmol, 2.0 eq) were mixed together under air, dry DMF (10 mL) was added and the mixture was stirred at 85° C. After one week, it was cooled down to room temperature and filtered over pall-seitz thick filter paper. The resulting cake was washed with EtOAc. The obtained filtrate was washed with H$_2$O. Aqueous layer was extracted with EtOAc. Combined organic layers were washed with brine, dried over MgSO$_4$, filtered and concentrated to dryness. Crude material was purified by column chromatography (EtOAc//DCM, 10% till 100% EtOAc) to afford the desired product.

Step 2: N-[5-(2-Fluoro-4-methanesulfonyl-6-methyl-phenoxy)-3-methyl-3H-imidazo[4,5-b]pyridin-7-yl]-pyrimidine-4,6-diamine 7-Chloro-5-(2-fluoro-4-methanesulfonyl-6-methyl-phenoxy)-3-methyl-3H-imidazo[4,5-b]pyridine (50 mg, 0.136 mmol, 1.0 eq), Pyrimidine-4,6-diamine (CAS [79364-63-9], 30 mg, 0.271 mmol, 2.0 eq), MorDALPhos Pd G3 (2 mg, 0.002 mmol, 0.02 eq), MorDALPhos (1 mg, 0.002 mmol, 0.02 eq) and Cs$_2$CO$_3$ (53 mg, 0.163 mmol, 1.2 eq) were mixed together under N2,1,4-dioxane (1 mL) was added. The resulting mixture was stirred at 110° C. After one night, it was cooled down to room temperature. The mixture was diluted with 2 mL of DMSO and purified preparative-HPLC to afford the desired product. LCMS: m/z=444 [M+H]$^+$.

Compound 3: 6-[7-(6-Amino-pyrimidin-4-ylamino)-3-methyl-3H-imidazo[4,5-b]pyridin-5-yloxy]-5-methyl-pyridazine-3-carbonitrile

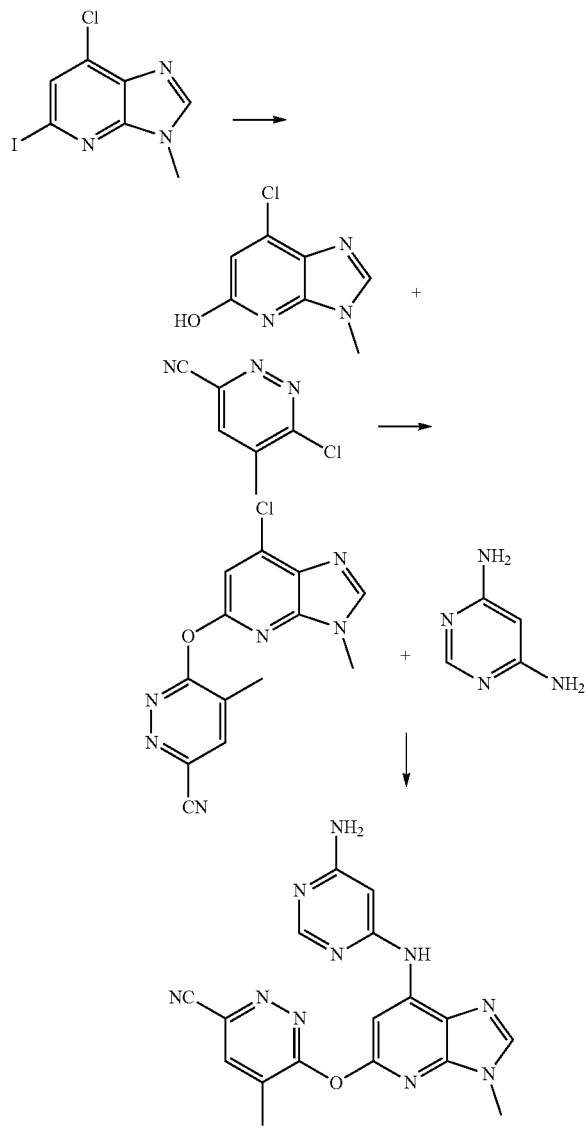

Step 1: 7-Chloro-3-methyl-3H-imidazo[4,5-b]pyridin-5-ol

Intermediate 1 (6.0 g, 20.48 mmol, 1.0 eq), tBuBrettPhos Pd G3 (348 mg, 0.410 mmol, 0.02 eq) and CsOH monohydrate (10.08 g, 61.44 mmol, 3.0 eq) were mixed in 1,4-dioxane (40 mL) and H$_2$O (3.68 mL, 204.80 mmol, 10 eq) was added. The mixture was mechanically stirred at room temperature. After one night, reaction mixture was quenched with H$_2$O and impurities were extracted with EtOAc. Aqueous layer was acidified to pH=5 and extracted with EtOAc. Organic layer was dried over MgSO$_4$, filtered and concentrated to dryness to afford the desired product. LCMS: m/z=184 [M+H]$^+$.

Step 2: 6-(7-Chloro-3-methyl-3H-imidazo[4,5-b]pyridin-5-yloxy)-5-methyl-pyridazine-3-carbonitrile 7-Chloro-3-methyl-3H-imidazo[4,5-b]pyridin-5-ol (500 mg, 2.73 mmol, 1.0 eq), 6-Chloro-5-methyl-pyridazine-3-carbonitrile (627 mg, 4.10 mmol, 1.5 eq) and K$_2$CO$_3$ (566 mg, 4.10 mmol, 1.5 eq) were mixed together under N$_2$. Next, dry DMF (8 mL) was added and the mixture was stirred at 100° C. After 3 h, it was cooled down to room temperature and quenched with H$_2$O to give rise to a suspension. Filtration gave a solid that was washed with H$_2$O then dried in the vacuum oven to afford the desired product. LCMS: m/z=301 [M+H]$^+$.

Step 3: 6-[7-(6-Amino-pyrimidin-4-ylamino)-3-methyl-3H-imidazo[4,5-b]pyridin-5-yloxy]-5-methyl-pyridazine-3-carbonitrile 6-(7-Chloro-3-methyl-3H-imidazo[4,5-b]pyridin-5-yloxy)-5-methyl-pyridazine-3-carbonitrile (50 mg, 0.167 mmol, 1.0 eq), Pyrimidine-4,6-diamine [79364-63-9] (37 mg, 0.333 mmol, 2.0 eq), Pd$_2$(dba)$_3$ (3 mg, 0.003 mmol, 0.02 eq), MorDALPhos (3 mg, 0.006 mmol, 0.04 eq) and Cs$_2$CO$_3$ (65 mg, 0.200 mmol, 1.2 eq) were mixed together under N$_2$, dioxane (1 mL) was added and the mixture was stirred at 110° C. After one night, it was cooled down to room temperature. The mixture was diluted with 2 mL of DMSO and purified preparative-HPLC to afford the desired product. LCMS: m/z=375 [M+H]$^+$.

Compound 4: 5-[[7-(6-Amino-pyrimidin-4-ylamino)-3-methyl-3H-imidazo[4,5-b]pyridin-5-yl]-(3-methoxy-propyl)-amino]-4-methyl-pyridine-2-carbonitrile

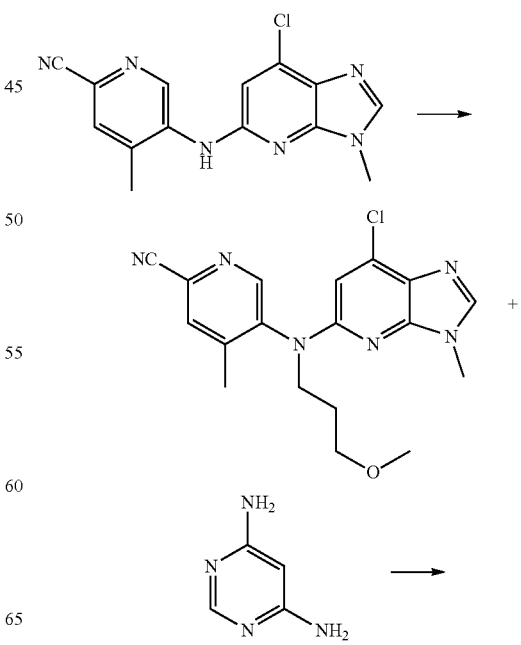

-continued

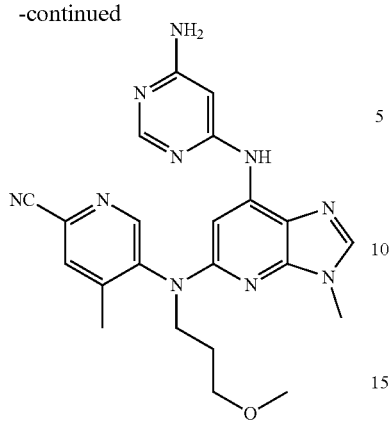

Step 1: 5-[(7-Chloro-3-methyl-3H-imidazo[4,5-b]pyridin-5-yl)-(3-methoxy-propyl)-amino]-4-methyl-pyridine-2-carbonitrile To a solution of intermediate 4 (150 mg, 0.48 mmol, 1.0 eq) and $Cs_2CO_3$ (186 mg, 0.57 mmol, 1.2 eq) in dry DMF (3 mL) under $N_2$ was added 1-bromo-3-methoxypropane (CAS [36865-41-5], 147 mg, 0.96 mmol, 2.0 eq). The mixture was stirred at 50° C. for 3 h. It was then cooled down to room temperature and quenched with $H_2O$. Compound was extracted with EtOAc. Organic layer was washed with brine, dried over $MgSO_4$, filtered and concentrated to dryness. Crude was purified by column chromatography (MeOH/DCM, 2% MeOH) to afford the desired product. LCMS: m/z=371 $[M+H]^+$.

Step 2: 5-[[7-(6-Amino-pyrimidin-4-ylamino)-3-methyl-3H-imidazo[4,5-b]pyridin-5-yl]-(3-methoxy-propyl)-amino]-4-methyl-pyridine-2-carbonitrile 5-[(7-Chloro-3-methyl-3H-imidazo[4,5-b]pyridin-5-yl)-(3-methoxy-propyl)-amino]-4-methyl-pyridine-2-carbonitrile (113 mg, 0.30 mmol, 1.0 eq), Pyrimidine-4,6-diamine (CAS [79364-63-9], 66 mg, 0.60 mmol, 2.0 eq), $Pd_2(dba)_3$ (5 mg, 0.006 mmol, 0.02 eq), MorDALPhos (5 mg, 0.012 mmol, 0.04 eq) and $Cs_2CO_3$ (117 mg, 0.36 mmol, 1.2 eq) were mixed together under $N_2$ after which 1.4-dioxane (2 mL) was added and the mixture was stirred at 110° C. After one night, it was cooled down to room temperature and DMSO (1 mL) was added. Mixture was filtered and purified by preparative HPLC to afford the desired product. LCMS: m/z=445 $[M+H]^+$.

Compound 5: 5-[[7-(6-Amino-pyrimidin-4-ylamino)-3-methyl-3H-imidazo[4,5-b]pyridin-5-yl]-(3-hydroxy-propyl)-amino]-4-methyl-pyridine-2-carbonitrile

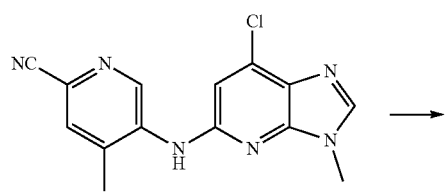

-continued

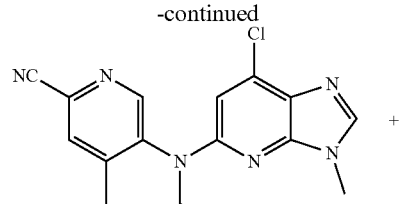

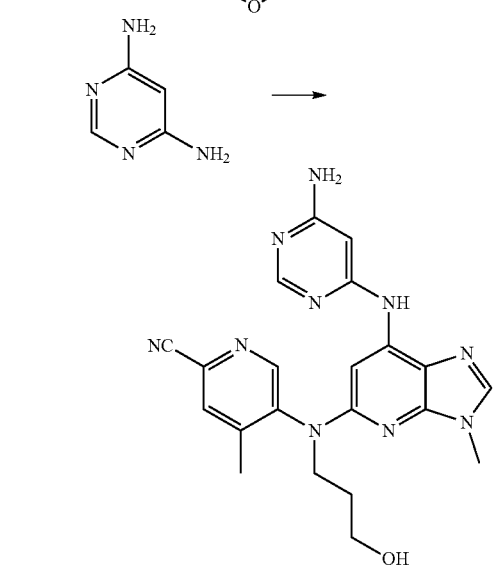

Step 1: 5-[[3-(tert-Butyl-dimethyl-silanyloxy)-propyl]-(7-chloro-3-methyl-3H-imidazo[4,5-b]pyridin-5-yl)-amino]-4-methyl-pyridine-2-carbonitrile To a solution of intermediate 4 (100 mg, 0.33 mmol, 1.0 eq) in dry DMF (1 mL) under $N_2$ was added LHMDS (1M in THF, 390 µL, 0.39 mmol, 1.2 eq). The mixture was stirred at room temperature for 5 min then 3-bromopropoxy-tert-butyl-dimethyl-silane(CAS [89031-84-5], 98 mg, 0.39 mmol, 1.2 eq) was added and the mixture was stirred at 50° C. for 3 h. It was then cooled down to room temperature and quenched with $H_2O$. The mixture was extracted with EtOAc. Organic layer was washed with brine, dried over $MgSO_4$, filtered and concentrated to dryness. Crude was purified by column chromatography (EtOAc/petroleum ether, 6:4) to afford the desired product. LCMS: m/z=471 $[M+H]^+$.

Step 2: 5-[[7-(6-Amino-pyrimidin-4-ylamino)-3-methyl-3H-imidazo[4,5-b]pyridin-5-yl]-(3-hydroxy-propyl)-amino]-4-methyl-pyridine-2-carbonitrile 5-[[3-(tert-Butyl-dimethyl-silanyloxy)-propyl]-(7-chloro-3-methyl-3H-imidazo[4,5-b]pyridin-5-yl)-amino]-4-methyl-pyridine-2-carbonitrile (102 mg, 0.217 mmol, 1.0 eq), Pyrimidine-4,6-diamine (CAS [79364-63-9], 48 mg, 0.434 mmol, 2.0 eq), $Pd_2(dba)_3$ (4 mg, 0.046 mmol, 0.02 eq), MorDALPhos (4 mg, 0.08 mmol, 0.04 eq) and $Cs_2CO_3$ (85 mg, 0.26 mmol, 1.2 eq) were mixed together under $N_2$ after which 1,4-dioxane (2 mL) was added. Next, the mixture was stirred at 110° C. during overnight. After letting the mixture cool down till room temperature, DMSO (1 mL) and TBAF (1M in THF, 0.6 mL, 0.6 mmol, 2.8 eq) were added. The mixture was stirred for 10 min at room temperature. Reaction mixture was then filtered and purified by preparative HPLC to afford the desired product. LCMS: m/z=431 [M+H]+.

Compound 6: 4-methyl-5-[3-methyl-7-[[5-[4-(trideuteriomethyl)piperazine-1-carbonyl]pyridin-2-yl]amino]imidazo[4,5-b]pyridin-5-yl]oxypyridine-2-carbonitrile

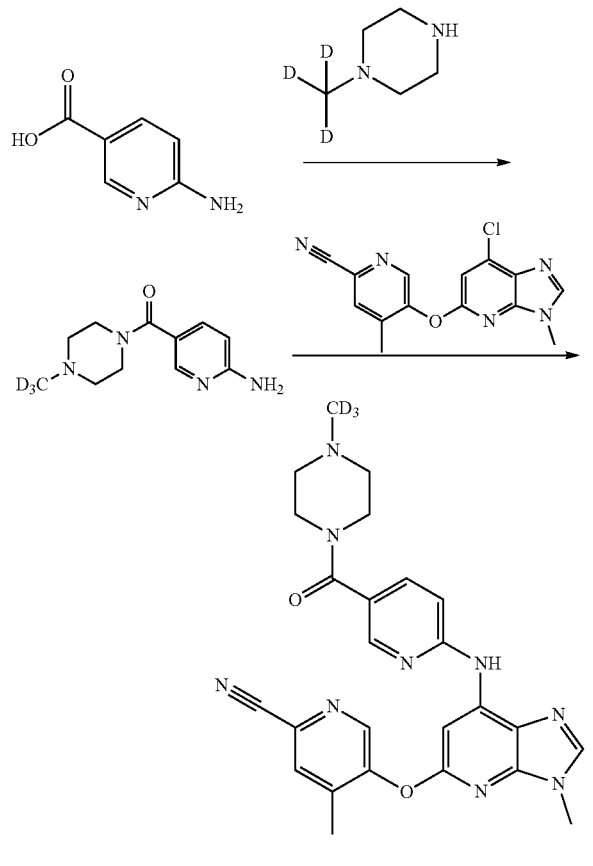

Step 1: (6-Amino-pyridin-3-yl)-(4-trideuteriomethyl-piperazin-1-yl)-methanone

6-Amino-nicotinic acid (CAS [3167-49-5], 447 mg, 3.236 mmol, 1.0 eq), N-methyl-D3-piperazine (CAS [1093380-08-5], 444 µL, 3.883, 1.2 eq) and DIPEA (1.24 mL, 7.119 mmol, 2.2 eq) were stirred in dry EtOH (5 mL) after which HATU (1.844 g, 4.854 mmol, 1.5 eq) was added. The mixture was stirred at room temperature for 18 h. It was then concentrated to dryness and redissolved in DCM. A precipitate formed and was filtered. Filtrate was purified by column chromatography using DCM/EtOH/25% aqueous NH3 (7/1/0.1) as eluent to obtain the desired product.

Step 2: 4-methyl-5-[3-methyl-7-[[5-[4-(trideuteriomethyl)piperazine-1-carbonyl]pyridin-2-yl]amino]imidazo[4,5-b]pyridin-5-yl]oxypyridine-2-carbonitrile Intermediate 2 (201 mg, 0.673 mmol, 1.0 eq), (6-Amino-pyridin-3-yl)-(4-trideuteriomethyl-piperazin-1-yl)-methanone (150 mg, 0.673 mmol, 1.0 eq), Pd2Cl2(allyl)2 (5 mg, 0.013 mmol, 0.02 eq), MorDALPhos (12 mg, 0.026 mmol, 0.04 eq) and Cs2CO3 (263 mg, 0.808 mmol, 1.2 eq) were mixed together under N after which 1,4-dioxane (3 mL) was added. The mixture was stirred at 110° C. After one night, it was cooled down to room temperature followed by the addition of 0.5 mL of DMSO. Mixture was filtered and filtrate was purified by preparative HPLC to afford the desired product. LCMS: m/z=487 [M+H]+.

Compound 7: 4-Ethyl-5-{3-methyl-7-[5-(morpholine-4-carbonyl)-pyridin-2-ylamino]-3H-imidazo[4,5-b]pyridin-5-yloxy}-pyridine-2-carbonitrile

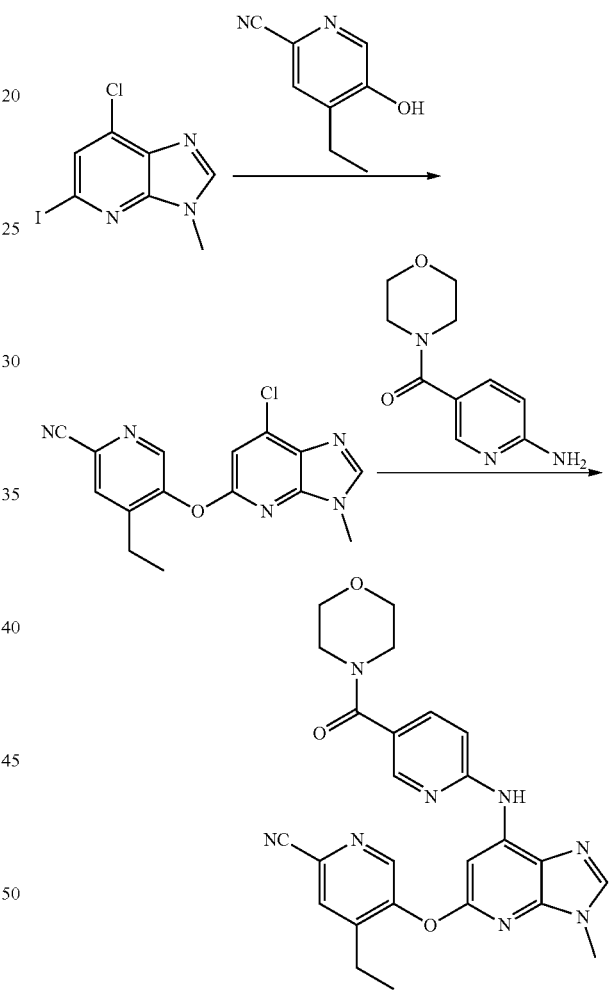

Step 1: 5-(7-Chloro-3-methyl-3H-imidazo[4,5-b]pyridin-5-yloxy)-4-ethyl-pyridine-2-carbonitrile Intermediate 1 (215 mg, 0.733 mmol, 1.0 eq), 4-Ethyl-5-hydroxy-pyridine-2-carbonitrile (Int 87, 141 mg, 0.953 mmol, 1.3 eq), CuI (28 mg, 0.147 mmol, 0.2 eq), TMHD (CAS [1118-71-4],305 µL, 1.466 mmol, 2.0 eq) and Cs2CO3 (478 g, 1.466 mmol, 2.0 eq) were mixed together under air, solvent was added and the mixture was stirred at 85° C. After 48 h, it was cooled down to room temperature and quenched with 10% aq. TMEDA solution and compound was extracted with EtOAc. Organic layer was washed with brine, dried over MgSO₄, filtered and concentrated to dryness. Crude material was purified by column chromatography (EtOAc/DCM, 7:3) to afford the desired product. LCMS: m/z=314 [M+H]+.

Step 2: 4-Ethyl-5-{3-methyl-7-[5-(morpholine-4-carbonyl)-pyridin-2-ylamino]-3H-imidazo[4,5-b]pyridin-5-yloxy}-pyridine-2-carbonitrile 5-(7-Chloro-3-methyl-3H-imidazo[4,5-b]pyridin-5-yloxy)-4-ethyl-pyridine-2-carbonitrile (82 mg, 0.263 mmol, 1.0 eq), 5-[(morpholin-4-yl)carbonyl]pyridin-2-amine (CAS [827587-90-6], 55 mg, 0.263 mmol, 1.0 eq), MorDALPhos Pd G3 (CAS [6035-47-8], 5 mg, 0.005 mmol, 0.02 eq), MorDALPhos (CAS [1237588-12-3] (2 mg, 0.005 mmol, 0.02 eq) and Cs₂CO₃ (103 mg, 0.316 mmol, 1.2 eq) were mixed together under N2 after which 1,4-dioxane (1 mL) was added and the mixture was stirred at 110° C. After one night, the mixture was allowed to cool down till room temperature and was then diluted with 2 mL of DMSO. Resulting mixture was filtered and filtrate was purified by preparative HPLC to afford the desired product. LCMS: m/z=485 [M+H]+.

Compound 79 and 80: 5-[7-[[5-[1-(dimethylamino)-2,2,2-trifluoroethyl]pyridin-2-yl]amino]-3-methylimidazo[4,5-b]pyridin-5-yl]oxy-4-methylpyridine-2-carbonitrile and 5-[7-[[5-[1-(ethylamino)-2,2,2-trifluoroethyl]pyridin-2-yl]amino]-3-methylimidazo[4,5-b]pyridin-5-yl]oxy-4-methylpyridine-2-carbonitrile

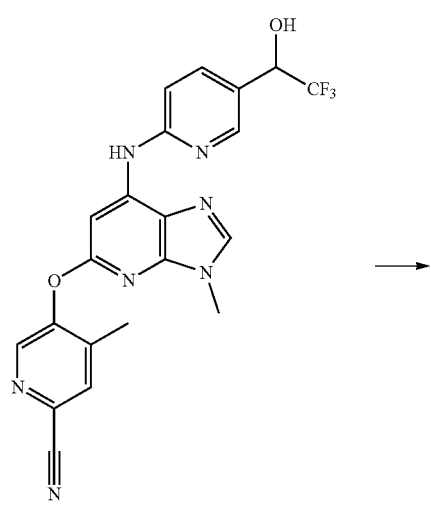

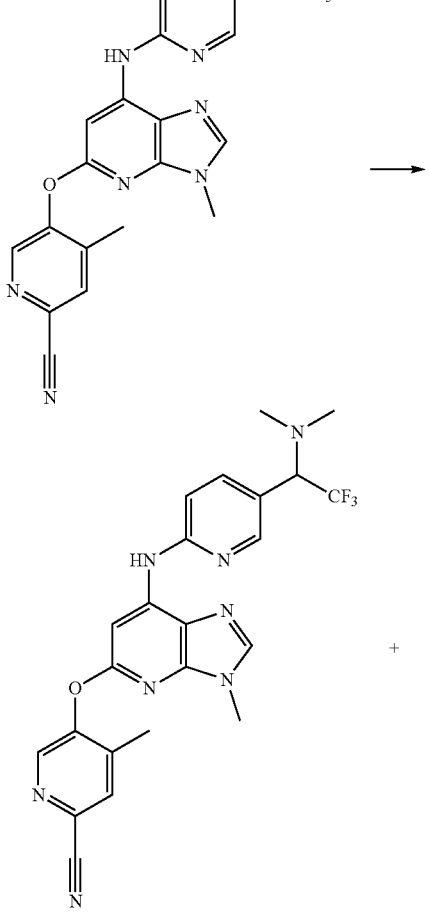

Compound 79

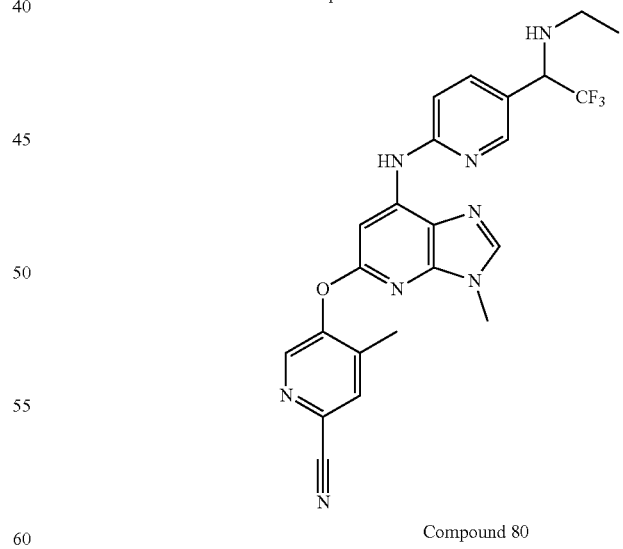

Compound 80

Step 1: A solution of Int 49 (75 mg, 0.16 mmol, 1.0 eq) and Et₃N (46 µL, 0.33 mmol, 2.0 eq) in anhydrous DCM (1 mL, 0.2 M) was cooled to 0° C. under N₂. MsCl (CAS [124-63-0], 25 µL, 0.33 mmol, 2.0 eq) in 0.1 mL of anhydrous DCM was added dropwise and the mixture was allowed to warm to room temperature. After 1 h, the reaction was diluted with DCM (5 mL) and quenched with saturated aqueous NaHCO₃ (5 mL). The organic layer was washed with brine (5 mL), dried and evaporated in vacuo to afford the desired product which was used as such. MS m/z 474/476 (75/25%).

Step 2: 5-[7-[[5-(1-chloro-2,2,2-trifluoro-ethyl)-2-pyridyl]amino]-3-methyl-imidazo[4,5-b]pyridin-5-yl]oxy-4-methyl-pyridine-2-carbonitrile (31 mg, 0.066 mmol, 1.0 eq), Me₂NH₂Cl (53 mg, 0.66 mmol, 10 eq) and K₂CO₃ (182 mg, 1.32 mmol, 20 eq) were mixed together in anhydrous DMF (0.3 mL). The mixture was stirred for 1 h at 80° C. under N₂ atmosphere. Next, the reaction mixture was diluted with water (5 mL) and extracted with EtOAc (2×5 mL). The combined organic extracts were dried and evaporated in vacuo. The residue was dissolved in MeOH, filtered purified by preparative HPLC to afford the desired products. LCMS 79: m/z=483 [M+H]⁺; LCMS 80: m/z=483 [M+H]⁺.

Compound 187: 5-[[7-[(6-aminopyrimidin-4-yl)amino]-3-methyl-imidazo[4,5-b]pyridin-5-yl]-(2-hydroxypropyl)amino]-4-methyl-pyridine-2-carbonitrile

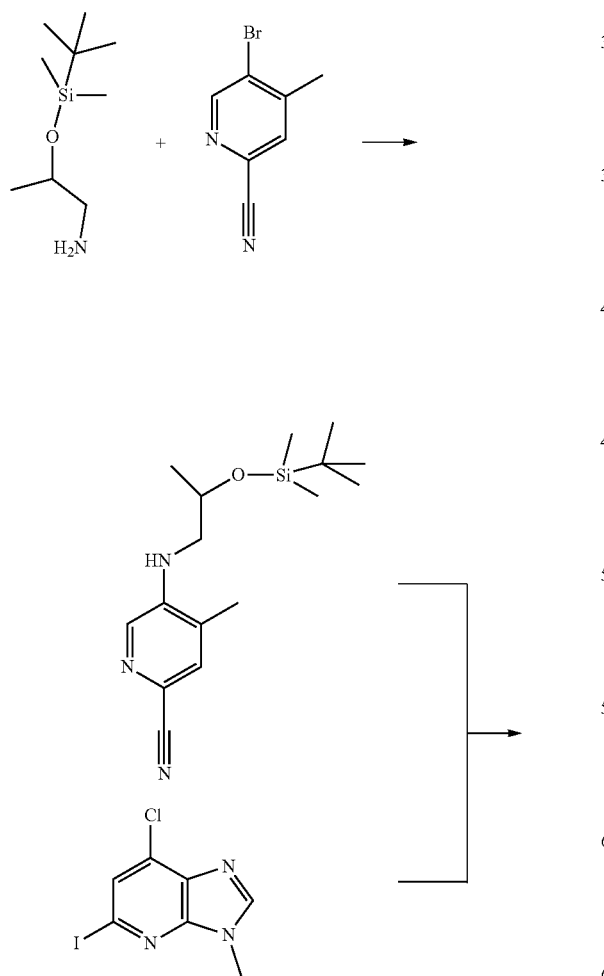

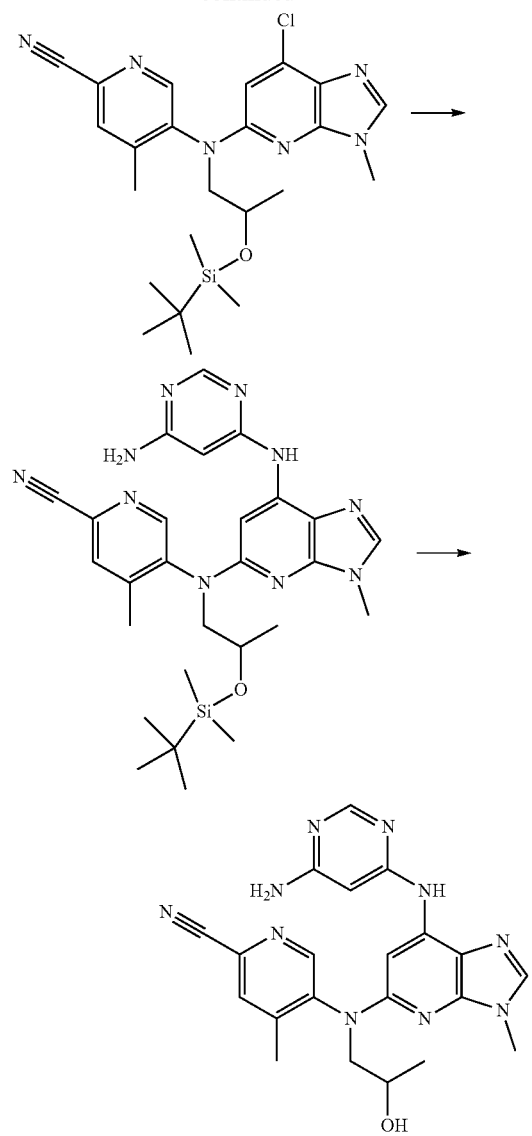

Step 1: 5-[2-[tert-butyl(dimethyl)silyl]oxypropylamino]-4-methyl-pyridine-2-carbonitrile In a 5 mL vial, 2-[tert-butyl(dimethyl)silyl]oxypropylamine (CAS [1789680-15-4], 380 mg, 2 mmol, 2.0 eq), 2-cyano-4-methyl-5-bromopyridine (CAS [886364-86-9], 200 mg, 1 mmol, 1.0 eq), XantPhosPd G3 (CAS [1445085-97-1], 29 mg, 0.03 mmol, 0.03 eq), XantPhos (CAS [161265-03-8], 17.5 mg, 0.03 mmol, 0.03 eq), and Cs₂CO₃ (975 mg, 3.0 mmol, 3.0 eq) were added. Dry 1,4-dioxane (3 mL) was added and the mixture was brought under N₂ and degassed. The mixture was stirred overnight at 70° C. Water and ethyl acetate were added, after shaking, the water layer was separated. The organic layer was washed once more with water. The precipitate in the organic layer was filtered away. The organic layer was dried over MgSO₄, filtered and evaporated. Purification column chromatogratography 5- to 25% of EtOAc in PE afforded the desired product (200 mg, yield 33%). LCMS: m/z=306 [M+H]⁺.

Step 2: 5-[2-[tert-butyl(dimethyl)silyl]oxypropyl-(7-chloro-3-methyl-imidazo[4,5-b]pyridin-5-yl)amino]-4-methyl-pyridine-2-carbonitrile In a 5 mL vial, 5-[2-[tert-butyl(dimethyl)silyl]oxypropylamino]-4-methyl-pyridine-2-carbonitrile (50 mg, 0.16 mmol, 1.0 eq), Int 1 (48 mg, 0.16 mmol, 1.0 eq), Pd2dba3 (15 mg, 0.016 mmol, 0.1 eq), P(tBu)₃·HBF₄ (9.3 mg, 0.032 mmol, 0.2 eq) and NaOtBu (16 mg, 0.192 mmol, 1.2 eq) were added. Dry toluene was added and the mixture was brought under N₂. It was degassed and stirred for 5 h at 110° C. Water and ethyl acetate were added, the mixture was filtered over celite. The layers were separated and the organic layer was dried over MgSO₄, filtered and evaporated. Crude was purified with column chromatography using an eluent from 5% EtOAc to 70% EtOAc in PE to afford the desired product. LCMS: m/z=471 [M+H]⁺.

Step 3: 5-[[7-[(6-aminopyrimidin-4-yl)amino]-3-methyl-imidazo[4,5-b]pyridin-5-yl]-[2-[tert-butyl(dimethyl)silyl]oxypropyl]amino]-4-methyl-pyridine-2-carbonitrile In a 5 mL vial, 5-[2-[tert-butyl(dimethyl)silyl]oxypropyl-(7-chloro-3-methyl-imidazo[4,5-b]pyridin-5-yl)amino]-4-methyl-pyridine-2-carbonitrile (50 mg, 0.22 mmol, 1 eq), 4,6-diaminopyrimidine (49 mg, 0.44 mmol, 2 eq), MorDalPhos Pd G3 (18 mg, 0.022 mmol, 0.1 eq), MorDalPhos (10 mg, 0.022 mmol, 0.1 eq) and Cs₂CO₃ (143 mg, 0.44 mmol, 2 eq) were added. Anhydrous 1,4-dioxane was added, the mixture was brought under N₂ and degassed. It was subsequently stirred at 110° C. for 2 h. The mixture was cooled to room temperature, water and ethyl acetate were added, the layers were separated and the water layer was washed with EtOAc. The combined organic layers were dried over sodium sulphate, filtered and evaporated to give the desired product which was used as such. LCMS (M+1): 545.3

Step 4: 5-[[7-[(6-aminopyrimidin-4-yl)amino]-3-methyl-imidazo[4,5-b]pyridin-5-yl]-(2-hydroxypropyl)amino]-4-methyl-pyridine-2-carbonitrile A 1 M solution of TBAF in THF (0.2 mL, 0.2 mmol, 2 eq) was added to a solution of 5-[[7-[(6-aminopyrimidin-4-yl)amino]-3-methyl-imidazo[4,5-b]pyridin-5-yl]-[2-[tert-butyl(dimethyl)silyl]oxypropyl]amino]-4-methyl-pyridine-2-carbonitrile (50 mg, 0.1 mmol, 1 equiv) in anhydrous THF (10 mL) at room temperature and the mixture was stirred overnight. The volatiles were evaporated and the mixture was purified by preparative chromatography to give the desired product. LCMS: m/z=431 [M+H]⁺.

Compound 38: 4-Methyl-5-[3-methyl-7-(6-morpholin-4-yl-pyridazin-3-ylamino)-3H-imidazo[4,5-b]pyridin-5-yloxy]-pyridine-2-carbonitrile

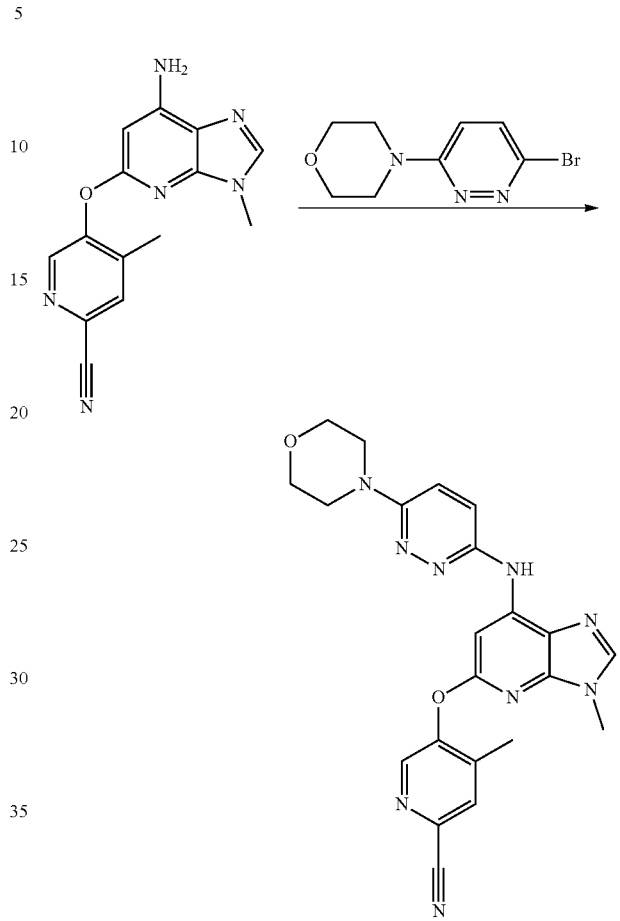

Route 1

Intermediate 3 (1.0 eq, 409 g, 1.459 moles) and 4-(6-bromopyridazin-3-yl)morpholine (CAS [66346-91-6], 1.1 eq, 392 g) were added to xylene mix of isomers (8 L) at room temperature. To the mixture was added, under stirring at room temperature, potassium phosphate tribasic (3.0 eq, 929 g). The reaction mixture was heated from room temperature to 135° C. in 2 h 30. Then a suspension of Pd(OAc)₂ (2 mol %, 6.6 g) and Xantphos (4 mol %, 33.8 g) in xylene (50 mL) was added to the hot mixture. The reaction was heated at reflux for 1 h 30. Then a suspension of Pd(OAc)₂ (2 mol %, 6.6 g) and Xantphos (4 mol %, 33.8 g) in xylenes (50 mL) was added and the reaction was heated at reflux for an additional 1 h 30. Then a suspension of Pd(OAc)₂ (2 mol %, 6.6 g) and Xantphos (4 mol %, 33.8 g) in xylenes (50 mL) was added one last time. The reaction was refluxed for an additional 1 h 30. The reaction mixture was cooled down to room temperature and stirred overnight. The suspension was filtered, washed with acetonitrile (5 L). The solid was washed with water (15 L) until obtaining a neutral pH, dried under suction, then suspended in acetonitrile (6.5 L) and stirred at room temperature for 1 h. The suspension was filtered, washed with acetonitrile (2 L) and dried. Chromatography on SiO₂ (1 g of SiO₂ for 1 g of crude) using eluent CHCl₃/acetone (70/30) and then CHCl₃/MeOH (96/4) afforded the desired product.

Route 2

Intermediate 3 (280 mg, 1 mmol, 1.0 eq), 4-(6-bromopyridazin-3-yl)morpholine (268 mg, 1.1 mmol, 1.1 eq) and CsCO₃ (977 mg, 3 mmol, 3 eq) are mixed under argon at room temperature and degassed tert-amyl alcohol or DMF (5 mL) is added. [Pd(cinnamyl)Cl]₂ (5.18 mg, 0.010 mmol, 0.01 eq) and JosiPhos (CAS[1702311-34-9]) (13 mg, 0.024 mmol, 0.024 eq) are added under argon either as solid or as pre-mixed solution in 1 mL degassed tert-amyl alcohol or DMF. The mixture is heated to 100° C. for at least 2 h.

The reaction mixture is then cooled to room temperature and acetonitrile is added. The suspension is filtered, the solid is triturated first with water then acetonitrile, and dried to afford the desired product.

TABLE III

Illustrative compounds of the invention

| Cpd # | Structure | Name | SM | Mtd | MW | Mes |
|---|---|---|---|---|---|---|
| 8 | 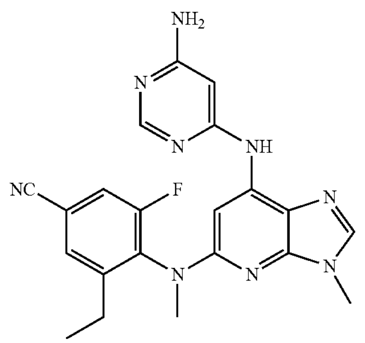 [SMILES: CCc1cc(C#N)cc(F)c1N(C)c1cc(Nc2cc(N)ncn2)c2ncn(C)c2n1] | 4-{[7-(6-Amino-pyrimidin-4-ylamino)-3-methyl-3H-imidazo[4,5-b]pyridin-5-yl]-methyl-amino}-3-ethyl-5-fluoro-benzonitrile | Int 16 | C1 | 417 | 418 |
| 9 | 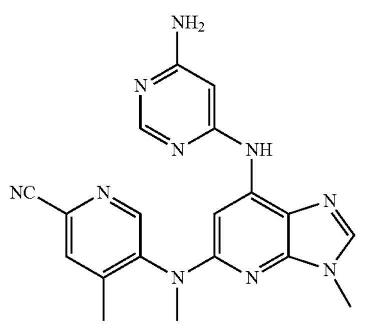 [SMILES: Cc1cc(C#N)ncc1N(C)c1cc(Nc2cc(N)ncn2)c2ncn(C)c2n1] | 5-{[7-(6-Amino-pyrimidin-4-ylamino)-3-methyl-3H-imidazo[4,5-b]pyridin-5-yl]-methyl-amino}-4-methyl-pyridine-2-carbonitrile | Int 4 | C2 | 386 | 387 |
| 10 | 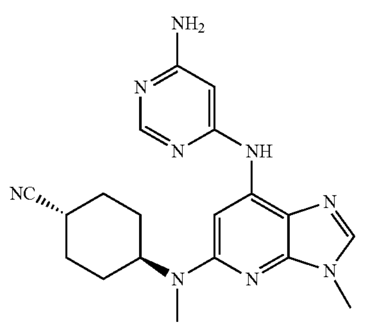 [SMILES: Cn1cnc2c(Nc3cc(N)ncn3)cc(N(C)[C@H]3CC[C@H](C#N)CC3)nc21] | 4-{[7-(6-Amino-pyrimidin-4-ylamino)-3-methyl-3H-imidazo[4,5-b]pyridin-5-yl]-methyl-amino}-cyclohexanecarbonitrile | Int 6 | C2 | 378 | 378 |
| 11 | 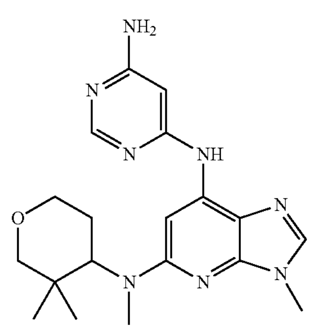 [SMILES: CN(c1cc(Nc2cc(N)ncn2)c2ncn(C)c2n1)C1CCOCC1(C)C] | N7-(6-Amino-pyrimidin-4-yl)-N5-(3,3-dimethyl-tetrahydro-pyran-4-yl)-3,N5-dimethyl-3H-imidazo[4,5-b]pyridine-5,7-diamine | Int 7 | C2 | 383 | 383 |

TABLE III-continued

Illustrative compounds of the invention

| Cpd # | Structure | Name | SM | Mtd | MW | Mes |
|---|---|---|---|---|---|---|
| 12 | 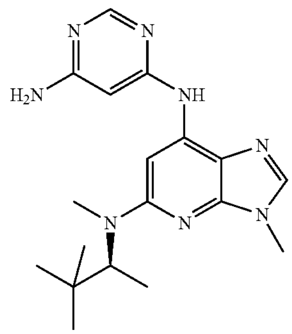 [SMILES: C[C@H](N(C)c1cc(Nc2cc(N)ncn2)c2ncn(C)c2n1)C(C)(C)C] | N7-(6-aminopyrimidin-4-yl)-N5,3-dimethyl-N5-[(1S)-1,2,2-trimethylpropyl]imidazo[4,5-b]pyridine-5,7-diamine | Int 33, [79364-63-9] | B1 | 355 | 355 |
| 13 | 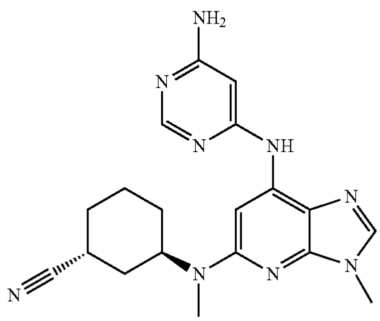 [SMILES: CN(c1cc(Nc2cc(N)ncn2)c2ncn(C)c2n1)[C@@H]1CCC[C@@H](C#N)C1] | (±)-(1R,3R)-3-{[7-(6-Amino-pyrimidin-4-ylamino)-3-methyl-3H-imidazo[4,5-b]pyridin-5-yl]-methyl-amino}-cyclohexanecarbonitrile | Int 9 | C2 | 378 | 378 |
| 14 | 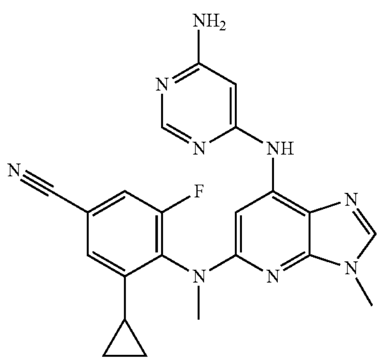 [SMILES: CN(c1cc(Nc2cc(N)ncn2)c2ncn(C)c2n1)c1c(F)cc(C#N)cc1C1CC1] | 4-{[7-(6-Amino-pyrimidin-4-ylamino)-3-methyl-3H-imidazo[4,5-b]pyridin-5-yl]-methyl-amino}-3-cyclopropyl-5-fluoro-benzonitrile | Int 10 | C2 | 430 | 430 |
| 15 | 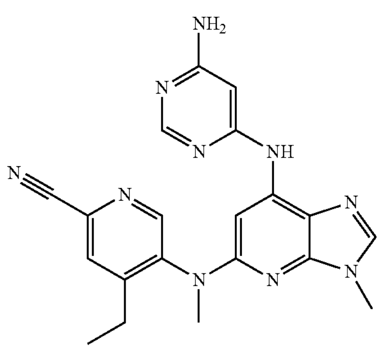 [SMILES: CCc1cc(C#N)ncc1N(C)c1cc(Nc2cc(N)ncn2)c2ncn(C)c2n1] | 5-{[7-(6-Amino-pyrimidin-4-ylamino)-3-methyl-3H-imidazo[4,5-b]pyridin-5-yl]-methyl-amino}-4-methyl-pyridine-2-carbonitrile | Int 11 | C2 | 400 | 401 |

TABLE III-continued

Illustrative compounds of the invention

| Cpd # | Structure | Name | SM | Mtd | MW | Mes |
|---|---|---|---|---|---|---|
| 16 | 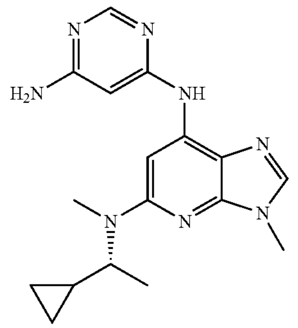 [SMILES: C[C@H](C1CC1)N(C)c1cc(Nc2cc(N)ncn2)c2ncn(C)c2n1] | N7-(6-aminopyrimidin-4-yl)-N5-[(1R)-1-cyclopropylethyl]-N5,3-dimethyl-imidazo[4,5-b]pyridine-5,7-diamine | Int 34, [79364-63-9] | B1 | 338 | 339 |
| 17 | 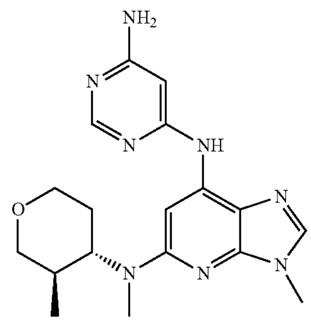 [SMILES: C[C@H]1COCC[C@@H]1N(C)c1cc(Nc2cc(N)ncn2)c2ncn(C)c2n1] | N7-(6-Amino-pyrimidin-4-yl)-3,N5-dimethyl-N5-((3R,4S)-3-methyl-tetrahydro-pyran-4-yl)-3H-imidazo[4,5-b]pyridine-5,7-diamine | Int 13 | C2 | 368 | 369 |
| 18 | 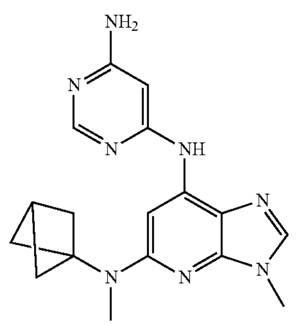 [SMILES: CN(c1cc(Nc2cc(N)ncn2)c2ncn(C)c2n1)C12CC(C1)C2] | N7-(6-Amino-pyrimidin-4-yl)-N5-bicyclo[1.1.1]pent-1-yl-3,N5-dimethyl-3H-imidazo[4,5-b]pyridine-5,7-diamine | Int 24 | C2 | 336 | 337 |
| 19 | 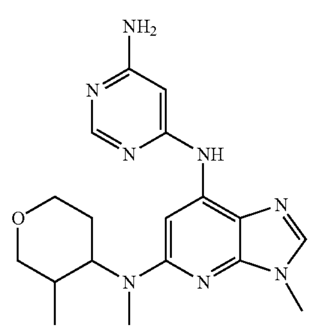 [SMILES: CC1COCCC1N(C)c1cc(Nc2cc(N)ncn2)c2ncn(C)c2n1] | N7-(6-Amino-pyrimidin-4-yl)-3,N5-dimethyl-N5-(3-methyl-tetrahydro-pyran-4-yl)-3H-imidazo[4,5-b]pyridine-5,7-diamine | Int 25 | C2 | 368 | 369 |

TABLE III-continued

Illustrative compounds of the invention

| Cpd # | Structure | Name | SM | Mtd | MW | Mes |
|---|---|---|---|---|---|---|
| 20 | 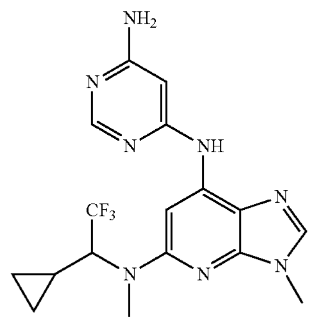 [SMILES: CN(c1cc(Nc2cc(N)ncn2)c2ncn(C)c2n1)C(C1CC1)C(F)(F)F] | N7-(6-Amino-pyrimidin-4-yl)-N5-(1-cyclopropyl-2,2,2-trifluoro-ethyl)-3,N5-dimethyl-3H-imidazo[4,5-b]pyridine-5,7-diamine | Int 26 | C2 | 392 | 393 |
| 21 | 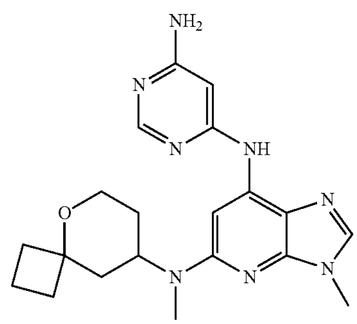 [SMILES: CN(c1cc(Nc2cc(N)ncn2)c2ncn(C)c2n1)C1CCOC2(CCC2)C1] | N7-(6-Amino-pyrimidin-4-y)-3,N5-dimethyl-N5-(5-oxa-spiro[3.5]non-8-yl)-3H-imidazo[4,5-b]pyridine-5,7-diamine | Int 27 | C2 | 395 | 395 |
| 22 | 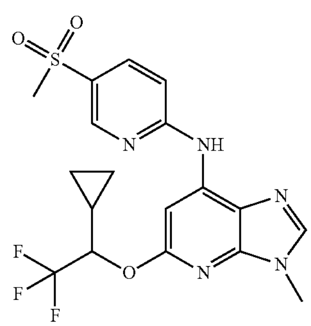 [SMILES: Cn1cnc2c(Nc3ccc(S(C)(=O)=O)cn3)cc(OC(C3CC3)C(F)(F)F)nc21] | 5-(1-cyclopropyl-2,2,2-trifluoro-ethoxy)-3-methyl-N-(5-methylsulfonyl-2-pyridyl)imidazo[4,5-b]pyridin-7-amine | Int 28, [35196-11-3] | B1 | 441 | 442 |
| 23 | 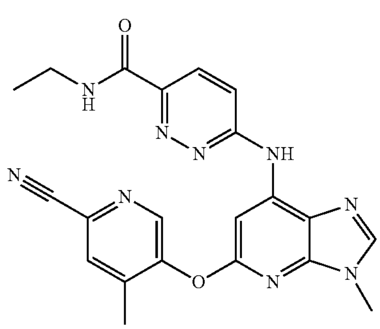 [SMILES: CCNC(=O)c1ccc(Nc2cc(Oc3cnc(C#N)cc3C)nc3c2ncn3C)nn1] | 6-[5-(6-Cyano-4-methyl-pyridin-3-yloxy)-3-methyl-3H-imidazo[4,5-b]pyridin-7-ylamino]-pyridazine-3-carboxylic acid ethylamide | Int 2, Int 29 | B1 | 429 | 430 |

TABLE III-continued

Illustrative compounds of the invention

| Cpd # | Structure | Name | SM | Mtd | MW | Mes |
|---|---|---|---|---|---|---|
| 24 | 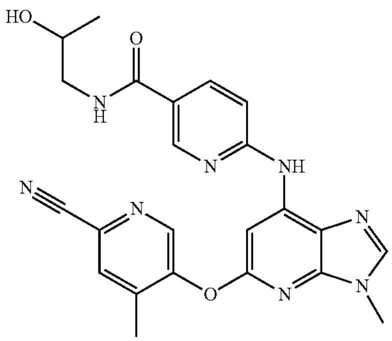 | 6-[5-(6-Cyano-4-methyl-pyridin-3-yloxy)-3-methyl-3H-imidazo[4,5-b]pyridin-7-ylamino]-N-(2-hydroxy-propyl)-nicotinamide | Int 2, Int 30 | B1 | 459 | 459 |
| 25 | 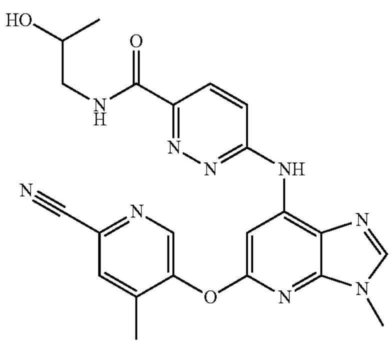 [SMILES: Cc1cc(C#N)ncc1Oc1cc(Nc2ccc(C(=O)NCC(C)O)nn2)c2ncn(C)c2n1] | 6-[5-(6-Cyano-4-methyl-pyridin-3-yloxy)-3-methyl-3H-imidazo[4,5-b]pyridin-7-ylamino]-pyridazine-3-carboxylic acid (2-hydroxy-propyl)-amide | Int 2, Int 31 | B1 | 460 | 460 |
| 26 | 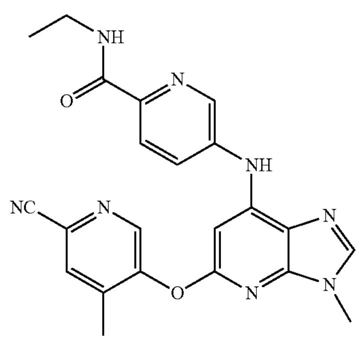 [SMILES: CCNC(=O)c1ccc(Nc2cc(Oc3cnc(C#N)cc3C)nc3c2ncn3C)cn1] | 5-[5-(6-Cyano-4-methyl-pyridin-3-yloxy)-3-methyl-3H-imidazo[4,5-b]pyridin-7-ylamino]-pyridine-2-carboxylic acid ethylamide | Int 2, Int 32 | B1 | 429 | 429 |
| 27 | 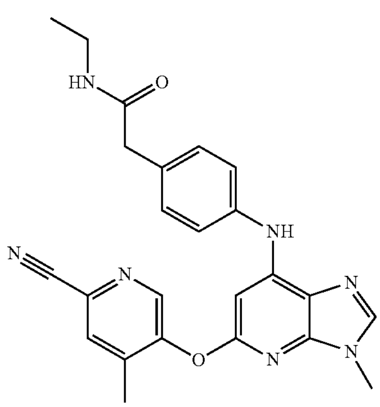 [SMILES: CCNC(=O)Cc1ccc(Nc2cc(Oc3cnc(C#N)cc3C)nc3c2ncn3C)cc1] | 2-{4-[5-(6-Cyano-4-methyl-pyridin-3-yloxy)-3-methyl-3H-imidazo[4,5-b]pyridin-7-ylamino]-phenyl}-N-ethyl-acetamide | Int 3, Int 83 | B1 | 442 | 442 |

TABLE III-continued

Illustrative compounds of the invention

| Cpd # | Structure | Name | SM | Mtd | MW | Mes |
|---|---|---|---|---|---|---|
| 28 | 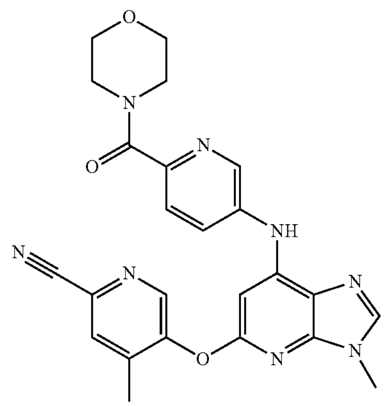 [SMILES: Cc1cc(C#N)ncc1Oc1cc(Nc2ccc(C(=O)N3CCOCC3)nc2)c2ncn(C)c2n1] | 4-Methyl-5-{3-methyl-7-[6-(morpholine-4-carbonyl)-pyridin-3-ylamino]-3H-imidazo[4,5-b]pyridin-5-yloxy}-pyridine-2-carbonitrile | Int 2, [1180131-89-8] | B1 | 471 | 471 |
| 29 | 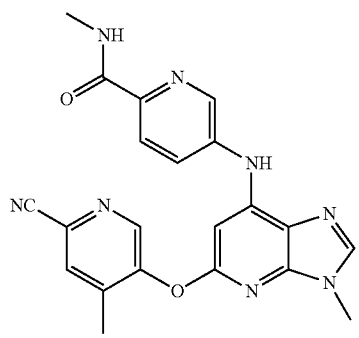 [SMILES: CNC(=O)c1ccc(Nc2cc(Oc3cnc(C#N)cc3C)nc3c2ncn3C)cn1] | 5-[5-(6-Cyano-4-methyl-pyridin-3-yloxy)-3-methyl-3H-imidazo[4,5-b]pyridin-7-ylamino]-pyridine-2-carboxylic acid methylamide | Int 2, [941284-74-8] | B1 | 414 | 415 |
| 30 | 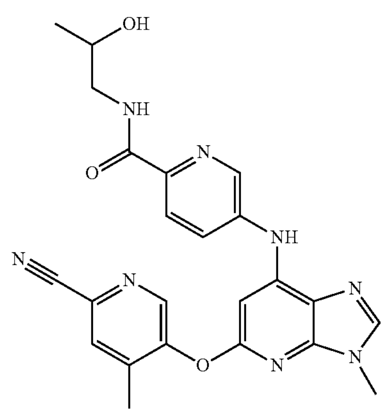 [SMILES: Cc1cc(C#N)ncc1Oc1cc(Nc2ccc(C(=O)NCC(C)O)nc2)c2ncn(C)c2n1] | 5-[5-(6-Cyano-4-methyl-pyridin-3-yloxy)-3-methyl-3H-imidazo[4,5-b]pyridin-7-ylamino]-pyridine-2-carboxylic acid (2-hydroxy-propyl)-amide | Int 2, Int 22 | B1 | 459 | 459 |
| 31 | 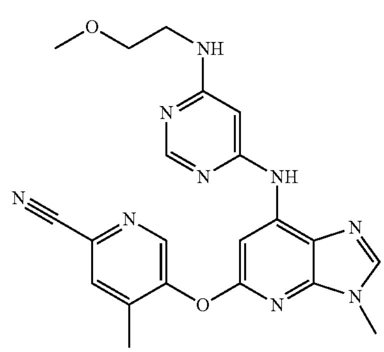 [SMILES: COCCNc1cc(Nc2cc(Oc3cnc(C#N)cc3C)nc3c2ncn3C)ncn1] | 5-{7-[6-(2-Methoxy-ethylamino)-pyrimidin-4-ylamino]-3-methyl-3H-imidazo[4,5-b]pyridin-5-yloxy}-4-methyl-pyridine-2-carbonitrile | Int 2, Int 33 | B1 | 431 | 432 |

TABLE III-continued

Illustrative compounds of the invention

| Cpd # | Structure | Name | SM | Mtd | MW | Mes |
|---|---|---|---|---|---|---|
| 32 | 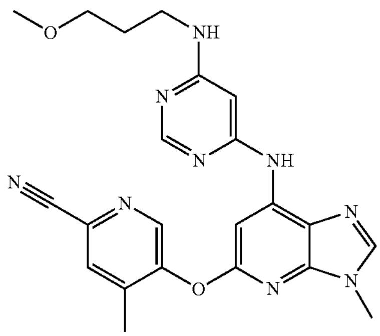 [SMILES: COCCCNc1cc(Nc2cc(Oc3cnc(C#N)cc3C)nc3c2ncn3C)ncn1] | 5-{7-[6-(3-Methoxy-propylamino)-pyrimidin-4-ylamino]-3-methyl-3H-imidazo[4,5-b]pyridin-5-yloxy}-4-methyl-pyridine-2-carbonitrile | Int 2, Int 34 | B1 | 445 | 446 |
| 33 | 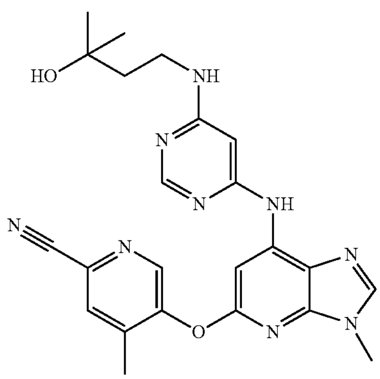 [SMILES: Cc1cc(C#N)ncc1Oc1cc(Nc2cc(NCCC(C)(C)O)ncn2)c2ncn(C)c2n1] | 5-{7-[6-(3-Hydroxy-3-methyl-butylamino)-pyrimidin-4-ylamino]-3-methyl-3H-imidazo[4,5-b]pyridin-5-yloxy}-4-methyl-pyridine-2-carbonitrile | Int 2, Int 35 | B1 | 459 | 460 |
| 34 | 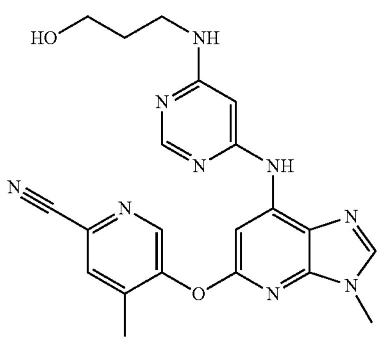 [SMILES: Cc1cc(C#N)ncc1Oc1cc(Nc2cc(NCCCO)ncn2)c2ncn(C)c2n1] | 5-{7-[6-(3-Hydroxy-propylamino)-pyrimidin-4-ylamino]-3-methyl-3H-imidazo[4,5-b]pyridin-5-yloxy}-4-methyl-pyridine-2-carbonitrile | Int 2, Int 36 | B1 | 431 | 432 |
| 35 | 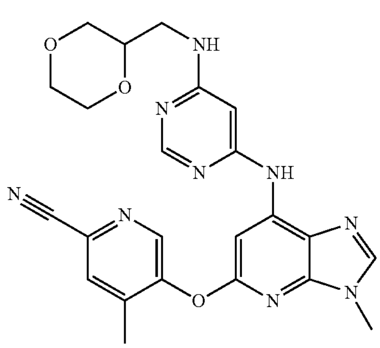 [SMILES: Cc1cc(C#N)ncc1Oc1cc(Nc2cc(NCC3COCCO3)ncn2)c2ncn(C)c2n1] | 5-(7-{6-[([1,4]Dioxan-2-ylmethyl)-amino]-pyrimidin-4-ylamino}-3-methyl-3H-imidazo[4,5-b]pyridin-5-yloxy)-4-methyl-pyridine-2-carbonitrile | Int 2, Int 37 | B1 | 473 | 474 |

TABLE III-continued

Illustrative compounds of the invention

| Cpd # | Structure | Name | SM | Mtd | MW | Mes |
|---|---|---|---|---|---|---|
| 36 | 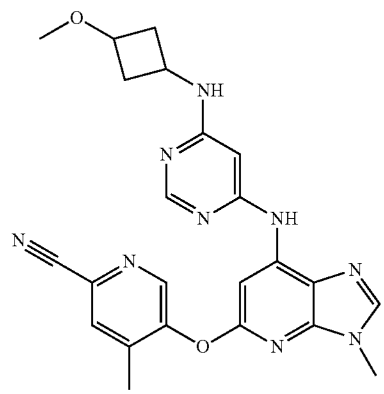 [SMILES: COC1CC(Nc2cc(Nc3cc(Oc4cnc(C#N)cc4C)nc4c3ncn4C)ncn2)C1] | 5-{7-[6-(3-Methoxy-cyclobutylamino)-pyrimidin-4-ylamino]-3-methyl-3H-imidazo[4,5-b]pyridin-5-yloxy}-4-methyl-pyridine-2-carbonitrile | Int 2, Int 38 | B1 | 457 | 458 |
| 37 | 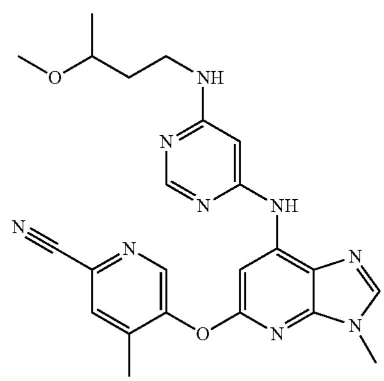 [SMILES: COC(C)CCNc1cc(Nc2cc(Oc3cnc(C#N)cc3C)nc3c2ncn3C)ncn1] | 5-{7-[6-(3-Methoxy-butylamino)-pyrimidin-4-ylamino]-3-methyl-3H-imidazo[4,5-b]pyridin-5-yloxy}-4-methyl-pyridine-2-carbonitrile | Int 2, Int 39 | B1 | 459 | 460 |
| 38 | 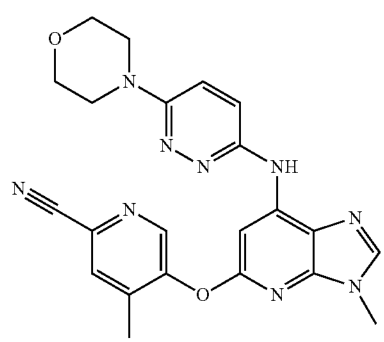 [SMILES: Cc1cc(C#N)ncc1Oc1cc(Nc2ccc(N3CCOCC3)nn2)c2ncn(C)c2n1] | 4-Methyl-5-[3-methyl-7-(6-morpholin-4-yl-pyridazin-3-ylamino)-3H-imidazo[4,5-b]pyridin-5-yloxy]-pyridine-2-carbonitrile | Int 2, [66346-91-6] or Int 3, [66346-91-6] | B1 Or see above | 443 | 444 |
| 39 | 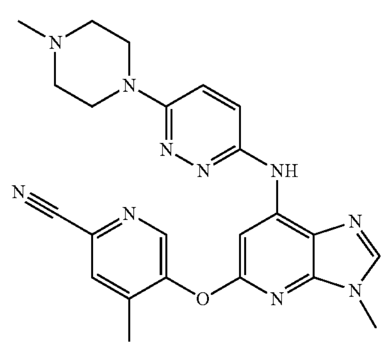 [SMILES: Cc1cc(C#N)ncc1Oc1cc(Nc2ccc(N3CCN(C)CC3)nn2)c2ncn(C)c2n1] | 4-Methyl-5-{3-methyl-7-[6-(4-methyl-piperazin-1-yl)-pyridazin-3-ylamino]-3H-imidazo[4,5-b]pyridin-5-yloxy}-pyridine-2-carbonitrile | Int 2, [66346-94-9] | B1 | 456 | 457 |

TABLE III-continued

Illustrative compounds of the invention

| Cpd # | Structure | Name | SM | Mtd | MW | Mes |
|---|---|---|---|---|---|---|
| 40 | 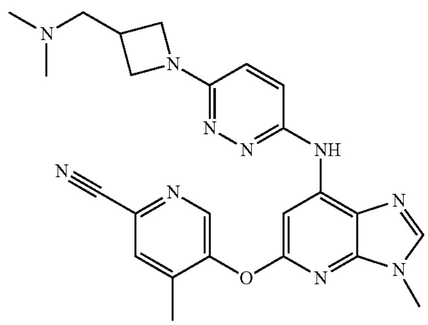 [SMILES: Cc1cc(C#N)ncc1Oc1cc(Nc2ccc(N3CC(CN(C)C)C3)nn2)c2ncn(C)c2n1] | 5-{7-[6-(3-Dimethylaminomethyl-azetidin-1-yl)-pyridazin-3-ylamino]-3-methyl-3H-imidazo[4,5-b]pyridin-5-yloxy}-4-methyl-pyridine-2-carbonitrile | Int 2, Int 40 | B1 | 470 | 471 |
| 41 | 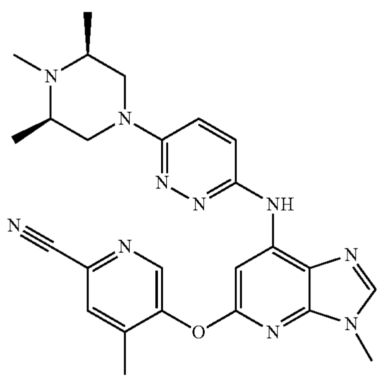 [SMILES: Cc1cc(C#N)ncc1Oc1cc(Nc2ccc(N3C[C@@H](C)N(C)[C@@H](C)C3)nn2)c2ncn(C)c2n1] | (±)-4-Methyl-5-{3-methyl-7-[6-((3R,5S)-3,4,5-trimethyl-piperazin-1-yl)-pyridazin-3-ylamino]-3H-imidazo[4,5-b]pyridin-5-yloxy}-pyridine-2-carbonitrile | Int 2, Int 41 | B1 | 484 | 485 |
| 42 | 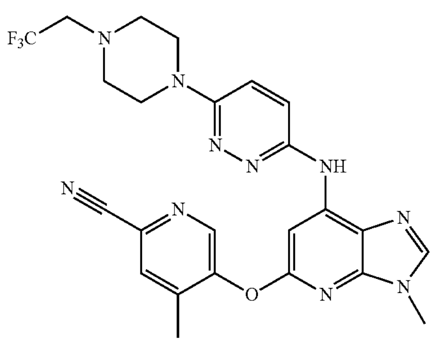 [SMILES: Cc1cc(C#N)ncc1Oc1cc(Nc2ccc(N3CCN(CC(F)(F)F)CC3)nn2)c2ncn(C)c2n1] | 4-Methyl-5-(3-methyl-7-{6-[4-(2,2,2-trifluoro-ethyl)-piperazin-1-yl]-pyridazin-3-ylamino}-3H-imidazo[4,5-b]pyridin-5-yloxy)-pyridine-2-carbonitrile | Int 2, Int 42 | B1 | 524 | 525 |
| 43 | 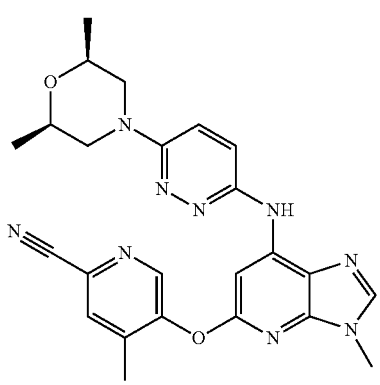 [SMILES: Cc1cc(C#N)ncc1Oc1cc(Nc2ccc(N3C[C@@H](C)O[C@@H](C)C3)nn2)c2ncn(C)c2n1] | (±)-5-{7-[6-((2R,6S)-2,6-Dimethyl-morpholin-4-yl)-pyridazin-3-ylamino]-3-methyl-3H-imidazo[4,5-b]pyridin-5-yloxy}-4-methyl-pyridine-2-carbonitrile | Int 2, Int 43 | B1 | 471 | 472 |

TABLE III-continued

Illustrative compounds of the invention

| Cpd # | Structure | Name | SM | Mtd | MW | Mes |
|---|---|---|---|---|---|---|
| 44 | 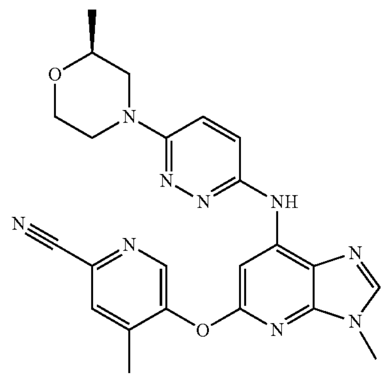 [SMILES: Cc1cc(C#N)ncc1Oc1cc(Nc2ccc(N3CCO[C@@H](C)C3)nn2)c2ncn(C)c2n1] | 4-Methyl-5-{3-methyl-7-[6-((S)-2-methyl-morpholin-4-yl)-pyridazin-3-ylamino]-3H-imidazo[4,5-b]pyridin-5-yloxy}-pyridine-2-carbonitrile | Int 2, Int 44 | B1 | 457 | 458 |
| 45 | 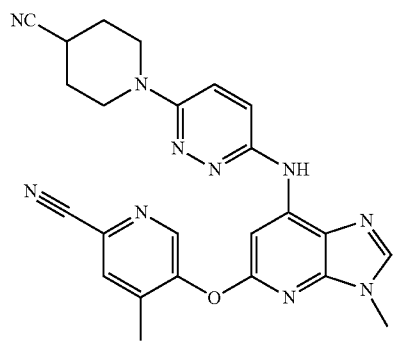 [SMILES: Cc1cc(C#N)ncc1Oc1cc(Nc2ccc(N3CCC(C#N)CC3)nn2)c2ncn(C)c2n1] | 5-{7-[6-(4-Cyano-piperidin-1-yl)-pyridazin-3-ylamino]-3-methyl-3H-imidazo[4,5-b]pyridin-5-yloxy}-4-methyl-pyridine-2-carbonitrile | Int 2, Int 45 | B1 | 466 | 467 |
| 46 | 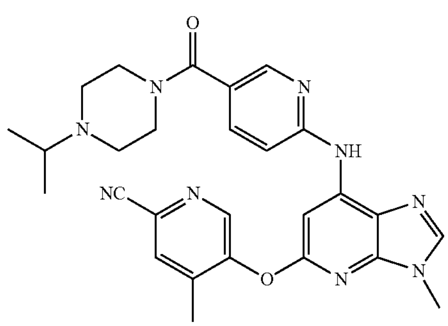 [SMILES: Cc1cc(C#N)ncc1Oc1cc(Nc2ccc(C(=O)N3CCN(C(C)C)CC3)cn2)c2ncn(C)c2n1] | 4-methyl-5-[3-methyl-7-[[5-(4-propan-2-ylpiperazine-1-carbonyl)pyridin-2-yl]amino]imidazo[4,5-b]pyridin-5-yloxy]pyridine-2-carbonitrile | Int 61, [4318-42-7] | A1-a | 512 | 513 |
| 47 | 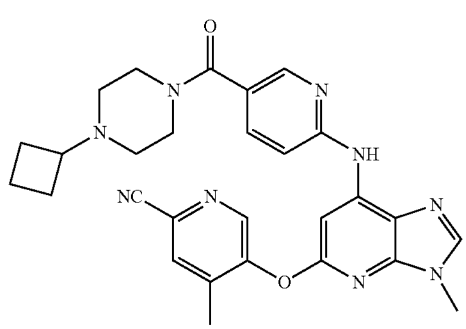 [SMILES: Cc1cc(C#N)ncc1Oc1cc(Nc2ccc(C(=O)N3CCN(C4CCC4)CC3)cn2)c2ncn(C)c2n1] | 5-[7-[[5-(4-cyclobutylpiperazine-1-carbonyl)pyridin-2-yl]amino]-3-methylimidazo[4,5-b]pyridin-5-yl]oxy-4-methylpyridine-2-carbonitrile | Int 61, [799557-65-6] | A1-a | 524 | 525 |

TABLE III-continued

Illustrative compounds of the invention

| Cpd # | Structure | Name | SM | Mtd | MW | Mes |
|---|---|---|---|---|---|---|
| 48 | 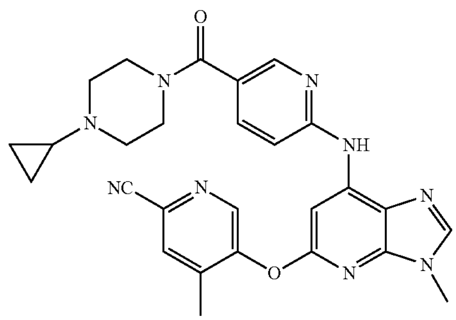 [SMILES: Cc1cc(C#N)ncc1Oc1cc(Nc2ccc(C(=O)N3CCN(C4CC4)CC3)cn2)c2ncn(C)c2n1] | 5-[7-[[5-(4-cyclopropylpiperazine-1-carbonyl)pyridin-2-yl]amino]-3-methylimidazo[4,5-b]pyridin-5-yl]oxy-4-methylpyridine-2-carbonitrile | Int 61, [20327-23-5] | A1-a | 510 | 511 |
| 49 | 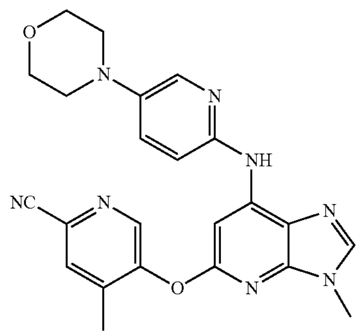 [SMILES: Cc1cc(C#N)ncc1Oc1cc(Nc2ccc(N3CCOCC3)cn2)c2ncn(C)c2n1] | 4-methyl-5-[3-methyl-7-[(5-morpholin-4-ylpyridin-2-yl)amino]imidazo[4,5-b]pyridin-5-yl]oxypyridine-2-carbonitrile | Int 2, [571189-78-1] | B1 | 442 | 443 |
| 50 | 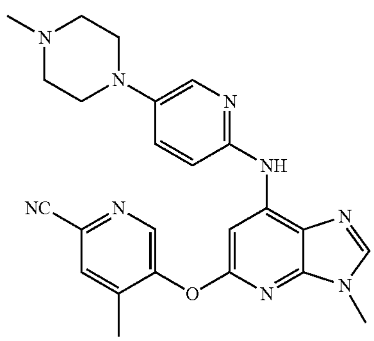 [SMILES: Cc1cc(C#N)ncc1Oc1cc(Nc2ccc(N3CCN(C)CC3)cn2)c2ncn(C)c2n1] | 4-methyl-5-[3-methyl-7-[[5-(4-methylpiperazin-1-yl)pyridin-2-yl]amino]imidazo[4,5-b]pyridin-5-yl]oxypyridine-2-carbonitrile | Int 2, [571189-49-6] | B1 | 456 | 457 |
| 51 | 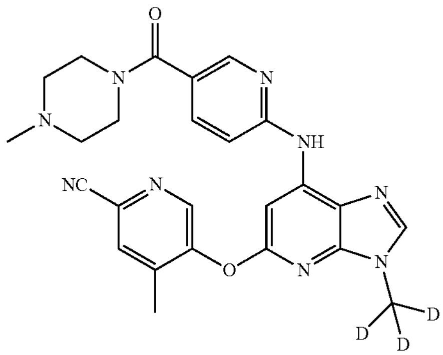 [SMILES: [2H]C([2H])([2H])n1cnc2c(Nc3ccc(C(=O)N4CCN(C)CC4)cn3)cc(Oc3cnc(C#N)cc3C)nc21] | 4-methyl-5-[7-[[5-(4-methylpiperazine-1-carbonyl)pyridin-2-yl]amino]-3-(trideuteriomethyl)imidazo[4,5-b]pyridin-5-yl]oxypyridine-2-carbonitrile | Int 84, Int 89 | B1 | 487 | 487 |

TABLE III-continued

Illustrative compounds of the invention

| Cpd # | Structure | Name | SM | Mtd | MW | Mes |
|---|---|---|---|---|---|---|
| 52 | 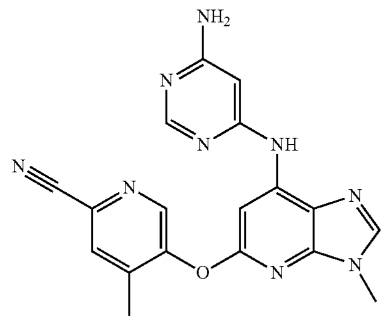 [SMILES: Cc1cc(C#N)ncc1Oc1cc(Nc2cc(N)ncn2)c2ncn(C)c2n1] | 5-[7-[(6-aminopyrimidin-4-yl)amino]-3-methyl-imidazo[4,5-b]pyridin-5-yl]oxy-4-methyl-pyridine-2-carbonitrile | Int 2, [79364-63-9] | B1 | 373 | 374 |
| 53 | 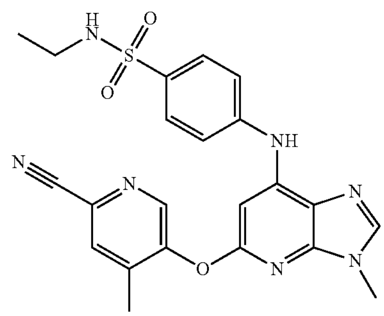 [SMILES: CCNS(=O)(=O)c1ccc(Nc2cc(Oc3cnc(C#N)cc3C)nc3c2ncn3C)cc1] | 4-[[5-[(6-cyano-4-methyl-3-pyridyl)oxy]-3-methyl-imidazo[4,5-b]pyridin-7-yl]amino]-N-ethyl-benzenesulfonamide | Int 2, [1709-53-1] | B1 | 464 | 464 |
| 54 | 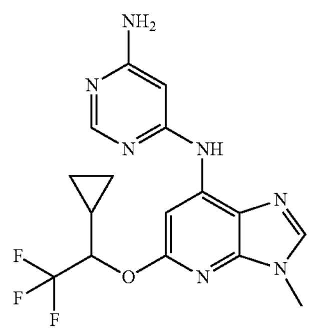 [SMILES: Cn1cnc2c(Nc3cc(N)ncn3)cc(OC(C3CC3)C(F)(F)F)nc21] | N4-[5-(1-cyclopropyl-2,2,2-trifluoro-ethoxy)-3-methyl-imidazo[4,5-b]pyridin-7-yl]pyrimidine-4,6-diamine | Int 28, [79364-63-9] | B1 | 379 | 380 |
| 55 | 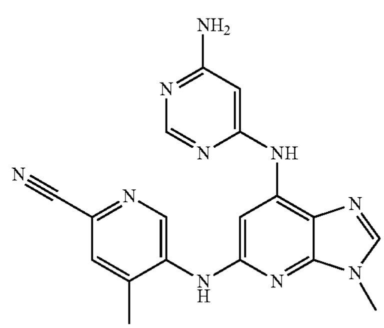 [SMILES: Cc1cc(C#N)ncc1Nc1cc(Nc2cc(N)ncn2)c2ncn(C)c2n1] | 5-[[7-[(6-aminopyrimidin-4-yl)amino]-3-methyl-imidazo[4,5-b]pyridin-5-yl]amino]-4-methyl-pyridine-2-carbonitrile | Int 4, [79364-63-9] | B1 | 372 | 373 |

TABLE III-continued

Illustrative compounds of the invention

| Cpd # | Structure | Name | SM | Mtd | MW | Mes |
|---|---|---|---|---|---|---|
| 57 | 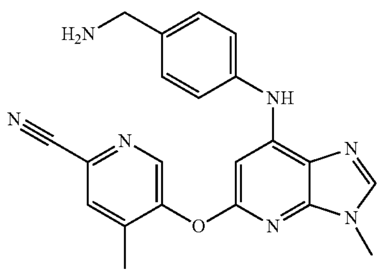 | 5-[7-[4-(aminomethyl)anilino]-3-methyl-imidazo[4,5-b]pyridin-5-yl]oxy-4-methyl-pyridine-2-carbonitrile formate salt | Int 47 | D1 | 385 | 369 (M − $NH_2^-$) |
| 58 | 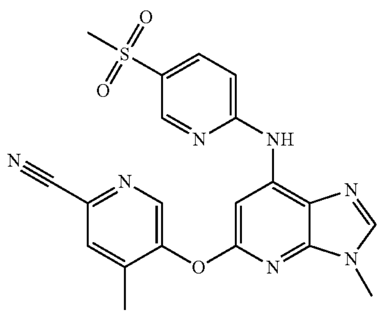 [SMILES: Cc1cc(C#N)ncc1Oc1cc(Nc2ccc(S(C)(=O)=O)cn2)c2ncn(C)c2n1] | 4-methyl-5-[3-methyl-7-[(5-methylsulfonyl-2-pyridyl)amino]imidazo[4,5-b]pyridin-5-yl]oxy-pyridine-2-carbonitrile | Int 2, [35196-11-3] | B1 | 436 | 436 |
| 59 | 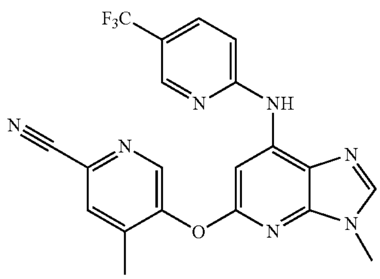 [SMILES: Cc1cc(C#N)ncc1Oc1cc(Nc2ccc(C(F)(F)F)cn2)c2ncn(C)c2n1] | 4-methyl-5-[3-methyl-7-[[5-(trifluoromethyl)-2-pyridyl]amino]imidazo[4,5-b]pyridin-5-yl]oxy-pyridine-2-carbonitrile | Int 2, [74784-70-6] | B1 | 425 | 426 |
| 60 | 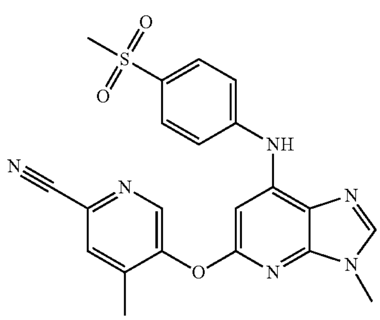 [SMILES: Cc1cc(C#N)ncc1Oc1cc(Nc2ccc(S(C)(=O)=O)cc2)c2ncn(C)c2n1] | 4-methyl-5-[3-methyl-7-(4-methylsulfonylanilino)imidazo[4,5-b]pyridin-5-yl]oxy-pyridine-2-carbonitrile | Int 2, [5470-49-5] | B1 | 435 | 435 |
| 61 | 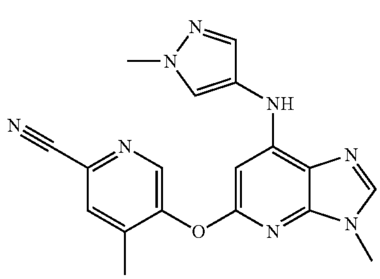 [SMILES: Cc1cc(C#N)ncc1Oc1cc(Nc2cnn(C)c2)c2ncn(C)c2n1] | 4-methyl-5-[3-methyl-7-[(1-methylpyrazol-4-yl)amino]imidazo[4,5-b]pyridin-5-yl]oxy-pyridine-2-carbonitrile | Int 2, [69843-13-6] | B1 | 360 | 361 |

TABLE III-continued

Illustrative compounds of the invention

| Cpd # | Structure | Name | SM | Mtd | MW | Mes |
|---|---|---|---|---|---|---|
| 62 | 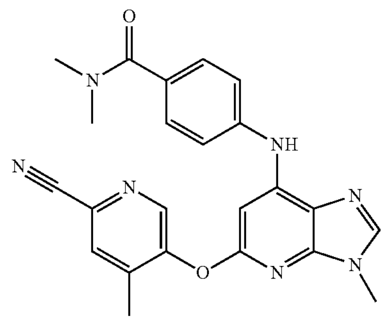 [SMILES: Cc1cc(C#N)ncc1Oc1cc(Nc2ccc(C(=O)N(C)C)cc2)c2ncn(C)c2n1] | 4-[[5-[(6-cyano-4-methyl-3-pyridyl)oxy]-3-methyl-imidazo[4,5-b]pyridin-7-yl]amino]-N,N-dimethyl-benzamide | Int 2, [6331-71-1] | B1 | 428 | 428 |
| 63 | 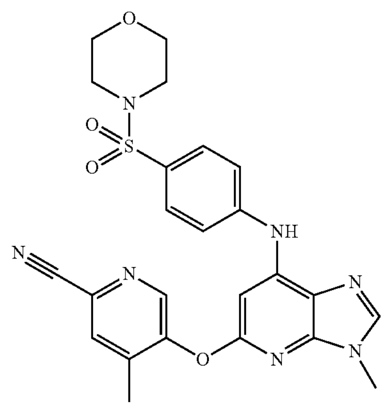 [SMILES: Cc1cc(C#N)ncc1Oc1cc(Nc2ccc(S(=O)(=O)N3CCOCC3)cc2)c2ncn(C)c2n1] | 4-methyl-5-[3-methyl-7-(4-morpholinosulfonyl)anilino)imidazo[4,5-b]pyridin-5-yl]oxy-pyridine-2-carbonitrile | Int 2, [21626-70-0] | B1 | 506 | 506 |
| 64 | 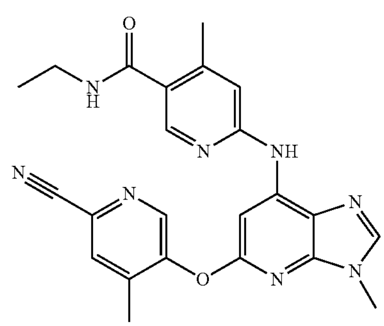 [SMILES: CCNC(=O)c1cnc(Nc2cc(Oc3cnc(C#N)cc3C)nc3c2ncn3C)cc1C] | 6-[[5-[(6-cyano-4-methyl-3-pyridyl)oxy]-3-methyl-imidazo[4,5-b]pyridin-7-yl]amino]-N-ethyl-4-methyl-pyridine-3-carboxamide | Int 2, Int 50 | B1 | 443 | 443 |
| 65 | 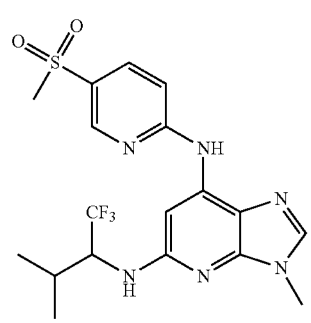 [SMILES: CC(C)C(Nc1cc(Nc2ccc(S(C)(=O)=O)cn2)c2ncn(C)c2n1)C(F)(F)F] | 3-methyl-N7-(5-methylsulfonyl-2-pyridiyl)-N5-[2-methyl-1-(trifluoromethyl)propyl]imidazo[4,5-b]pyridine-5,7-diamine | Int 46, [35196-11-3] | B1 | 443 | 443 |

TABLE III-continued

Illustrative compounds of the invention

| Cpd # | Structure | Name | SM | Mtd | MW | Mes |
|---|---|---|---|---|---|---|
| 66 | 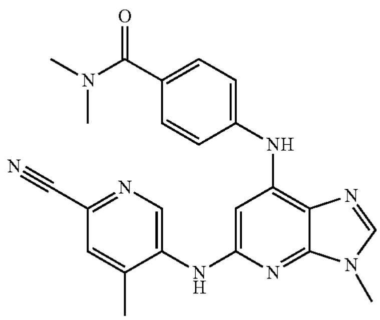 [SMILES: Cc1cc(C#N)ncc1Nc1cc(Nc2ccc(C(=O)N(C)C)cc2)c2ncn(C)c2n1] | 4-[[5-[(6-cyano-4-methyl-3-pyridyl)amino]-3-methyl-imidazo[4,5-b]pyridin-7-yl]amino]-N,N-dimethyl-benzamide | Int 4, [6331-71-1] | B1 | 427 | 427 |
| 67 | 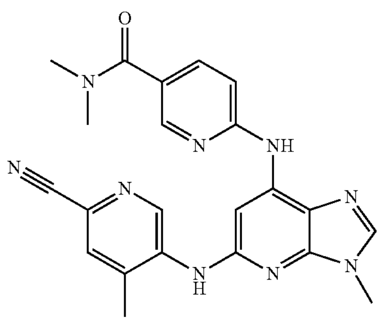 [SMILES: Cc1cc(C#N)ncc1Nc1cc(Nc2ccc(C(=O)N(C)C)cn2)c2ncn(C)c2n1] | 6-[[5-[(6-cyano-4-methyl-3-pyridyl)amino]-3-methyl-imidazo[4,5-b]pyridin-7-yl]amino]-N,N-dimethyl-pyridine-3-carboxamide | Int 4, [827588-33-0] | B1 | 428 | 428 |
| 68 | 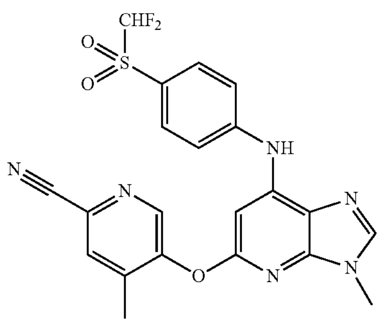 [SMILES: Cc1cc(C#N)ncc1Oc1cc(Nc2ccc(S(=O)(=O)C(F)F)cc2)c2ncn(C)c2n1] | 5-[7-[4-(difluoromethylsulfonyl)anilino]-3-methyl-imidazo[4,5-b]pyridin-5-yl]oxy-4-methyl-pyridine-2-carbonitrile | Int 2, [24906-77-2] | B1 | 471 | 471 |
| 69 | 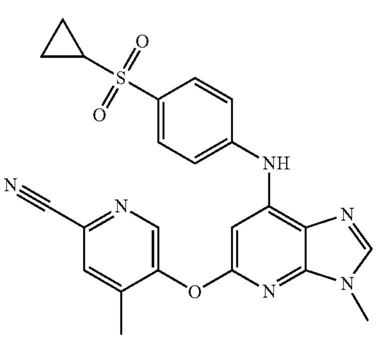 [SMILES: Cc1cc(C#N)ncc1Oc1cc(Nc2ccc(S(=O)(=O)C3CC3)cc2)c2ncn(C)c2n1] | 5-[7-(4-cyclopropylsulfonylanilino)-3-methyl-imidazo[4,5-b]pyridin-5-yl]oxy-4-methyl-pyridine-2-carbonitrile | Int 2, [1147558-13-1] | B1 | 461 | 461 |

TABLE III-continued

Illustrative compounds of the invention

| Cpd # | Structure | Name | SM | Mtd | MW | Mes |
|---|---|---|---|---|---|---|
| 71 | 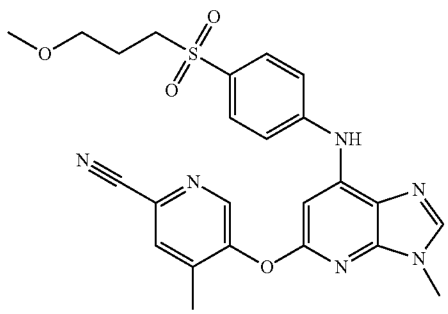 [SMILES: COCCCS(=O)(=O)c1ccc(Nc2cc(Oc3cnc(C#N)cc3C)nc3c2ncn3C)cc1] | 5-[7-[4-(3-methoxypropylsulfonyl)anilino]-3-methyl-imidazo[4,5-b]pyridin-5-yl]oxy-4-methyl-pyridine-2-carbonitrile | Int 2, [1247164-58-4] | B1 | 493 | 493 |
| 72 | 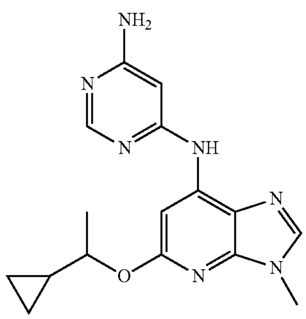 [SMILES: CC(Oc1cc(Nc2cc(N)ncn2)c2ncn(C)c2n1)C1CC1] | N4-[5-(1-cyclopropylethoxy)-3-methyl-imidazo[4,5-b]pyridin-7-yl]pyrimidine-4,6-diamine | Int 48, [79364-63-9] | B1 | 325 | 326 |
| 73 | 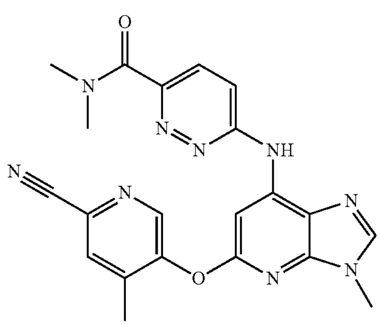 [SMILES: Cc1cc(C#N)ncc1Oc1cc(Nc2ccc(C(=O)N(C)C)nn2)c2ncn(C)c2n1] | 6-[[5-[(6-cyano-4-methyl-3-pyridyl)oxy]-3-methyl-imidazo[4,5-b]pyridin-7-yl]amino]-N,N-dimethyl-pyridazine-3-carboxamide | Int 2, [1250216-83-1] | B1 | 429 | 429 |
| 74 | 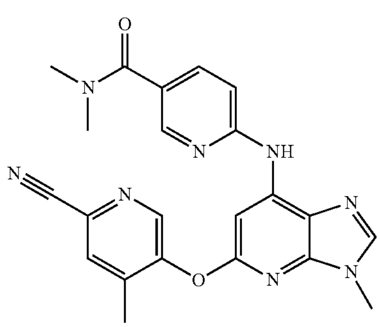 [SMILES: Cc1cc(C#N)ncc1Oc1cc(Nc2ccc(C(=O)N(C)C)cn2)c2ncn(C)c2n1] | 6-[[5-[(6-cyano-4-methyl-3-pyridyl)oxy]-3-methyl-imidazo[4,5-b]pyridin-7-yl]amino]-N,N-dimethyl-pyridine-3-carboxamide | Int 2, [827588-33-0] | B1 | 429 | 429 |

TABLE III-continued

Illustrative compounds of the invention

| Cpd # | Structure | Name | SM | Mtd | MW | Mes |
|---|---|---|---|---|---|---|
| 75 | 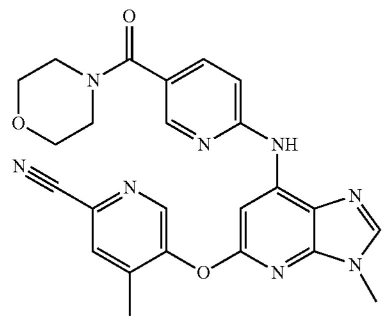 [SMILES: Cc1cc(C#N)ncc1Oc1cc(Nc2ccc(C(=O)N3CCOCC3)cn2)c2ncn(C)c2n1] | 4-methyl-5-[3-methyl-7-[[5-(morpholine-4-carbonyl)-2-pyridyl]amino]imidazo[4,5-b]pyridin-5-yl]oxy-pyridine-2-carbonitrile | Int 2, [827587-90-6] | B1 | 471 | 471 |
| 76 | 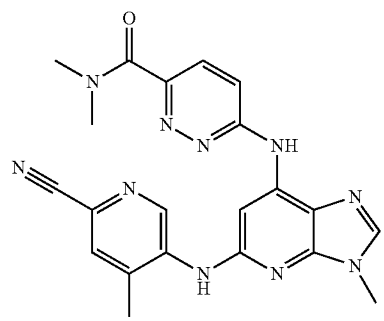 [SMILES: Cc1cc(C#N)ncc1Nc1cc(Nc2ccc(C(=O)N(C)C)nn2)c2ncn(C)c2n1] | 6-[[5-[(6-cyano-4-methyl-3-pyridyl)amino]-3-methyl-imidazo[4,5-b]pyridin-7-yl]amino]-N,N-dimethyl-pyridazine-3-carboxamide | Int 4, [1250216-83-1] | B1 | 429 | 429 |
| 77 | 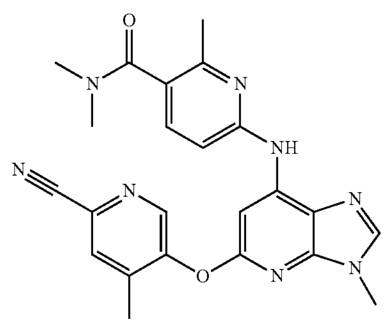 [SMILES: Cc1cc(C#N)ncc1Oc1cc(Nc2ccc(C(=O)N(C)C)c(C)n2)c2ncn(C)c2n1] | 6-[[5-[(6-cyano-4-methyl-3-pyridyl)oxy]-3-methyl-imidazo[4,5-b]pyridin-7-yl]amino]-N,N,2-trimethyl-pyridine-3-carboxamide | Int 52, [506-59-2] | A1 | 443 | 443 |
| 78 | 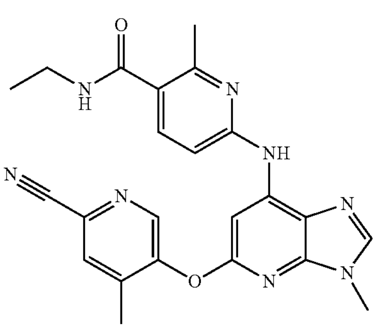 [SMILES: CCNC(=O)c1ccc(Nc2cc(Oc3cnc(C#N)cc3C)nc3c2ncn3C)nc1C] | 6-[[5-[(6-cyano-4-methyl-3-pyridyl)oxy]-3-methyl-imidazo[4,5-b]pyridin-7-yl]amino]-N-ethyl-2-methyl-pyridine-3-carboxamide | Int 52, [557-66-4] | A1 | 443 | 443 |

TABLE III-continued

Illustrative compounds of the invention

| Cpd # | Structure | Name | SM | Mtd | MW | Mes |
|---|---|---|---|---|---|---|
| 81 | 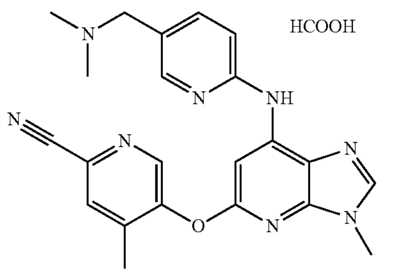 [SMILES: Cc1cc(C#N)ncc1Oc1cc(Nc2ccc(CN(C)C)cn2)c2ncn(C)c2n1 ; "HCOOH"] | 5-[7-[[5-[(dimethylamino)methyl]pyridin-2-yl]amino]-3-methylimidazo[4,5-b]pyridin-5-yl]oxy-4-methylpyridine-2-carbonitrile formate salt | Int 2, [1384429-17-7] | B1 | 415 | 415 |
| 82 | 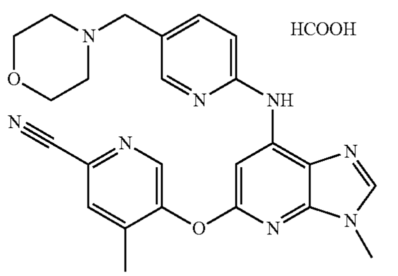 [SMILES: Cc1cc(C#N)ncc1Oc1cc(Nc2ccc(CN3CCOCC3)cn2)c2ncn(C)c2n1 ; "HCOOH"] | 4-methyl-5-[3-methyl-7-[[5-(morpholin-4-ylmethyl)pyridin-2-yl]amino]imidazo[4,5-b]pyridin-5-yl]oxypyridine-2-carbonitrile formate salt | Int 2, [400775-78-2] | B1 | 457 | 457 |
| 83 | 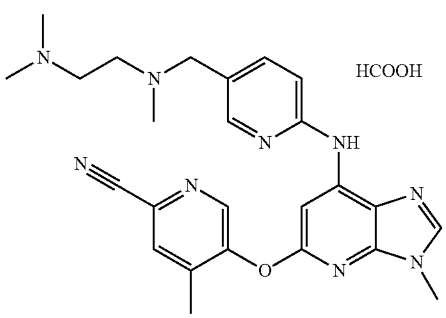 [SMILES: Cc1cc(C#N)ncc1Oc1cc(Nc2ccc(CN(C)CCN(C)C)cn2)c2ncn(C)c2n1 ; "HCOOH"] | 5-[7-[[5-[[2-(dimethylamino)ethyl-methylamino]methyl]pyridin-2-yl]amino]-3-methylimidazo[4,5-b]pyridin-5-yl]oxy-4-methylpyridine-2-carbonitrile formate salt | Int 2, [1197332-20-9] | B1 | 472 | 472 |
| 84 | 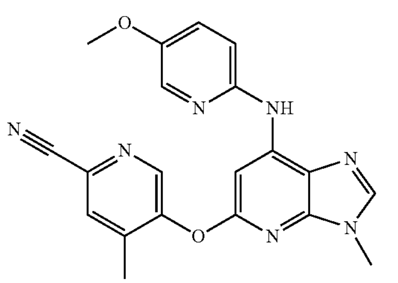 [SMILES: COc1ccc(Nc2cc(Oc3cnc(C#N)cc3C)nc3c2ncn3C)nc1] | 5-[7-[(5-methoxypyridin-2-yl)amino]-3-methylimidazo[4,5-b]pyridin-5-yl]oxy-4-methylpyridine-2-carbonitrile | Int 2, [10167-97-2] | B1 | 387 | 388 |
| 85 | 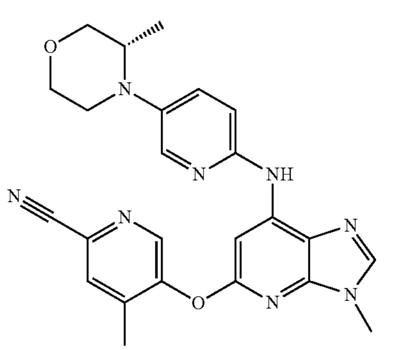 [SMILES: Cc1cc(C#N)ncc1Oc1cc(Nc2ccc(N3CCOC[C@@H]3C)cn2)c2ncn(C)c2n1] | 4-methyl-5-[3-methyl-7-[[5-[(3S)-3-methylmorpholin-4-yl]pyridin-2-yl]amino]imidazo[4,5-b]pyridin-5-yl]oxypyridine-2-carbonitrile | Int 2, Int 53 | B1 | 457 | 457 |

TABLE III-continued

Illustrative compounds of the invention

| Cpd # | Structure | Name | SM | Mtd | MW | Mes |
|---|---|---|---|---|---|---|
| 86 | 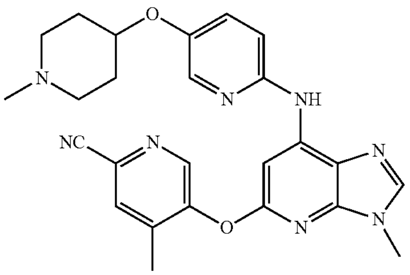 [SMILES: Cc1cc(C#N)ncc1Oc1cc(Nc2ccc(OC3CCN(C)CC3)cn2)c2ncn(C)c2n1] | 4-methyl-5-[3-methyl-7-[[5-(1-methylpiperidin-4-yl)oxypyridin-2-yl]amino]imidazo[4,5-b]pyridin-5-yl]oxypyridine-2-carbonitrile | Int 2, [1249322-37-9] | B1 | 471 | 471 |
| 87 | 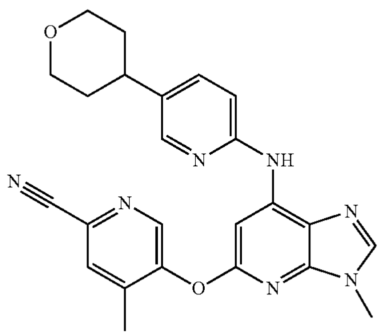 [SMILES: Cc1cc(C#N)ncc1Oc1cc(Nc2ccc(C3CCOCC3)cn2)c2ncn(C)c2n1] | 4-methyl-5-[3-methyl-7-[[5-(oxan-4-yl)pyridin-2-yl]amino]imidazo[4,5-b]pyridin-5-yl]oxypyridine-2-carbonitrile | Int 2, Int 55 | B1 | 442 | 442 |
| 88 | 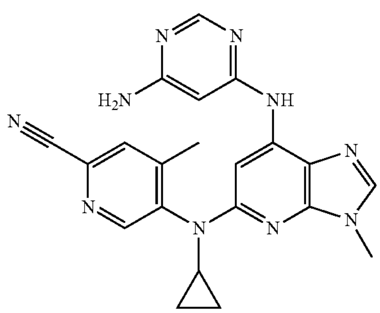 [SMILES: Cc1cc(C#N)ncc1N(c1cc(Nc2cc(N)ncn2)c2ncn(C)c2n1)C1CC1] | 5-[[7-[(6-aminopyrimidin-4-yl)amino]-3-methyl-imidazo[4,5-b]pyridin-5-yl]-cyclopropyl-amino]-4-methyl-pyridine-2-carbonitrile | Int 86, [156-81-0] | B1 | 413 | 414 |
| 89 | 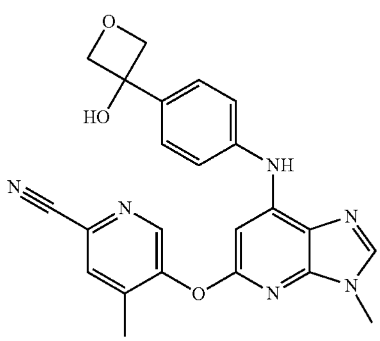 [SMILES: Cc1cc(C#N)ncc1Oc1cc(Nc2ccc(C3(O)COC3)cc2)c2ncn(C)c2n1] | 5-[7-[4-(3-hydroxyoxetan-3-yl)anilino]-3-methylimidazo[4,5-b]pyridin-5-yl]oxy-4-methylpyridine-2-carbonitrile | Int 2, [1111735-05-7] | B1 | 429 | 429 |
| 90 | 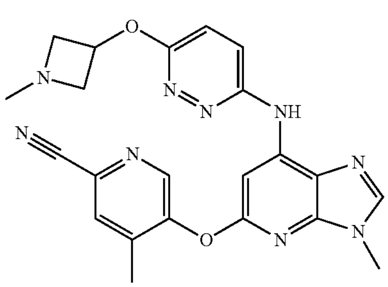 [SMILES: Cc1cc(C#N)ncc1Oc1cc(Nc2ccc(OC3CN(C)C3)nn2)c2ncn(C)c2n1] | 4-methyl-5-[3-methyl-7-[[6-(1-methylazetidin-3-yl)oxypyridazin-3-yl]amino]imidazo[4,5-b]pyridin-5-yl]oxypyridine-2-carbonitrile | Int 3, Int 56 | B2-a | 444 | 444 |

TABLE III-continued

Illustrative compounds of the invention

| Cpd # | Structure | Name | SM | Mtd | MW | Mes |
|---|---|---|---|---|---|---|
| 91 | 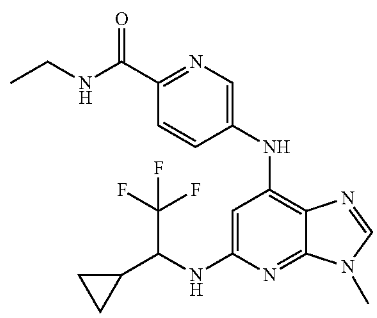 [SMILES: CCNC(=O)c1ccc(Nc2cc(NC(C3CC3)C(F)(F)F)nc3c2ncn3C)cn1] | 5-[[5-[(1-cyclopropyl-2,2,2-trifluoro-ethyl)amino]-3-methyl-imidazo[4,5-b]pyridin-7-yl]amino]-N-ethyl-pyridine-2-carboxamide | Int 26, Int 32 | B1 | 433 | 434 |
| 92 | 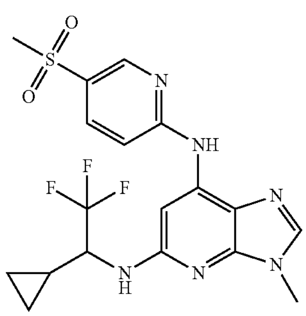 [SMILES: Cn1cnc2c(Nc3ccc(S(C)(=O)=O)cn3)cc(NC(C3CC3)C(F)(F)F)nc21] | N5-(1-cyclopropyl-2,2,2-trifluoro-ethyl)-3-methyl-N7-(5-methylsulfonyl-2-pyridyl)imidazo[4,5-b]pyridine-5,7-diamine | Int 26, [35196-11-3] | B1 | 440 | 441 |
| 93 | 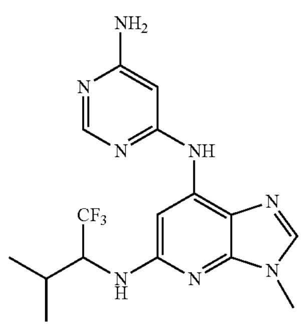 [SMILES: CC(C)C(Nc1cc(Nc2cc(N)ncn2)c2ncn(C)c2n1)C(F)(F)F] | N7-(6-aminopyrimidin-4-yl)-3-methyl-N5-[2-methyl-1-(trifluoromethyl)propyl]imidazo[4,5-b]pyridine-5,7-diamine | Int 46, [79364-63-9] | B1 | 380 | 381 |
| 94 | 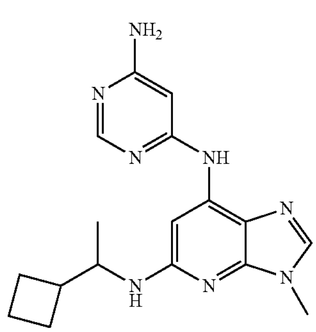 [SMILES: CC(Nc1cc(Nc2cc(N)ncn2)c2ncn(C)c2n1)C1CCC1] | N7-(6-aminopyrimidin-4-yl)-N5-(1-cyclobutylethyl)-3-methyl-imidazo[4,5-b]pyridine-5,7-diamine | Int 58, [79364-63-9] | B1 | 338 | 339 |

TABLE III-continued

Illustrative compounds of the invention

| Cpd # | Structure | Name | SM | Mtd | MW | Mes |
|---|---|---|---|---|---|---|
| 95 | 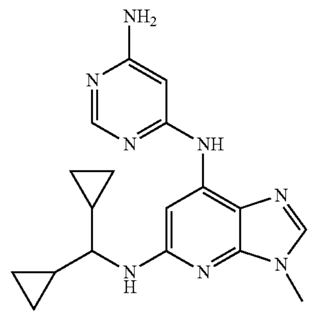 [SMILES: Cn1cnc2c(Nc3cc(N)ncn3)cc(NC(C3CC3)C3CC3)nc21] | N7-(6-aminopyrimidin-4-yl)-N5-(dicyclopropylmethyl)-3-methyl-imidazo[4,5-b]pyridine-5,7-diamine | Int 59, [79364-63-9] | B1 | 350 | 351 |
| 96 | 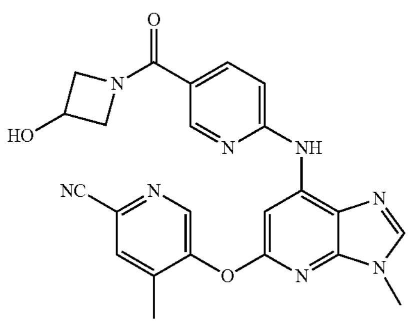 [SMILES: Cc1cc(C#N)ncc1Oc1cc(Nc2ccc(C(=O)N3CC(O)C3)cn2)c2ncn(C)c2n1] | 5-[7-[[5-(3-hydroxyazetidine-1-cabonyl)-2-pyridyl]amino]-3-methyl-imidazo[4,5-b]pyridin-5-yl]oxy-4-methyl-pyridine-2-carbonitrile | Int 2, [45347-82-8] | A1-a | 457 | 457 |
| 97 | 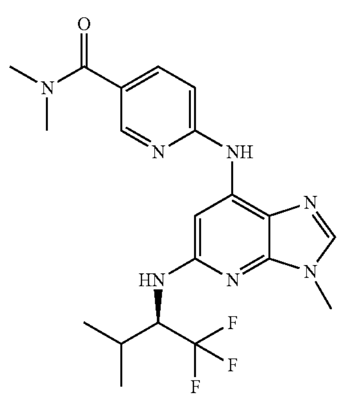 [SMILES: CC(C)[C@@H](Nc1cc(Nc2ccc(C(=O)N(C)C)cn2)c2ncn(C)c2n1)C(F)(F)F] | N,N-dimethyl-6-[[3-methyl-5-[[(1R)-2-methyl-1-(trifluoromethyl)propyl]amino]imidazo[4,5-b]pyridin-7-yl]amino]pyridine-3-carboxamide | Int 64, [827588-33-0] | B1 | 436 | 436 |
| 98 | 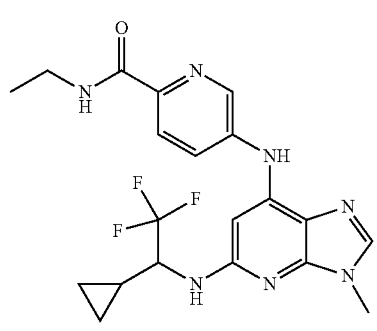 [SMILES: CCNC(=O)c1ccc(Nc2cc(NC(C3CC3)C(F)(F)F)nc3c2ncn3C)cn1] | N7-(6-aminopyrimidin-4-yl)-3-methyl-N5-[(1R)-2-methyl-1-(trifluoromethyl)propyl]imidazo[4,5-b]pyridine-5,7-diamine | Int 64, [79364-63-9] | B1 | 380 | 381 |

TABLE III-continued

Illustrative compounds of the invention

| Cpd # | Structure | Name | SM | Mtd | MW | Mes |
|---|---|---|---|---|---|---|
| 99 | 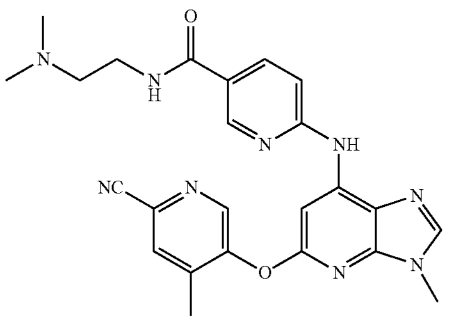 [SMILES: Cc1cc(C#N)ncc1Oc1cc(Nc2ccc(C(=O)NCCN(C)C)cn2)c2ncn(C)c2n1] | 6-[[5-[(6-cyano-4-methyl-3-pyridyl)oxy]-3-methyl-imidazo[4,5-b]pyridin-7-yl]amino]-N-(2-dimethylaminoethyl)pyridine-3-carboxamide | Int 61, [108-00-9] | A1-a | 472 | 472 |
| 100 | 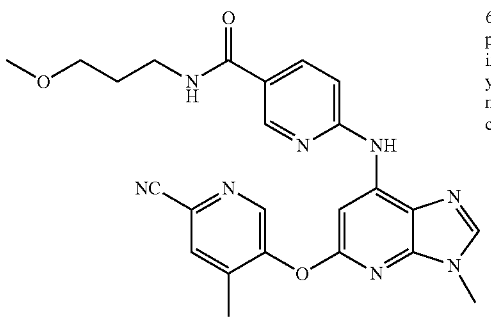 | 6-[[5-[(6-cyano-4-methyl-3-pyridyl)oxy]-3-methyl-imidazo[4,5-b]pyridin-7-yl]amino]-N-(3-methoxypropyl)pyridine-3-carboxamide | Int 61, [5332-73-0] | A1-a | 473 | 473 |
| 101 | 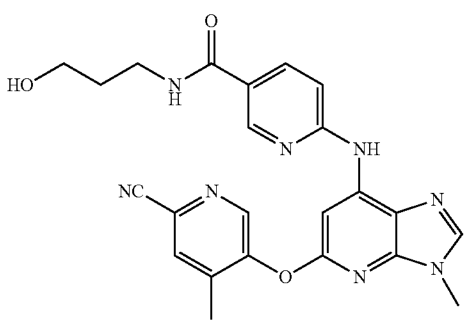 [SMILES: Cc1cc(C#N)ncc1Oc1cc(Nc2ccc(C(=O)NCCCO)cn2)c2ncn(C)c2n1] | 6-[[5-[(6-cyano-4-methyl-3-pyridyl)oxy]-3-methyl-imidazo[4,5-b]pyridin-7-yl]amino]-N-(3-hydroxypropyl)pyridine-3-carboxamide | Int 61, [156-87-6] | A1-a | 459 | 459 |
| 102 | 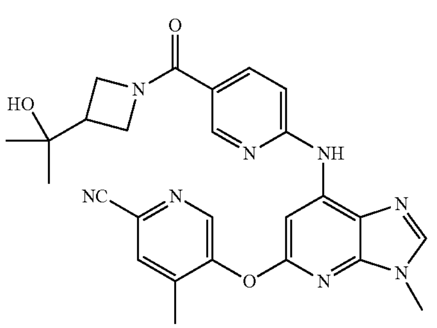 [SMILES: Cc1cc(C#N)ncc1Oc1cc(Nc2ccc(C(=O)N3CC(C(C)(C)O)C3)cn2)c2ncn(C)c2n1] | 5-[7-[[5-[3-(1-hydroxy-1-methyl-ethyl)azetidine-1-carbonyl]-2-pyridyl]amino]-3-methyl-imidazo[4,5-b]pyridin-5-yl]oxy-4-methyl-pyridine-2-carbonitrile | Int 61, [1357923-33-1] | A1-a | 499 | 499 |

TABLE III-continued

Illustrative compounds of the invention

| Cpd # | Structure | Name | SM | Mtd | MW | Mes |
|---|---|---|---|---|---|---|
| 103 | 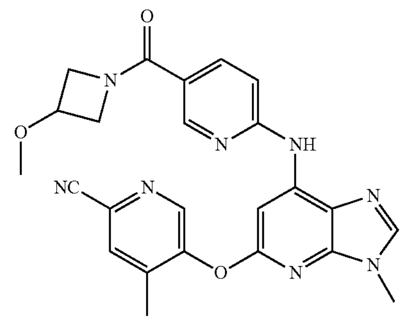 [SMILES: COC1CN(C(=O)c2ccc(Nc3cc(Oc4cnc(C#N)cc4C)nc4c3ncn4C)nc2)C1] | 5-[7-[[5-(3-methoxyazetidine-1-carbonyl)-2-pyridyl]amino]-3-methyl-imidazo[4,5-b]pyridin-5-yl]oxy-4-methyl-pyridine-2-carbonitrile | Int 61, [110925-17-2] | A1-a | 471 | 471 |
| 104 | 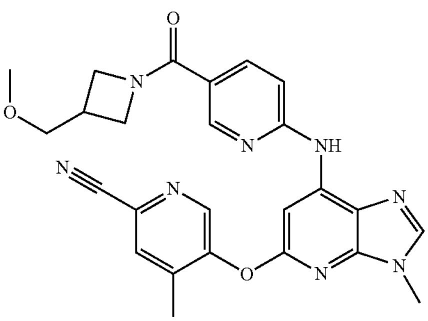 [SMILES: COCC1CN(C(=O)c2ccc(Nc3cc(Oc4cnc(C#N)cc4C)nc4c3ncn4C)nc2)C1] | 5-[7-[[5-[3-(methoxymethyl)azetidine-1-carbonyl]-2-pyridyl]amino]-3-methyl-imidazo[4,5-b]pyridin-5-yl]oxy-4-methyl-pyridine-2-carbontrile | Int 61, [942308-06-7] | A1-a | 485 | 485 |
| 105 | 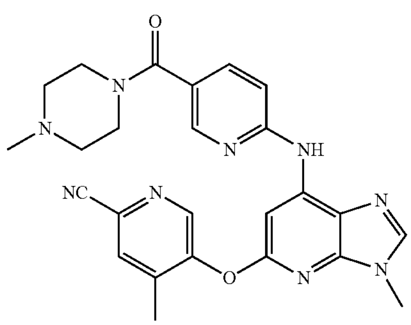 [SMILES: Cc1cc(C#N)ncc1Oc1cc(Nc2ccc(C(=O)N3CCN(C)CC3)cn2)c2ncn(C)c2n1] | 4-methyl-5-[3-methyl-7-[[5-(4-methylpiperazine-1-carbonyl)-2-pyridyl]amino]imidazo[4,5-b]pyridin-5-yl]oxy-pyridine-2-carbonitrile | Int 61, [5332-73-0] | A1-a | 484 | 484 |
| 106 | 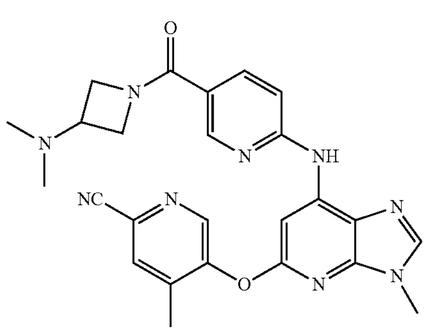 [SMILES: Cc1cc(C#N)ncc1Oc1cc(Nc2ccc(C(=O)N3CC(N(C)C)C3)cn2)c2ncn(C)c2n1] | 5-[7-[[5-[3-(dimethylamino)azetidine-1-carbonyl]-2-pyridyl]amino]-3-methyl-imidazo[4,5-b]pyridin-5-yl]oxy-4-methyl-pyridine-2-carbonitrile | Int 61, [124668-49-1] | A1-a | 484 | 484 |

TABLE III-continued

Illustrative compounds of the invention

| Cpd # | Structure | Name | SM | Mtd | MW | Mes |
|---|---|---|---|---|---|---|
| 107 | 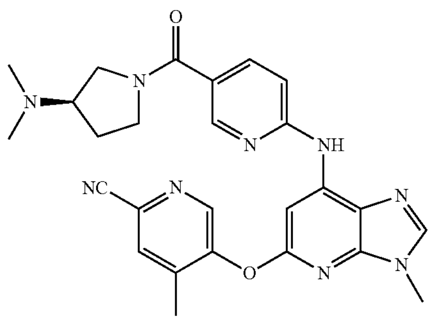 [SMILES: Cc1cc(C#N)ncc1Oc1cc(Nc2ccc(C(=O)N3CC[C@@H](N(C)C)C3)cn2)c2ncn(C)c2n1] | 5-[7-[[5-[(3R)-3-(dimethylamino)pyrrolidine-1-carbonyl]pyridin-2-yl]amino]-3-methylimidazo[4,5-b]pyridin-5-yl]oxy-4-methylpyridine-2-carbonitrile | Int 61, [132958-72-6] | A1-a | 498 | 498 |
| 108 | 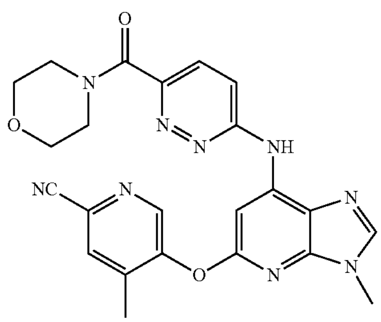 [SMILES: Cc1cc(C#N)ncc1Oc1cc(Nc2ccc(C(=O)N3CCOCC3)nn2)c2ncn(C)c2n1] | 4-methyl-5-[3-methyl-7-[[6-(morpholine-4-carbonyl)pyridazin-3-yl]amino]imidazo[4,5-b]pyridin-5-yl]oxypyridine-2-carbonitrile | Int 63, [110-91-8] | A1-a | 472 | 472 |
| 109 | 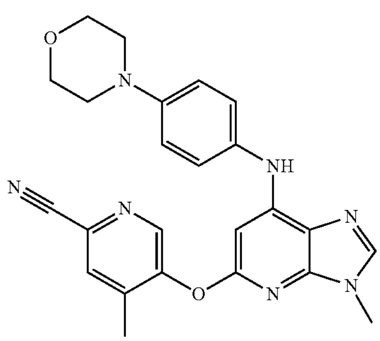 [SMILES: Cc1cc(C#N)ncc1Oc1cc(Nc2ccc(N3CCOCC3)cc2)c2ncn(C)c2n1] | 4-methyl-5-[3-methyl-7-(4-morpholinoanilino)imidazo[4,5-b]pyridin-5-yl]oxy-pyridine-2-carbonitrile | Int 2, [2524-67-6] | B1 | 442 | 442 |
| 110 | 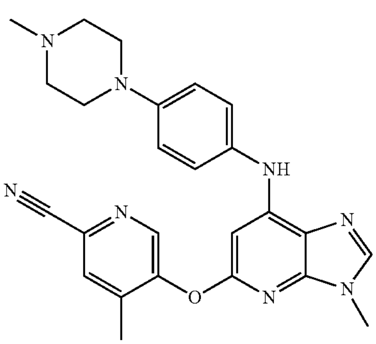 [SMILES: Cc1cc(C#N)ncc1Oc1cc(Nc2ccc(N3CCN(C)CC3)cc2)c2ncn(C)c2n1] | 4-methyl-5-[3-methyl-7-[4-(4-methylpiperazin-1-yl)anilino]imidazo[4,5-b]pyridin-5-yl]oxy-pyridine-2-carbonitrile | Int 2, [16153-81-4] | B1 | 455 | 455 |

TABLE III-continued

Illustrative compounds of the invention

| Cpd # | Structure | Name | SM | Mtd | MW | Mes |
|---|---|---|---|---|---|---|
| 111 | 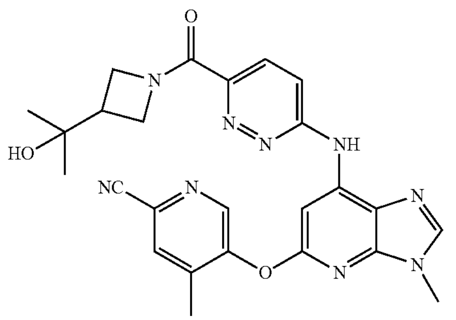 [SMILES: Cc1cc(C#N)ncc1Oc1cc(Nc2ccc(C(=O)N3CC(C(C)(C)O)C3)nn2)c2ncn(C)c2n1] | 5-[7-[[6-[3-(1-hydroxy-1-methyl-ethyl)azetidine-1-carbonyl]pyridazin-3-yl]amino]-3-methyl-imidazo[4,5-b]pyridin-5-yl]oxy-4-methyl-pyridine-2-carbonitrile | Int 63, [1357923-33-1] | A1-a | 500 | 500 |
| 112 | 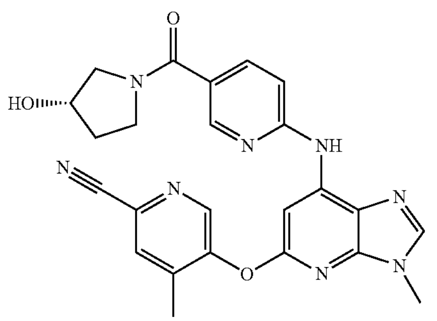 [SMILES: Cc1cc(C#N)ncc1Oc1cc(Nc2ccc(C(=O)N3CC[C@H](O)C3)cn2)c2ncn(C)c2n1] | 5-[7-[[5-[(3S)-3-hydroxypyrrolidine-1-carbonyl]-2-pyridyl]amino]-3-methyl-imidazo[4,5-b]pyridin-5-yl]oxy-4-methyl-pyridine-2-carbonitrile | Int 61, [100243-39-8] | A1-a | 471 | 471 |
| 113 | 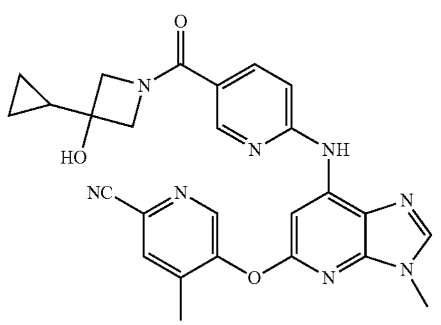 [SMILES: Cc1cc(C#N)ncc1Oc1cc(Nc2ccc(C(=O)N3CC(O)(C4CC4)C3)cn2)c2ncn(C)c2n1] | 5-[7-[[5-(3-cyclopropyl-3-hydroxy-azetidine-1-carbonyl)-2-pyridyl]amino]-3-methyl-imidazo[4,5-b]pyridin-5-yl]oxy-4-methyl-pyridine-2-carbonitrile | Int 61, [848192-93-8] | A1-a | 497 | 497 |
| 114 | 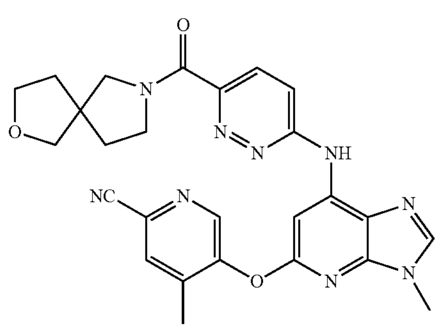 [SMILES: Cc1cc(C#N)ncc1Oc1cc(Nc2ccc(C(=O)N3CCC4(CCOC4)C3)nn2)c2ncn(C)c2n1] | 4-methyl-5-[3-methyl-7-[[5-(8-oxa-3-azaspiro[4.4]nonane-3-carbonyl)-2-pyridyl]amino]imidazo[4,5-b]pyridin-5-yl]oxy-pyridine-2-carbonitrile | Int 61, [175-97-3] | A1-a | 511 | 511 |

TABLE III-continued

Illustrative compounds of the invention

| Cpd # | Structure | Name | SM | Mtd | MW | Mes |
|---|---|---|---|---|---|---|
| 115 | 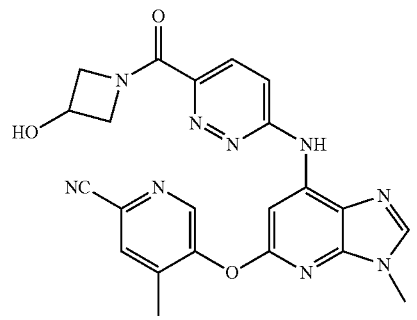 [SMILES: Cc1cc(C#N)ncc1Oc1cc(Nc2ccc(C(=O)N3CC(O)C3)nn2)c2ncn(C)c2n1] | 5-[7-[[6-(3-hydroxyazetidine-1-carbonyl)pyridazin-3-yl]amino]-3-methyl-imidazo[4,5-b]pyridin-5-yl]oxy-4-methyl-pyridine-2-carbonitrile | Int 63, [45347-82-8] | A1-a | 458 | 458 |
| 116 | 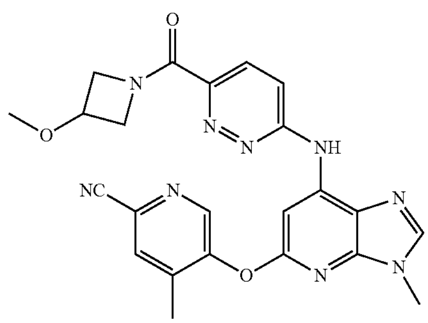 [SMILES: COC1CN(C(=O)c2ccc(Nc3cc(Oc4cnc(C#N)cc4C)nc4c3ncn4C)nn2)C1] | 5-[7-[[6-(3-methoxyazetidine-1-carbonyl)pyridazin-3-yl]amino]-3-methyl-imidazo[4,5-b]pyridin-5-yl]oxy-4-methyl-pyridine-2-carbonitrile | Int 63, [45347-82-8] | A1-a | 472 | 472 |
| 117 | 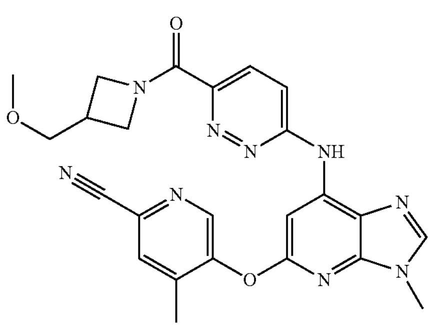 | 5-[7-[[6-[3-(methoxymethyl)azetidine-1-carbonyl]pyridazin-3-yl]amino]-3-methyl-imidazo[4,5-b]pyridin-5-yl]oxy-4-methyl-pyridine-2-carbonitrile | Int 63, [942308-06-7] | A1-a | 486 | 486 |
| 118 | 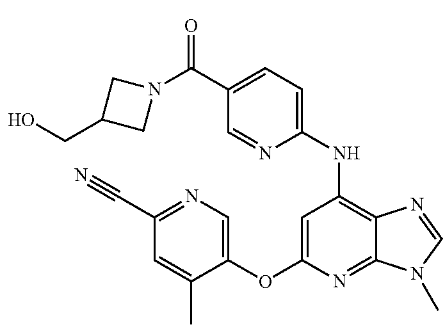 [SMILES: Cc1cc(C#N)ncc1Oc1cc(Nc2ccc(C(=O)N3CC(CO)C3)cn2)c2ncn(C)c2n1] | 5-[7-[[5-[3-(hydroxymethyl)azetidine-1-carbonyl]-2-pyridyl]amino]-3-methyl-imidazo[4,5-b]pyridin-5-yl]oxy-4-methyl-pyridine-2-carbonitrile | Int 61, [928038-44-2] | A1-a | 471 | 471 |

TABLE III-continued

Illustrative compounds of the invention

| Cpd # | Structure | Name | SM | Mtd | MW | Mes |
|---|---|---|---|---|---|---|
| 119 | 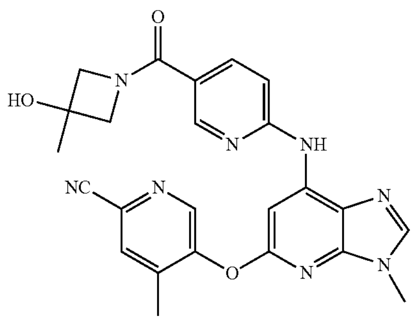 [SMILES: Cc1cc(C#N)ncc1Oc1cc(Nc2ccc(C(=O)N3CC(C)(O)C3)cn2)c2ncn(C)c2n1] | 5-[7-[[5-(3-hydroxy-3-methyl-azetidine-1-carbonyl)-2-pyridyl]amino]-3-methyl-imidazo[4,5-b]pyridin-5-yl]oxy-4-methyl-pyridine-2-carbonitrile | Int 61, [124668-46-8] | A1-a | 471 | 471 |
| 120 | 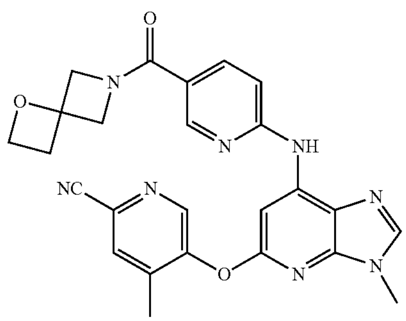 [SMILES: Cc1cc(C#N)ncc1Oc1cc(Nc2ccc(C(=O)N3CC4(CCO4)C3)cn2)c2ncn(C)c2n1] | 4-methyl-5-[3-methyl-7-[[5-(3-oxa-6-azaspiro[3.3]heptane-6-carbonyl)-2-pyridyl]amino]imidazo[4,5-b]pyridin-5-yl]oxy-pyridine-2-carbonitrile | Int 61, [936947-34-1] | A1-a | 483 | 483 |
| 121 | 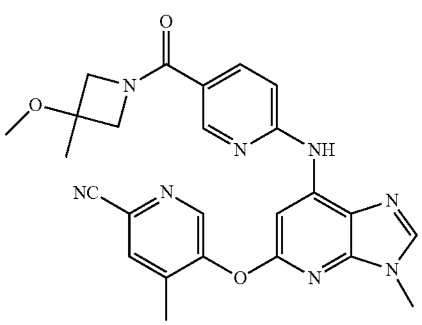 [SMILES: COC1(C)CN(C(=O)c2ccc(Nc3cc(Oc4cnc(C#N)cc4C)nc4c3ncn4C)nc2)C1] | 5-[7-[[5-(3-methoxy-3-methyl-azetidine-1-carbonyl)-2-pyridyl]amino]-3-methyl-imidazo[4,5-b]pyridin-5-yl]oxy-4-methyl-pyridine-2-carbonitrile | Int 61, [905832-93-8] | A1-a | 485 | 485 |
| 122 | 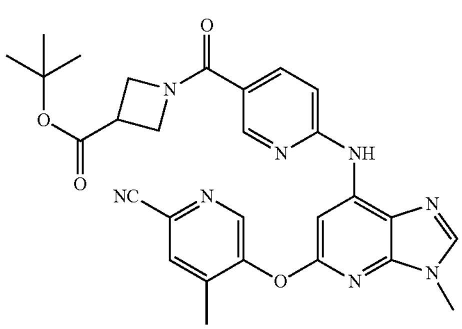 [SMILES: Cc1cc(C#N)ncc1Oc1cc(Nc2ccc(C(=O)N3CC(C(=O)OC(C)(C)C)C3)cn2)c2ncn(C)c2n1] | tert-butyl 1-[6-[[5-[(6-cyano-4-methyl-3-pyridyl)oxy]-3-methyl-imidazo[4,5-b]pyridin-7-yl]amino]pyridine-3-carbonyl]azetidine-3-carboxylate | Int 61, [53871-08-2] | A1-a | 541 | 541 |

TABLE III-continued

Illustrative compounds of the invention

| Cpd # | Structure | Name | SM | Mtd | MW | Mes |
|---|---|---|---|---|---|---|
| 123 | 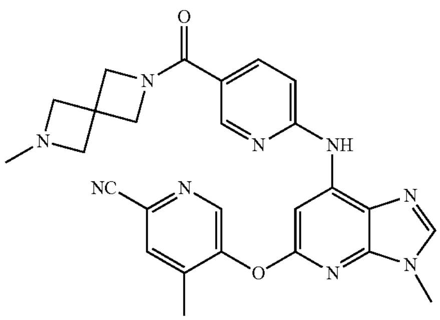 [SMILES: Cc1cc(C#N)ncc1Oc1cc(Nc2ccc(C(=O)N3CC4(CN(C)C4)C3)cn2)c2ncn(C)c2n1] | 4-methyl-5-[3-methyl-7-[[5-(6-methyl-2,6-diazaspiro[3.3]heptane-2-carbonyl)-2-pyridyl]amino]imidazo[4,5-b]pyridin-5-yl]oxy-pyridine-2-carbonitrile | Int 61, [1203567-11-6] | A1-a | 496 | 496 |
| 124 | 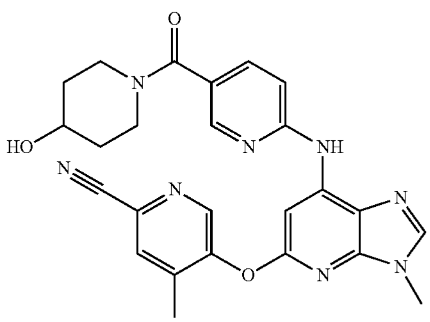 [SMILES: Cc1cc(C#N)ncc1Oc1cc(Nc2ccc(C(=O)N3CCC(O)CC3)cn2)c2ncn(C)c2n1] | 5-[7-[[5-(4-hydroxypiperidine-1-carbonyl)pyridin-2-yl]amino]-3-methylimidazo[4,5-b]pyridin-5-yl]oxy-4-methylpyridine-2-carbonitrile | Int 61, [5382-16-1] | A1-a | 485 | 485 |
| 125 | 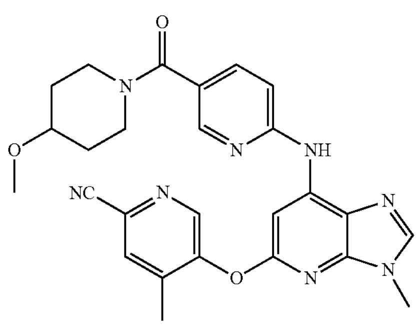 [SMILES: COC1CCN(C(=O)c2ccc(Nc3cc(Oc4cnc(C#N)cc4C)nc4c3ncn4C)nc2)CC1] | 5-[7-[[5-(4-methoxypiperidine-1-carbonyl)pyridin-2-yl]amino]-3-methylimidazo[4,5-b]pyridin-5-yl]oxy-4-methylpyridine-2-carbonitrile | Int 61, [4045-24-3] | A1-a | 499 | 499 |
| 126 | 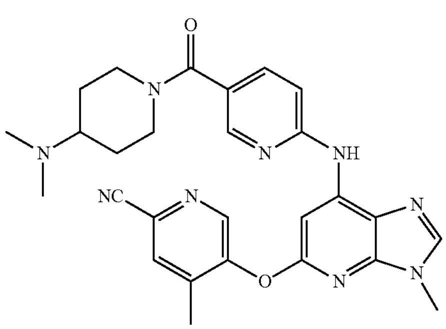 [SMILES: Cc1cc(C#N)ncc1Oc1cc(Nc2ccc(C(=O)N3CCC(N(C)C)CC3)cn2)c2ncn(C)c2n1] | 5-[7-[[5-[4-(dimethylamino)piperidine-1-carbonyl]pyridin-2-yl]amino]-3-methylimidazo[4,5-b]pyridin-5-yl]oxy-4-methylpyridine-2-carbonitrile | Int 61, [50533-97-6] | A1-a | 512 | 512 |

TABLE III-continued

Illustrative compounds of the invention

| Cpd # | Structure | Name | SM | Mtd | MW | Mes |
|---|---|---|---|---|---|---|
| 127 | 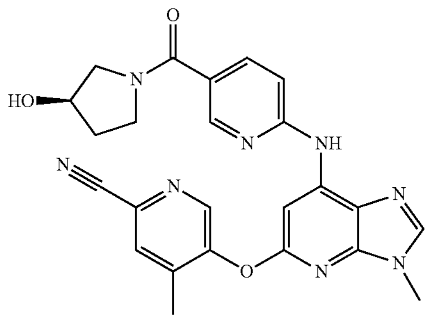 [SMILES: Cc1cc(C#N)ncc1Oc1cc(Nc2ccc(C(=O)N3CC[C@@H](O)C3)cn2)c2ncn(C)c2n1] | 5-[7-[[5-[(3R)-3-hydroxypyrrolidine-1-carbonyl]pyridin-2-yl]amino]-3-methylimidazo[4,5-b]pyridin-5-yl]oxy-4-methylpyridine-2-carbonitrile | Int 61, [2799-21-5] | A1-a | 471 | 471 |
| 128 | 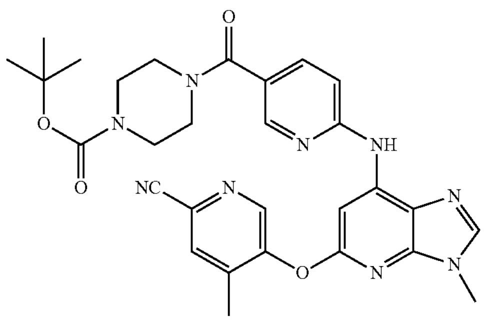 [SMILES: Cc1cc(C#N)ncc1Oc1cc(Nc2ccc(C(=O)N3CCN(C(=O)OC(C)(C)C)CC3)cn2)c2ncn(C)c2n1] | 4-{6-[5-(6-Cyano-4-methyl-pyridin-3-yloxy)-3-methyl-3H-imidazo[4,5-b]pyridin-7-ylamino]-pyridine-3-carbonyl}-piperazine-1-carboxylic acid tert-butyl ester | Int 61, [57260-71-6] | A1-a | 570 | 570 |
| 129 | 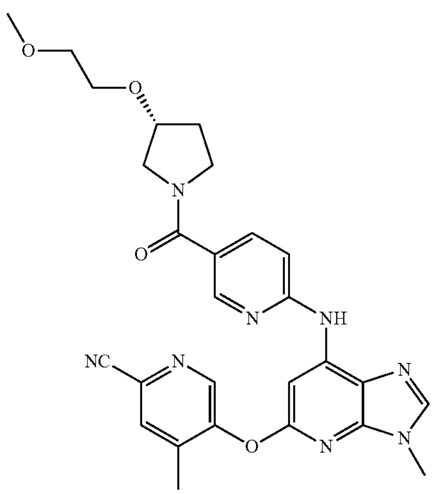 [SMILES: COCCO[C@@H]1CCN(C(=O)c2ccc(Nc3cc(Oc4cnc(C#N)cc4C)nc4c3ncn4C)nc2)C1] | 5-[7-[[5-[(3R)-3-(2-methoxyethoxy)pyrrolidine-1-carbonyl]pyridin-2-yl]amino]-3-methylimidazo[4,5-b]pyridin-5-yl]oxy-4-methylpyridine-2-carbonitrile | Int 61, [942618-26-0] | A1-a | 529 | 529 |
| 130 | 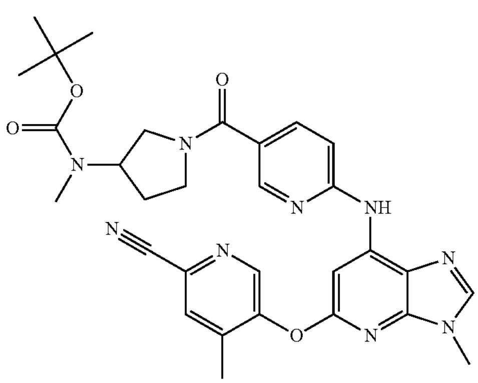 [SMILES: Cc1cc(C#N)ncc1Oc1cc(Nc2ccc(C(=O)N3CCC(N(C)C(=O)OC(C)(C)C)C3)cn2)c2ncn(C)c2n1] | (1-{6-[5-(6-Cyano-4-methyl-pyridin-3-yloxy)-3-methyl-3H-imidazo[4,5-b]pyridin-7-ylamino]-pyridine-3-carbonyl}-pyrrolidin-3-yl)-methyl-carbamic acid tert-butyl ester | Int 61, [172478-00-1] | A1-a | 584 | 584 |

TABLE III-continued

Illustrative compounds of the invention

| Cpd # | Structure | Name | SM | Mtd | MW | Mes |
|---|---|---|---|---|---|---|
| 131 | 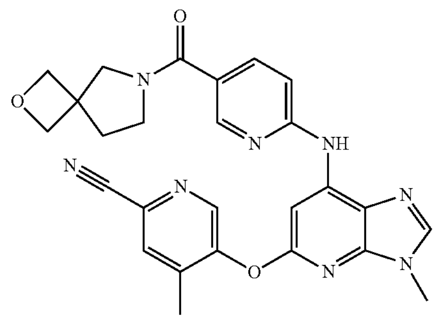 [SMILES: Cc1cc(C#N)ncc1Oc1cc(Nc2ccc(C(=O)N3CCC4(COC4)C3)cn2)c2ncn(C)c2n1] | 4-methyl-5-[3-methyl-7-[[5-(2-oxa-7-azaspiro[3.4]octane-7-carbonyl)pyridin-2-yl]amino]imidazo[4,5-b]pyridin-5-yl]oxypyridine-2-carbonitrile | Int 61, [39640-71-6] | A1-a | 497 | 497 |
| 132 | 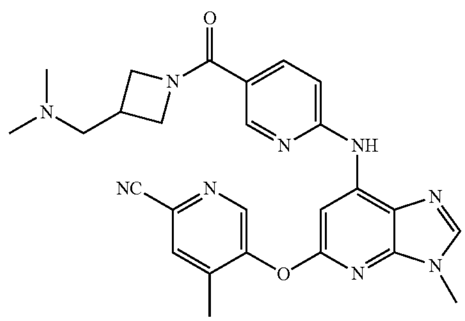 [SMILES: Cc1cc(C#N)ncc1Oc1cc(Nc2ccc(C(=O)N3CC(CN(C)C)C3)cn2)c2ncn(C)c2n1] | 5-[7-[[5-[3-[(dimethylamino)methyl]azetidine-1-carbonyl]pyridin-2-yl]amino]-3-methylimidazo[4,5-b]pyridin-5-yl]oxy-4-methylpyridine-2-carbonitrile | Int 61, [321890-22-6] | A1-a | 498 | 498 |
| 133 | 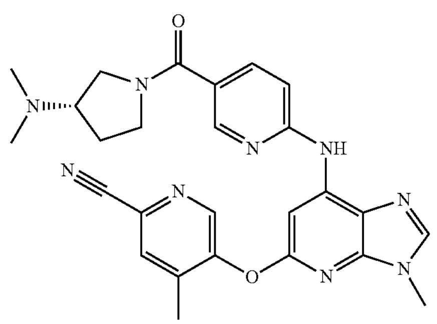 [SMILES: Cc1cc(C#N)ncc1Oc1cc(Nc2ccc(C(=O)N3CC[C@H](N(C)C)C3)cn2)c2ncn(C)c2n1] | 5-[7-[[5-[(3S)-3-(dimethylamino)pyrrolidine-1-carbonyl]pyridin-2-yl]amino]-3-methylimidazo[4,5-b]pyridin-5-yl]oxy-4-methylpyridine-2-carbonitrile | Int 61, [132883-44-4] | A1-a | 498 | 498 |
| 134 | 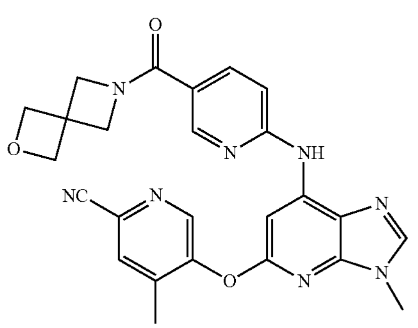 [SMILES: Cc1cc(C#N)ncc1Oc1cc(Nc2ccc(C(=O)N3CC4(COC4)C3)cn2)c2ncn(C)c2n1] | 4-methyl-5-[3-methyl-7-[[5-(2-oxa-6-azaspiro[3.3]heptane-6-carbonyl)pyridin-2-yl]amino]imidazo[4,5-b]pyridin-5-yl]oxypyridine-2-carbonitrile | Int 61, [1045709-32-7] | A1-a | 483 | 483 |

TABLE III-continued

Illustrative compounds of the invention

| Cpd # | Structure | Name | SM | Mtd | MW | Mes |
|---|---|---|---|---|---|---|
| 135 | 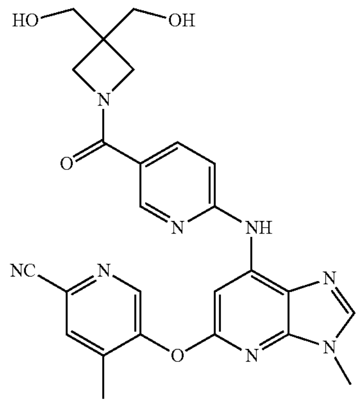 [SMILES: Cc1cc(C#N)ncc1Oc1cc(Nc2ccc(C(=O)N3CC(CO)(CO)C3)cn2)c2ncn(C)c2n1] | 5-[7-[[5-[3,3-bis(hydroxymethyl)azetidine-1-carbonyl]pyridin-2-yl]amino]-3-methylimidazo[4,5-b]pyridin-5-yl]oxy-4-methylpyridine-2-carbonitrile | Int 61, [1016232-92-0] | A1-a | 501 | 501 |
| 136 | 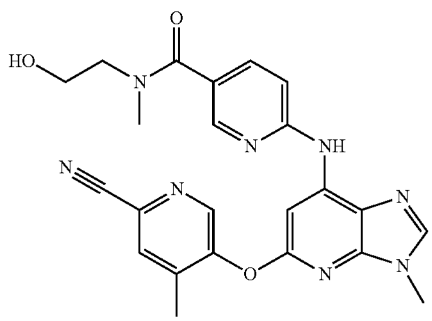 [SMILES: Cc1cc(C#N)ncc1Oc1cc(Nc2ccc(C(=O)N(C)CCO)cn2)c2ncn(C)c2n1] | 6-[[5-(6-cyano-4-methylpyridin-3-yl)oxy-3-methylimidazo[4,5-b]pyridin-7-yl]amino]-N-(2-hydroxyethyl)-N-methylpyridine-3-carboxamide | Int 61, [109-83-1] | A1-a | 459 | 459 |
| 137 | 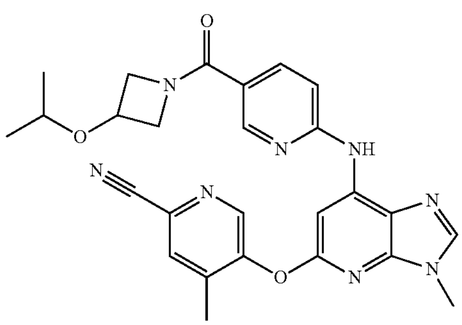 [SMILES: Cc1cc(C#N)ncc1Oc1cc(Nc2ccc(C(=O)N3CC(OC(C)C)C3)cn2)c2ncn(C)c2n1] | 4-methyl-5-[3-methyl-7-[[5-(3-propan-2-yloxyazetidine-1-carbonyl)pyridin-2-yl]amino]imidazo[4,5-b]pyridin-5-yl]oxypyridine-2-carbonitrile | Int 61, [871657-49-7] | A1-a | 499 | 499 |
| 138 | 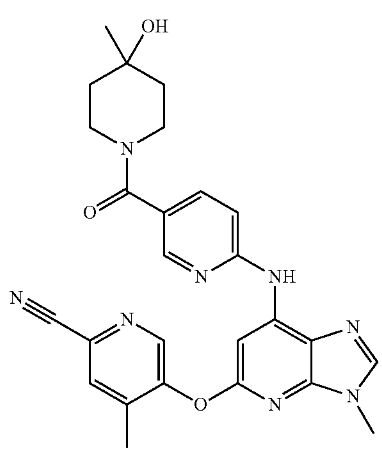 [SMILES: Cc1cc(C#N)ncc1Oc1cc(Nc2ccc(C(=O)N3CCC(C)(O)CC3)cn2)c2ncn(C)c2n1] | 5-[7-[[5-(4-hydroxy-4-methylpiperidine-1-carbonyl)pyridin-2-yl]amino]-3-methylimidazo[4,5-b]pyridin-5-yl]oxy-4-methylpyridine-2-carbonitrile | Int 61, [3970-68-1] | A1-a | 499 | 499 |

TABLE III-continued

Illustrative compounds of the invention

| Cpd # | Structure | Name | SM | Mtd | MW | Mes |
|---|---|---|---|---|---|---|
| 139 | 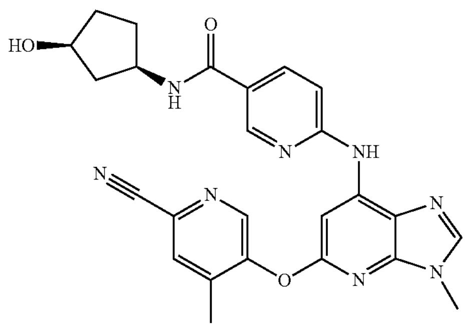 [SMILES: Cc1cc(C#N)ncc1Oc1cc(Nc2ccc(C(=O)N[C@@H]3CC[C@H](O)C3)cn2)c2ncn(C)c2n1] | 6-[[5-(6-cyano-4-methylpyridin-3-yl)oxy-3-methylimidazo[4,5-b]pyridin-7-yl]amino]-N-[rac-(1R,3R)-3-hydroxycyclopentyl]pyridine-3-carboxamide | Int 61, [124555-33-5] | A1-a | 485 | 485 |
| 140 | 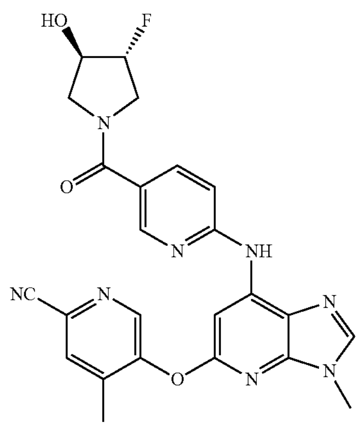 [SMILES: Cc1cc(C#N)ncc1Oc1cc(Nc2ccc(C(=O)N3C[C@@H](O)[C@H](F)C3)cn2)c2ncn(C)c2n1] | 4-methyl-5-[3-methyl-7-[[5-[rac-(3R,4R)-3-fluoro-4-hydroxypyrrolidine-1-carbonyl]pyridin-2-yl]amino]imidazo[4,5-b]pyridin-5-yl]oxypyridine-2-carbonitrile | Int 61, [1334320-82-9] | A1-a | 489 | 489 |
| 141 | 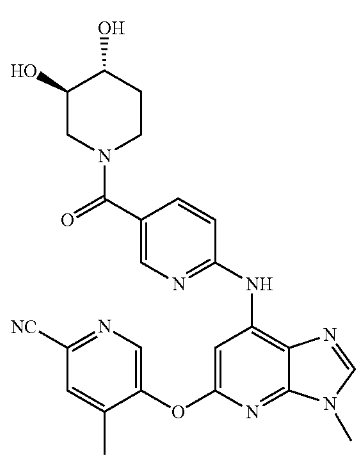 [SMILES: Cc1cc(C#N)ncc1Oc1cc(Nc2ccc(C(=O)N3CC[C@@H](O)[C@H](O)C3)cn2)c2ncn(C)c2n1] | 4-methyl-5-[3-methyl-7-[[5-[rac-(3R,4R)-3,4-dihydroxypiperidine-1-carbonyl]pyridin-2-yl]amino]imidazo[4,5-b]pyridin-5-yl]oxypyridine-2-carbonitrile | Int 61, [39640-71-6] | A1-a | 501 | 501 |

TABLE III-continued

Illustrative compounds of the invention

| Cpd # | Structure | Name | SM | Mtd | MW | Mes |
|---|---|---|---|---|---|---|
| 142 | 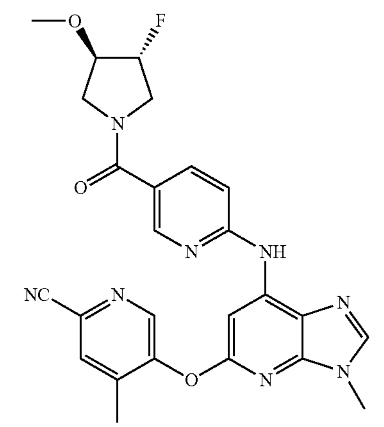 [SMILES: CO[C@@H]1CN(C(=O)c2ccc(Nc3cc(Oc4cnc(C#N)cc4C)nc4c3ncn4C)nc2)C[C@H]1F] | 4-methyl-5-[3-methyl-7-[[5-[rac-(3R,4R)-3-fluoro-4-methoxypyrrolidine-1-carbonyl]pyridin-2-yl]amino]imidazo[4,5-b]pyridin-5-yl]oxypyridine-2-carbonitrile | Int 61, [1203566-98-6] | A1-a | 503 | 503 |
| 143 | 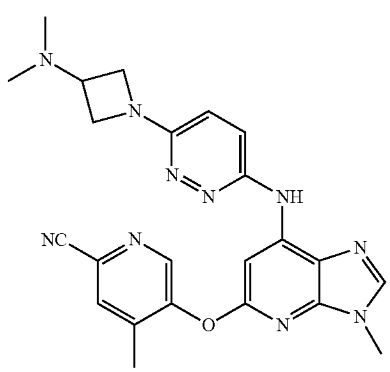 [SMILES: Cc1cc(C#N)ncc1Oc1cc(Nc2ccc(N3CC(N(C)C)C3)nn2)c2ncn(C)c2n1] | 5-[7-[[6-[3-(dimethylamino)azetidin-1-yl]pyridazin-3-yl]amino]-3-methylimidazo[4,5-b]pyridin-5-yl]oxy-4-methylpyridine-2-carbonitrile | Int 2, Int 90 | B1 | 457 | 457 |
| 144 | 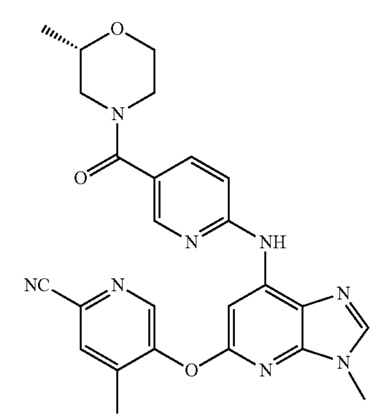 [SMILES: Cc1cc(C#N)ncc1Oc1cc(Nc2ccc(C(=O)N3CCO[C@@H](C)C3)cn2)c2ncn(C)c2n1] | 4-methyl-5-[3-methyl-7-[[5-[(2S)-2-methylmorpholine-4-carbonyl]pyridin-2-yl]amino]imidazo[4,5-b]pyridin-5-yl]oxypyridine-2-carbonitrile | Int 61, [74572-13-7] | A1-a | 485 | 485 |

TABLE III-continued

Illustrative compounds of the invention

| Cpd # | Structure | Name | SM | Mtd | MW | Mes |
|---|---|---|---|---|---|---|
| 145 | 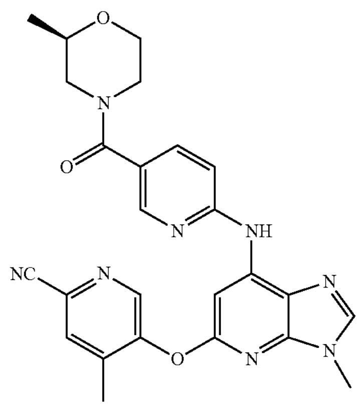 [SMILES: Cc1cc(C#N)ncc1Oc1cc(Nc2ccc(C(=O)N3CCO[C@H](C)C3)cn2)c2ncn(C)c2n1] | 4-methyl-5-[3-methyl-7-[[5-[(2R)-2-methylmorpholine-4-carbonyl]pyridin-2-yl]amino]imidazo[4,5-b]pyridin-5-yl]oxypyridine-2-carbonitrile | Int 61, [168038-14-0] | A1-a | 485 | 485 |
| 146 | 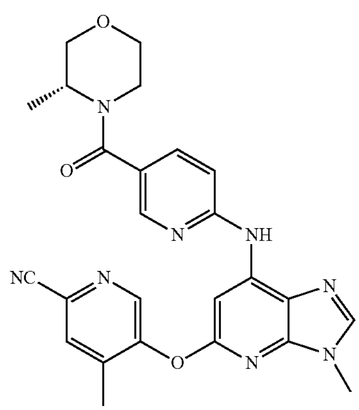 [SMILES: Cc1cc(C#N)ncc1Oc1cc(Nc2ccc(C(=O)N3CCOC[C@H]3C)cn2)c2ncn(C)c2n1] | 4-methyl-5-[3-methyl-7-[[5-[(3R)-3-methylmorpholine-4-carbonyl]pyridin-2-yl]amino]imidazo[4,5-b]pyridin-5-yl]oxypyridine-2-carbonitrile | Int 61, [74572-04-6] | A1-a | 485 | 485 |
| 147 | 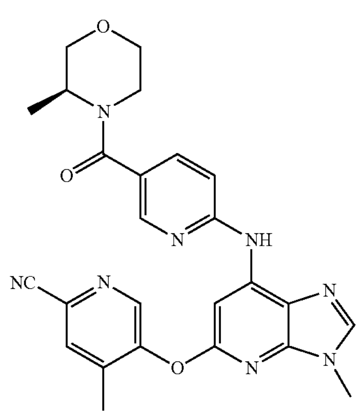 [SMILES: Cc1cc(C#N)ncc1Oc1cc(Nc2ccc(C(=O)N3CCOC[C@@H]3C)cn2)c2ncn(C)c2n1] | 4-methyl-5-[3-methyl-7-[[5-[(3S)-3-methylmorpholine-4-carbonyl]pyridin-2-yl]amino]imidazo[4,5-b]pyridin-5-yl]oxypyridine-2-carbonitrile | Int 61, [350595-57-2] | A1-a | 485 | 485 |

TABLE III-continued

Illustrative compounds of the invention

| Cpd # | Structure | Name | SM | Mtd | MW | Mes |
|---|---|---|---|---|---|---|
| 148 | 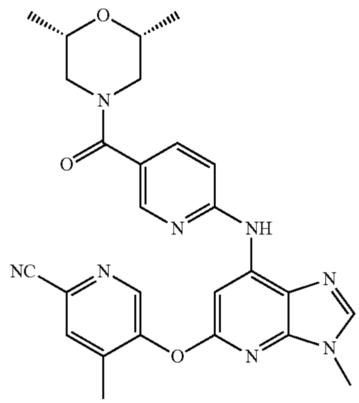 [SMILES: Cc1cc(C#N)ncc1Oc1cc(Nc2ccc(C(=O)N3C[C@@H](C)O[C@@H](C)C3)cn2)c2ncn(C)c2n1] | 4-methyl-5-[3-methyl-7-[[5-[rac-(2R,6S)-2,6-dimethylmorpholine-4-carbonyl]pyridin-2-yl]amino]imidazo[4,5-b]pyridin-5-yl]oxypyridine-2-carbonitrile | Int 61, [6485-55-8] | A1-a | 499 | 499 |
| 149 | 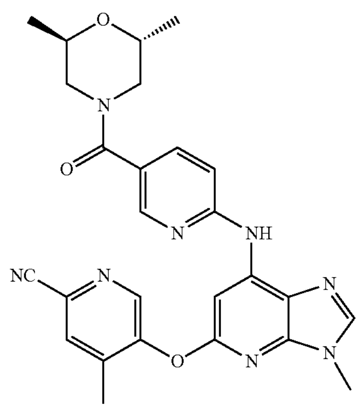 [SMILES: Cc1cc(C#N)ncc1Oc1cc(Nc2ccc(C(=O)N3C[C@@H](C)O[C@H](C)C3)cn2)c2ncn(C)c2n1] | 4-methyl-5-[3-methyl-7-[[5-[rac-(2R,6R)-2,6-dimethylmorpholine-4-carbonyl]pyridin-2-yl]amino]imidazo[4,5-b]pyridin-5-yl]oxypyridine-2-carbonitrile | Int 61, [6485-45-6] | A1-a | 499 | 499 |
| 150 | 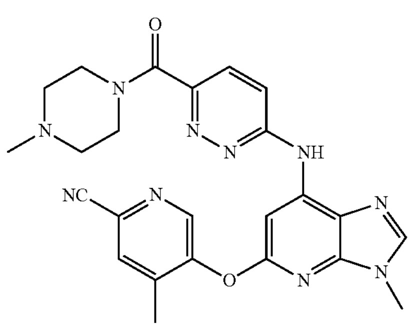 [SMILES: Cc1cc(C#N)ncc1Oc1cc(Nc2ccc(C(=O)N3CCN(C)CC3)nn2)c2ncn(C)c2n1] | 4-methyl-5-[3-methyl-7-[[6-(4-methylpiperazine-1-carbonyl)pyridazin-3-yl]amino]imidazo[4,5-b]pyridin-5-yl]oxypyridine-2-carbonitrile | Int 66 Int 2 | B1 | 485 | 485 |
| 151 | 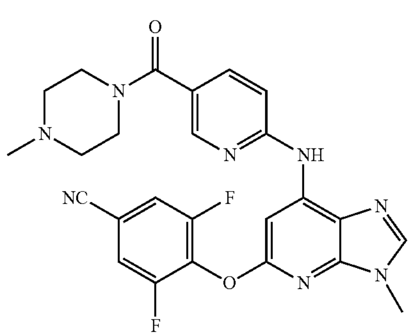 [SMILES: CN1CCN(C(=O)c2ccc(Nc3cc(Oc4c(F)cc(C#N)cc4F)nc4c3ncn4C)nc2)CC1] | 3,5-difluoro-4-[3-methyl-7-[[5-(4-methylpiperazine-1-carbonyl)pyridin-2-yl]amino]imidazo[4,5-b]pyridin-5-yl]oxybenzonitrile | Int 92, Int 84 | B1 | 505 | 505 |

TABLE III-continued

Illustrative compounds of the invention

| Cpd # | Structure | Name | SM | Mtd | MW | Mes |
|---|---|---|---|---|---|---|
| 152 | 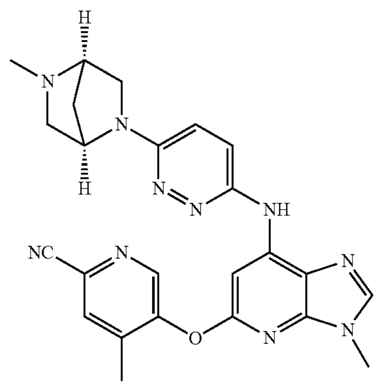 [SMILES: Cc1cc(C#N)ncc1Oc1cc(Nc2ccc(N3C[C@H]4C[C@@H]3CN4C)nn2)c2ncn(C)c2n1] | 4-methyl-5-[3-methyl-7-[[6-[(1R,4R)-5-methyl-2,5-diazabicyclo[2.2.1]heptan-2-yl]pyridazin-3-yl]amino]imidazo[4,5-b]pyridin-5-yl]oxypyridine-2-carbonitrile | Int 3, Int 91 | B2-a | 469 | 469 |
| 153 | 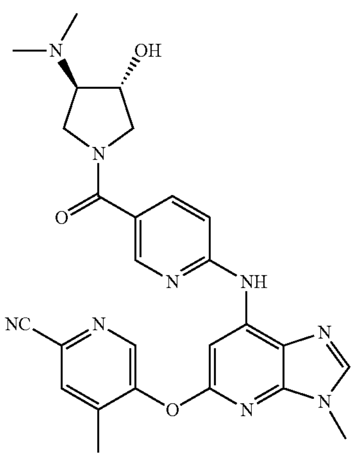 [SMILES: Cc1cc(C#N)ncc1Oc1cc(Nc2ccc(C(=O)N3C[C@@H](O)[C@H](N(C)C)C3)cn2)c2ncn(C)c2n1] | 5-{7-[5-((3R,4R)-3-Dimethylamino-4-hydroxy-pyrrolidine-1-carbonyl)-pyridin-2-ylamino]-3-methyl-3H-imidazo[4,5-b]pyridin-5-yloxy}-4-methyl-pyridine-2-carbonitrile | Int 61, [960289-61-6] | A1-a | 514 | 514 |
| 154 | 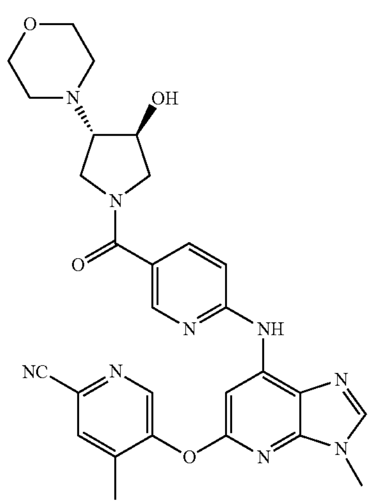 [SMILES: Cc1cc(C#N)ncc1Oc1cc(Nc2ccc(C(=O)N3C[C@H](O)[C@@H](N4CCOCC4)C3)cn2)c2ncn(C)c2n1] | 5-{7-[5-((3S,4S)-3-Hydroxy-4-morpholin-4-yl-pyrrolidine-1-carbonyl)-pyridin-2-ylamino]-3-methyl-3H-imidazo[4,5-b]pyridin-5-yloxy}-4-methyl-pyridine-2-carbonitrile | Int 61, [1187339-81-6] | A1-a | 556 | 556 |

TABLE III-continued

Illustrative compounds of the invention

| Cpd # | Structure | Name | SM | Mtd | MW | Mes |
|---|---|---|---|---|---|---|
| 155 | 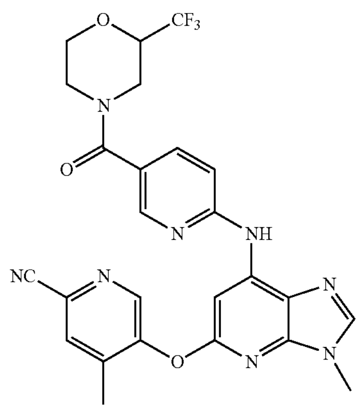 [SMILES: Cc1cc(C#N)ncc1Oc1cc(Nc2ccc(C(=O)N3CCOC(C(F)(F)F)C3)cn2)c2ncn(C)c2n1] | 4-methyl-5-[3-methyl-7-[[5-[2-(trifluoromethyl)morpholine-4-carbonyl]pyridin-2-yl]amino]imidazo[4,5-b]pyridin-5-yl]oxypyridine-2-carbonitrile | Int 61, [1196152-51-8] | A1-a | 539 | 539 |
| 156 | 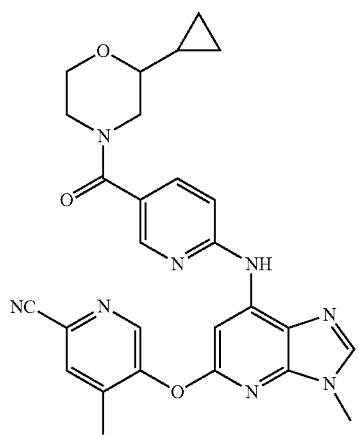 [SMILES: Cc1cc(C#N)ncc1Oc1cc(Nc2ccc(C(=O)N3CCOC(C4CC4)C3)cn2)c2ncn(C)c2n1] | 5-[7-[[5-(2-cyclopropylmorpholine-4-carbonyl)pyridin-2-yl]amino]-3-methylimidazo[4,5-b]pyridin-5-yl]oxy-4-methylpyridine-2-carbonitrile | Int 61, [1063734-79-1] | A1-a | 511 | 511 |
| 157 | 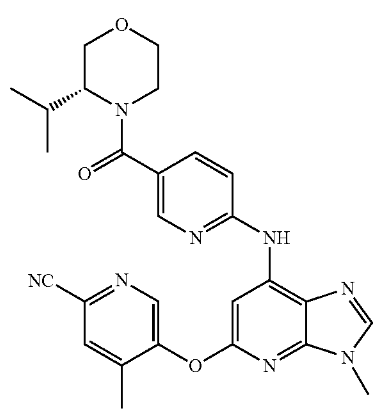 [SMILES: Cc1cc(C#N)ncc1Oc1cc(Nc2ccc(C(=O)N3CCOC[C@H]3C(C)C)cn2)c2ncn(C)c2n1] | 4-methyl-5-[3-methyl-7-[[5-[(3R)-3-propan-2-ylmorpholine-4-carbonyl]pyridin-2-yl]amino]imidazo[4,5-b]pyridin-5-yl]oxypyridine-2-carbonitrile | Int 61, [74572-01-3] | A1-a | 513 | 513 |

TABLE III-continued

Illustrative compounds of the invention

| Cpd # | Structure | Name | SM | Mtd | MW | Mes |
|---|---|---|---|---|---|---|
| 158 | 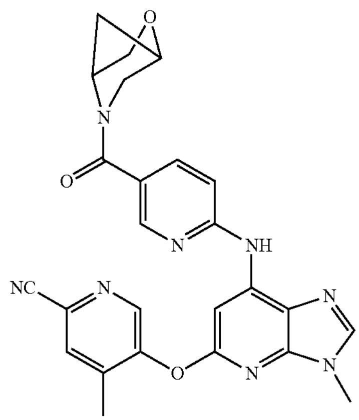 [SMILES: Cc1cc(C#N)ncc1Oc1cc(Nc2ccc(C(=O)N3CC4CC3CO4)cn2)c2ncn(C)c2n1] | 4-methyl-5-[3-methyl-7-[[5-(2-oxa-5-azabicyclo[2.2.1]heptane-5-carbonyl)pyridin-2-yl]amino]imidazo[4,5-b]pyridin-5-yl]oxypyridine-2-carbonitrile | Int 61, [31560-06-2] | A1-a | 483 | 483 |
| 159 | 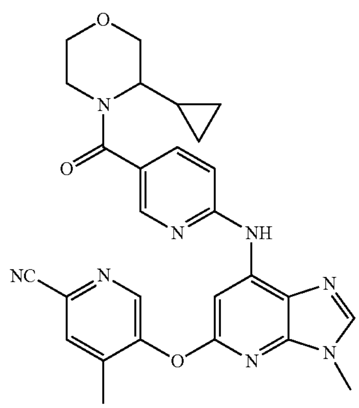 [SMILES: Cc1cc(C#N)ncc1Oc1cc(Nc2ccc(C(=O)N3CCOCC3C3CC3)cn2)c2ncn(C)c2n1] | 5-[7-[[5-(3-cyclopropylmorpholine-4-carbonyl)pyridin-2-yl]amino]-3-methylimidazo[4,5-b]pyridin-5-yl]oxy-4-methylpyridine-2-carbonitrile | Int 61, [260667-05-7] | A1-a | 511 | 511 |
| 160 | 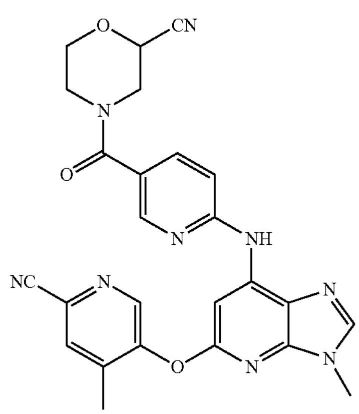 [SMILES: Cc1cc(C#N)ncc1Oc1cc(Nc2ccc(C(=O)N3CCOC(C#N)C3)cn2)c2ncn(C)c2n1] | 4-[6-[[5-(6-cyano-4-methylpyridin-3-yl)oxy-3-methylimidazo[4,5-b]pyridin-7-yl]amino]pyridine-3-carbonyl]morpholine-2-carbonitrile | Int 61, [1205751-07-0] | A1-a | 496 | 496 |

TABLE III-continued

Illustrative compounds of the invention

| Cpd # | Structure | Name | SM | Mtd | MW | Mes |
|---|---|---|---|---|---|---|
| 161 | 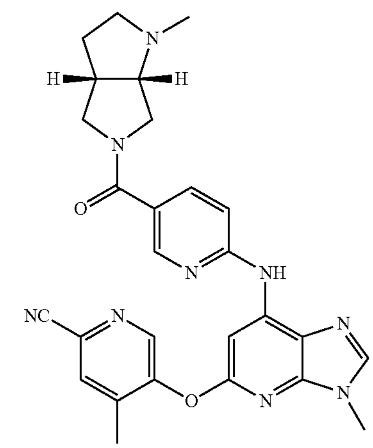 [SMILES: Cc1cc(C#N)ncc1Oc1cc(Nc2ccc(C(=O)N3C[C@@H]4CCN(C)[C@@H]4C3)cn2)c2ncn(C)c2n1] | 4-Methyl-5-{3-methyl-7-[5-((3aS,6aS)-1-methyl-hexahydro-pyrrolo[3,4-b]pyrrole-5-carbonyl)-pyridin-2-ylamino]-3H-imidazo[4,5-b]pyridin-5-yloxy}-pyridine-2-carbonitrile | Int 61, [877212-98-1] | A1-a | 510 | 510 |
| 162 | 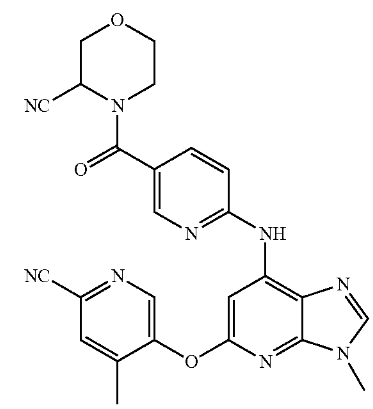 [SMILES: Cc1cc(C#N)ncc1Oc1cc(Nc2ccc(C(=O)N3CCOCC3C#N)cn2)c2ncn(C)c2n1] | 4-[6-[[5-(6-cyano-4-methylpyridin-3-yl)oxy-3-methylimidazo[4,5-b]pyridin-7-yl]amino]pyridine-3-carbonyl]morpholine-3-carbonitrile | Int 61, [97039-63-9] | A1-a | 496 | 496 |
| 163 | 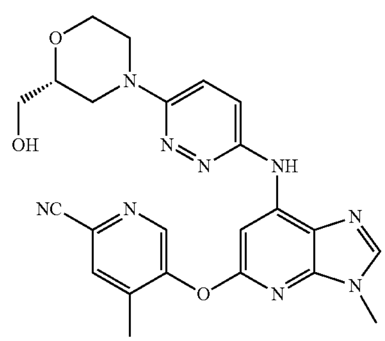 [SMILES: Cc1cc(C#N)ncc1Oc1cc(Nc2ccc(N3CCO[C@@H](CO)C3)nn2)c2ncn(C)c2n1] | 5-[7-[[6-[(2R)-2-(hydroxymethyl)morpholin-4-yl]pyridazin-3-yl]amino]-3-methylimidazo[4,5-b]pyridin-5-yl]oxy-4-methylpyridine-2-carbonitrile | Int 3, Int 68 | B2-a | 474 | 474 |
| 164 | 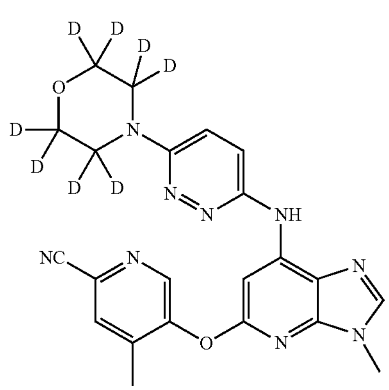 [SMILES: [2H]C1([2H])OC([2H])([2H])C([2H])([2H])N(c2ccc(Nc3cc(Oc4cnc(C#N)cc4C)nc4c3ncn4C)nn2)C1([2H])[2H]] | 4-methyl-5-[3-methyl-7-[[6-(2,2,3,3,5,5,6,6-octadeuteriomorpholin-4-yl)pyridazin-3-yl]amino]imidazo[4,5-b]pyridin-5-yl]oxy-pyridine-2-carbonitrile | Int 3, Int 69 | B2-a | 452 | 452 |

TABLE III-continued

Illustrative compounds of the invention

| Cpd # | Structure | Name | SM | Mtd | MW | Mes |
|---|---|---|---|---|---|---|
| 165 | 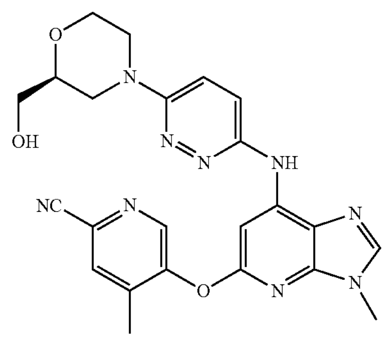 [SMILES: Cc1cc(C#N)ncc1Oc1cc(Nc2ccc(N3CCO[C@H](CO)C3)nn2)c2ncn(C)c2n1] | 5-[7-[[6-[(2S)-2-(hydroxymethyl)morpholin-4-yl]pyridazin-3-yl]amino]-3-methylimidazo[4,5-b]pyridin-5-yl]oxy-4-methylpyridine-2-carbonitrile | Int 3, Int 70 | B20a | 474 | 474 |
| 166 | 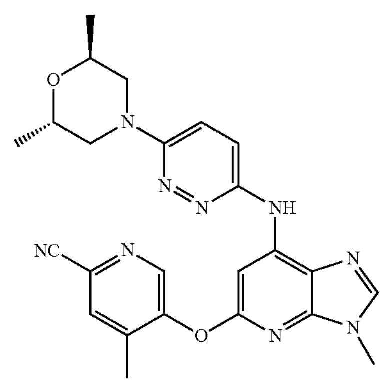 [SMILES: Cc1cc(C#N)ncc1Oc1cc(Nc2ccc(N3C[C@H](C)O[C@@H](C)C3)nn2)c2ncn(C)c2n1] | 5-[7-[[6-[(2S,6S)-2,6-dimethylmorpholin-4-yl]pyridazin-3-yl]amino]-3-methylimidazo[4,5-b]pyridin-5-yl]oxy-4-methylpyridine-2-carbonitrile | Int 3, Int 71 | B2-a | 472 | 472 |
| 167 | 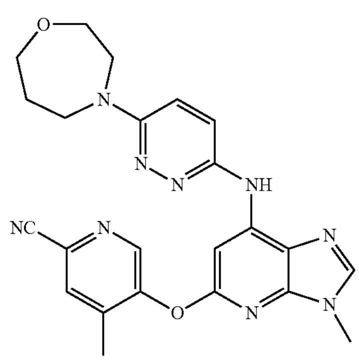 [SMILES: Cc1cc(C#N)ncc1Oc1cc(Nc2ccc(N3CCCOCC3)nn2)c2ncn(C)c2n1] | 4-methyl-5-[3-methyl-7-[[6-(1,4-oxazepan-4-yl)pyridazin-3-yl]amino]imidazo[4,5-b]pyridin-5-yl]oxypyridine-2-carbonitrile | Int 3, Int 72 | B2-a | 458 | 458 |
| 168 | 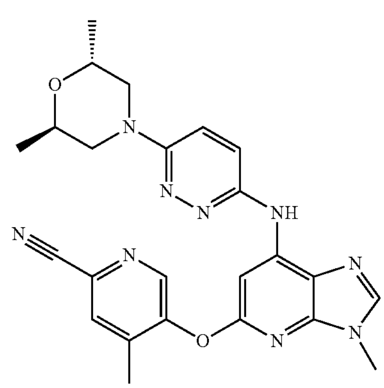 [SMILES: Cc1cc(C#N)ncc1Oc1cc(Nc2ccc(N3C[C@@H](C)O[C@H](C)C3)nn2)c2ncn(C)c2n1] | 5-[7-[[6-[(2R,6R)-2,6-dimethylmorpholin-4-yl]pyridazin-3-yl]amino]-3-methylimidazo[4,5-b]pyridin-5-yl]oxy-4-methylpyridine-2-carbonitrile | Int 3, Int 73 | B2-a | 472 | 472 |

TABLE III-continued

Illustrative compounds of the invention

| Cpd # | Structure | Name | SM | Mtd | MW | Mes |
|---|---|---|---|---|---|---|
| 169 | 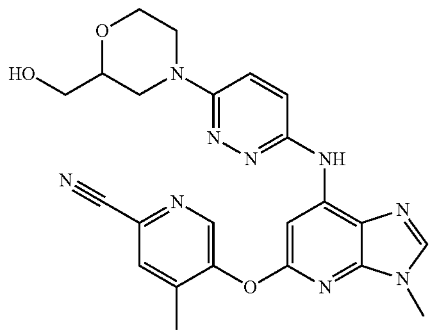 [SMILES: Cc1cc(C#N)ncc1Oc1cc(Nc2ccc(N3CCOC(CO)C3)nn2)c2ncn(C)c2n1] | 5-[7-[[6-[2-(hydroxymethyl)morpholin-4-yl]pyridazin-3-yl]amino]-3-methylimidazo[4,5-b]pyridin-5-yl]oxy-4-methylpyridine-2-carbonitrile | Int 3, Int 74 | B2-a | 474 | 474 |
| 170 | 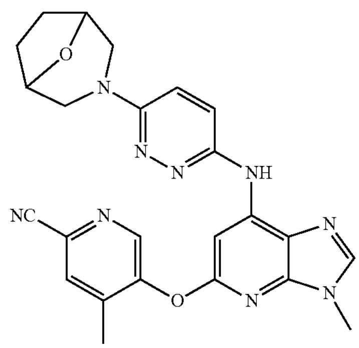 [SMILES: Cc1cc(C#N)ncc1Oc1cc(Nc2ccc(N3CC4CCC(C3)O4)nn2)c2ncn(C)c2n1] | 4-methyl-5-[3-methyl-7-[[6-(8-oxa-3-azabicyclo[3.2.1]octan-3-yl)pyridazin-3-yl]amino]imidazo[4,5-b]pyridin-5-yl]oxypyridine-2-carbonitrile | Int 3, Int 75 | B2-a | 470 | 470 |
| 171 | 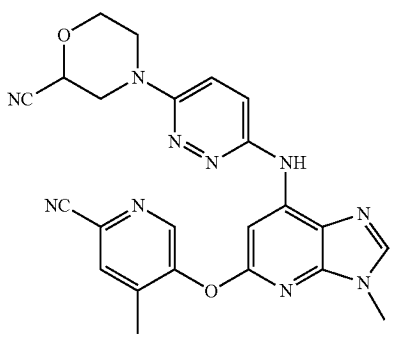 [SMILES: Cc1cc(C#N)ncc1Oc1cc(Nc2ccc(N3CCOC(C#N)C3)nn2)c2ncn(C)c2n1] | 4-[6-[[5-(6-cyano-4-methylpyridin-3-yl)oxy-3-methylimidazo[4,5-b]pyridin-7-yl]amino]pyridazin-3-yl]morpholine-2-carbonitrile | Int 3, Int 76 | B2-a | 468 | 469 |
| 172 | 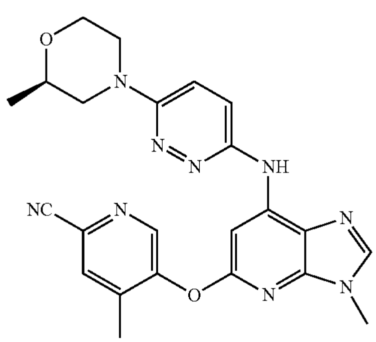 [SMILES: Cc1cc(C#N)ncc1Oc1cc(Nc2ccc(N3CCO[C@H](C)C3)nn2)c2ncn(C)c2n1] | 4-methyl-5-[3-methyl-7-[[6-[(2R)-2-methylmorpholin-4-yl]pyridazin-3-yl]amino]imidazo[4,5-b]pyridin-5-yl]oxypyridine-2-carbonitrile | Int 3, Int 77 | B2-a | 458 | 458 |

TABLE III-continued

Illustrative compounds of the invention

| Cpd # | Structure | Name | SM | Mtd | MW | Mes |
|---|---|---|---|---|---|---|
| 173 | 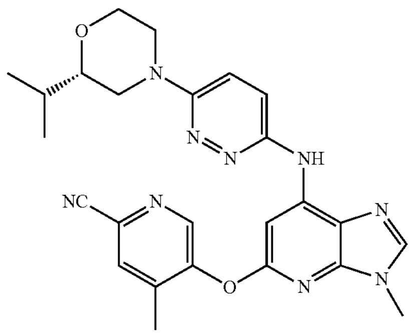 [SMILES: Cc1cc(C#N)ncc1Oc1cc(Nc2ccc(N3CCO[C@@H](C(C)C)C3)nn2)c2ncn(C)c2n1] | 4-methyl-5-[3-methyl-7-[[6-[(2R)-2-propan-2-ylmorpholin-4-yl]pyridazin-3-yl]amino]imidazo[4,5-b]pyridin-5-yl]oxypyridine-2-carbonitrile | Int 3, Int 78 | B2-a | 486 | 486 |
| 174 | 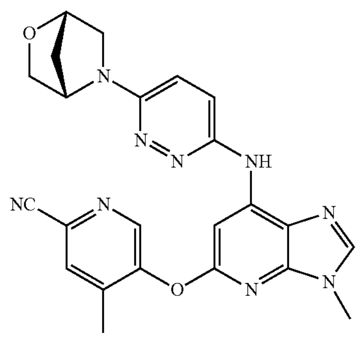 [SMILES: Cc1cc(C#N)ncc1Oc1cc(Nc2ccc(N3C[C@@H]4C[C@H]3CO4)nn2)c2ncn(C)c2n1] | 4-methyl-5-[3-methyl-7-[[6-[(1S,4S)-2-oxa-5-azabicyclo[2.2.1]heptan-5-yl]pyridazin-3-yl]amino]imidazo[4,5-b]pyridin-5-yl]oxypyridine-2-carbonitrile | Int 3, Int 79 | B2-a | 455 | 456 |
| 175 | 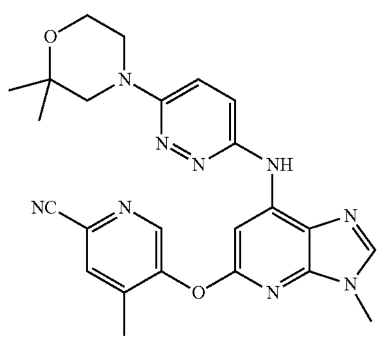 [SMILES: Cc1cc(C#N)ncc1Oc1cc(Nc2ccc(N3CCOC(C)(C)C3)nn2)c2ncn(C)c2n1] | 5-[7-[[6-(2,2-dimethylmorpholin-4-yl)pyridazin-3-yl]amino]-3-methylimidazo[4,5-b]pyridin-5-yl]oxy-4-methylpyridine-2-carbonitrile | Int 3, Int 80 | B2-a | 472 | 472 |
| 176 | 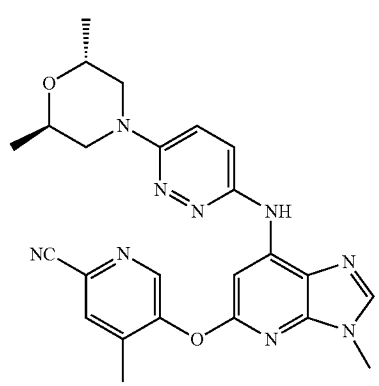 [SMILES: Cc1cc(C#N)ncc1Oc1cc(Nc2ccc(N3C[C@@H](C)O[C@H](C)C3)nn2)c2ncn(C)c2n1] | 4-methyl-5-[3-methyl-7-[[6-[rac-(2R,6R)-2,6-dimethylmorpholin-4-yl]pyridazin-3-yl]amino]imidazo[4,5-b]pyridin-5-yl]oxypyridine-2-carbonitrile | Int 3, Int 81 | B2-a | 472 | 472 |

TABLE III-continued

Illustrative compounds of the invention

| Cpd # | Structure | Name | SM | Mtd | MW | Mes |
|---|---|---|---|---|---|---|
| 177 | 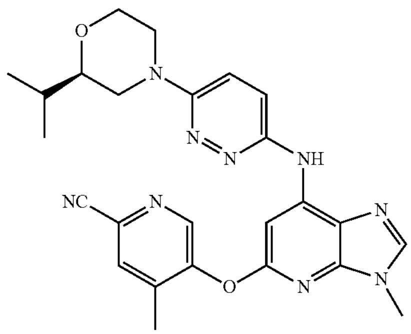 [SMILES: Cc1cc(C#N)ncc1Oc1cc(Nc2ccc(N3CCO[C@H](C(C)C)C3)nn2)c2ncn(C)c2n1] | 4-methyl-5-[3-methyl-7-[[6-[(2S)-2-propan-2-ylmorpholin-4-yl]pyridazin-3-yl]amino]imidazo[4,5-b]pyridin-5-yl]oxypyridine-2-carbonitrile | Int 3, Int 82 | B2-a | 486 | 486 |
| 178 | 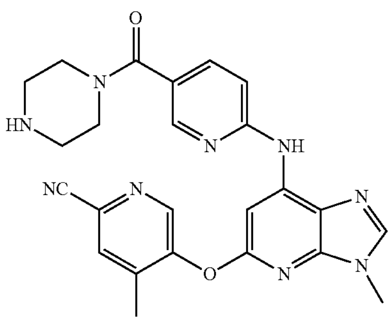 [SMILES: Cc1cc(C#N)ncc1Oc1cc(Nc2ccc(C(=O)N3CCNCC3)cn2)c2ncn(C)c2n1] | 4-methyl-5-[3-methyl-7-[[5-(piperazine-1-carbonyl)pyridin-2-yl]amino]imidazo[4,5-b]pyridin-5-yl]oxypyridine-2-carbonitrile | Cmpd 128 | D1 | 470 | 470 |
| 179 | 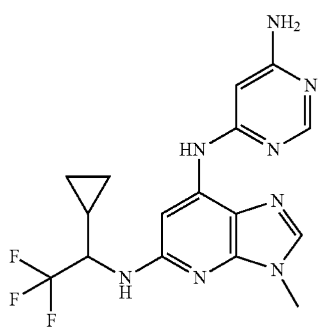 [SMILES: Cn1cnc2c(Nc3cc(N)ncn3)cc(NC(C3CC3)C(F)(F)F)nc21] | N7-(6-aminopyrimidin-4-yl)-N5-(1-cyclopropyl-2,2,2-trifluoro-ethyl)-3-methyl-imidazo[4,5-b]pyridine-5,7-diamine | Int 26, [156-81-0] | B1 | 378 | 380 |
| 180 | 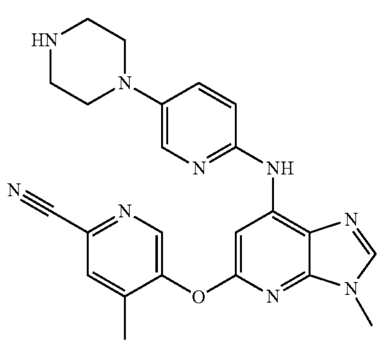 [SMILES: Cc1cc(C#N)ncc1Oc1cc(Nc2ccc(N3CCNCC3)cn2)c2ncn(C)c2n1] | 4-methyl-5-[3-methyl-7-[(5-piperazin-1-yl-2-pyridyl)amino]imidazo[4,5-b]pyridin-5-yl]oxy-pyridine-2-carbonitrile | Int 88 | D1 | 442 | 443 |

TABLE III-continued

Illustrative compounds of the invention

| Cpd # | Structure | Name | SM | Mtd | MW | Mes |
|---|---|---|---|---|---|---|
| 181 | 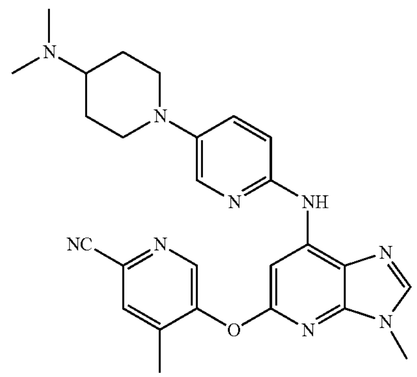 [SMILES: Cc1cc(C#N)ncc1Oc1cc(Nc2ccc(N3CCC(N(C)C)CC3)cn2)c2ncn(C)c2n1] | 5-[7-[[5-[4-(dimethylamino)-1-piperidyl]-2-pyridyl]amino]-3-methyl-imidazo[4,5-b]pyridin-5-yl]oxy-4-methyl-pyridine-2-carbonitrile | Int 2, [1002317-13-6] | B1 | 484 | 485 |
| 182 | 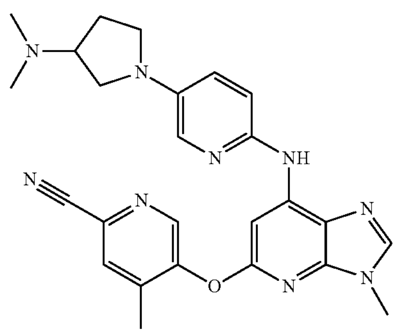 [SMILES: Cc1cc(C#N)ncc1Oc1cc(Nc2ccc(N3CCC(N(C)C)C3)cn2)c2ncn(C)c2n1] | 5-[7-[[5-[3-(dimethylamino)pyrrolidin-1-yl]-2-pyridyl]amino]-3-methyl-imidazo[4,5-b]pyridin-5-yl]oxy-4-methyl-pyridine-2-carbonitrile | Int 2, [748183-23-5] | B1 | 470 | 471 |
| 183 | 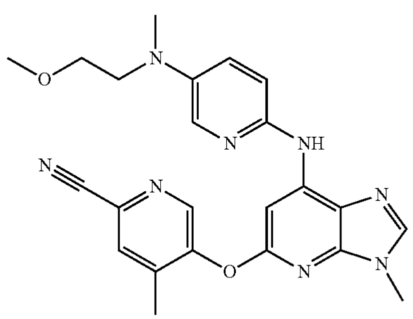 [SMILES: COCCN(C)c1ccc(Nc2cc(Oc3cnc(C#N)cc3C)nc3c2ncn3C)nc1] | 5-[7-[[5-[2-methoxyethyl(methyl)amino]-2-pyridyl]amino]-3-methyl-imidazo[4,5-b]pyridin-5-yl]oxy-4-methyl-pyridine-2-carbonitrile | Int 2, [866620-42-0] | B1 | 445 | 446 |
| 184 | 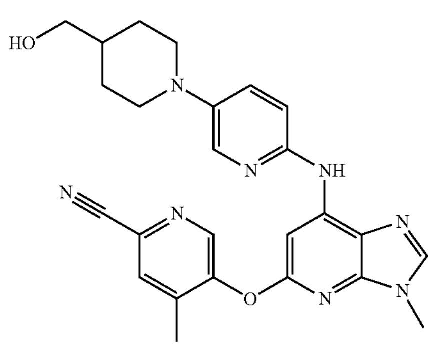 [SMILES: Cc1cc(C#N)ncc1Oc1cc(Nc2ccc(N3CCC(CO)CC3)cn2)c2ncn(C)c2n1] | 5-[7-[[5-[4-(hydroxymethyl)-1-piperidyl]-2-pyridyl]amino]-3-methyl-imidazo[4,5-b]pyridin-5-yl]oxy-4-methyl-pyridine-2-carbonitrile | Int 2, [1152501-47-7] | B1 | 471 | 472 |

TABLE III-continued

Illustrative compounds of the invention

| Cpd # | Structure | Name | SM | Mtd | MW | Mes |
|---|---|---|---|---|---|---|
| 185 | 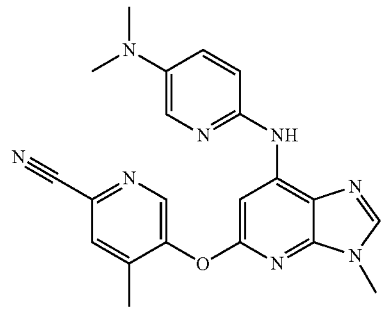 [SMILES: Cc1cc(C#N)ncc1Oc1cc(Nc2ccc(N(C)C)cn2)c2ncn(C)c2n1] | 5-[7-[[5-(dimethylamino)-2-pyridyl]amino]-3-methyl-imidazo[4,5-b]pyridin-5-yl]oxy-4-methyl-pyridine-2-carbonitrile | Int 2, [39856-52-5] | B1 | 400 | 402 |
| 186 | 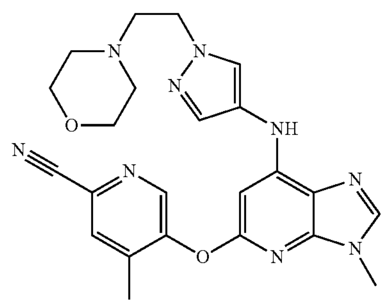 [SMILES: Cc1cc(C#N)ncc1Oc1cc(Nc2cnn(CCN3CCOCC3)c2)c2ncn(C)c2n1] | 4-methyl-5-[3-methyl-7-[[1-(2-morpholinoethyl)pyrazol-4-yl]amino]imidazo[4,5-b]pyridin-5-yl]oxy-pyridine-2-carbonitrile | Int 2, [1152961-27-7] | B1 | 460 | 461 |
| 187 | 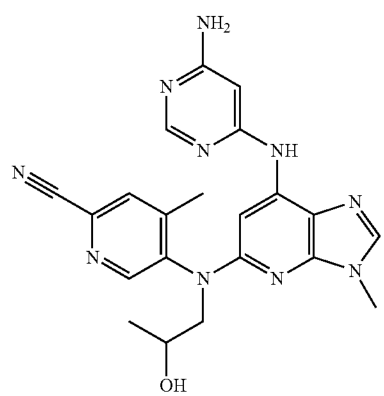 [SMILES: Cc1cc(C#N)ncc1N(CC(C)O)c1cc(Nc2cc(N)ncn2)c2ncn(C)c2n1] | 5-[[7-[(6-aminopyrimidin-4-yl)amino]-3-methyl-imidazo[4,5-b]pyridin-5-yl]-(2-hydroxypropyl)amino]-4-methyl-pyridine-2-carbonitrile | Exemplified | Exemplified | 430 | 431 |
| 188 | 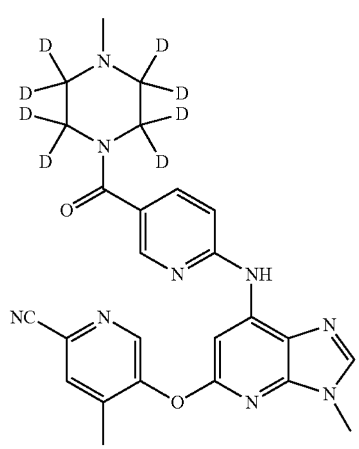 [SMILES: [2H]C1([2H])N(C)C([2H])([2H])C([2H])([2H])N(C(=O)c2ccc(Nc3cc(Oc4cnc(C#N)cc4C)nc4c3ncn4C)nc2)C1([2H])[2H]] | 4-methyl-5-[3-methyl-7-[[5-(2,2,3,3,5,5,6,6,-octadeuterio-4-methyl-piperazine-1-carbonyl)-2-pyridyl]amino]imidazo[4,5-b]pyridin-5-yl]oxy-pyridine-2-carbonitrile | Int 61, [917358-67-7] | A1-a | 492 | 492 |

TABLE III-continued

Illustrative compounds of the invention

| Cpd # | Structure | Name | SM | Mtd | MW | Mes |
|---|---|---|---|---|---|---|
| 189 | 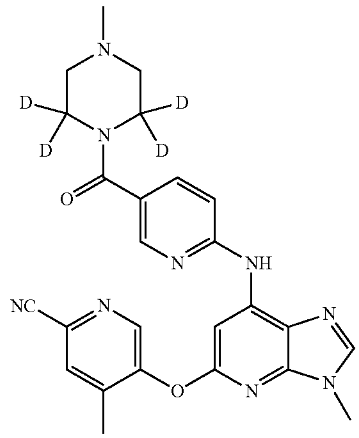 [SMILES: [2H]C1([2H])CN(C)CC([2H])([2H])N1C(=O)c1ccc(Nc2cc(Oc3cnc(C#N)cc3C)nc3c2ncn3C)nc1] | 4-methyl-5-[3-methyl-7-[[5-(2,2,6,6-tetradeuterio-4-methyl-piperazine-1-carbonyl)-2-pyridyl]amino]imidazo[4,5-b]pyridin-5-yl]oxy-pyridine-2-carbonitrile | Int 61, [343864-02-8] | A1-a | 488 | 488 |
| 190 | 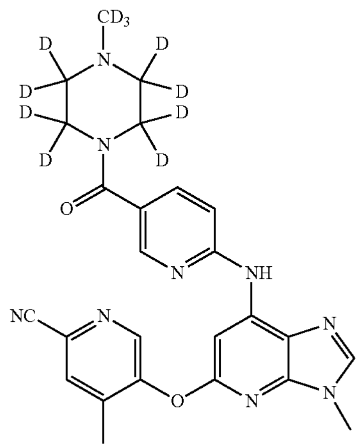 [SMILES: [2H]C([2H])([2H])N1C([2H])([2H])C([2H])([2H])N(C(=O)c2ccc(Nc3cc(Oc4cnc(C#N)cc4C)nc4c3ncn4C)nc2)C([2H])([2H])C1([2H])[2H]] | 4-methyl-5-[3-methyl-7-[[5-[2,2,3,3,5,5,6,6-octadeuterio-4-(trideuteriomethyl)piperazine-1-carbonyl]-2-pyridyl]amino]imidazo[4,5-b]pyridin-5-yl]oxy-pyridine-2-carbonitrile | Int 3, Int 93 | B2-a | 495 | 495 |

TABLE IV

1H NMR of final compounds

| Cpd# | 1H NMR |
|---|---|
| 1 | 1H NMR (400 MHz, DMSO-d$_6$) δ ppm 9.74 (s, 1H), 8.54 (s, 1H), 8.21 (d, J = 0.9 Hz, 1H), 8.17 (s, 1H), 8.17 (s, 1H), 7.97 (s, 1H), 6.63 (s, 2H), 6.34 (d, J = 1.1 Hz, 1H), 3.59 (s, 3H), 2.32 (s, 3H). |
| 2 | 1H NMR (400 MHz, DMSO-d$_6$) δ ppm 9.71 (s, 1H), 8.22 (d, J = 0.9 Hz, 1H), 8.16 (s, 1H), 8.14 (s, 1H), 7.80 (d, J = 7.4 Hz, 2H), 6.63 (s, 2H), 6.34 (d, J = 1.0 Hz, 1H), 3.54 (s, 3H), 3.32 (s, 3H), 2.30 (s, 3H). |
| 3 | 1H NMR (400 MHz, DMSO-d$_6$) δ ppm 9.83 (s, 1H), 8.37 (d, J = 1.0 Hz, 1H), 8.29 (s, 1H), 8.23 (s, 1H), 8.16 (d, J = 1.0 Hz, 1H), 6.64 (s, 2H), 6.35 (d, J = 1.0 Hz, 1H), 3.70 (s, 3H), 2.42 (d, J = 1.0 Hz, 3H). |
| 4 | 1H NMR (400 MHz, DMSO-d$_6$) δ ppm 9.36 (s, 1H), 8.70 (s, 1H), 8.15 (s, 1H), 8.04 (s, 1H), 7.93 (d, J = 0.9 Hz, 1H), 7.41 (s, 1H), 6.52 (s, 2H), 6.22 (d, J = 1.1 Hz, 1H), 4.08 (dd, J = 8.2, 6.4 Hz, 2H), 3.72 (s, 3H), 3.47 (d, J = 12.2 Hz, 2H), 3.26 (s, 3H), 2.21 (s, 3H), 1.98 (p, J = 6.3 Hz, 2H). |
| 5 | 1H NMR (400 MHz, DMSO-d$_6$) δ 9.31 (s, 1H), 8.65 (s, 1H), 8.10 (s, 1H), 7.99 (s, 1H), 7.88 (d, J = 0.9 Hz, 1H), 7.36 (s, 1H), 6.48 (s, 2H), 6.17 (d, J = 1.0 Hz, 1H), 4.62 (s, 1H), 4.08-4.02 (m, 2H), 3.67 (s, 3H), 3.51 (t, J = 6.2 Hz, 2H), 2.16 (s, 3H), 1.82 (q, J = 6.8, 6.3 Hz, 2H). |
| 6 | 1H NMR (400 MHz, DMSO-d$_6$) δ ppm 10.20 (s, 1H), 8.54 (s, 1H), 8.39 (dd, J = 2.3, 0.7 Hz, 1H), 8.29 (s, 1H), 8.22 (s, 1H), 8.13 (s, 1H), 7.77 (dd, J = 8.6, 2.4 Hz, 1H), 7.51 (dd, J = 8.7, 0.8 Hz, 1H), 3.61 (s, 3H), 3.52 (s, 4H), 2.34 (s, 4H), 2.29 (d, J = 0.7 Hz, 3H). |
| 7 | 1H NMR (400 MHz, DMSO-d$_6$) δ ppm 10.21 (s, 1H), 8.54 (s, 1H), 8.42 (dd, J = 2.4, 0.7 Hz, 1H), 8.29 (s, 1H), 8.21 (s, 1H), 8.14 (s, 1H), 7.80 (dd, J = 8.6, 2.4 Hz, 1H), 7.52 (dd, J = 8.6, 0.8 Hz, 1H), 3.67-3.61 (m, 4H), 3.61 (s, 3H), 3.55 (s, 4H), 2.68 (q, J = 7.5 Hz, 2H), 1.19 (t, J = 7.5 Hz, 3H). |
| 8 | 1H NMR (400 MHz, DMSO-d$_6$) δ ppm 9.23 (s, 1H), 7.96 (s, 1H), 7.87-7.81 (m, J = 15.66, 9.85, 7.33 Hz, 3H), 7.36 (s, 1H), 6.45 (s, 2H), 6.16 (s, 1H), 3.68 (s, 3H), 3.35 (s, 3H), 2.59 (q, J = 7.45 Hz, 2H), 1.14 (t, J = 7.58 Hz, 3H). |
| 9 | 1H NMR (400 MHz, DMSO-d$_6$) δ ppm 9.3 (s, 1H), 8.63 (s, 1H), 8.08 (t, J = 0.7 Hz, 1H), 8.0 (s, |

TABLE IV-continued

¹H NMR of final compounds

| Cpd# | 1H NMR |
|---|---|
| | 1H), 7.92 (d, J = 0.9 Hz, 1H), 7.43 (s, 1H), 6.48 (s, 2H), 6.18 (d, J = 1.0 Hz, 1H), 3.67 (s, 3H), 3.48 (s, 3H), 2.18 (s, 3H). |
| 10 | ¹H NMR (400 MHz, DMSO-$d_6$) δ ppm 9.01 (s, 1H), 8.15 (d, J = 0.73 Hz, 1H), 7.87 (s, 1H), 7.61 (s, 1H), 6.46 (s, 2H), 6.21 (d, J = 0.78 Hz, 1H), 4.42-4.36 (m, J = 0.0 Hz, 1H), 3.67 (s, 3H), 2.73-2.66 (m, J = 0.0 Hz, 1H), 2.15 (td, J = 3.03, 2.52 Hz, 2H), 1.73-1.58 (m, J = 0.0 Hz, 6H). |
| 11 | ¹H NMR (400 MHz, DMSO-$d_6$) δ ppm 9.01 (s, 1H), 8.14 (d, J = 0.9 Hz, 1H), 7.87 (s, 1H), 7.69 (s, 1H), 6.45 (s, 2H), 6.22 (d, J = 0.9 Hz, 1H), 4.8 (dd, J = 12.63, 3.79 Hz, 1H), 4.01 (dd, J = 11.12, 4.55 Hz, 1H), 3.67 (s, 3H), 3.46-3.4 (m, J = 11.37, 11.37 Hz, 2H), 3.23 (d, J = 11.12 Hz, 1H), 2.92 (s, 3H), 2.22 (dt, J = 25.01, 7.58 Hz, 1H), 1.39-1.32 (m, J = 7.71 Hz, 1H), 1.08 (s, 3H), 0.79 (s, 3H). |
| 12 | 1H NMR (400 MHz, DMSO-$d_6$) δ ppm: 8.97 (s, 1H), 8.14 (d, J = 0.72 Hz, 1H), 7.85 (s, 1H), 7.61 (s, 1H), 6.45 (s, 2H), 6.22 (d, J = 0.81 Hz, 1H), 4.87 (q, J = 7.07 Hz, 1H), 3.67 (s, 3H), 2.89 (s, 3H), 1.16 (d, J = 7.07 Hz, 9H), 0.95 (s, 9H). |
| 13 | ¹H NMR (400 MHz, DMSO-$d_6$) δ ppm 9.04 (s, 1H), 8.15 (d, J = 1.0 Hz, 1H), 7.88 (s, 1H), 7.67 (s, 1H), 6.45 (s, 2H), 6.22 (d, J = 1.0 Hz, 1H), 3.68 (s, 3H), 3.35 (s, 1H), 2.87 (s, 3H), 2.01-1.44 (m, J = 0.0 Hz, 8H). |
| 15 | 1H NMR (400 MHz, DMSO-$d_6$) δ ppm 9.29 (s, 1H), 8.61 (s, 1H), 8.14 (s, 1H), 7.99 (s, 1H), 7.89 (d, J = 1.0 Hz, 1H), 7.40 (s, 1H), 6.47 (s, 2H), 6.18 (d, J = 1.0 Hz, 1H), 3.67 (s, 3H), 3.47 (s, 3H), 2.53 (s, 2H), 1.14 (t, J = 7.5 Hz, 3H). |
| 16 | 1H NMR (400 MHz, DMSO-$d_6$) δ ppm: 8.95 (s, 1H), 8.13 (d, J = 0.73 Hz, 1H), 7.84 p (s, 1H), 7.53 (s, 1H), 6.45 (s, 2H), 6.21 (d, J = 0.95 Hz, 1H), 4.15-4.08 (m, J = 5.3 Hz, 1H), 3.65 (s, 3H), 2.95 (s, 3H), 1.19 ppm (d, J = 6.79 Hz, 3H), 1.1-1.04 (m, 1H), 0.58-0.51 (m, 1H), 0.4-0.29 (m, 2H), 0.27-0.21 (m, 1H). |
| 17 | 1H NMR (400 MHz, DMSO-$d_6$) δ ppm 9.02 (s, 1H), 8.16 (d, J = 0.9 Hz, 1H), 7.88 (s, 1H), 7.66 (s, 1H), 6.46 (s, 2H), 6.23 (d, J = 1.0 Hz, 1H), 4.39 (td, J = 11.2, 3.8 Hz, 1H), 3.98 (dd, J = 11.3, 4.5 Hz, 1H), 3.89 (dd, J = 11.2, 4.4 Hz, 1H), 3.68 (s, 3H), 3.52-3.41 (m, 1H), 3.08 (t, J = 11.0 Hz, 1H), 2.88 (s, 3H), 2.02-1.88 (m, 1H), 1.78 (qd, J = 12.3, 4.7 Hz, 1H), 1.56 (d, J = 9.0 Hz, 1H), 0.69 (d, J = 6.6 Hz, 3H). |
| 18 | 1H NMR (400 MHz, DMSO-$d_6$) δ ppm 9.14 (s, 1H), 8.14 (d, J = 0.76 Hz, 1H), 8.0 (s, 1H), 7.9 (s, 1H), 6.47 (s, 2H), 6.23 (d, J = 0.76 Hz, 1H), 3.68 (s, 3H), 3.0 (s, 3H), 2.49 (s, 1H), 2.23 (s, 6H). |
| 20 | 1H NMR (400 MHz, DMSO-$d_6$) δ ppm 9.17 (s, 1H), 8.16 (d, J = 0.9 Hz, 1H), 7.93 (s, 1H), 7.73 (s, 1H) 6.49 (s, 2H), 6.25 (d, J = 1.0 Hz, 1H), 4.99 (q, J = 9.0 Hz, 1H), 3.64 (s, 3H), 3.06 (s, 3H), 1.48-1.35 (m, 1H), 0.87-0.69 (m, 1H), 0.64 (dt, J = 9.7, 4.7 Hz, 1H), 0.57 (dt, J = 9.6, 4.8 Hz, 1H), 0.20 (dd, J = 4.7, 1.3 Hz, 1H). |
| 21 | 1H NMR (400 MHz, DMSO-$d_6$) δ ppm 9.05 (s, 1H), 8.10 (d, J = 0.9 Hz, 1H), 7.88 (s, 1H), 7.71 (s, 1H), 6.46 (s, 2H), 6.23 (d, J = 1.0 Hz, 1H), 4.60 (t, J = 12.3 Hz, 1H), 3.77 (dd, J = 11.8, 3.8 Hz, 1H), 3.67 (s, 3H), 3.50 (dd, J = 12.4, 10.2 Hz, 1H), 2.91 (s, 3H), 2.36-2.21 (m, 2H), 2.11-1.47 (m, 9H). |
| 22 | 1H NMR (400 MHz, DMSO-$d_6$) δ ppm: 10.4 (d, J = 7.32 Hz, 1H), 8.82 (d, J = 2.3 Hz, 1H), 8.2 (s, 1H), 8.13 (dd, J = 8.85, 2.53 Hz, 1H), 7.98 (s, 1H), 7.6 (d, J = 8.85 Hz, 1H), 5.46 (ddd, J = 24.49, 2.8, 2.02 Hz, 1H), 3.76 (d, J = 8.1 Hz, 1H), 3.27 (dd, J = 2.53, 1.52 Hz, 3H), 1.34-1.25 (m, 1H), 0.77-0.59 ppm (m, 4H). |
| 23 | 1H NMR (400 MHz, DMSO-$d_6$) δ ppm 10.53 (s, 1H), 9.12 (t, J = 6.0 Hz, 1H), 8.60 (s, 1H), 8.38 (s, 1H), 8.28 (s, 1H), 8.13 (s, 1H), 8.09 (d, J = 9.2 Hz, 1H), 7.89 (d, J = 9.2 Hz, 1H), 3.64 (s, 3H), 3.33 (m, J = 7.3 Hz, 2H), 2.31 (s, 3H), 1.16 (t, J = 7.2 Hz, 3H). |
| 24 | 1H NMR (400 MHz, DMSO-$d_6$) δ ppm 10.23 (s, 1H), 8.82 (d, J = 2.4 Hz, 1H), 8.56 (s, 1H), 8.51 (dd, J = 9.8, 4.1 Hz, 1H), 8.29 (s, 1H), 8.22 (s, 1H), 8.19-8.04 (m, 2H), 7.49 (d, J = 8.7 Hz, 1H), 4.96-4.73 (m, 1H), 3.80 (dt, J = 12.3, 6.0 Hz, 1H), 3.61 (s, 3H), 3.28-3.08 (m, 2H), 2.30 (s, 3H), 1.07 (s, 3H). |
| 25 | 1H NMR (400 MHz, DMSO-$d_6$) δ ppm 10.48 (s, 1H), 8.88 (t, J = 5.9 Hz, 1H), 8.59 (s, 1H), 8.37 (s, 1H), 8.28 (s, 1H), 8.13 (s, 1H), 8.10 (d, J = 9.2 Hz, 1H), 7.89 (d, J = 9.2 Hz, 1H), 4.89 (s, 1H), 3.91-3.77 (m, 1H), 3.64 (s, 3H), 3.33-3.21 (m, 2H), 2.31 (s, 3H), 1.09 (d, J = 6.2 Hz, 3H). |
| 26 | 1H NMR (400 MHz, DMSO-$d_6$) δ ppm 9.76 (s, 1H), 8.68 (dd, J = 2.6, 0.8 Hz, 1H), 8.64 (t, J = 6.1 Hz, 1H) 8.54 (s, 1H), 8.18 (s, 1H), 8.11 (d, J = 0.8 Hz, 1H), 8.00 (dd, J = 8.6, 0.8 Hz, 1H), 7.95 (dd, J = 8.5, 2.6 Hz, 1H), 6.70 (s, 1H), 3.60 (s, 3H), 3.38-3.27 (m, 2H), 2.28 (d, J = 0.7 Hz, 3H), 1.13 (td, J = 7.2, 3.5 Hz, 3H). |
| 27 | 1H NMR (400 MHz, DMSO-$d_6$) δ ppm 9.21 (s, 1H), 8.49 (s, 1H), 8.11 (s, 1H), 8.07 (d, J = 0.7 Hz, 1H), 8.01 (t, J = 5.4 Hz, 1H), 7.33 (d, J = 8.5 Hz, 2H), 7.26 (d, J = 8.5 Hz, 2H), 6.45 (s, 1H), 3.58 (s, 3H), 3.37 (s, 2H), 3.14-3.02 (m, 2H), 2.25 (d, J = 0.7 Hz, 3H), 1.03 (t, J = 7.2 Hz, 3H). |
| 28 | 1H NMR (400 MHz, DMSO-$d_6$) δ ppm 9.69 (s, 1H), 8.64 (dd, J = 2.7, 0.7 Hz, 1H), 8.53 (s, 1H), 8.18 (s, 1H), 8.10 (t, J = 0.8 Hz, 1H), 7.93 (dd, J = 8.5, 2.7 Hz, 1H), 7.66 (dd, J = 8.5, 0.7 Hz, 1H), 6.68 (s, 1H), 3.63 (m, J = 22.7 Hz, 11H), 2.28 (s, 3H). |
| 29 | 1H NMR (400 MHz, DMSO-$d_6$) δ ppm 9.68 (s, 1H), 8.67 (dd, J = 2.6, 0.8 Hz, 1H), 8.61 (q, J = 4.9 Hz, 1H), 8.54 (s, 1H), 8.18 (s, 1H), 8.10 (s, 1H), 8.04-7.97 (m, 1H), 7.95 (dd, J = 8.5, 2.6 Hz, 1H), 6.70 (s, 1H), 3.60 (s, 3H), 2.83 (d, J = 4.7 Hz, 3H), 2.28 (s, 3H). |
| 30 | 1H NMR (400 MHz, DMSO-$d_6$) δ ppm 9.78 (s, 1H), 8.69 (dd, J = 2.6, 0.8 Hz, 1H), 8.54 (s, 1H), 8.47 (t J = 6.0 Hz, 1H), 8.18 (s, 1H), 8.10 (d, J = 0.7 Hz, 1H), 8.01 (dd, J = 8.5, 0.7 Hz, 1H), 7.95 (dd, J = 8.5, 2.6 Hz, 1H), 6.70 (s, 1H), 4.85 (s, 1H), 3.86-3.74 (m, 1H), 3.60 (s, 3H), 3.41-3.29 (m, 1H), 3.24-3.14 (m, 1H), 2.28 (d, J = 0.7 Hz, 3H), 1.07 (s, 3H). |
| 32 | 1H NMR (400 MHz, DMSO-$d_6$) δ ppm 9.73 (s, 1H), 8.52 (s, 1H), 8.25 (s, 1H), 8.18 (s, 2H), 8.11 (s, 1H), 7.17 (s, 1H), 6.41 (s, 1H), 3.59 (s, 3H), 3.41-3.38 (m, J = 6.39, 6.23 Hz, 4H), 3.25 (s, 3H), 2.28 (s, 3H), 1.8-1.73 (m, J = 6.59 Hz, 2H). |
| 33 | 1H NMR (400 MHz, DMSO-$d_6$) δ ppm 9.72 (s, 1H), 8.52 (s, 1H), 8.24 (s, 1H), 8.19 (s, 1H), 8.18 (s, 1H), 8.11 (s, 1H), 7.07 (s, 1H), 6.38 (s, 1H), 4.35 (s, 1H), 3.31-3.22 (m, 4H), 2.28 (s, 3H), 1.65 (dd, J = 7.87, 5.86 Hz, 2H), 1.15 (s, 6H). |
| 35 | 1H NMR (400 MHz, DMSO-$d_6$) δ ppm 9.75 (s, 1H), 8.53 (s, 1H), 8.28 (s, 1H), 8.19 (s, 2H), 8.18 (s, 2H), 8.12 (t, J = 0.7 Hz, 1H), 7.28 (s, 1H), 6.44 (s, 1H), 3.76 (d, J = 11.3 Hz, 2H), 3.72-3.46 (m, 7H), 3.44 (s, 1H), 3.25 (d, J = 11.4, 9.8 Hz, 2H), 2.29 (d, J = 0.7 Hz, 3H). |
| 36 | 1H NMR (400 MHz, DMSO-$d_6$) δ ppm 9.77 (s, 1H), 8.53 (s, 1H), 8.26 (s, 1H), 8.19 (s, 2H), 8.11 (s, 1H), 7.44 (d, J = 6.7 Hz, 1H), 6.37 (s, 1H), 3.59 (s, 4H), 3.29 (d, J = 1.7 Hz, 1H), 3.16 (d, J = 6.8 Hz, 3H), 2.73-2.63 (m, 2H), 2.29 (d, J = 0.7 Hz, 3H), 1.80 (dt, J = 11.6, 8.8 Hz, 2H). |
| 37 | 1H NMR (400 MHz, DMSO-$d_6$) δ ppm 9.72 (s, 1H), 8.53 (s, 1H), 8.25 (s, 1H), 8.19 (s, 1H), 8.15-8.08 (m, 1H), 7.12 (s, 1H), 6.89 (s, 1H), 6.40 (s, 1H), 4.55 (d, J = 4.8 Hz, 1H), 3.70 (s, 1H), 3.59 |

TABLE IV-continued

¹H NMR of final compounds

| Cpd# | 1H NMR |
|---|---|
| | (s, 3H), 3.30 (d, J = 16.8 Hz, 2H), 2.29 (d, J = 0.7 Hz, 3H), 1.58 (dq, J = 13.7, 7.0, 6.6 Hz, 2H), 1.11 (s, 3H). |
| 38 | 1H NMR (400 MHz, DMSO-d₆) δ ppm 9.86 (s, 1H), 8.53 (s, 1H), 8.20 (s, 1H), 8.19 (s, 1H), 8.15-8.08 (m, 1H), 7.64 (d, J = 9.7 Hz, 1H), 7.43 (d, J = 9.7 Hz, 1H), 3.75 (t, J = 4.8 Hz, 4H), 3.61 (s, 3H), 3.50-3.42 (m, 4H), 2.31 (d, J = 0.7 Hz, 3H). |
| 39 | 1H NMR (400 MHz, DMSO-d₆) δ ppm 9.83 (s, 1H), 8.53 (s, 1H), 8.19 (s, 1H), 8.18 (s, 1H), 8.11 (d, J = 0.7 Hz, 1H), 7.60 (d, J = 9.7 Hz, 1H), 7.42 (d, J = 9.8 Hz, 1H), 3.61 (s, 3H), 3.50 (t, J = 5.0 Hz, 4H), 2.44 (t, J = 4.9 Hz, 4H), 2.31 (d, J = 0.7 Hz, 3H), 2.24 (s, 3H). |
| 41 | 1H NMR (400 MHz, DMSO-d₆) δ ppm 9.81 (s, 1H), 8.53 (s, 1H), 8.19 (s, 1H), 8.18 (s, 1H), 8.11 (s, 1H), 7.60 (d, J = 9.7 Hz, 1H), 7.44 (d, J = 9.8 Hz, 1H), 4.14-4.03 (m, 2H), 3.61 (s, 3H), 2.65-2.54 (m, 2H), 2.31 (s, 3H), 2.26-2.14 (m, 5H), 1.09 (d, J = 6.1 Hz, 6H). |
| 42 | 1H NMR (400 MHz, DMSO-d₆) δ ppm 9.84 (s, 1H), 8.53 (s, 1H), 8.19 (s, 1H), 8.19 (s, 1H), 8.11 (d, J = 0.7 Hz, 1H), 7.62 (d, J = 9.8 Hz, 1H), 7.43 (d, J = 9.8 Hz, 1H), 3.61 (s, 3H), 3.52 (t, J = 5.0 Hz, 4H), 3.26 (q, J = 10.2 Hz, 2H), 2.76 (t, J = 5.0 Hz, 4H), 2.31 (d, J = 0.7 Hz, 3H). |
| 43 | 1H NMR (400 MHz, DMSO-d₆) δ ppm 9.83 (s, 1H), 8.53 (s, 1H), 8.19 (s, 1H), 8.19 (s, 1H), 8.11 (t, J = 0.7 Hz, 1H), 7.62 (d, J = 9.7 Hz, 1H), 7.42 (d, J = 9.8 Hz, 1H), 4.21-3.97 (m, 2H), 3.67 (ddd, J = 10.5, 6.3, 2.4 Hz, 2H), 3.62 (s, 3H), 2.49-2.40 (m, 2H), 2.31 (d, J = 0.7 Hz, 3H), 1.17 (d, J = 6.2 Hz, 6H). |
| 44 | 1H NMR (400 MHz, DMSO-d₆) δ ppm 9.84 (s, 1H), 8.53 (s, 1H), 8.19 (s, 1H), 8.19 (s, 1H), 8.12 (t, J = 0.7 Hz, 1H), 7.63 (d, J = 9.8 Hz, 1H), 7.43 (d, J = 9.8 Hz, 1H), 4.10 (d, J = 12.4 Hz, 1H), 3.99 (d, J = 12.8 Hz, 1H), 3.94 (ddd, J = 11.5, 3.7, 1.2 Hz, 1H), 3.71-3.53 (m, 4H), 2.87 (td, J = 12.4, 3.5 Hz, 1H), 2.60-2.52 (m, 2H), 2.31 (d, J = 0.7 Hz, 3H), 1.17 (d, J = 6.2 Hz, 3H). |
| 45 | 1H NMR (400 MHz, DMSO-d₆) δ ppm 9.84 (s, 1H), 8.53 (s, 1H), 8.19 (d, J = 0.9 Hz, 2H), 8.12 (s, 1H), 7.62 (d, J = 9.8 Hz, 1H), 7.45 (d, J = 9.8 Hz, 1H), 3.81 (ddd, J = 13.3, 6.5, 3.6 Hz, 2H), 3.61 (s, 3H), 3.40 (d, J = 9.0, 3.5 Hz, 2H), 3.20-3.09 (m, 1H), 2.37-2.25 (m, 3H), 2.06-1.89 (m, 2H), 1.78 (dtd, J = 12.5, 8.6, 3.5 Hz, 2H). |
| 49 | 1H NMR (400 MHz, (DMSO-d₆) δ ppm: 9.69 (s, 1H), 8.5 (s, 1H), 8.14 (s, 1H), 8.11 (s, 1H), 8.1 (s, 1H), 8.01 (d, J = 2.8 Hz, 1H), 7.46 (dd, J = 9.1, 3.0 Hz, 1H), 7.37 (d, J = 9.1 Hz, 1H), 3.75 (m, 4H), 3.58 (s, 3H), 3.09 (m, 4H), 2.28 (s, 3H). |
| 50 | 1H NMR (400 MHz, (DMSO-d₆) δ ppm: 9.66 (s, 1H), 8.50 (s, 1H), 8.25 (s, 1H), 8.13 (s, 1H), 8.1 (s, 2H), 7.99 (d, J = 3.0 Hz, 1H), 7.45 (dd, J = 9.1, 3.0 Hz, 1H), 7.34 (d, J = 8.9 Hz, 1H), 3.58 (s, 3H), 3.11 (m, 4H), 2.47 (m, 4H), 2.27 (s, 3H), 2.22 (s, 3H). |
| 51 | 1H NMR (400 MHz, (DMSO-d₆) δ ppm: 10.19 (s, 1H), 8.53 (s, 1H), 8.38 (d, J = 2.0 Hz, 1H), 8.28 (s, 1H), 8.20 (s, 2H), 8.10 (s, 1H), 7.76 (dd, J = 8.6, 2.5 Hz, 1H), 3.53 (s br, 3H), 2.35 (s, 4H), 2.28 (s, 3H), 2.2 (s, 3H). |
| 52 | ¹H NMR 400 MHz, (DMSO-d₆) δ ppm): 9.71 (s, 1H), 8.52 (s, 1H), 8.2 (d, J = 0.6 Hz, 1H), 8.17 (s, 1H), 8.16 (s, 1H), 8.1 (s, 1H), 6.6 (s, 2H), 6.34 (d, J = 0.6 Hz, 1H), 3.58 (s, 3H), 2.28 (s, 3H). |
| 53 | 1H NMR (400 MHz, CDC13) δ ppm: 8.49 (s, 1H), 8.01 (s, 1H), 7.90 (dd, J = 6.8, 2.0 Hz, 2H), 7.86 (s, 1H), 7.64 (s, 1H), 7.46 (dd, J = 6.8, 2.0 Hz, 2H), 6.83 (s, 1H), 4.68 (t, J = 6.1 Hz, 1H), 3.69 (s, 3H), 3.06 (dq, J = 7.3, 6.8 Hz, 2H), 2.33 (s, 3H), 1.15 (t, J = 7.3 Hz, 3H). |
| 54 | 1H NMR (400 MHz, DMSO-d₆) δ ppm: 9.55 (s, 1H), 8.22 (s, 1H), 8.12 (d, J = 5.11 Hz, 1H), 7.85 (s, 1H), 6.60 (m, 2H), 6.3 (d, J = 0.94 Hz, 1H), 5.43 (dt, J = 15.42, 6.82 Hz, 1H), 3.72 ppm (s, 3H), 1.32-1.23 ppm (m, 1H), 0.75-0.69 ppm (m, 1H), 0.67-0.57 ppm (m, 3H). |
| 55 | ¹H NMR (400 MHz, DMSO-d₆) δ ppm: 9.45 (s, 1H), 9.39 (s, 1H), 8.73 (s, 1H), 8.21 p (s, 1H), 8.08 (s, 1H), 8.02 (s, 1H), 7.82 (s, 1H), 6.57 (s, 2H), 6.28 (d, J = 0.8 Hz, 1H), 3.72 (s, 3H), 2.37 (s, 3H). |
| 56 | ¹H NMR (400 MHz, DMSO-d₆) δ ppm: 9.61 (s, 1H), 8.52 (s, 1H), 8.39 (s, 1H), 8.16 (s, 1H), 8.09 (s, 1H), 7.63 (d, J = 8.1 Hz, 1H), 7.58 (d, J = 1.6 Hz, 1H), 7.49 (dd, J = 8.1, 1.6 Hz, 1H), 6.7 (s, 1H), 4.36 (s, 2H), 3.58 ppm (s, 3H), 2.25 ppm (s, 3H). |
| 57 | ¹H NMR (400 MHz, DMSO-d₆) δ ppm: 9.34 (s, 1H), 8.49 (s, 1H), 8.40 (s, 1H), 8.12 (s, 1H), 8.07 (s, 1H), 7.43 (d, J = 8.6 Hz, 2H), 7.39 (d, J = 8.6 Hz, 2H), 6.48 (s, 1H), 4.32 (s, 3H), 3.90 (s, 2H), 3.57 (s, 3H), 2.24 (s, 3H). |
| 58 | ¹H NMR (400 MHz, DMSO-d₆) δ ppm: 10.55 (s, 1H), 8.79 (d, J = 2.5 Hz, 1H), 8.57 (s, 1H), 8.27 (s, 1H), 8.25 (s, 1H), 8.15 (dd, J = 8.8, 2.5 Hz, 1H), 8.13 (s, 1H), 7.64 (d, J = 8.8 Hz, 1H), 3.62 (s, 3H), 3.26 (s, 3H), 2.30 (s, 3H). |
| 59 | ¹H NMR (400 MHz, DMSO-d₆) δ ppm: 10.43 (s, 1H), 8.72 (d, J = 2.0 Hz, 1H), 8.56 (s, 1H), 8.28 (s, 1H), 8.24 (s, 1H), 8.12 (s, 1H), 8.07 (dd, J = 9.0, 2.0 Hz, 1H), 7.64 (d, J = 9.0 Hz, 1H), 3.62 (s, 3H), 2.29 (s, 3H). |
| 60 | ¹H NMR (400 MHz, DMSO-d₆) δ ppm: 9.85 (s, 1H), 8.59 (s, 1H), 8.24 (s, 1H), 8.15 (s, 1H), 7.92 (d, J = 8.8 Hz, 2H), 7.66 (d, J = 8.8 Hz, 2H), 6.83 (s, 1H), 3.65 (s, 3H), 3.37 (s, 3H), 2.33 (s, 3H). |
| 61 | ¹H NMR (400 MHz, DMSO-d₆) δ ppm: 8.81 (s, 1H), 8.39 (s, 1H), 8.0 (s, 1H), 7.99 (s, 1H), 7.79 (s, 1H), 7.43 (s, 1H), 6.17 (s, 1H), 3.77 (s, 3H), 3.49 (s, 3H), 2.18 (s, 3H). |
| 62 | ¹H NMR (400 MHz, DMSO-d₆) δ ppm 9.46 (s, 1H), 8.51 (s, 1H), 8.14 (s, 1H), 8.08 (s, 1H), 7.45 (d, J = 8.8 Hz, 2H), 7.42 (d, J = 8.8 Hz, 2H), 6.63 (s, 1H), 3.58 (s, 3H), 2.98 (s, 6H), 2.26 (s, 3H). |
| 63 | ¹H NMR (400 MHz, DMSO-d₆) δ ppm: 9.81 (s, 1H), 8.54 (s, 1H), 8.19 (s, 1H), 8.1 (s, 1H), 7.69 (d, J = 8.9 Hz, 2H), 7.63 (d, J = 8.9 Hz, 2H), 6.81 (s, 1H), 3.65 (t, J = 4.7 Hz, 4H), 3.60 (s, 3H), 2.88 (t, J = 4.7 Hz, 4H), 2.28 (s, 3H). |
| 64 | ¹H NMR (400 MHz, DMSO-d₆) δ ppm: 9.94 (s, 1H), 8.54 (s, 1H), 8.30 (s, 1H), 8.30 (t, J = 5.4 Hz, 1H), 8.23 (s, 1H), 8.19 (s, 1H), 8.11 (s, 1H), 7.32 (s, 1H), 3.6 (s, 3H), 3.25 (qd, J = 7.2, 5.4 Hz, 2H), 2.35 (s, 3H), 2.28 (s, 3H), 1.12 (t, J = 7.2 Hz, 3H). |
| 65 | 1H NMR (400 MHz, DMSO-d₆) δ ppm: 10.0 (s, 1H), 8.71 (d, J = 2.31 Hz, 1H), 8.08 (dd, J = 8.97, 2.54 Hz, 1H), 7.93 (s, 1H), 7.8 (s, 1H), 7.5 (d, J = 8.85 Hz, 1H), 6.98 (d, J = 9.83 Hz, 1H), 5.01 (td, J = 9.1, 5.81 Hz, 1H), 3.72-3.69 (s, 3H), 3.25 (s, 3H), 2.17 (td, J = 12.63, 6.81 Hz, 1H), 1.01 (t, J = 7.7 Hz, 6H). |
| 66 | ¹H NMR (400 MHz, DMSO-d₆) δ ppm: 9.62 (s, 1H), 9.14 (s, 1H), 8.48 (s, 1H), 8.04 (s, 1H), 7.79 (s, 1H), 7.45 (d, J = 9.1 Hz, 2H), 7.42 (d, J = 9.1 Hz, 2H), 6.92 (s, 1H), 3.72 (s, 3H), 2.99 (s, 6H), 2.33 (s, 3H). |
| 67 | ¹H NMR (400 MHz, DMSO-d₆) δ ppm: 9.82 (s, 1H), 9.47 (s, 1H), 8.73 (s, 1H), 8.39 (dd, J = 2.4, 0.5 Hz, 1H), 8.17 (s, 1H), 8.09 (s, 1H), 7.82 (s, 1H), 7.77 (dd, J = 8.6, 2.4 Hz, 1H), 7.43 (dd, J = 8.6, 0.5 Hz, 1H), 3.72 (s, 3H), 3.0 (s, 6H), 2.37 (s, 3H). |
| 68 | ¹H NMR (400 MHz, DMSO-d₆) δ ppm: 10.09 (s, 1H), 8.56 (s, 1H), 8.23 (s, 1H), 8.12 (s, 1H), 7.86 (d, J = 9.0 Hz, 2H), 7.67 (d, J = 9.0 Hz, 2H), 7.24 (t, JHF = 52.4 Hz, 1H), 6.87 (s, 1H), 3.60 (s, 3H), 2.27 (s, 3H). |
| 69 | ¹H NMR (400 MHz, DMSO-d₆) δ ppm: 9.83 (s, 1H), 8.54 (s, 1H), 8.19 (s, 1H), 8.11 (s, 1H), 7.82 |

TABLE IV-continued

¹H NMR of final compounds

| Cpd# | 1H NMR |
|---|---|
| | (dt, J = 9.5, 2.4 Hz, 2H), 7.6 (dt, J = 9.5, 2.4 Hz, 2H), 6.78 (s, 1H), 3.59 (s, 3H), 2.85-2.79 (m, 1H), 2.27 (s, 3H), 1.13-1.09 (m, 2H), 1.07-1.01 (m, 2H). |
| 70 | ¹H NMR (400 MHz, DMSO-$d_6$) δ ppm: 10.33 (s, 1H), 9.29 (s, 1H), 8.48 (s, 1H), 8.11 (s, 1H), 8.08 (s, 1H), 7.26 (d, J = 8.1 Hz, 1H), 6.99 (dd, J = 8.1, 2.0 Hz, 1H), 6.91 (d, J = 2.0 Hz, 1H), 6.52 (s, 1H), 3.57 (s, 3H), 2.24 (s, 3H), 1.25 (s, 6H). |
| 71 | ¹H NMR (400 MHz, DMSO-$d_6$) δ ppm: 9.85 (s, 1H), 8.53 (s, 1H), 8.19 (s, 1H), 8.09 (s, 1H), 7.82 (dt, J = 9.5, 2.6 Hz, 2H), 7.61 (dt, J = 9.5, 2.6 Hz, 2H), 6.79 (s, 1H), 3.59 (s, 3H), 3.34 (t, J = 6.7 Hz, 2H), 3.28-3.24 (m, 2H), 3.17 (s, 3H), 2.26 (s, 3H), 1.81-1.74 (m, 2H). |
| 73 | ¹H NMR (400 MHz, DMSO-$d_6$) δ ppm: 10.43 (s, 1H), 8.56 (s, 1H), 8.34 (s, 1H), 8.25 (s, 1H), 8.11 (s, 1H), 7.85 (d, J = 9.2 Hz, 1H), 7.78 (d, J = 9.2 Hz, 1H), 3.62 (s, 3H), 3.08 (s, 3H), 3.06 (s, 3H), 2.30 (s, 3H). |
| 74 | ¹H NMR (400 MHz, DMSO-$d_6$) δ ppm: 10.19 (s, 1H), 8.54 (s, 1H), 8.42 (d, J = 2.3 Hz, 1H), 8.29 (s, 1H), 8.21 (s, 1H), 8.12 (s, 1H), 7.79 (dd, J = 8.6, 2.3 Hz, 1H), 7.5 (dd, J = 8.6, 0.5 Hz, 1H), 3.6 (s, 3H), 3.0 (s, 6H), 2.28 (s, 3H). |
| 75 | ¹H NMR (400 MHz, DMSO-$d_6$) δ ppm: 10.21 (s, 1H), 8.53 (s, 1H), 8.42 (d, J = 2.4 Hz, 1H), 8.29 (s, 1H), 8.21 (s, 1H), 8.12 (s, 1H), 7.79 (dd, J = 8.6, 2.4 Hz, 1H), 7.51 (dd, J = 8.6, 0.5 Hz, 1H), 3.64-3.61 (m, 4H), 3.6 (s, 3H), 3.55-3.52 (m, 4H), 2.28 (s, 3H). |
| 76 | ¹H NMR (400 MHz, DMSO-$d_6$) δ ppm: 10.08 (s, 1H), 9.48 (s, 1H), 8.91 (s, 1H), 8.29 (s, 1H), 8.13 (s, 1H), 7.82 (s, 1H), 7.81 (d, J = 9.2 Hz, 1H), 7.74 (d, J = 9.2 Hz, 1H), 3.73 (s, 3H), 3.10 (s, 3H), 3.06 (s, 3H), 2.37 (s, 3H). |
| 77 | ¹H NMR (400 MHz, DMSO-$d_6$) δ ppm: 10.04 (s, 1H), 8.59 (s, 1H), 8.3 (s, 1H), 8.21 (s, 1H), 8.15 (s, 1H), 7.54 (d, J = 8.4 Hz, 1H), 7.27 (d, J = 8.4 Hz, 1H), 3.65 (s, 3H), 3.0 (s, 3H), 2.82 (s, 3H), 2.28 (s, 3H), 2.27 (s, 3H). |
| 78 | ¹H NMR (400 MHz, DMSO-$d_6$) δ ppm: 10.04 (s, 1H, NH), 8.60 (s, 1H), 8.29 (s, 1H), 8.25 (t, J = 5.4 Hz, 1H, NH), 8.21 (s, 1H), 8.16 (s, 1H), 7.66 (d, J = 8.5 Hz, 1H), 7.26 (d, J = 8.5 Hz, 1H), 3.65 (s, 3H), 3.25 (m, 2H), 2.43 (s, 3H), 2.28 (s, 3H), 1.11 (t, J = 7.2 Hz, 3H). |
| 79 | ¹H NMR (400 MHz, DMSO-$d_6$) δ ppm: 10.09 (s, 1H), 8.54 (s, 1H), 8.33 (d, J = 2.2 Hz, 1H), 8.28 (s, 1H), 8.20 (s, 1H), 8.12 (s, 1H), 7.74 (dd, J = 8.6, 2.2 Hz, 1H), 7.53 (d, J = 8.6 Hz, 1H), 4.51 (q, JHF = 9.7 Hz, 1H), 3.60 (s, 3H) 2.29 (s, 3H), 2.25 (s, 6H). |
| 80 | ¹H NMR (400 MHz, DMSO-$d_6$) δ ppm: 10.01 (s, 1H), 8.54 (s, 1H), 8.40 (d, J = 2.0 Hz, 1H), 8.26 (s, 1H), 8.19 (s, 1H), 8.11 (s, 1H), 7.83 (dd, J = 8.5, 2.0 Hz, 1H), 7.49 (d, J = 8.5 Hz, 1H), 4.47-4.35 (m, 1H), 3.60 (s, 3H), 2.53-2.46 (m, 2H), 2.83-2.73 (m, 1H), 2.29 (s, 3H), 1.01 (t, J = 7.1 Hz, 3H). |
| 81 | ¹H NMR (400 MHz, DMSO-$d_6$) δ ppm: 9.93 (s, 1H), 8.52 (s, 1H), 8.25 (s, 1H), 8.23 (s, 2H), 8.17 (s, 1H), 8.08 (s, 1H), 7.66 (dd, J = 8.5, 2.3 Hz, 1H), 7.43 (d, J = 8.5 Hz, 1H), 4.81 (s, 1H), 3.59 (s, 3H), 3.53 (s, 2H), 2.27 (s, 3H), 2.25 (s, 6H). |
| 82 | ¹H NMR (400 MHz, DMSO-$d_6$) δ ppm: 9.89 (s, 1H), 8.52 (s, 1H), 8.24 (s, 2H), 8.21 (d, J = 2.0 Hz, 1H), 8.17 (s, 1H), 8.10 (s, 1H), 7.63 (dd, J = 8.6, 2.3 Hz, 1H), 7.42 (d, J = 8.6 Hz, 1H), 4.51 (s, 1H), 3.59 (s, 3H), 3.56 (t, J = 4.4 Hz, 4H), 3.42 (s, 2H), 2.35 (t, J = 4.0 Hz, 4H), 2.28 (s, 3H). |
| 83 | ¹H NMR (400 MHz, DMSO-$d_6$) δ ppm: 9.89 (s, 1H), 8.52 (s, 1H), 8.25 (s, 2H), 8.22 (d, J = 2.2 Hz, 1H), 8.17 (s, 1H), 8.1 (s, 1H), 7.65 (dd, J = 8.5, 2.2 Hz, 1H), 7.43 (d, J = 8.5 Hz, 1H), 4.27-4.15 (m, 1H), 3.59 (s, 3H), 3.48 (s, 2H), 2.67 (t, J = 6.8 Hz, 2H), 2.52 (t, J = 6.8 Hz, 2H), 2.35 (s, 6H), 2.28 (s, 3H), 2.14 (s, 3H). |
| 84 | ¹H NMR (400 MHz, DMSO-$d_6$) δ ppm: 9.76 (s, 1H), 8.51 (s, 1H), 8.14 (s, 1H), 8.11 (s, 1H), 8.10 (s, 1H), 8.06 (t, J = 1.9 Hz, 1H), 7.43 (s, 1H), 7.42 (s, 1H), 3.80 (s, 3H), 3.58 (s, 3H), 2.28 (s, 3H). |
| 85 | ¹H NMR (400 MHz, DMSO-$d_6$) δ ppm: 9.70 (s, 1H), 8.50 (s, 1H), 8.14 (s, 1H), 8.12 (s, 1H), 8.10 (s, 1H), 7.98 (d, J = 2.8 Hz, 1H), 7.44 (dd, J = 9.0, 2.8 Hz, 1H), 7.38 (d, J = 9.0 Hz, 1H), 3.88-3.61 (m, 5H), 3.58 (s, 3H), 3.12-3.00 (m, 2H), 2.28 (s, 3H), 0.95 (d, J = 6.3 Hz, 3H). |
| 86 | ¹H NMR (400 MHz, DMSO-$d_6$) δ ppm: 9.77 (s, 1H), 8.50 (s, 1H), 8.14 (s, 1H), 8.11 (s, 1H), 8.10 (s, 1H), 8.06 (d, J = 2.8 Hz, 1H), 7.45 (dd, J = 8.9, 2.8 Hz, 1H), 7.41 (d, J = 8.9 Hz, 1H), 4.33 (septuplet, J = 4.0 Hz, 1H), 3.58 (s, 3H), 2.69-2.61 (m, J = 3.8 Hz, 2H), 2.28 (s, 3H), 2.18 (s, 3H), 1.95-1.91 (m, 1H), 1.65-1.62 (m, 2H), 1.67-1.59 (m, 2H). |
| 87 | ¹H NMR (400 MHz, DMSO-$d_6$) δ ppm: 9.84 (s, 1H), 8.52 (s, 1H), 8.23 (s, 1H), 8.22 (d, J = 2.5 Hz, 1H), 8.16 (s, 1H), 8.11 (s, 1H), 7.65 (dd, J = 8.7, 2.5 Hz, 1H), 7.41 (d, J = 8.7 Hz, 1H), 3.95 (td, J = 5.8, 3.0 Hz, 2H), 3.59 (s, 3H), 3.47-3.40 (m, 2H), 2.81-2.74 (m, J = 5.2 Hz, 1H), 2.28 (s, 3H), 1.72-1.66 (m, 4H). |
| 88 | ¹H NMR (300MHz, DMSO-$d_6$,) δ ppm 9.34 (s, 1H), 8.61 (s, 1H), 8.43 (s, 1H), 8.16 (s, 1H), 7.97 (s, 1H), 7.95 (s, 1H), 6.51 (br. s., 2H), 6.25 (s, 1H), 3.46 (s, 3H), 3.22-3.12 (m, 1H), 2.09 (s, 3H), 1.05-0.95 (m, 2H), 0.57-0.48 (m, 2H). |
| 89 | ¹H NMR (400 MHz, DMSO-$d_6$) δ ppm: 9.31 (s, 1H), 8.49 (s, 1H), 8.11 (s, 1H), 8.07 (s, 1H), 7.59 (d, J = 8.6 Hz, 2H), 7.42 (d, J = 8.6 Hz, 2H), 6.50 (s, 1H), 6.33 (s, 1H), 4.77 (d, J = 6.6 Hz, 2H), 4.71 (d, J = 6.6 Hz, 2H), 3.57 (s, 3H), 2.24 (s, 3H). |
| 90 | ¹H NMR (400 MHz, DMSO-$d_6$) δ ppm: 10.05 (s, 1H), 8.53 (s, 1H), 8.22 (s, 1H), 8.2 (s, 1H), 8.11 (s, 1H), 7.79 (d, J = 9.5 Hz, 1H), 7.25 (d, J = 9.5 Hz, 1H), 5.2 (quintuplet, J = 5.7 Hz, 1H), 3.76-3.72 (m, 2H), 3.60 (s, 3H), 3.06-3.02 ppm (m, 2H), 2.30 ppm (s, 6H). |
| 94 | ¹H NMR (400 MHz, DMSO-$d_6$) δ ppm: 8.89 (s, 1H), 8.14 (s, 1H), 7.79 (s, 1H), 7.31 (s, 1H), 6.47 (s, 2H), 6.17 (d, J = 0.79 Hz, 1H), 6.15 (d, J = 8.34 Hz, 1H), 4.03-3.98 (m, 1H), 3.65 (s, 3H), 2.41-2.33 (m, 1H), 1.98-1.9 (m, 2H), 1.86-1.69 (m, 4H), 1.02 (d, J = 6.34 Hz, 3H). |
| 96 | ¹H NMR (400 MHz, DMSO-$d_6$) δ ppm: 10.29 (s, 1H), 8.6 (d, J = 2.03 Hz, 1H), 8.55 (s, 1H), 8.32 (s, 1H), 8.23 (s, 1H), 8.13 (s, 1H), 7.95 (dd, J = 8.77, 2.45 Hz, 1H), 7.51 (d, J = 8.82 Hz, 1H), 5.8 (d, J = 5.81 Hz, 1H), 4.58-4.5 (m, 2H), 4.28-4.24 (m, 1H), 4.15-4.12 (m, 1H), 3.82-3.78 (m, 1H), 3.61 (s, 3H), 2.29 (s, 3H). |
| 97 | ¹H NMR (400 MHz, DMSO-$d_6$) δ ppm: 9.54 (s, 1H), 8.37 (d, J = 2.27 Hz, 1H), 7.89 (s, 1H), 7.77 (d, J = 2.73 Hz, 1H), 7.77 (s, 1H), 7.39 (d, J = 8.61 Hz, 1H), 6.95 (d, J = 9.83 Hz, 1H), 5.07-4.96 (m, 1H), 3.69 (s, 3H), 2.99 (s, 6H), 2.21-2.13 (m, 1H), 1.02 (dd, J = 16.67, 9.61 Hz, 6H). |
| 98 | ¹H NMR (400 MHz, DMSO-$d_6$) δ ppm: 9.05 ppm (s, 1H), 8.17 (d, J = 0.5 Hz, 1H), 7.86 (s, 1H), 7.57 (s, 1H), 6.92 (d, J = 9.61 Hz, 1H), 6.5 (s, 2H), 6.21 (d, J = 0.74 Hz, 1H), 5.02-4.95 (m, 1H), 3.66 (s, 3H), 2.16 (dq, J = 19.47, 6.59 Hz, 1H), 1.0 (t, J = 6.83 Hz, 6H). |
| 100 | ¹H NMR (400 MHz, DMSO-$d_6$) δ ppm: 10.26 (s, 1H), 8.79 (d, J = 2.28 Hz, 1H), 8.57 (s, 1H), 8.46 (t, J = 5.56 Hz, 1H), 8.27 (d, J = 10.39 Hz, 2H), 8.14 (d, J = 2.27 Hz, 1H), 8.1 (dd, J = 8.8, 2.48 Hz, 1H), 7.48 (d, J = 8.61 Hz, 1H), 3.62 (s, 3H), 3.41-3.29 (m, 4H), 3.25 (s, 3H), 3.31 (s, 3H), 1.80-1.73 (m, 2H). |
| 101 | ¹H NMR (400 MHz, DMSO-$d_6$) δ ppm: 10.27-10.2 (m, 1H), 8.79 (d, J = 2.04 Hz, 1H), 8.57 (s, 1H), 8.44 (t, J = 5.56 Hz, 1H), 8.3 (d, J = 3.45 Hz, |

TABLE IV-continued

¹H NMR of final compounds

| Cpd# | 1H NMR |
|---|---|
|  | 1H), 8.22 (s, 1H), 8.13 (s, 1H), 8.1 (dd, J = 8.8, 2.48 Hz, 1H), 7.5 (d, J = 8.83 Hz, 1H), 4.55-4.47 (m, 1H), 3.6 (s, 3H), 3.49-3.33 ppm (m, 4H), 2.3 ppm (s, 3H), 1.72-1.66 (m, 2H). |
| 102 | ¹H NMR (400 MHz, DMSO-$d_6$) δ ppm: 10.29 (s, 1H), 8.62 (d, J = 2.28 Hz, 1H), 8.55 (s, 1H), 8.31 (s, 1H) 8.26 (s, 1H), 8.13 (s, 1H), 7.96 (dd, J = 8.78, 2.45 Hz, 1H), 7.51 (d, J = 8.82 Hz, 1H), 4.37-4.32 (m, 1H), 4.27-4.23 (m, 1H), 4.0-3.91 (m, 2H), 3.61 (s, 3H), 2.65-2.57 (m, 1H), 2.29 (s, 3H), 1.05 (d, J = 4.3 Hz, 6H). |
| 103 | ¹H NMR (400 MHz, DMSO-$d_6$) δ ppm: 10.31 (s, 1H), 8.63 (d, J = 2.49 Hz, 1H), 8.55 (s, 1H), 8.3 (s, 1H) 8.27 (s, 1H), 8.14 (s, 1H), 7.97 (dd, J = 8.76, 2.45 Hz, 1H), 7.51 (d, J = 8.61 Hz, 1H), 4.60-4.54 ppm (m, 1H), 4.30-4.24 (m, 3H), 3.84-382 (m, 3H), 3.61 (s, 3H), 3.25 (s, 3H), 2.29 ppm (s, 3H). |
| 105 | ¹H NMR (400 MHz, DMSO-$d_6$) δ ppm: 10.19 (s, 1H), 8.53 (s, 1H), 8.38 (d, J = 2.27 Hz, 1H), 8.28 (s, 1H), 8.2 (s, 1H), 8.11 (s, 1H), 7.76 (dd, J = 8.59, 2.33 Hz, 1H), 7.51-7.49 (m, 1H), 3.6 (s, 3H), 3.52 (s, 4H), 2.34 (s, 4H), 2.28 (s, 3H), 2.2 (s, 3H) |
| 107 | ¹H NMR (400 MHz, DMSO-$d_6$) δ ppm: 10.23 (s, 1H), 8.55 (s, 1H), 8.31 (d, J = 3.29 Hz, 1H), 8.22 (s, 1H) 8.15 (s, 1H), 8.14 (d, J = 5.5 Hz, 2H), 7.92-7.89 (m, 1H), 7.51 (d, J = 8.64 Hz, 1H), 3.85-3.52 (m, 6H), 2.96-2.66 (m, 2H), 2.3 (s, 3H), 2.26 (s, 3H), 2.17 (s, 3H), 2.15-2.02 (m, 1H), 1.84-1.7 (m, 1H). |
| 108 | ¹H NMR (400 MHz, DMSO-$d_6$) δ ppm: 8.58 (s, 1H), 8.35 (s, 1H), 8.28 (s, 1H), 8.14 (s, 1H), 7.86 (dd, J = 16.05, 9.2 Hz, 2H), 3.71 (s, 4H), 3.63 (s, 8H), 2.31 (s, 3H). |
| 113 | ¹H NMR (400 MHz, DMSO-$d_6$) δ ppm: 8.37 (d, J = 2.06 Hz, 1H), 8.31 (s, 1H), 8.15-8.06 (m, 2H), 7.98 (s, 1H), 7.89 (s, 1H), 7.72 (dd, J = 8.66, 2.34 Hz, 1H), 7.27 (d, J = 8.78 Hz, 1H), 3.99-3.84 (m,2H), 3.66-3.53 (m, 2H), 3.36 ppm (s, 3H), 2.03 (s, 3H), 0.96 (dq, J = 13.73, 5.35 Hz, 1H), 0.19-0.05 (m, 4H). |
| 125 | ¹H NMR (400 MHz, DMSO-$d_6$) δ ppm: 10.34 (s, 1H), 8.67 (s, 1H), 8.58 (s, 1H), 8.43 (d, J = 2.19 Hz, 1H), 8.14 (s, 1H), 8.03 (s, 1H), 7.83 (dd, J = 8.44, 2.21 Hz, 1H), 7.37 (d, J = 8.6 Hz, 1H), 4.00-3.77 (m, 2H), 3.67 (s, 3H), 3.51-3.33 (s, 1H), 3.33-3.24 (m, 5H), 2.28 (s, 3H), 1.94-1.82 (m, 2H), 1.53-1.45 (m, 2H). |
| 126 | ¹H NMR (400 MHz, DMSO-$d_6$) δ ppm: 10.22 (s, 1H), 8.54 (s, 1H), 8.43 (d, J = 2.19 Hz, 1H), 8.3 (s, 1H), 8.22 (s, 1H), 8.13 (s, 1H), 7.79 ppm (dd, J = 8.6, 2.37 Hz, 0H), 7.53 (d, J = 8.6 Hz, 0H), 4.61-3.78 (m, 2H), 3.60 (s, 3H), 3.33-2.79 (m, 3H), 2.69 (s, 6H), 2.32 (s, 3H), 2.08-1.81 (m, 2H), 1.69-1.5 (m, 2H). |
| 134 | ¹H NMR (400 MHz, DMSO-$d_6$) δ ppm: 10.28 (s, 1H), 8.59 (d, J = 2.37 Hz, 1H), 8.55 (s, 1H), 8.28 (s, 1H), 8.24 (s, 1H), 8.12 (s, 1H), 7.93 (dd, J = 8.77, 2.37 Hz, 1H), 7.5 (d, J = 8.61 Hz, 1H), 4.73-4.66 (m, 4H), 4.57 (s, 2H), 4.22 (s, 2H), 3.61 (s, 3H), 2.29 (s, 3H). |
| 137 | 1H NMR (400 MHz, DMSO-$d_6$) δ ppm: 10.32 (s, 1H), 8.62 (d, J = 2.37 Hz, 1H), 8.56 (s, 1H), 8.38 (s, 1H), 8.22 (s, 1H), 8.13 (s, 1H), 7.97 (dd, J = 8.77, 2.38 Hz, 1H), 7.46 (d, J = 8.78 Hz, 1H), 4.62-4.53 (m, 1H), 4.43 (m, 1H), 4.35-4.21 (m, 2H), 3.88-3.77 (m, 1H), 3.65-3.45 (m, 1H), 2.29 (s, 3H), 1.1 (d, J = 6.04 Hz, 6H). |
| 138 | 1H NMR (400 MHz, DMSO-$d_6$) δ ppm: 10.32 (s, 1H), 8.65 (s, 1H), 8.58 (s, 1H), 8.42 (d, J = 2.19 Hz, 1H), 8.14 (s, 1H), 8.03 (s, 1H), 7.82 (dd, J = 8.59, 2.37 Hz, 1H), 7.37 (d, J = 8.6 Hz, 1H), 3.67 (s, 3H), 3.55-3.17 (m, 4H), 2.28 (s, 3H), 1.59-1.42 (m, 4H), 1.17 (s, 3H). |
| 142 | 1H NMR (400 MHz, DMSO-$d_6$) δ ppm: 10.36 (s, 1H), 8.61-8.56 (m, 3H), 8.14 (s, 1H), 8.11 (s, |
|  | 1H), 7.98 (d, J = 8.6 Hz, 1H), 7.41 (d, J = 8.6 Hz, 1H), 5.35-5.18 (m, 1H), 4.17-3.56 (m, 8H), 3.34 (d, J = 36.77 Hz, 3H), 2.29 (s, 3H). |
| 143 | 1H NMR (400 MHz, DMSO-$d_6$) δ ppm: 9.79 (s, 1H), 8.53 (s, 1H), 8.19 (s, 1H), 8.14 (s, 1H), 8.11 (s, 1H), 7.6 (d, J = 9.54 Hz, 1H), 6.94 (d, J = 9.43 Hz, 1H), 4.07-4.03 (m, 2H), 3.8-3.77 (m, 2H), 3.64 (s, 3H), 3.28-3.17 (m, 1H), 2.3 (d, J = 4.54 Hz, 3H), 2.13 (s, 6H). |
| 144 | 1H NMR (400 MHz, DMSO-$d_6$) δ ppm: 10.24 (s, 1H), 8.55 (s, 1H), 8.42-8.4 (m, 1H), 8.29 (s, 1H), 8.25 (s, 1H), 8.13 (s, 1H), 7.81-7.78 (m, 1H), 7.5 (d, J = 8.81 Hz, 1H), 4.4-3.97 (m, , 2H), 3.61 (s, 3H), 3.69-3.38 ppm (m, 4H), 3.3-2.74 (m, 1H), 2.29 (s, 3H), 1.19-1.0 (m, 3H). |
| 145 | 1H NMR (400 MHz, DMSO-$d_6$) δ ppm: 10.24 (s, 1H), 8.55 (s, 1H), 8.42-8.4 (m, 1H), 8.29 (s, 1H), 8.25 (s, 1H), 8.13 (s, 1H), 7.81-7.78 (m, 1H), 7.5 (d, J = 8.81 Hz, 1H), 4.4-3.97 (m, , 2H), 3.61 (s, 3H), 3.69-3.38 ppm (m, 4H), 3.3-2.74 (m, 1H), 2.29 (s, 3H), 1.19-1.0 (m, 3H). |
| 146 | 1H NMR (400 MHz, DMSO-$d_6$) δ ppm: 10.21 (s, 1H), 8.54 (s, 1H), 8.4 (d, J = 2.04 Hz, 1H), 8.3 (s, 1H), 8.21 (s, 1H), 8.13 (s, 1H), 7.78 (dd, J = 8.59, 2.33 Hz, 1H), 7.52 (dd, J = 8.6, 0.46 Hz, 1H), 4.24-4.09 (m, 1H), 3.87-3.56 (m, 2H), 3.64-3.56 (m, 5H), 3.46-3.33 (m, 2H), 2.29 (s, 3H), 1.26 (s, 3H). |
| 147 | 1H NMR (400 MHz, DMSO-$d_6$) δ ppm: 10.21 (s, 1H), 8.54 (s, 1H), 8.4 (d, J = 2.04 Hz, 1H), 8.3 (s, 1H), 8.21 (s, 1H), 8.13 (s, 1H), 7.78 (dd, J = 8.59, 2.33 Hz, 1H), 7.52 (dd, J = 8.6, 0.46 Hz, 1H), 4.24-4.09 (m, 1H), 3.87-3.56 (m, 2H), 3.64-3.56 (m, 5H), 3.46-3.33 (m, 2H), 2.29 (s, 3H), 1.26 (s, 3H). |
| 148 | 1H NMR (400 MHz, DMSO-$d_6$) δ ppm: 10.24 (s, 1H), 8.55 (s, 1H), 8.41 (d, J = 0.46 Hz, 1H), 8.29 (s, 1H), 8.26 (s, 1H), 8.13 (s, 1H), 7.8 (dd, J = 8.6, 2.33 Hz, 1H), 7.5 (d, J = 8.36 Hz, 1H), 4.47-3.45 (m, 8H), 3.0-2.71 (m, 1H), 2.28 (s, 3H), 1.26-0.92 (m, 6H). |
| 149 | 1H NMR (400 MHz, DMSO-$d_6$) δ ppm: 10.2 (s, 1H), 8.54 (d, J = 5.32 Hz, 1H), 8.4 (d, J = 2.73 Hz, 1H), 8.29 (s, 1H), 8.2 (s, 1H), 8.11 (s, 1H), 7.77 (dd, J = 8.6, 2.33 Hz, 1H), 7.51 (d, J = 8.34 Hz, 1H), 4.0-3.9 (m, 1H), 3.66-3.53 (m, 5H), 3.32-3.15 (m, 2H), 2.28 (s, 3H), 1.18-1.04 (m, 6H). |
| 151 | 1H NMR (400 MHz, DMSO-$d_6$) δ ppm: 10.23 (s, 1H), 8.42 (d, J = 2.27 Hz, 1H), 8.34 (s, 1H), 8.21 (s, 1H), 8.06 (td, J = 8.32, 3.0 Hz, 1H), 7.78 (dd, J = 8.59, 2.44 Hz, 1H), 7.52 (d, J = 8.6 Hz, 1H), 3.65-3.44 (m, 7H), 2.39-2.3 (m, 4H), 2.21 (s, 3H). |
| 152 | 1H NMR (400 MHz, DMSO-$d_6$) δ ppm: 9.73 (s, 1H), 8.52 (s, 1H), 8.18 (s, 1H), 8.15 (s, 1H), 8.11 (d, J = 0.48 Hz, 1H), 7.57 (d, J = 9.62 Hz, 1H), 7.09 (d, 1H), 4.61 (s, 1H), 3.61 (s, 3H), 3.54-3.48 (m, 2H), 3.39-3.31 (m, 2H), 2.83 (dd, J = 9.6, 2.01 Hz, 1H), 2.31 (s, 3H), 2.30 (s, 3H), 1.92 (d, J = 9.34 Hz, 1H), 1.79 (d, J = 9.35 Hz, 1H). |
| 153 | 1H NMR (400 MHz, DMSO-$d_6$) δ ppm: 10.21 (s, 1H), 8.53 (s, 1H), 8.52 (s, 1H), 8.3 (d, J = 3.54 Hz, 1H), 8.21 (s, 1H), 8.12 (s, 1H), 7.89 (d, J = 8.34 Hz, 1H), 7.5 (d, J = 8.6 Hz, 1H), 5.26-5.15 (m, 1H), 4.25-4.12 (m, 1H), 3.78-3.65 (m, 2H), 3.6 (s, 3H), 3.5-3.33 (m, 2H), 2.66-2.57 (m, 1H), 2.29 (s, 3H), 2.24 (s, 3H), 2.15 (s, 3H). |
| 154 | 1H NMR (400 MHz, DMSO-$d_6$) δ ppm: 10.2 ppm (s, 1H), 8.53 (s, 1H), 8.52 (s, 1H), 8.3 (d, J = 2.28 Hz, 1H), 8.2 (s, 1H), 8.11 (s, 1H), 7.88 (d, J = 4.55 Hz, 1H), 7.49 (d, J = 8.6 Hz, 1H), 5.28-5.18 (m, 1H), 4.29-4.15 (m, 1H), 3.8-3.68 (m, 2H), 3.64-3.48 (m, 7H), 2.78-2.53 (, 4H), 3.48-3.3 (m, 2H), 2.28 (s, 3H). |
| 155 | 1H NMR (400 MHz, DMSO-$d_6$) δ ppm: 10.26 (s, 1H), 8.55 (s, 1H), 8.47 (d, J = 2.26 Hz, 1H), 8.28 (s, 1H), 8.25 (s, 1H), 8.13 (s, 1H), 7.83 (dd, |

TABLE IV-continued

¹H NMR of final compounds

| Cpd# | 1H NMR |
|---|---|
| | J = 8.6, 2.29 Hz, 1H), 7.53 (dd, J = 8.61, 0.45 Hz, 1H), 4.49-3.65 (m, 5H), 3.61 (s, 3H), 3.38-3.02 (m, 2H), 2.29 (s, 3H). |
| 156 | 1H NMR (400 MHz, DMSO-$d_6$) δ ppm: 10.21 (s, 1H), 8.54 (s, 1H), 8.41 (d, J = 2.27 Hz, 1H), 8.26 (s, 1H), 8.25 (s, 1H), 8.12 (s, 1H), 7.79 (dd, J = 8.6, 2.31 Hz, 1H), 7.5 (d, J = 8.35 Hz, 1H), 4.47-3.67 (m, 3H), 3.62 ppm (s, 3H), 3.4-2.72 ppm (m, 4H), 2.28 (s, 3H), 0.93-0.79 (m, 1H), 0.53-0.14 (m, 4H). |
| 157 | 1H NMR (400 MHz, DMSO-$d_6$) δ ppm: 10.2 (s, 1H), 8.53 (s, 1H), 8.38 (d, J = 1.52 Hz, 1H), 8.29 (s, 1H), 8.21 (s, 1H), 8.11 (s, 1H), 7.76 (dd, J = 8.34, 1.76 Hz, 1H), 7.51 (d, J = 8.35 Hz, 1H), 4.15-3.64 (m, 3H), 3.6 (s, 3H), 3.55-2.95 (m, 4H), 2.34-2.24 (m, 4H), 1.08-0.63 (m, 6H). |
| 158 | 1H NMR (400 MHz, DMSO-$d_6$) δ ppm: 10.24 (s, 1H), 8.58-8.49 (m, 2H), 8.31-8.24 (m, 2H), 8.13 (d, J = 4.5 Hz, 1H), 7.94-7.84 (m, 1H), 7.54-7.47 (m, J = 4.3 Hz, 1H), 4.83-4.54 (m, 2H), 3.99-3.65 (m, 2H), 3.61 ppm (s, 3H), 3.59-3.25 ppm (m, 2H), 2.28 (s, 3H), 1.94-1.75 (m, 2H). |
| 159 | 1H NMR (400 MHz, DMSO-$d_6$) δ ppm: 10.22 (s, 1H), 8.54 (s, 1H), 8.38 (d, J = 2.05 Hz, 1H), 8.29 (s, 1H), 8.23 (s, 1H), 8.12 (s, 1H), 7.76 (dd, J = 8.59, 2.33 Hz, 1H), 7.52-7.5 (m, J = 2.51 Hz, 1H), 3.9-3.57 (m, 7H), 3.56-3.27 (m, 3H), 2.28 (s, 3H), 1.57-1.48 (m, 1H), 0.55-0.43 (m, 2H), 0.32-0.25 (m, 1H), 0.15-0.06 (m, 1H). |
| 160 | 1H NMR (400 MHz, DMSO-$d_6$) δ ppm: 10.28 (s, 1H), 8.55 (s, 1H), 8.45-8.45 (m, J = 1.83, 0.44 Hz, 1H), 8.45 (dd, J = 2.28, 0.44 Hz, 1H), 8.27 (s, 2H), 8.12 (s, 1H), 7.81 (dd, J = 8.61, 2.33 Hz, 1H), 7.53 (dd, J = 8.6, 0.45 Hz, 1H), 5.09-4.99 (m, 1H), 4.09-3.57 (m, 8H), 3.43-3.32 (m, 1H), 2.27 (s, 3H). |
| 161 | 1H NMR (400 MHz, DMSO-$d_6$) δ ppm: 10.19 (s, 1H), 8.53 (s, 1H), 8.49 (s, 1H), 8.29 (s, 1H), 8.2 (s, 1H), 8.11 (s, 1H), 7.86 (dd, J = 8.6, 2.28 Hz, 1H), 7.49 (d, J = 8.59 Hz, 1H), 3.77-3.4 (m, 6H), 3.04-2.96 (m, 1H), 2.83-2.69 (m, 3H), 2.31-2.09 (m, 7H), 2.06-1.85 (m, 1H), 1.59-1.45 (m, 1H). |
| 163 | 1H NMR (400 MHz, DMSO-$d_6$) δ ppm: 9.84 (s, 1H), 8.53 (s, 1H), 8.19 (d, J = 1.59 Hz, 2H), 8.1 (s, 1H), 7.63 (d, J = 9.66 Hz, 1H), 7.41 (d, J = 9.67 Hz, 1H), 4.83-4.81 (m, 1H), 4.16 (d, J = 12.59 Hz, 1H), 3.97 (d, J = 10.88 Hz, 2H), 3.64-3.58 (m, 0.61 Hz, 4H), 3.56-3.49 (m, 2H), 3.48-3.43 (m, 1H), 2.9 (td, J = 12.23, 3.06 Hz, 1H), 2.64 (dd, J = 12.59, 10.39 Hz, 1H), 2.31 (s, 3H) |
| 164 | 1H NMR (400 MHz, DMSO-$d_6$) δ ppm: 9.83 (s, 1H), 8.52 (s, 1H), 8.18 (s, 1H), 8.17 (s, 1H), 8.1 (s, 1H), 7.62 (d, J = 9.78 Hz, 1H), 7.4 (d, J = 9.77 Hz, 1H), 3.6 (s, 3H), 2.29 (s, 3H) |
| 165 | 1H NMR (400 MHz, DMSO-$d_6$) δ ppm: 9.82 (s, 1H), 8.51 (s, 1H), 8.17 (s, 1H), 8.17 (s, 1H), 8.09 (s, 1H), 7.62 (d, J = 9.66 Hz, 1H), 7.4 (d, J = 9.78 Hz, 1H), 4.81 (s, 1H), 4.14 (d, J = 12.47 Hz, 1H), 3.96 (d, J = 10.88 Hz, 2H), 3.63-3.57 (m, 4H), 3.52 (ddd, J = 20.17, 5.26, 2.81 Hz, 2H), 3.43 (td, J = 11.0, 5.5 Hz, 1H), 2.89 (td, J = 12.35, 3.06 Hz, 1H), 2.66-2.6 (m, 1H), 2.29 (s, 3H) |
| 166 | 1H NMR (400 MHz, DMSO-$d_6$) δ ppm: 9.79 (s, 1H), 8.51 (s, 1H), 8.17 (s, 1H), 8.15 (s, 1H), 8.09 (s, 1H), 7.59 (d, J = 9.66 Hz, 1H), 7.39 (d, J = 9.66 Hz, 1H), 4.07-4.03 (m, 2H), 3.62-3.58 (m, 5H), 3.21 (dd, J = 12.72, 6.23 Hz, 2H), 2.29 (s, 3H), 1.17 (d, J = 6.48 Hz, 6H) |
| 167 | 1H NMR (400 MHz, DMSO-$d_6$) δ ppm: 9.72 (s, 1H), 8.5 (s, 1H), 8.16 (s, 1H), 8.14 (s, 1H), 8.09 (s, 1H), 7.57 (d, J = 9.78 Hz, 1H), 7.27 (d, J = 9.78 Hz, 1H), 3.81-3.78 (m, 2H), 3.76-3.72 (m, 4H), 3.61-3.58 (m, 5H), 2.3 (s, 3H), 1.9-1.87 (m, 2H) |
| 168 | 1H NMR (400 MHz, DMSO-$d_6$) δ ppm: 9.79 (s, 1H), 8.51 (s, 1H), 8.17 (s, 1H), 8.15 (s, 1H), 8.09 (s, 1H), 7.6 (d, J = 9.78 Hz, 1H), 7.39 (d, J = 9.78 Hz, 1H), 4.07-4.03 (m, 2H), 3.62-3.57 (m, 5H), 3.21 (dd, J = 12.72, 6.24 Hz, 2H), 2.29 (s, 3H), 1.17 (d, J = 6.36 Hz, 6H) |
| 169 | 1H NMR (400 MHz, DMSO-$d_6$) δ ppm: 9.83 (s, 1H), 8.52 (s, 1H), 8.18 (s, 1H), 8.18 (s, 1H), 8.1 (s, 1H), 7.62 (d, J = 9.77 Hz, 1H), 7.4 (d, J = 9.78 Hz, 1H), 4.8 (t, J = 5.38 Hz, 1H), 4.15 (d, J = 12.47 Hz, 1H), 3.98-3.95 (m, 2H), 3.64-3.57 (m, 4H), 3.55-3.48 (m, 2H), 3.47-3.42 (m, 1H), 2.93-2.86 (m, 1H), 2.63 (dd, J = 12.48, 10.27 Hz, 1H), 2.3 (s, 3H) |
| 170 | 1H NMR (400 MHz, DMSO-$d_6$) δ ppm: 9.78 (s, 1H), 8.51 (s, 1H), 8.17 (s, 1H), 8.14 (s, 1H), 8.1 (s, 1H), 7.59 (d, J = 9.77 Hz, 1H), 7.3 (d, J = 9.78 Hz, 1H), 4.45 (s, 2H), 3.79 (d, J = 11.98 Hz, 2H), 3.6 (s, 3H), 3.0 (dd, J = 12.23, 2.21 Hz, 2H), 2.3 (s, 3H), 1.86-1.78 (m, 4H) |
| 171 | 1H NMR (400 MHz, DMSO-$d_6$) δ ppm:9.9 (s, 1H), 8.52 (s, 1H), 8.19 (s, 1H), 8.18 (s, 1H), 8.1 (s, 1H), 7.67 (d, J = 9.77 Hz, 1H), 7.5 (d, J = 9.58 Hz, 1H), 5.17 (t, J = 3.55 Hz, 1H), 4.09 (dd, J = 13.46, 3.42 Hz, 1H), 3.94-3.9 (m, 2H), 3.87-3.84 (m, 1H), 3.6 (s, 3H), 3.49 (dd, J = 13.47, 3.43 Hz, 1H), 3.28-3.21 (m, 1H), 2.3 (s, 3H) |
| 172 | 1H NMR (400 MHz, DMSO-$d_6$) δ ppm: 9.82 (s, 1H), 8.52 (s, 1H), 8.18 (s, 1H), 8.17 (s, 1H), 8.1 (s, 1H), 7.62 (d, J = 9.78 Hz, 1H), 7.41 (d, J = 9.78 Hz, 1H), 4.11-4.07 (m, 1H), 4.01-3.96 (m, 1H), 3.95-3.91 (m, 1H), 3.67-3.55 (m, 5H), 2.9-2.82 (m, 1H), 2.57-2.52 (m, 1H), 2.3 (s, 3H), 1.16 (d, J = 6.12 Hz, 3H) |
| 173 | 1H NMR (400 MHz, DMSO-$d_6$) δ ppm: 9.82 (s, 1H), 8.52 (s, 1H), 8.18 (s, 1H), 8.18 (s, 1H), 8.1 (s, 1H), 7.63 (d, J = 9.78 Hz, 1H), 7.45 (d, J = 9.78 Hz, 1H), 4.16-4.1 (m, 1H), 4.0-3.94 (m, 2H), 3.6 (s, 3H), 3.58-3.55 (m, 1H), 3.24-3.17 (m, 1H), 2.9-2.82 (m, 1H), 2.66-2.58 (m, 1H), 2.3 (s, 3H), 1.79-1.69 (m, 1H), 0.98-0.95 (m, 6H) |
| 174 | 1H NMR (400 MHz, DMSO-$d_6$) δ ppm: 9.74 (s, 1H), 8.51 (s, 1H), 8.17 (s, 2H), 8.17 (s, 3H), 8.17 (s, 1H), 8.14 (s, 1H), 8.1 (s, 1H), 7.59 (d, J = 9.65 Hz, 1H), 7.13 (d, J = 9.54 Hz, 1H), 4.85 (s, 1H), 4.67 (s, 1H), 3.79-3.78 (m, 1H), 3.68 (d, J = 7.46 Hz, 1H), 3.6 (s, 3H), 3.53-3.5 (m, 1H), 3.32-3.32 (m, 1H), 2.31 (s, 3H), 1.96-1.93 (m, 1H), 1.89-1.87 (m, 1H) |
| 175 | 1H NMR (400 MHz, DMSO-$d_6$) δ ppm: 9.8 (s, 1H), 8.52 (s, 1H), 8.18 (s, 1H), 8.16 (s, 1H), 8.1 (s, 1H), 7.6 (d, J = 9.78 Hz, 1H), 7.4 (d, J = 9.67 Hz, 1H), 3.76-3.74 (m, 2H), 3.6 (s, 3H), 3.46-3.44 (m, 2H), 3.35 (s, 2H), 2.3 (s, 3H), 1.21 (s, 6H) |
| 176 | 1H NMR (400 MHz, DMSO-$d_6$) δ ppm: 9.79 (s, 1H), 8.52 (s, 1H), 8.17 (s, 1H), 8.16 (s, 1H), 8.09 (s, 1H), 7.6 (d, J = 9.67 Hz, 1H), 7.39 (d, J = 9.78 Hz, 1H), 4.05 (q, J = 6.24, 3.3 Hz, 2H), 3.62-3.58 (m, 5H), 3.21 (dd, J = 12.72, 6.24 Hz, 2H), 2.3 (s, 3H), 1.17 (d, J = 6.36 Hz, 6H) |
| 177 | 1H NMR (400 MHz, DMSO-$d_6$) δ ppm: 9.82 (s, 1H), 8.51 (s, 1H), 8.18 (s, 2H), 8.09 (s, 1H), 7.62 (d, J = 9.78 Hz, 1H), 7.44 (d, J = 9.78 Hz, 1H), 4.13 (d, J = 12.59 Hz, 1H), 3.97 (td, J = 3.18, 2.69 Hz, 2H), 3.6 (s, 3H), 3.58-3.54 (m, 1H), 3.2 (ddd, J = 10.27, 6.6, 2.2 Hz, 1H), 2.91-2.81 (m, 1H), 2.65-2.57 (m, 1H), 2.3 (s, 3H), 1.79-1.68 (m, 1H), 0.97-0.94 (m, 6H) |
| 179 | 1H NMR (300MHz, DMSO-$d_6$) δ ppm 9.03 (s, 1H), 8.14 (s, 1H), 7.84 (s, 1H), 7.50 (s, 1H), 6.99 (d, J = 9.00 Hz, 1H), 6.47 (s, 2H), 6.19 (s, 1H), 4.64-4.53 (m, 1H), 3.62 (s, 3H), 1.19-1.09 (m, 1H), 0.63-0.55 (m, 1H), 0.50-0.37 (m, 3H). |
| 180 | 1H NMR (300 MHz, DMSO-$d_6$) δ ppm 9.67 (s, 1H), 8.52 (s, 1H), 8.26 (s, 1H), 8.15 (s, 1H), 8.11 (s, 2H), 8.01 (br. s., 1H), 7.45 (br. s., 1H), 7.33-7.41 (m, 3H), 3.59 (s, 3H), 3.11 (br. s., 3H), 2.96 (br. s., 4H), 2.29 (s, 4H). |
| 181 | 1H NMR (300 MHz, DMSO-$d_6$) δ ppm 9.62 (br. s., 1H), 8.49 (br. s., 1H), 8.08 (br. s., 3H), 7.99 |

TABLE IV-continued

¹H NMR of final compounds

| Cpd# | 1H NMR |
|---|---|
|  | (br. s., 1H), 7.24-7.55 (m, 2H), 3.50-3,68 (br. s., 6H), 2.24-2.29 (br.s., 2H), 2.11-2.22 (m, 6H), 1.81 (br. s., 2H), 1.50 (br. s., 2H), 1.23 (br. s., 2H), 0.84 (br. s., 1H) |
| 182 | 1H NMR (300 MHz, DMSO-$d_6$) δ ppm 9.46 (br. s., 1H), 8.48 (s, 1H), 8.09 (d, J = 4.01 Hz, 2H), 7.95 (s, 1H), 7.68 (br. s., 1H), 7.30 (d, J = 8.71 Hz, 1H), 7.04 (d, J = 6.62 Hz, 1H), 3.57 (br. s., 3H), 2.95-3.10 (m, J = 7.50 Hz, 2H), 2.79 (br. s., 2H), 2.27 (br. s., 3H), 2.19 (br. s., 6H), 1.70-1.90 (m, J = 9.80 Hz, 1H), 1.23 (br. s., 1H), 0.84 (br. s., 1H). |
| 183 | 1H NMR (300 MHz, DMSO-$d_6$) δ ppm 9.49 (s, 1H), 8.48 (s, 1H), 8.09 (d, J = 5.40 Hz, 2H), 7.99 (s, 1H), 7.82 (d, J = 2.61 Hz, 1H), 7.13-7.35 (m, 2H), 3.57 (s, 3H), 3.47 (s, 3H), 3.24 (s, 3H), 2.90 (s, 3H), 2.27 (s, 4H). |
| 184 | 1H NMR (300 MHz, DMSO-$d_6$): δ ppm 9.61 (s, 1H), 8.49 (s, 1H), 8.12 (s, 1H), 8.08 (d, J = 3.83 Hz, 2H), 7.99 (br. s., 1H), 7.37-7.51 (m, 1H), 7.23-7.36 (m, 1H), 4.35-4.56 (m, 1H), 3.64 (br. s., 2H), 3.57 (s, 3H), 2.55-2.79 (m, 2H), 2.27 (s, 3H), 1.74 (d, J = 12.37 Hz, 2H), 1.48 (br. s., 1H), 1.26 (br. s., 2H), 0.72-0.93 (m, 2H). |
| 185 | 1H NMR (300 MHz, DMSO-$d_6$) δ ppm 9.52 (s, 1H), 8.48 (s, 1H), 8.09 (d, J = 6.62 Hz, 2H), 8.01 (s, 1H), 7.85 (d, J = 2.61 Hz, 1H), 7.19-7.39 (m, 2H), 3.57 (s, 3H), 2.86 (s, 6H), 2.27 (s, 3H). |
| 186 | 1H NMR (300 MHz, DMSO-$d_6$) δ ppm 8.88 (br. s., 1H), 8.44 (s, 1H), 8.05 (br. s., 2H), 7.92 (br. s., 1H), 7.47 (s, 1H), 6.23 (s, 1H), 4.20 (br. s., 2H), 3.54 (br. s., 7H), 2.68 (br. s., 2H), 2.40 (br. s., 4H), 2.24 (br. s., 3H). |
| 187 | 1H NMR (400MHz, DMSO-$d_6$) δ ppm: 9.18 (br s, 1H), 8.57 (s, 1H), 7.89 (s, 1H), 7.82 (s, 1H), 7.69 (s, 1H), 7.13 (s, 1H), 6.34 (br s, 2H), 5.97 (d, 1H), 4.66 (d, 1H), 3.97-3.90 (m, 2H), 3.54-3.46 (m, 1H), 3.48 (s, 3H), 1.99 (s, 3H), 0.96 (d, 3H). |

BIOLOGICAL EXAMPLES

Example 1. In Vitro Assays 1.1. JAK1 Inhibition Assay

Recombinant human JAK1 (catalytic domain, amino acids 866-1154; catalog number PV4774) is purchased from Invitrogen. 1 ng of JAK1 (or 2 ng of JAK1 depending of the enzyme lot number) is incubated with 20 nM Ulight-JAK1 (tyr1023) peptide (Perkin Elmer catalog number TRF0121) in kinase reaction buffer (15 mM MOPS pH6.8, 0.01% Brij-35, 5 mM $MgCl_2$, 2 mM DTT, 20 μM ATP) with or without 4 μL containing test compound or vehicle (DMSO, 1% final concentration), in a total volume of 20 μL, in a white 384 Opti plate (Perkin Elmer, catalog number 6007290). After 60 min at room temperature, reactions are stopped by adding 20 μL/well of detection mixture (1× detection buffer (Perkin Elmer, catalog number CR97-100), 0.5 nM Europium-anti-phosphotyrosine (PT66) (Perkin Elmer, catalog number AD0068/AD0069), 10 mM EDTA). Readout is performed after 60 min incubation at room temperature using the Envision with excitation at 320 nm and measuring emission at 615 nm and 665 nm (Perkin Elmer). The ratio of the relative fluorescence units (RFU) at 665 nm and 615 nm (RFU 665/RFU 615 multiplied with a factor 1000) is used to do further calculations. Kinase activity is calculated by subtracting the ratio obtained in the presence of a positive control inhibitor (1 μM staurosporine) from the ratio obtained in the presence of vehicle. The ability of a test compound to inhibit this activity (or percentage inhibition) is determined as:

$$\left(1 - \frac{\text{(Fluorescent ratio test compound} - \text{Fluorescent ratio control)}}{\text{(Fluorescent ratio vehicle} - \text{Fluorescent ratio control)}}\right) * 100$$

wherein

Fluorescent ratio test compound=ratio RFU665/RFU615*1000 determined for sample with test compound present Fluorescent ratio control=ratio RFU665/RFU615*1000 determined for sample with positive control inhibitor Fluorescent ratio vehicle=ratio RFU665/RFU615*1000 determined in the presence of vehicle Dose dilution series were prepared for the compounds enabling the testing of dose-response effects in the JAK1 assay and the calculation of the $IC_{50}$ for the compound. Each compound is routinely tested at concentration of 20 μM followed by a 1/5 serial dilution, 10 points in a final concentration of 1% DMSO. When potency of compound series increases, more dilutions are prepared and/or the top concentration are lowered (e.g. 5 μM, 1 μM). The data are expressed as the average $IC_{50}$ from the assays.

TABLE V

JAK1 potency of illustrative compounds of the invention

| Cpd | $IC_{50}$ (nM) |
|---|---|
| 1 | 153.4 |
| 2 | 70.3 |
| 3 | 110.3 |
| 4 | 92.3 |
| 5 | 23.4 |
| 6 | 49.7 |
| 7 | 8.5 |
| 8 | 23.1 |
| 9 | 47.2 |
| 10 | 83.9 |
| 11 | 27.2 |
| 12 | 26.9 |
| 13 | 24.4 |
| 14 | 91.4 |
| 15 | 12.2 |
| 16 | 71.0 |
| 17 | 64.6 |
| 18 | 293.9 |
| 19 | 80.9 |
| 20 | 8.6 |
| 21 | 208.2 |
| 22 | 23.0 |
| 23 | 234.2 |
| 24 | 61.8 |
| 25 | 243.1 |
| 26 | 338.4 |
| 27 | 347.6 |
| 28 | 348.7 |
| 29 | 505.0 |
| 30 | 398.8 |
| 31 | 186.5 |
| 32 | 117.0 |
| 33 | 67.6 |
| 34 | 100.7 |
| 35 | 52.4 |
| 36 | 40.5 |
| 37 | 84.3 |
| 38 | 40.9 |
| 39 | 101.6 |
| 40 | 269.4 |

TABLE V-continued

JAK1 potency of illustrative compounds of the invention

| Cpd | IC$_{50}$ (nM) |
|---|---|
| 41 | 268.2 |
| 42 | 145.9 |
| 43 | 53.8 |
| 44 | 54.1 |
| 45 | 80.6 |
| 46 | 66.8 |
| 47 | 77.5 |
| 48 | 35.5 |
| 49 | 34.9 |
| 50 | 85.6 |
| 51 | 29.2 |
| 52 | 37.9 |
| 53 | 68.0 |
| 54 | 11.2 |
| 55 | 100.1 |
| 56 | 99.2 |
| 57 | 780.9 |
| 58 | 97.8 |
| 59 | 460.7 |
| 60 | 85.5 |
| 61 | 60.3 |
| 62 | 86.7 |
| 63 | 102.4 |
| 64 | 343.3 |
| 65 | 69.4 |
| 66 | 146.4 |
| 67 | 51.4 |
| 68 | 112.6 |
| 69 | 61.3 |
| 70 | 115.7 |
| 71 | 103.2 |
| 72 | 8.9 |
| 73 | 60.2 |
| 74 | 23.6 |
| 75 | 32.7 |
| 76 | 199.5 |
| 77 | 43.8 |
| 78 | 60.2 |
| 79 | 18.5 |
| 80 | 19.9 |
| 81 | 150.0 |
| 82 | 103.2 |
| 83 | 277.7 |
| 84 | 57.1 |
| 85 | 30.4 |
| 86 | 197.5 |
| 87 | 73.1 |
| 88 | 5.3 |
| 89 | 71.5 |
| 90 | 199.7 |
| 91 | 156.8 |
| 92 | 9.6 |
| 93 | 57.1 |
| 94 | 217.2 |
| 95 | 249.8 |
| 96 | 21.8 |
| 97 | 21.8 |
| 98 | 28.2 |
| 99 | 110.7 |
| 100 | 63.5 |
| 101 | 48.9 |
| 102 | 52.0 |
| 103 | 46.2 |
| 104 | 54.0 |
| 105 | 54.1 |
| 106 | 38.9 |
| 107 | 132.9 |
| 108 | 91.7 |
| 109 | 215.8 |
| 110 | 314.9 |
| 111 | 310.4 |
| 112 | 55.9 |
| 113 | 44.0 |
| 114 | 78.8 |
| 115 | 107.3 |
| 116 | 151.2 |
| 117 | 204.8 |
| 118 | 29.1 |
| 119 | 26.8 |
| 120 | 30.2 |
| 121 | 25.2 |
| 122 | 48.3 |
| 123 | 124.4 |
| 124 | 36.4 |
| 125 | 47.8 |
| 126 | 121.9 |
| 127 | 43.6 |
| 128 | 176.8 |
| 129 | 105.6 |
| 130 | 123.8 |
| 131 | 52.7 |
| 132 | 139.7 |
| 133 | 178.2 |
| 134 | 55.4 |
| 135 | 28.2 |
| 136 | 43.0 |
| 137 | 54.6 |
| 138 | 37.8 |
| 139 | 33.8 |
| 140 | 51.5 |
| 141 | 52.6 |
| 142 | 85.1 |
| 143 | 92.1 |
| 144 | 44.4 |
| 145 | 43.9 |
| 146 | 22.3 |
| 147 | 40.6 |
| 148 | 52.2 |
| 149 | 79.3 |
| 150 | 136.9 |
| 151 | 97.0 |
| 152 | 205.4 |
| 153 | 54.4 |
| 154 | 62.0 |
| 155 | 41.4 |
| 156 | 34.8 |
| 157 | 19.8 |
| 158 | 23.6 |
| 159 | 34.6 |
| 160 | 37.3 |
| 161 | 137.1 |
| 162 | 34.3 |
| 163 | 51.5 |
| 164 | 53.6 |
| 165 | 39.1 |
| 166 | 76.2 |
| 167 | 52.4 |
| 168 | 50.0 |
| 169 | 62.8 |
| 170 | 59.0 |
| 171 | 27.2 |
| 172 | 45.2 |
| 173 | 53.4 |
| 174 | 37.2 |
| 175 | 73.6 |
| 176 | 37.8 |
| 177 | 74.5 |
| 178 | 85.3 |
| 179 | 14.5 |
| 180 | 81.7 |
| 181 | 151.0 |
| 182 | 164.7 |
| 183 | 95.4 |
| 184 | 59.0 |
| 185 | 93.6 |
| 186 | 77.2 |
| 187 | 126.9 |
| 188 | 41.8 |

TABLE V-continued

JAK1 potency of illustrative compounds of the invention

| Cpd | IC$_{50}$ (nM) |
|---|---|
| 189 | 43.3 |
| 190 | 41.6 |

1.2. JAK2 Inhibition Assay

Recombinant human JAK2 (catalytic domain, amino acids 808-1132; catalog number PV4210) is purchased from Invitrogen. 0.83 ng of JAK2 is incubated with 25 nM Ulight-JAK1(tyr1023) peptide (Perkin Elmer catalog number TRF0121) in kinase reaction buffer 25 mM MOPS pH7.0, 0.01% Triton X-100, 7.5 mM MgCl$_2$, 2 mM DTT, 0.7 µM ATP) with or without 4 µL containing test compound or vehicle (DMSO, 1% final concentration), in a total volume of 20 µL, in a white 384 Opti plate (Perkin Elmer, catalog number 6007290). After 60 min at room temperature, reactions are stopped by adding 20 µL/well of detection mixture (1× detection buffer (Perkin Elmer, catalog number CR97-100) with 0.5 nM Europium-anti-phosphotyrosine (PT66) (Perkin Elmer, catalog number AD0068/AD0069) and 10 mM EDTA). Readout is performed after 60 min incubation at room temperature using the Envision with excitation at 320 nm and measuring emission at 615 nm and 665 nm (Perkin Elmer). The ratio of the relative fluorescence units (RFU) at 665 nm and 615 nm (RFU 665/RFU 615 multiplied with a factor 1000) is used to do further calculations. Kinase activity is calculated by subtracting the ratio obtained in the presence of a positive control inhibitor (1 µM staurosporine) from the ratio obtained in the presence of vehicle. The ability of a test compound to inhibit this activity (or percentage inhibition) is determined as:

$$\left(1 - \frac{\text{(Fluorescent ratio test compound} - \text{Fluorenscent } ration control)}{\text{(Fluorescent ratio vehicle} - \text{Fluorescent ratio control)}}\right) * 100$$

wherein

Fluorescent ratio test compound=ratio RFU665/RFU615*1000 determined for sample with test compound present Fluorescent ratio control=ratio RFU665/RFU615*1000 determined for sample with positive control inhibitor Fluorescent ratio vehicle=ratio RFU665/RFU615*1000 determined in the presence of vehicle Dose dilution series are prepared for compound enabling the testing of dose-response effects in the JAK2 assay and the calculation of the IC$_{50}$ for the compound. Each compound is routinely tested at concentration of 20 µM followed by a 1/5 serial dilution, 10 points in a final concentration of 1% DMSO. When potency of compound series increases, more dilutions are prepared and/or the top concentration are lowered (e.g. 5 µM, 1 µM). The data are expressed as the average IC$_{50}$ from the assays.

TABLE VI

JAK2 potency of illustrative compounds of the invention

| Cpd | IC$_{50}$ (nM) |
|---|---|
| 1 | 67.3 |
| 2 | 19.36 |
| 3 | 77.99 |
| 4 | 16.45 |
| 5 | 6.96 |
| 6 | 8.46 |
| 7 | 3.17 |
| 8 | 2.39 |
| 9 | 16.52 |
| 10 | 8.35 |
| 11 | 4.75 |
| 12 | 3.04 |
| 13 | 3.16 |
| 14 | 17.02 |
| 15 | 2.4 |
| 16 | 24.97 |
| 17 | 14.6 |
| 18 | 31.48 |
| 19 | 11.19 |
| 20 | 1.3 |
| 21 | 18.29 |
| 22 | 3.35 |
| 23 | 66.66 |
| 24 | 43.9 |
| 25 | 78.31 |
| 26 | 872.85 |
| 27 | 280.15 |
| 28 | 207.65 |
| 29 | 906.75 |
| 30 | 777.1 |
| 31 | 43.8 |
| 32 | 26.18 |
| 33 | 23.09 |
| 34 | 23.38 |
| 35 | 20.44 |
| 36 | 9.17 |
| 37 | 20.13 |
| 38 | 7.72 |
| 39 | 10.65 |
| 40 | 27.09 |
| 41 | 21.96 |
| 42 | 14.37 |
| 43 | 7.42 |
| 44 | 10.98 |
| 45 | 11.11 |
| 46 | 7.29 |
| 47 | 18.25 |
| 48 | 9.7 |
| 49 | 14.59 |
| 50 | 25.91 |
| 51 | 7.16 |
| 52 | 21.41 |
| 53 | 72.66 |
| 54 | 2.03 |
| 55 | 45.5 |
| 56 | 179.5 |
| 57 | 229.07 |
| 58 | 35.5 |
| 59 | 133.2 |
| 60 | 98.89 |
| 61 | 58.44 |
| 62 | 139.05 |
| 63 | 69.95 |
| 64 | 213.6 |
| 65 | 12.42 |
| 66 | 198.73 |
| 67 | 28.23 |
| 68 | 175.1 |
| 69 | 69.97 |
| 70 | 81.29 |
| 71 | 86.15 |
| 72 | 1.91 |
| 73 | 13.13 |
| 74 | 13.84 |
| 75 | 8.56 |

TABLE VI-continued

JAK2 potency of illustrative compounds of the invention

| Cpd | IC$_{50}$ (nM) |
|---|---|
| 76 | 19.85 |
| 77 | 16.65 |
| 78 | 31.62 |
| 79 | 5.58 |
| 80 | 5.2 |
| 81 | 10.44 |
| 82 | 17.69 |
| 83 | 27.06 |
| 84 | 45.46 |
| 85 | 10.48 |
| 86 | 22.86 |
| 87 | 38.82 |
| 88 | 1.42 |
| 89 | 110.41 |
| 90 | 15.04 |
| 91 | 42.03 |
| 92 | 1.17 |
| 93 | 16.4 |
| 94 | 39.68 |
| 95 | 37.97 |
| 96 | 15.74 |
| 97 | 6.29 |
| 98 | 6.31 |
| 99 | 51.07 |
| 100 | 39.44 |
| 101 | 37.76 |
| 102 | 13.28 |
| 103 | 19.42 |
| 104 | 17.11 |
| 105 | 10.15 |
| 106 | 14.48 |
| 107 | 27.12 |
| 108 | 9.66 |
| 109 | 197.43 |
| 110 | 237.47 |
| 111 | 29.72 |
| 112 | 21.58 |
| 113 | 15.07 |
| 114 | 19.96 |
| 115 | 29.13 |
| 116 | 28.32 |
| 117 | 32.26 |
| 118 | 17.27 |
| 119 | 13.18 |
| 120 | 13.28 |
| 121 | 18.85 |
| 122 | 23.67 |
| 123 | 40.24 |
| 124 | 7.71 |
| 125 | 13.27 |
| 126 | 16.76 |
| 127 | 18.26 |
| 128 | 16.85 |
| 129 | 32 |
| 130 | 21.82 |
| 131 | 14.8 |
| 132 | 36.48 |
| 133 | 25.8 |
| 134 | 14.46 |
| 135 | 12.64 |
| 136 | 19.62 |
| 137 | 12.88 |
| 138 | 8.22 |
| 139 | 23.7 |
| 140 | 14.55 |
| 141 | 10.45 |
| 142 | 21.26 |
| 143 | 22.89 |
| 144 | 15.85 |
| 145 | 14.64 |
| 146 | 6.95 |
| 147 | 11.78 |
| 148 | 15.81 |
| 149 | 21.23 |
| 150 | 10.84 |
| 151 | 9.32 |
| 152 | 26.59 |
| 153 | 16.7 |
| 154 | 22.18 |
| 155 | 17.83 |
| 156 | 12.3 |
| 157 | 5.95 |
| 158 | 11.74 |
| 159 | 7.25 |
| 160 | 11.23 |
| 161 | 17.48 |
| 162 | 11.33 |
| 163 | 5.77 |
| 164 | 5.99 |
| 165 | 4.43 |
| 166 | 11.47 |
| 167 | 6.22 |
| 168 | 5.94 |
| 169 | 6.61 |
| 170 | 5.27 |
| 171 | 5.97 |
| 172 | 6.99 |
| 173 | 5.22 |
| 174 | 3.01 |
| 175 | 8.77 |
| 176 | 4.86 |
| 177 | 6.91 |
| 178 | 11.58 |
| 179 | 2.23 |
| 180 | 18.23 |
| 181 | 36.91 |
| 182 | 76.4 |
| 183 | 41.22 |
| 184 | 22.11 |
| 185 | 41.39 |
| 186 | 22.22 |
| 187 | 42.33 |
| 188 | 7.53 |
| 189 | 9.7 |
| 190 | 7.98 |

1.3. JAK3 Inhibition Assay

Recombinant human JAK3 catalytic domain (amino acids 781-1124; catalog number PV3855) is purchased from Invitrogen. 0.5 ng JAK3 protein is incubated with 2.5 µg polyGT substrate (Sigma catalog number P0275) in kinase reaction buffer (25 mM Tris pH 7.5, 0.5 mM EGTA, 10 mM MgCL$_2$, 2.5 mM DTT, 0.5 mM Na3VO4, 5 mM b-glycerolphosphate, 0.01% Triton X-100, 1 µM non-radioactive ATP, 0.25 µCi 33P-gamma-ATP (Perkin Elmer, catalog number NEG602K001MC) final concentrations) with or without 5 µL containing test compound or vehicle (DMSO, 1% final concentration), in a total volume of 25 µL, in a polypropylene 96-well plate (Greiner, catalog number 651201). After 45 min at 30° C., reactions are stopped by adding 25 µL/well of 150 mM phosphoric acid. All of the terminated kinase reaction is transferred to prewashed (75 mM phosphoric acid) 96 well filter plates (Perkin Elmer catalog number 6005177) using a cell harvester (Perkin Elmer). Plates are washed 6 times with 300 µL per well of a 75 mM phosphoric acid solution and the bottom of the plates is sealed. 40 µL/well of Microscint-20 (Perkin Elmer, catalog number 6013621) is added, the top of the plates is sealed and readout is performed using the Topcount (Perkin Elmer). Kinase activity is calculated by subtracting counts per min (cpm) obtained in the presence of a positive control inhibitor (10 µM staurosporine) from cpm obtained in the presence of vehicle. The ability of a test compound to inhibit this activity (or percentage inhibition) is determined as:

$$\left(1 - \frac{(cpm \text{ test compound} - cpm \text{ control})}{(cpm \text{ vehicle} - cpm \text{ control})}\right) * 100$$

cpm test compound=cpm determined for sample with test compound present cpm control=cpm determined for sample with positive control inhibitor cpm vehicle=cpm determined in the presence of vehicle Dose dilution series were prepared for the compounds enabling the testing of dose-response effects in the JAK3 assay and the calculation of the $IC_{50}$ for each compound. Each compound is routinely tested at concentration of 20 µM followed by a 1/5 serial dilution, 10 points in a final concentration of 1% DMSO. When potency of compound series increased, more dilutions were prepared and/or the top concentration is lowered (e.g. 5 µM, 1 µM).

The following compounds have been tested for their activity against JAK3 and the average $IC_{50}$ values, as determined using the assays described herein, are given in the table below.

TABLE VII

JAK3 $IC_{50}$ Values of Illustrative Compounds of the invention

| Cpd | $IC_{50}$ (nM) |
|---|---|
| 1 | 1493.67 |
| 2 | 130.7 |
| 3 | 2159.67 |
| 4 | 783.97 |
| 5 | 329.15 |
| 6 | 210.47 |
| 7 | 65.73 |
| 8 | 47.51 |
| 9 | 499.78 |
| 10 | 459.3 |
| 11 | 142.9 |
| 12 | 36.68 |
| 13 | 9.66 |
| 14 | 278.75 |
| 15 | 73.98 |
| 16 | 220.8 |
| 17 | 237.1 |
| 18 | 187.25 |
| 19 | 231.4 |
| 20 | 13.05 |
| 21 | 437.43 |
| 22 | 97.93 |
| 23 | 2925.5 |
| 24 | 919.2 |
| 25 | 2295.5 |
| 26 | 4000 |
| 27 | 1855 |
| 28 | 3152 |
| 29 | 4000 |
| 30 | 4000 |
| 31 | 1046.45 |
| 32 | 601.35 |
| 33 | 503.4 |
| 34 | 1109 |
| 35 | 452.47 |
| 36 | 417.27 |
| 37 | 439.15 |
| 38 | 395.91 |
| 39 | 363.16 |
| 40 | 759.45 |
| 41 | 389.13 |
| 42 | 912.57 |
| 43 | 254.1 |
| 44 | 475.95 |
| 45 | 486.05 |
| 46 | 205 |
| 47 | 200.05 |
| 48 | 266.05 |
| 49 | 495.4 |
| 50 | 476.47 |
| 51 | 188.55 |
| 52 | 516.88 |
| 53 | 495.05 |
| 54 | 36.32 |
| 55 | 481.33 |
| 56 | 2868.33 |
| 57 | 3041 |
| 58 | 1102.67 |
| 59 | 3782 |
| 60 | 2061 |
| 61 | 1111.93 |
| 62 | 2374 |
| 63 | 583.9 |
| 64 | 3221.5 |
| 65 | 69.69 |
| 66 | 972.07 |
| 67 | 258.2 |
| 68 | 2762.5 |
| 69 | 1314.5 |
| 70 | 1262 |
| 71 | 1083 |
| 72 | 24.34 |
| 73 | 1065 |
| 74 | 466.45 |
| 75 | 283.94 |
| 76 | 579.03 |
| 77 | 591.63 |
| 78 | 736.7 |
| 79 | 573.07 |
| 80 | 391.53 |
| 81 | 386.3 |
| 82 | 207.8 |
| 83 | 368.03 |
| 84 | 907.8 |
| 85 | 478.55 |
| 86 | 445.7 |
| 87 | 979.35 |
| 88 | 188.5 |
| 89 | 1989.5 |
| 90 | 1128.75 |
| 91 | 207.85 |
| 92 | 13.01 |
| 93 | 77.4 |
| 94 | 87.08 |
| 95 | 177.25 |
| 96 | 457.97 |
| 97 | 36.36 |
| 98 | 48.23 |
| 99 | 915.97 |
| 100 | 911.73 |
| 101 | 909.57 |
| 102 | 334.13 |
| 103 | 560.2 |
| 104 | 449.67 |
| 105 | 258.76 |
| 106 | 270.4 |
| 107 | 364.98 |
| 108 | 666.17 |
| 109 | 2810.67 |
| 110 | 1968 |
| 111 | 1050.37 |
| 112 | 541.83 |
| 113 | 495.03 |
| 114 | 392.6 |
| 115 | 2113.5 |
| 116 | 1201 |
| 117 | 2030 |
| 118 | 432.35 |
| 119 | 481.15 |
| 120 | 536.2 |

TABLE VII-continued

JAK3 IC$_{50}$ Values of Illustrative Compounds of the invention

| Cpd | IC$_{50}$ (nM) |
|---|---|
| 121 | 781.45 |
| 122 | 586.6 |
| 123 | 657 |
| 124 | 203.5 |
| 125 | 225 |
| 126 | 316.7 |
| 127 | 587.15 |
| 128 | 258.6 |
| 129 | 730.7 |
| 130 | 416.5 |
| 131 | 256.55 |
| 132 | 463.35 |
| 133 | 314.55 |
| 134 | 370.5 |
| 135 | 402.65 |
| 136 | 526.85 |
| 137 | 491.35 |
| 138 | 272.85 |
| 139 | 672.95 |
| 140 | 500 |
| 141 | 334.15 |
| 142 | 639.95 |
| 143 | 579.87 |
| 144 | 391.23 |
| 145 | 372.33 |
| 146 | 215.5 |
| 147 | 385.33 |
| 148 | 301.2 |
| 149 | 567.33 |
| 151 | 136.62 |
| 152 | 539.9 |
| 153 | 229.25 |
| 154 | 300.8 |
| 155 | 238.55 |
| 156 | 194.4 |
| 157 | 90.07 |
| 158 | 186.45 |
| 159 | 255.85 |
| 160 | 514.15 |
| 161 | 455.15 |
| 162 | 452.97 |
| 178 | 291.77 |
| 179 | 25.36 |
| 180 | 408.6 |
| 181 | 396.5 |
| 182 | 721.4 |
| 183 | 561.03 |
| 184 | 487.33 |
| 185 | 871.13 |
| 186 | 256.87 |
| 187 | 659.7 |

1.4. TYK2 Inhibition Assay
1.4.1. TYK2 Radioactive Assay polyGT Substrate Recombinant human TYK2 catalytic domain (amino acids 871-1187; catalog number 08-147) is purchased from Carna Biosciences. 6 ng of TYK2 is incubated with 0.05 mg/mL polyGT substrate (Sigma catalog number P0275) in kinase reaction buffer (25 mM MOPS pH 7.2, 50 mM NaCl, 0.5 mM EDTA, 1 mM DTT, 5 mM MnCl$_2$, 10 mM MgCl$_2$, 0.01% Brij-35, 0.1 µM non-radioactive ATP, 0.125 µCi $^{33}$P-gamma-ATP (Perkin Elmer, catalog number NEG602K001MC) final concentrations) with or without 5 µL containing test compound or vehicle (DMSO, 1% final concentration), in a total volume of 25 µL, in a polypropylene 96-well plate (Greiner, catalog number 651201). After 120 min at 30° C., reactions were stopped by adding 25 µL/well of 150 mM phosphoric acid. All of the terminated kinase reaction is transferred to prewashed (75 mM phosphoric acid) 96 well filter plates (Perkin Elmer catalog number 6005177) using a cell harvester (Perkin Elmer). Plates were washed 6 times with 300 µL per well of a 75 mM phosphoric acid solution and the bottom of the plates is sealed. 40 µL/well of Microscint-20 (Perkin Elmer, catalog number 6013621) is added, the top of the plates is sealed and readout is performed using the Topcount (Perkin Elmer). Kinase activity is calculated by subtracting counts per min (cpm) obtained in the presence of a positive control inhibitor (10 µM staurosporine) from cpm obtained in the presence of vehicle. The ability of a test compound to inhibit this activity (or percentage inhibition) is determined as:

$$\left(1 - \left(\frac{(cpm \text{ test compound} - cpm \text{ control})}{(cpm \text{ vehicle} - cpm \text{ control})}\right)\right) * 100$$

wherein
cpm test compound=cpm determined for sample with test compound present
cpm control=cpm determined for sample with positive control inhibitor
cpm vehicle=cpm determined in the presence of vehicle Dose dilution series were prepared for the compounds enabling the testing of dose-response effects in the TYK2 assay and the calculation of the IC$_{50}$ for each compound. Each compound is routinely tested at concentration of 20 µM followed by a 1/5 serial dilution, 10 points in a final concentration of 1% DMSO. When potency of compound series increased, more dilutions were prepared and/or the top concentration is lowered (e.g. 5 µM, 1 µM).

The following compounds have been tested for their activity against TYK2; and the average IC$_{50}$ values as determined using the assays described herein, are given in the table below.

TABLE VIII

TYK2 IC$_{50}$ Values of Illustrative Compounds of the invention

| Cpd | IC$_{50}$ (nM) |
|---|---|
| 1 | 10.05 |
| 2 | 4.65 |
| 3 | 12.66 |
| 4 | 4.37 |
| 5 | 0.95 |
| 6 | 1.46 |
| 7 | 0.59 |
| 8 | 0.68 |
| 9 | 1.02 |
| 10 | 6.18 |
| 11 | 1.81 |
| 12 | 1.42 |
| 13 | 1.92 |
| 14 | 3.83 |
| 15 | 0.42 |
| 16 | 13.39 |
| 17 | 10.18 |
| 18 | 30.48 |
| 19 | 10.69 |
| 20 | 0.96 |
| 21 | 7.62 |
| 22 | 3.07 |
| 23 | 18.32 |
| 24 | 9.01 |
| 25 | 19.2 |
| 26 | 74.02 |
| 27 | 38.9 |
| 28 | 27.14 |
| 29 | 97.37 |
| 30 | 55.71 |

TABLE VIII-continued

TYK2 IC$_{50}$ Values of Illustrative Compounds of the invention

| Cpd | IC$_{50}$ (nM) |
|---|---|
| 31 | 8.01 |
| 32 | 6.08 |
| 33 | 2.93 |
| 34 | 5.49 |
| 35 | 2.3 |
| 36 | 1.41 |
| 37 | 3.62 |
| 38 | 2.51 |
| 39 | 2.43 |
| 40 | 9.69 |
| 41 | 3.37 |
| 42 | 2.74 |
| 43 | 1.58 |
| 44 | 1.97 |
| 45 | 2.17 |
| 46 | 1.47 |
| 47 | 2.02 |
| 48 | 0.84 |
| 49 | 3.6 |
| 50 | 5.54 |
| 51 | 1.19 |
| 52 | 2.87 |
| 53 | 9.22 |
| 54 | 1.18 |
| 55 | 5.27 |
| 56 | 14.43 |
| 57 | 45.35 |
| 58 | 7.42 |
| 59 | 69.16 |
| 60 | 9.72 |
| 61 | 10.27 |
| 62 | 12.68 |
| 63 | 7.58 |
| 64 | 51.59 |
| 65 | 7.84 |
| 66 | 11.72 |
| 67 | 3.38 |
| 68 | 15.65 |
| 69 | 6.07 |
| 70 | 12.05 |
| 71 | 13.56 |
| 72 | 1.41 |
| 73 | 3.44 |
| 74 | 3.66 |
| 75 | 1.96 |
| 76 | 6.71 |
| 77 | 2.98 |
| 78 | 9.69 |
| 79 | 3.57 |
| 80 | 2.22 |
| 81 | 6.83 |
| 82 | 8.15 |
| 83 | 16.26 |
| 84 | 10.98 |
| 85 | 4.81 |
| 86 | 9.06 |
| 87 | 8.81 |
| 88 | 0.52 |
| 89 | 10.97 |
| 90 | 12.38 |
| 91 | 24.09 |
| 92 | 1 |
| 93 | 4.99 |
| 94 | 30.74 |
| 95 | 26.3 |
| 96 | 2.51 |
| 97 | 3.08 |
| 98 | 3.04 |
| 99 | 17.81 |
| 100 | 8.06 |
| 101 | 9.36 |
| 102 | 1.98 |
| 103 | 2.73 |
| 104 | 2.88 |
| 105 | 1.87 |
| 106 | 1.43 |
| 107 | 5.44 |
| 108 | 2.63 |
| 109 | 24.38 |
| 110 | 26.68 |
| 111 | 5.53 |
| 112 | 4.29 |
| 113 | 2.05 |
| 114 | 3 |
| 115 | 8.88 |
| 116 | 5.41 |
| 117 | 8.47 |
| 118 | 2.81 |
| 119 | 2.56 |
| 120 | 1.57 |
| 121 | 1.9 |
| 122 | 3.03 |
| 123 | 9.38 |
| 124 | 2.51 |
| 125 | 2.26 |
| 126 | 5.54 |
| 127 | 3.36 |
| 128 | 5.87 |
| 129 | 5.84 |
| 130 | 4.67 |
| 131 | 2.87 |
| 132 | 8.93 |
| 133 | 6.67 |
| 134 | 2.1 |
| 135 | 2.08 |
| 136 | 2.76 |
| 137 | 2.32 |
| 138 | 1.66 |
| 139 | 5.64 |
| 140 | 2.87 |
| 141 | 3.34 |
| 142 | 4.53 |
| 143 | 4.55 |
| 144 | 2.15 |
| 145 | 2 |
| 146 | 1.15 |
| 147 | 1.66 |
| 148 | 2.08 |
| 149 | 3.66 |
| 152 | 12.47 |
| 153 | 1.83 |
| 154 | 3.36 |
| 155 | 2.05 |
| 156 | 1.75 |
| 157 | 0.97 |
| 158 | 1.21 |
| 159 | 1.02 |
| 160 | 1.39 |
| 161 | 2.14 |
| 162 | 2.06 |
| 178 | 3.39 |
| 179 | 1.1 |
| 180 | 6.61 |
| 181 | 7.08 |
| 182 | 17.16 |
| 183 | 12.9 |
| 184 | 6.42 |
| 185 | 16.96 |
| 186 | 6.27 |
| 187 | 6.54 |

1.4.2. TYK2 ADPglo™ Kinase Assay

Recombinant human TYK2 catalytic domain (amino acids 871-1187; catalog number 08-147) is purchased from Carna biosciences. 10 ng of TYK2 is incubated in kinase reaction buffer (25 mM MOPS pH7.2, 50 mM NaCl, 0.01% Brij-35, 0.5 mM EDTA, 10 mM MgCl$_2$, 1 mM DTT, 12 μM ultra pure ATP (Promega, catalog number V915B) final concentrations) with or without 1 µL containing test compound or vehicle (DMSO, 1% final concentration), in a total volume of 5 µL, in a white 384 Opti plate (Perkin Elmer, catalog number 6007290). After 120 min at room temperature, reactions were stopped and the remaining ATP is depleted by adding 5 µL/well of ADP Glo Reagent (Promega, catalog number V912B). After 40 min at room temperature, 10 µl Kinase Detection Reagent (Kinase Detection Substrate (Promega, catalog number V914B) dissolved in Kinase Detection Buffer (Promega, catalog number V913B)) is added to convert ADP to ATP and to measure this newly synthesized ATP in a luciferase/luciferin reaction. Readout is performed after 30 min incubation at room temperature using the Envision. Kinase activity is calculated by subtracting the relative light units (RLU) obtained in the presence of a positive control inhibitor (10 µM staurosporine) from the RLU obtained in the presence of vehicle. The ability of a test compound to inhibit this activity (or percentage inhibition) is determined as:

$$\left(1 - \left(\frac{(RLU \text{ test compound} - RLU \text{ control})}{(RLU \text{ vehicle} - RLU \text{ control})}\right)\right) * 100$$

wherein

RLU test compound=RLU determined for sample with test compound present

RLU control=RLU determined for sample with positive control inhibitor

RLU vehicle=RLU determined in the presence of vehicle

Dose dilution series were prepared for the compounds enabling the testing of dose-response effects in the TYK2 assay and the calculation of the $IC_{50}$ for the compound. Each compound is routinely tested at concentration of 20 µM followed by a 1/5 serial dilution, 10 points in a final concentration of 1% DMSO. When potency of compound series increases, more dilutions are prepared and/or the top concentration are lowered (e.g. 5 µM, 1 µM). The data are expressed as the average $IC_{50}$ from the assays.

TABLE IX

| TYK2 $IC_{50}$ Values of Illustrative Compounds of the invention | |
|---|---|
| Cpd | $IC_{50}$ (nM) |
| 8 | 0.32 |
| 38 | 1.1 |
| 48 | 0.48 |
| 88 | 0.11 |
| 92 | 0.58 |
| 105 | 0.68 |
| 150 | 1.1 |
| 163 | 1.06 |
| 164 | 1.84 |
| 165 | 1.09 |
| 166 | 2.28 |
| 167 | 2.55 |
| 168 | 2.39 |
| 169 | 1.47 |
| 170 | 1.46 |
| 171 | 0.88 |
| 172 | 0.92 |
| 173 | 1.3 |
| 174 | 1.03 |
| 175 | 2.64 |
| 176 | 0.93 |
| 177 | 1.2 |
| 188 | 0.79 |

TABLE IX-continued

| TYK2 $IC_{50}$ Values of Illustrative Compounds of the invention | |
|---|---|
| Cpd | $IC_{50}$ (nM) |
| 189 | 0.67 |
| 190 | 0.75 |

1.5. Conclusions

The in vitro assay reported above show the selectivity of the illustrative compounds of the invention towards TYK2 over the remaining JAK family members.

Example 2. Selectivity Assays

In order to determine the selectivity of the illustrative compounds of the invention, specific pathways inhibition is measured.

In particular, whereas both IFNα and IL-12 signalings are TYK2-dependent, IFNα can also be inhibited by a JAK1-selective inhibitor. However, the activation of STAT1 by IL-6 is strictly dependent on JAK1.

2.1. Cellular Assays 2.1.1. IFNα Activation of STAT1 in PBMC 2.1.1.1. Protocol

Pheripheral blood mononuclear cells (PBMC) are isolated from buffy coats under sterile conditions by density gradient centrifugation using LymphoPrep™ medium (Axis-Shield catalogue number 1114545) followed by 2 subsequent wash steps in PBS (Sigma catalogue number P4417-100TAB). After these 2 wash steps the cell pellet is dissolved in ammonium chloride buffer (1.5 M $NH_4Cl$, 100 mM $NaHCO_3$ and 10 mM $Na_2.EDTA$) for lysis of the red blood cells. Subsequently cells are centrifuged and the PBMC are resuspended in plain RPMI 1640 medium (Lonza catalogue number BE12-115F/U1) containing 10% (v/v) heat inactivated FBS (Sigma Aldrich catalogue number F7524).

Immediately after isolation, PBMC are seeded in 96 well plates at 1.0E06 cells/well in a volume of 180 µL RPMI 1640 containing 10% (v/v) FBS.

PBMC are treated with test compound for 30 min at 37° C. 5% $CO_2$. 0.6 µL of 333× concentrated compound dilution is added to the wells using the Mosquito. After 30 min of test compound/vehicle pre-treatment, PBMC are stimulated for 30 min at 37° C. 5% $CO_2$ with recombinant human IFNα (PeproTech, catalog number 300-02A) at a final concentration of 5 ng/mL by addition of 20 µL (10× concentrated) cytokine trigger to obtain a final volume of 200 µL per well.

All compounds are tested in single starting from 30 µM followed by a 1/3 serial dilution, 10 doses in total (30 µM, 10 µM, 3.3 µM, 1.11 µM, 0.370 µM, 0.123 µM, 0.0412 µM, 0.0137 µM, 0.0046 µM and 0.0015 µM) in a final concentration of 0.3% DMSO.

After 30 min of cytokine stimulation, 200 µL of cell suspension is transferred to a 96-well V-bottom plate, centrifugated for 5 min at 1000 rpm to pellet cells, followed by removal of supernatant. The cell pellet is reconstituted in 100 µL 1× Lysis buffer supplemented with EDTA-free Protease Inhibitor Cocktail (Roche Applied Sciences, Product Number 11836170001) followed by sample freezing and storage at −80° C. 1x Lysis buffer is provided with the Phospho-STAT1 Elisa Kit and contains phosphatase inhibitors. Endogenous levels of phosphorylated STAT1 are quantified using a 96-well PathScan® Phospho-STAT1 (Tyr701) Sandwich ELISA Kit (Cell Signaling, Product Number #7234) according to manufacturer's instructions.

HRP activity (HRP is conjugated to the secondary antibody) is measured by addition of 100 μL of freshly prepared luminol substrate (BM Chemiluminescence ELISA Substrate (POD), Roche, Product Number 11582950001), incubation for 5 min at room temperature in the dark and measured in an Envision (Perkin Elmer) (integration time of 100 msec).

2.1.1.2. Results

A positive control (CAS #[1187594-09-7], 10 μM in vehicle)] and a negative control (vehicle, 0% inhibition) are used to 'percent inhibition (PIN)' values.

The percentage inhibition is calculated as:

$$\left(1 - \left(\frac{RCLU(\text{test compound}) - RCLU(\text{positive control})}{RCLU(\text{vehicle control}) - RCLU(\text{positive control})}\right)\right) * 100$$

wherein

RCLU(vehicle control): Relative Chemiluminescent signal determined in presence of vehicle and trigger RCLU(test compound): Relative Chemiluminescent signal determined in presence of test compounds and trigger RCLU(positive control): Relative Chemiluminescent signal determined in presence of positive control and trigger PIN values are plotted for compounds tested in dose-response and average $IC_{50}$ values are derived using GraphiPad Prism Software applying non-linear regression (sigmoidal) curve fitting.

TABLE X

IFNα signaling inhibitory potency of illustrative compounds of the invention

| Cpd | $IC_{50}$ (nM) |
|---|---|
| 1 | 85.5 |
| 2 | 87 |
| 3 | 119 |
| 4 | 91 |
| 6 | 84.33 |
| 7 | 49 |
| 9 | 30 |
| 12 | 25 |
| 22 | 50 |
| 23 | 160 |
| 24 | 151 |
| 25 | 198 |
| 31 | 94 |
| 33 | 72 |
| 36 | 79 |
| 38 | 81.25 |
| 39 | 77.3 |
| 40 | 114.6 |
| 41 | 80.62 |
| 43 | 70 |
| 44 | 79 |
| 46 | 76 |
| 47 | 52 |
| 48 | 63 |
| 49 | 109 |
| 50 | 95 |
| 51 | 107.5 |
| 52 | 42.75 |
| 53 | 119 |
| 54 | 35 |
| 55 | 76 |
| 57 | 405 |
| 58 | 88 |
| 59 | 407 |
| 60 | 73 |
| 61 | 112 |
| 62 | 116 |
| 63 | 128 |

TABLE X-continued

IFNα signaling inhibitory potency of illustrative compounds of the invention

| Cpd | $IC_{50}$ (nM) |
|---|---|
| 65 | 96 |
| 66 | 138.5 |
| 67 | 51 |
| 68 | 128 |
| 69 | 90 |
| 71 | 111 |
| 72 | 124.5 |
| 73 | 81 |
| 74 | 62 |
| 75 | 65 |
| 80 | 93 |
| 81 | 56 |
| 82 | 126 |
| 83 | 137 |
| 84 | 178 |
| 85 | 114.97 |
| 86 | 121.16 |
| 87 | 158.47 |
| 88 | 14 |
| 89 | 266 |
| 90 | 288 |
| 92 | 67 |
| 93 | 65 |
| 96 | 73 |
| 98 | 38 |
| 102 | 75 |
| 103 | 68 |
| 104 | 65 |
| 105 | 73.89 |
| 106 | 102.5 |
| 107 | 110 |
| 108 | 52 |
| 111 | 123 |
| 112 | 130 |
| 115 | 144 |
| 116 | 113 |
| 117 | 148 |
| 118 | 110 |
| 119 | 81 |
| 133 | 121 |
| 137 | 62 |
| 138 | 91 |
| 144 | 119 |
| 145 | 134 |
| 146 | 122 |
| 147 | 121 |
| 148 | 142 |
| 149 | 218 |
| 150 | 278 |
| 153 | 234 |
| 154 | 351 |
| 158 | 87 |
| 161 | 96 |
| 166 | 84 |
| 167 | 129 |
| 168 | 82 |
| 169 | 147 |
| 170 | 83 |
| 171 | 45 |
| 172 | 66 |
| 173 | 114 |
| 174 | 72 |
| 175 | 94 |
| 176 | 66.5 |
| 177 | 71 |
| 178 | 189 |
| 179 | 51 |
| 180 | 84 |
| 186 | 229 |

2.1.2. IL-12 activation of STAT4 in NK-92 cells using AphaLISA SureFire technology 2.1.2.1. Protocol NK-92 cells (human malignant non-Hodgkin's lymphoma, interleukin-2 (IL-2) dependent Natural Killer Cell line, ATCC #CRL-2407).

NK-92 cells are maintained in Minimum Essential Medium (MEM) Alpha medium w/o ribonucleosides and deoxyribonucleosides, 2 mM L-glutamine, 2.2 g/L sodium bicarbonate (Invitrogen, Product Number 22561-021) containing 0.2 mM myo-inositol, 0.1 mM 2-mercapto-EtOH, 0.02 mM folic acid, 12.5% heat inactivated horse serum (Invitrogen, Catalogue Number 26050-088), 12.5% heat inactivated FBS (Sigma, catalogue number F7524), 1% Pen-Strep (100 U/mL Penicilium and 100 µg/mL Streptomycin) and 10 ng/mL recombinant human IL-2 (R&D Systems, Catalogue Number 202-IL). IL-2 is added freshly to the medium with each medium refreshment step. Cells are cultured in a humidified incubator at 37° C. 5% $CO_2$.

A subcultured fraction of NK-92 cells is washed once in culture medium without rhIL-2 the day before the experiment and incubated overnight in a culture flask. The day of the experiment cells are harvested by centrifugation, resuspended in Hank's Balanced Salt Solution (—Ca, —Mg) (Invitrogen, Catalogue Number 14170088) and seeded in 384-well plates at 60,000 cells/well in a volume of 30 µL.

NK-92 cells are treated with test compounds for 30 min prior to rhIL-12 stimulation by adding 180 nL of 333× concentrated compound dilution and incubation at 37° C. 5% $CO_2$. After 30 min of compound/vehicle pre-treatment, cells are stimulated with recombinant human IL-12 (R&D Systems, Product Number 219-IL) at a final concentration of 25 ng/mL by addition of 30 µL (2× concentrated) cytokine trigger to obtain a final volume of 60 µL per well. NK-92 cells are triggered with rhIL-12 for 30 min at 37° C. 5% $CO_2$.

After 30 min of cytokine stimulation the cells are lysed by addition of 15 µL 5× lysis buffer (supplemented with the AlphaLISA kit). After 10 minutes, plates are frozen at −80° C. overnight and the next day the levels of phospho-STAT4 are quantified using the AlphaLISA SureFire ULTRA p-STAT4 (Tyr693) (Perkin Elmer, Catalogue number ALSU-PST4-A10K) according to the manufacturers instructions. AlphaLISA signal (relative light units) is measured using an Envision (Perkin Elmer).

All compounds are tested in duplicate starting from 30 µM followed by a 1/3 serial dilution, 10 doses in total (30 µM, 10 µM, 3.3 µM, 1.11 µM, 0.370 µM, 0.123 µM, 0.0412 µM, 0.0137 µM, 0.0046 µM and 0.0015 µM) in a final concentration of 0.3% DMSO.

2.1.2.2. Results

A positive control (CAS #[1187594-09-7], 10 µM in vehicle)] and a negative control (vehicle, 0% inhibition) are used to 'percent inhibition (PIN)' values.

The percentage inhibition is calculated as:

$$\left(1 - \left(\frac{RLU(\text{test compound}) - RLU(\text{pos control})}{RLU(\text{trigger}/veh) - RLU(\text{pos control})}\right)\right) * 100$$

wherein

RLU(trigger/veh): Relative lumescent signal determined in presence of vehicle and trigger RLU(test compound): Relative luminescent signal determined in presence of test compounds and trigger RLU(pos control): Relative luminescent signal determined in presence of 10 µM CAS #[1187594-09-7] and trigger PIN values are plotted for compounds tested in dose-response and IC50 values are derived using GraphPad Prism Software applying non-linear regression (sigmoidal) curve fitting. The data are expressed as the average $IC_{50}$ from different experiments.

TABLE XI

IL12 signaling inhibitory potency of illustrative compounds of the invention

| Cpd | IL12 pSTAT4 $IC_{50}$ (nM) |
|---|---|
| 1 | 110.84 |
| 2 | 73.54 |
| 3 | 273.5 |
| 4 | 197.5 |
| 6 | 207.33 |
| 7 | 133 |
| 9 | 41 |
| 19 | 72 |
| 22 | 22 |
| 31 | 110 |
| 33 | 129 |
| 36 | 50 |
| 38 | 82 |
| 39 | 256 |
| 40 | 3528 |
| 41 | 314 |
| 43 | 49 |
| 44 | 50 |
| 46 | 210 |
| 47 | 84 |
| 48 | 56 |
| 49 | 150 |
| 50 | 248 |
| 51 | 274.5 |
| 52 | 50 |
| 54 | 16 |
| 55 | 77.75 |
| 61 | 221 |
| 62 | 100 |
| 65 | 80 |
| 66 | 205.35 |
| 67 | 54.14 |
| 68 | 122 |
| 69 | 42.77 |
| 71 | 127.5 |
| 72 | 57.23 |
| 73 | 158.05 |
| 74 | 62.94 |
| 75 | 159 |
| 80 | 83 |
| 81 | 224 |
| 82 | 195 |
| 83 | 987 |
| 84 | 87 |
| 85 | 153.5 |
| 86 | 505.5 |
| 87 | 265.5 |
| 88 | 22 |
| 89 | 476 |
| 90 | 1519 |
| 93 | 25.36 |
| 96 | 358 |
| 98 | 18.9 |
| 102 | 302 |
| 103 | 63.5 |
| 104 | 108 |
| 105 | 147.33 |
| 106 | 150.5 |
| 107 | 622 |
| 108 | 94 |
| 111 | 393 |
| 112 | 1103 |
| 113 | 190 |

TABLE XI-continued

IL12 signaling inhibitory potency of illustrative compounds of the invention

| Cpd | IL12 pSTAT4 IC$_{50}$ (nM) |
|---|---|
| 115 | 968 |
| 116 | 79 |
| 117 | 181 |
| 118 | 299 |
| 119 | 261 |
| 133 | 981 |
| 137 | 89 |
| 138 | 332 |
| 144 | 211 |
| 145 | 238 |
| 146 | 215 |
| 147 | 213 |
| 148 | 160 |
| 149 | 347 |
| 150 | 1021 |
| 153 | 7577 |
| 154 | 8720 |
| 158 | 204 |
| 161 | 864 |
| 166 | 97 |
| 167 | 88 |
| 168 | 87 |
| 169 | 665 |
| 170 | 73 |
| 171 | 127 |
| 172 | 58 |
| 173 | 33 |
| 174 | 61 |
| 175 | 137 |
| 176 | 40.5 |
| 177 | 24 |
| 178 | 2573 |
| 179 | 13 |
| 180 | 769 |
| 186 | 241 |

2.1.3. IL-12 Activation of STAT4 in NK-92 Cells Using MSD as Readout

NK-92 cells (human malignant non-Hodgkin's lymphoma, interleukin-2 (IL-2) dependent Natural Killer Cell line, ATCC #CRL-2407).

NK-92 cells are maintained in Minimum Essential Medium (MEM) Alpha medium w/o ribonucleosides and deoxyribonucleosides, 2 mM L-glutamine, 2.2 g/L sodium bicarbonate (Invitrogen, Product Number 22561-021) containing 0.2 mM myo-inositol, 0.1 mM 2-mercapto-EtOH, 0.02 mM folic acid, 12.5% heat inactivated horse serum (Invitrogen, Catalogue Number 26050-088), 12.5% heat inactivated FBS (Hyclone, catalogue number SV30160.03), 1% Pen-Strep (100 U/mL Penicilium and 100 µg/mL Streptomycin) and 10 ng/mL recombinant human IL-2 (R&D Systems, Catalogue Number 202-IL). IL-2 is added freshly to the medium with each medium refreshment step. Cells are cultured in a humidified incubator at 37° C. 5% $CO_2$.

A subcultured fraction of NK-92 cells is harvested by centrifugation, the cell pellet is resuspended in culture medium without rhIL-2 and 200,000 cells in 160 µL are seeded in a 96 well plate (Greiner, catalogue number 651201) already containing 20 µL diluted test compound or vehicle.

NK-92 cells are pre-incubated with test compounds or vehicle for 30 min at 37° C. 5% $CO_2$. Subsequently cells are stimulated with recombinant human IL-12 (R&D Systems, Product Number 219-IL) at a final concentration of 25 ng/mL by addition of 20 µL (10× concentrated) cytokine trigger to obtain a final volume of 200 µL per well. NK-92 cells are triggered with rhIL-12 for 45 min at 37° C. 5% $CO_2$.

After 45 min of cytokine stimulation the cells are lysed by addition of 50 µL ice-cold lysis buffer (supplemented with the MSD kit). Plates are frozen at −80° C. for minimal 1 hour to lyse the cells completely. After thawing the levels of phospho-STAT4 are quantified using the Phospho-STAT4 (Tyr693) kit (MSD, Catalogue number K150PAD-2) according to the manufacturer's instructions. Electroluminescent signal is measured on the MSD reader.

All compounds are tested in duplicate starting from 30 µM followed by a 1/3 serial dilution, 10 doses in total (30 µM, 10 µM, 3.3 µM, 1.11 µM, 0.370 µM, 0.123 µM, 0.0412 µM, 0.0137 µM, 0.0046 µM and 0.0015 µM) in a final concentration of 0.3% DMSO.

2.1.4. Results

A positive control (CAS #[1187594-09-7], 10 µM in vehicle)] and a negative control (vehicle, 0% inhibition) are used to 'percent inhibition (PIN)' values.

The percentage inhibition is calculated as:

$$\left(1 - \left(\frac{RLU(\text{test compound}) - RLU(\text{pos control})}{RLU(\text{trigger}/veh) - RLU(\text{pos control})}\right)\right) * 100$$

wherein

RLU (trigger/veh): Relative lumescent signal determined in presence of vehicle and trigger RLU (test compound): Relative luminescent signal determined in presence of test compounds)

RLU(pos control): Relative luminescent signal determined in presence of 10 µM CAS #[1187594-09-7] and trigger PIN values are plotted for compounds tested in dose-response and IC$_{50}$ values are derived using LIMS Software applying non-linear regression (sigmoidal) curve fitting. The data are expressed as the average IC$_{50}$ from different experiments.

TABLE XII

IL12 signaling inhibitory potency of illustrative compounds of the invention

| Cpd | IL12 pSTAT4 IC$_{50}$ (nM) |
|---|---|
| 1 | 538.8 |
| 2 | 259.3 |
| 8 | 416.2 |
| 9 | 252.0 |
| 10 | 529.8 |
| 11 | 377.3 |
| 12 | 540.0 |
| 14 | 1501.0 |
| 15 | 185.7 |
| 17 | 905.3 |
| 18 | 4683.0 |
| 19 | 805.9 |
| 20 | 377.8 |
| 21 | 1050.0 |
| 23 | 247.7 |
| 24 | 3371.0 |
| 25 | 1117.0 |
| 26 | 1527.0 |
| 52 | 400.9 |
| 53 | 409.3 |
| 54 | 290.9 |
| 55 | 264.6 |
| 57 | 7459.0 |
| 58 | 595.3 |
| 59 | 4724.0 |
| 60 | 1150.0 |

TABLE XII-continued

IL12 signaling inhibitory potency of illustrative compounds of the invention

| Cpd | IL12 pSTAT4 IC$_{50}$ (nM) |
|---|---|
| 62 | 809.2 |
| 63 | 1144.0 |
| 66 | 1654.0 |
| 67 | 232.8 |
| 68 | 1444.0 |
| 69 | 203.5 |
| 72 | 27.7 |
| 73 | 199.0 |
| 74 | 88.6 |
| 88 | 90.1 |
| 91 | 3150.0 |
| 92 | 281.5 |
| 93 | 200.6 |

2.2. Human Whole Blood Assay (hWBA)

2.2.1. IL-6 and IFNα Stimulation Protocol

A flow cytometry analysis is performed to establish JAK1 and TYK2 compound potency ex vivo using human whole blood. Therefore, blood is taken from human volunteers who gave informed consent, then equilibrated for 30 min at 37° C. under gentle rocking and aliquoted in Eppendorf tubes. Compound is added at different concentrations and incubated at 37° C. for 30 min under gentle rocking and subsequently stimulated for 20 min at 37° C. under gentle rocking with interleukin 6 (IL-6) for JAK-dependent pathway stimulation or IFNα for TYK2-dependent pathway stimulation. Phospho-STAT1 is then evaluated using FACS analysis.

2.2.1.1. Preparation of Reagents

The 5× Lyse/Fix buffer (BD PhosFlow, Cat. no 558049) is diluted 5-fold with distilled water and pre-warmed at 37° C. The remaining diluted Lyse/Fix buffer is discarded. 10 µg rhIL-6 (R&D Systems, Cat no 206-IL) is dissolved in 1 mL of PBS 0.1% BSA to obtain a 10 µg/mL stock solution. The stock solution of Universal type I IFN (R&D Systems, Cat no 11200-2) is aliquoted and stored at −80° C.

A 3-fold dilution series of the compound is prepared in DMSO (10 mM stock solution). Control-treated samples received DMSO instead of compound. All samples are incubated with a 1% final DMSO concentration.

2.2.1.2. Incubation of Blood with Compound and Stimulation with IL-6 or IFNα

Human blood is collected in heparinized tubes. The blood is divided in aliquots of 148.5 µL. Then, 1.5 µL of the test compound dilution is added to each blood aliquot and the blood samples are incubated for 30 min at 37° C. under gentle rocking. One and a half microliter of 10-fold diluted IL-6 stock solution or Universal type 1 IFN is added to the blood samples (final concentration 10 ng/mL and 1000 U/mL, respectively) and samples are incubated at 37° C. for 20 min under gentle rocking.

2.2.1.3. White Blood Cell Preparation

At the end of the stimulation period, 3 mL of 1× pre-warmed Lyse/Fix buffer is immediately added to the blood samples, vortexed briefly and incubated for 15 min at 37° C. in a water bath in order to lyse red blood cells and fix leukocytes.

Tubes are centrifuged for 5 min at 400×g at 4° C. The cell pellet is washed with 3 mL of cold 1×PBS, and after centrifugation the cell pellet is resuspended in 100 µL of ice-cold 1×PBS and 900 µL ice-cold 100% MeOH is added. Cells are then incubated at 4° C. for 30 min for permeabilization.

Permeabilized cells are then washed with 1×PBS containing 3% BSA and finally resuspended in 80 µL of 1×PBX containing 3% BSA.

2.2.1.4. Cell labeling with anti Phospho-STAT1 and anti-CD4 antibodies

[00395] 20 µL of PE mouse anti-STAT1 (pY701) or PE mouse IgG2aκ isotype control antibody (BD Biosciences, Cat. no 612564 and 559319, respectively) and FITC-conjugated anti-CD4 antibody or control FITC-conjugated isotype antibody are added and mixed, then incubated for 30 min at 4° C., in the dark.

Cells are then washed once with 1×PBS and analyzed on a FACSCanto II flow cytometer (BD Biosciences).

2.2.1.5. Fluorescence Analysis on FACSCanto II 50,000 total events are counted and Phospho-STAT1 positive cells are measured after gating on CD4+ cells, in the lymphocyte gate. Data are analyzed using the FACSDiva software and the percentage of inhibition of IL-6 or IFNα stimulation calculated from the percentage of positive cells for phospho-STAT1 on CD4+ cells.

2.2.1.6. Results

Using the above protocol, the following results are obtained.

| Cpd# | IFN α IC$_{50}$ (nM) | IL6 IC$_{50}$ (nM) |
|---|---|---|
| 38 | 622.41 | 8010.63 |
| 52 | 355.9 | 3589.22 |
| 75 | 476.43 | 3467.37 |
| 102 | 175.12 | ND |
| 105 | 137.54 | 2519.61 |
| 106 | 532.8 | ND |
| 112 | 446.68 | ND |
| 150 | 269.15 | 6812.92 |
| 166 | 1445.44 | ND |
| 168 | 1071.52 | ND |
| 176 | 756.83 | ND |

ND: not determined 2.3. Conclusions

Whereas JAK1 is a key driver in IFNα, IL6, IL10 and IL22 signaling, TYK2 is involved in type I interferons (including IFNα, INFβ), IL23 and IL12 signaling (Gillooly et al., 2016; Sohn et al., 2013). Although a similar inhibitory potency on IFNα and IL12 signalings is observed in the cell assay, a potency at least 7 times higher against the IFNα signalling than on IL-6 signalling for the illustrative compounds of the invention is measured, thus confirming the TYK2-selectivity over JAK1.

Example 3. In Vivo Assay 3.1. Murine Model of Psoriatic-Like Epidermal Hyperplasia Induced by Intradermal Injections of IL22 or IL23

3.1.1. Materials

Mouse recombinant IL22 (582-ML-CF), carrier free is provided by R&D systems. Mouse recombinant IL23, carrier free (14-8231, CF) is provided by e-Bioscience.

3.1.2. Animals

Balb/c mice (female, 18-20 g body weight) are obtained from CERJ (France). Mice are kept on a 12 h light/dark cycle (07:00-19:00). Temperature is maintained at 22° C., food and water are provided ad libitum.

3.1.3. Study Design

The design of the study is adapted from Rizzo et al, 2011.

On the first day (D1), the mice are shaved around the two ears.

For 4 consecutive days (D1 to D4), the mice received a daily intradermal dose of mouse recombinant IL22 or IL23 (1 μg/20 μL in PBS/0.1% BSA) in the right pinna ear and 20 μL of PBS/0.1% BSA in the left pinna ear under anesthesia induced by inhalation of isoflurane.

From D1 to D5, mice are dosed with test-compound (3, 10, 30, or 100 mg/kg, po, qd in MC 0.5%), 1 h prior IL23/IL22 injection or with vehicle.

3.1.4. Assessment of Disease

The thickness of both ears is measured daily with an automatic caliper. Body weight is assessed at initiation and at sacrifice. On fifth day, 2 hrs after the last dosing, the mice are sacrificed. The pinnae of the ear are cut, excluding cartilage. The pinnae are weighed and then, placed in vial containing 1 mL of RNAlater solution or in formaldehyde.

At D4, blood samples are also collected from the retroorbital sinus for PK profile just before dosing (T0) and 1 h, 3 h, 6 h post-dosing.

There are 10 mice per group. The results are expressed as mean seem and statistical analysis is performed using one-way Anova followed by Dunnett's post-hoc test versus IL22 or IL23 vehicle groups.

3.1.5. Histology

After sacrifice, ears are collected and fixed in 3.7% formaldehyde before embedding in paraffin. Two μm thick sections are done and stained with hematoxylin and eosin. Ear epidermis thickness is measured by image analysis (Sis'Ncom software) with 6 images per ear captured at magnification ×20. Data are expressed as mean seem and statistical analysis is performed using one-way Anova followed by Dunnett's post-hoc test versus IL22 or IL23 vehicle groups.

3.1.6. RNA Extraction, RT-PCR and Real-Time PCR

IL-17a, IL-22, IL-1β, LCN2 and S100A9 transcript levels in ear tissue are determined using real-time quantitative PCR.

3.1.7. Results

Using the above mentioned protocol using IL-23 injection, the ear thickness measurements below were obtained, showing for example that at 3, 10 and 30 mg/kg q.d., illustrative compound 38 prevented significantly IL-23 induced ear thickening.

TABLE XIII

| IL23-induced ear thickening (mm) | | | | | |
|---|---|---|---|---|---|
| | Day1 | Day2 | Day3 | Day4 | Day5 |
| PBS + Vehicle | 0.213 | 0.216 | 0.220 | 0.220 | 0.216 |
| sem | 0.002 | 0.002 | 0.002 | 0.002 | 0.002 |
| IL23 + Vehicle | 0.210 | 0.223 | 0.248 | 0.267 | 0.312 |
| sem | 0.002 | 0.002 | 0.003 | 0.003 | 0.004 |
| p value vs Vehicle at same day | ns | ns | *** | *** | *** |
| IL23 + Cpd 38 3 mg/kg q.d. | 0.210 | 0.220 | 0.236 | 0.258 | 0.260 |
| sem | 0.001 | 0.002 | 0.003 | 0.002 | 0.002 |
| p value vs Vehicle at same day | ns | ns | ** | ns | *** |
| IL23 + Cpd 38 10 mg/kg q.d. | 0.213 | 0.218 | 0.241 | 0.251 | 0.258 |
| sem | 0.002 | 0.002 | 0.002 | 0.003 | 0.005 |
| p value vs Vehicle at same day | ns | ns | ns | ** | *** |
| IL23 + Cpd 38 30 mg/kg q.d. | 0.212 | 0.219 | 0.236 | 0.243 | 0.255 |
| sem | 0.001 | 0.002 | 0.003 | 0.003 | 0.004 |
| p value vs Vehicle at same day | ns | ns | ** | *** | *** |

Sem: standard error of the mean
10 mice/group
*$p < 0.05$, $p < 0.01$, *$p < 0.001$ daily significance vs IL23-vehicle group by using ANOVA and Dunnett's test

FINAL REMARKS

It will be appreciated by those skilled in the art that the foregoing descriptions are exemplary and explanatory in nature, and intended to illustrate the invention and its preferred embodiments. Through routine experimentation, an artisan will recognize apparent modifications and variations that may be made without departing from the spirit of the invention. All such modifications coming within the scope of the appended claims are intended to be included therein. Thus, the invention is intended to be defined not by the above description, but by the following claims and their equivalents.

All publications, including but not limited to patents and patent applications, cited in this specification are herein incorporated by reference as if each individual publication are specifically and individually indicated to be incorporated by reference herein as though fully set forth.

It should be understood that factors such as the differential cell penetration capacity of the various compounds can contribute to discrepancies between the activity of the compounds in the in vitro biochemical and cellular assays.

At least some of the chemical names of compound of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

REFERENCES

Babon, J. J., Lucet, I. S., Murphy, J. M., Nicola, N. A., Varghese, L. N., 2014. The molecular regulation of Janus kinase (JAK) activation. Biochem. J. 462, 1-13. https://doi.org/10.1042/BJ20140712

Broekman, F., Giovannetti, E., Peters, G. J., 2011. Tyrosine kinase inhibitors: Multi-targeted or single-targeted? World J. Clin. Oncol. 2, 80-93. https://doi.org/10.5306/wjco.v2.i2.80

Dendrou, C. A., Cortes, A., Shipman, L., Evans, H. G., Attfield, K. E., Jostins, L., Barber, T., Kaur, G., Kuttikkatte, S. B., Leach, O. A., Desel, C., Faergeman, S. L., Cheeseman, J., Neville, M. J., Sawcer, S., Compston, A., Johnson, A. R., Everett, C., Bell, J. I., Karpe, F., Ultsch, M., Eigenbrot, C., McVean, G., Fugger, L., 2016. Resolving TYK2 locus genotype-to-phenotype differences in autoimmunity. Sci. Transl. Med. 8, 363ra149. https://doi.org/10.1126/scitranslmed.aag1974

Fabian, M. A., Biggs, W. H., Treiber, D. K., Atteridge, C. E., Azimioara, M. D., Benedetti, M. G., Carter, T. A., Ciceri, P., Edeen, P. T., Floyd, M., Ford, J. M., Galvin, M., Gerlach, J. L., Grotzfeld, R. M., Herrgard, S., Insko, D. E., Insko, M. A., Lai, A. G., Ldlias, J.-M., Mehta, S. A., Milanov, Z. V., Velasco, A. M., Wodicka, L. M., Patel, H. K., Zarrinkar, P. P., Lockhart, D. J., 2005. A small molecule-kinase interaction map for clinical kinase inhibitors. Nat. Biotechnol. 23, 329-336. https://doi.org/10.1038/nbt1068

Gillooly, K., Zhang, Y., Yang, X., Zupa-Fernandez, A., Cheng, L., Strnad, J., Cunningham, M., Heimrich, E., Zhou, X., Chen, J., Chaudhry, C., Li, S., McIntyre, K., Carman, J., Moslin, R., Wrobleski, S., Weinstein, D., Burke, J., 2016. BMS-986165 Is a Highly Potent and Selective Allosteric Inhibitor of Tyk2, Blocks IL-12, IL-23 and Type I Interferon Signaling and Provides for Robust Efficacy in Preclinical Models of Systemic Lupus Erythematosus and Inflammatory Bowel Disease. ACR Meet. Abstr.

Neubauer, H., Cumano, A., MGller, M., Wu, H., Huffstadt, U., Pfeffer, K., 1998. Jak2 Deficiency Defines an Essential Developmental Checkpoint in Definitive Hematopoiesis. Cell 93, 397-409. https://doi.org/10.1016/S0092-8674(00)81168-X O'Shea, J. J., Plenge, R., 2012. JAKs and STATs in Immunoregulation and Immune-Mediated Disease. Immunity 36, 542-550. https://doi.org/10.1016/j.immuni.2012.03.014 Parganas, E., Wang, D., Stravopodis, D., Topham, D. J., Marine, J.-C., Teglund, S., Vanin, E. F., Bodner, S., Colamonici, O. R., van Deursen, J. M., Grosveld, G., Ihle, J. N., 1998. Jak2 Is Essential for Signaling through a Variety of Cytokine Receptors. Cell 93, 385-395. https://doi.org/10.1016/S0092-8674(00)81167-8

Schwartz, D. M., Bonelli, M., Gadina, M., O'Shea, J. J., 2016. Type I/II cytokines, JAKs, and new strategies for treating autoimmune diseases. Nat. Rev. Rheumatol. 12, 25-36. https://doi.org/10.1038/nrrheum.2015.167

Sohn, S. J., Barrett, K., Abbema, A. V., Chang, C., Kohli, P. B., Kanda, H., Smith, J., Lai, Y., Zhou, A., Zhang, B., Yang, W., Williams, K., Macleod, C., Hurley, C. A., Kulagowski, J. J., Lewin-Koh, N., Dengler, H. S., Johnson, A. R., Ghilardi, N., Zak, M., Liang, J., Blair, W. S., Magnuson, S., Wu, L. C., 2013. A Restricted Role for TYK2 Catalytic Activity in Human Cytokine Responses Revealed by Novel TYK2-Selective Inhibitors. J. Immunol. 191, 2205-2216. https://doi.org/10.4049/jimmunol.1202859

Vainchenker, W., Dusa, A., Constantinescu, S. N., 2008. JAKs in pathology: Role of Janus kinases in hematopoietic malignancies and immunodeficiencies. Semin. Cell Dev. Biol. 19, 385-393. https://doi.org/10.1016/j.semcdb.2008.07.002

The invention claimed is:
1. A compound according to Formula I:

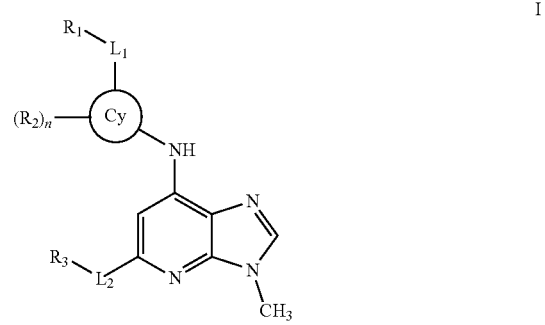

wherein
Cy is phenyl or 5-6 membered heteroaryl comprising one, two or three N atoms;
$L_1$ is a single bond, —O—, —C(=O)—, —C(=O)O—, —S(O)$_2$—, —NR$^{6a}$—, —C(=O)NR$^{6b}$—, —S(O)$_2$NR$^{6c}$—, or —C(=O)NR$^{6d}$S(O)$_2$—;
$R^1$ is:
 H,
 $C_{1-6}$ alkyl optionally substituted with one or more independently selected
 OH,
 halo,
 $C_{1-4}$ alkoxy,
 —NR$^{7a}$R$^{7b}$,
 —C(=O)OH—,
 —C(=O)NR$^{7c}$R$^{7d}$,
 —C(=O)OC$_{1-4}$ alkyl, or
 4-8 membered monocyclic heterocycloalkyl comprising one, two, or three heteroatoms independently selected from N, S, and O;
 $C_{3-7}$ cycloalkyl optionally substituted with one or more OH, $C_{1-4}$ alkoxy, or
 4-9 membered monocyclic heterocycloalkyl, spiro bicyclic heterocycloalkyl, bridged bicyclic heterocycloalkyl, or fused bicyclic heterocycloalkyl, wherein the heterocycloalkyl comprises one, two or three heteroatoms independently selected from N, S and O, and wherein the heterocycloalkyl is optionally substituted with one or more independently selected $R^{11}$ groups;
-$R^{11}$ is
 OH,
 CN,
 halo,
 oxo,
 —NR$^{8a}$R$^{8b}$
 $C_{3-7}$ cycloalkyl,
 $C_{1-4}$ alkyl optionally substituted with one or more independently selected halo, OH, $C_{1-4}$ alkoxy, —NR$^{9a}$R$^{9b}$,
 $C_{1-4}$ alkoxy optionally substituted with one $C_{1-4}$ alkoxy,
 4-7 membered monocyclic heterocycloalkyl comprising one, two, or three heteroatoms independently selected from N, S, and O,
 —C(=O)OC$_{1-4}$ alkyl, or
 —NR$^{8c}$C(=O)OC$_{1-4}$alkyl;
$R^2$ is
 halo,
 CN, or
 $C_{1-4}$ alkyl;

the subscript n is 0, or 1;

L² is O or —NR⁴—,

R³ is
- C$_{1-6}$ alkyl optionally substituted with one or more groups independently selected from
- halo, or
- C$_{3-7}$ cycloalkyl,
- phenyl substituted with one R$^{5a}$ a group and one or two independently selected R$^{5b}$ groups,
- 6-membered heteroaryl comprising one or two N atoms, substituted with one R$^{5a}$ group and one or two independently selected R$^{5b}$ groups,
- 4-10 membered monocyclic heterocycloalkyl, spiro bicyclic heterocycloalkyl, bridged bicyclic heterocycloalkyl, or fused bicyclic heterocycloalkyl, wherein the heterocycloalkyl comprises one or two heteroatoms independently selected from N, S and O, and wherein the heterocycloalkyl is optionally substituted with one, two, or three groups independently selected from R$^{5a}$ and R$^{5b}$, or
- 4-10 membered monocyclic or fused, bridged or spiro bicyclic cycloalkyl, optionally substituted with one, two or three groups independently selected from R5a and R$^{5b}$;

R⁴ is
- H,
- C$_{1-4}$ alkyl optionally substituted with one or more groups selected from OH or C$_{1-4}$ alkoxy, or
- C$_{3-7}$ cycloalkyl;

R$^{5a}$ is —CN, —SO$_2$—C$_{1-4}$ alkyl, or —CF$_3$;

R$^{5b}$ is halo, C$_{1-4}$ alkyl, and C$_{3-7}$ cycloalkyl;

R$^{7a}$, or R$^{7b}$ are independently selected from
- H, and
- C$_{1-4}$ alkyl optionally substituted with one —NR$^{10a}$R$^{10b}$;
and R$^{6a}$, R$^{6b}$, R$^{6c}$, R$^{6d}$, R$^{7c}$, R$^{7d}$, R$^{8a}$, R$^{8b}$, R$^{8c}$, R$^{9a}$, R$^{9b}$, R$^{10a}$, and R$^{10b}$ are independently selected from H, and C$_{1-4}$ alkyl;

or a pharmaceutically acceptable salt thereof, solvate thereof, or a solvate of a pharmaceutically acceptable salt thereof.

2. The compound or pharmaceutically acceptable salt thereof according to claim 1, wherein L$_2$ is O.

3. The compound or pharmaceutically acceptable salt thereof according to claim 1, wherein R³ is:

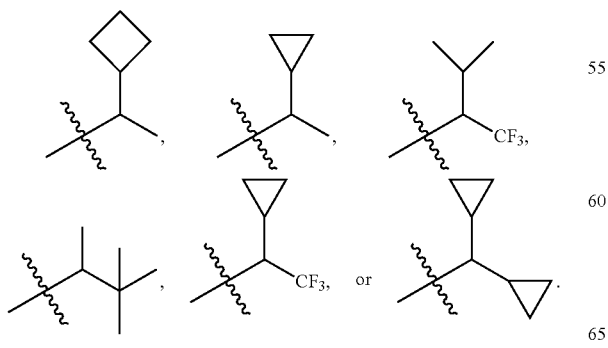

4. The compound or pharmaceutically acceptable salt thereof according to claim 1, wherein R³ is

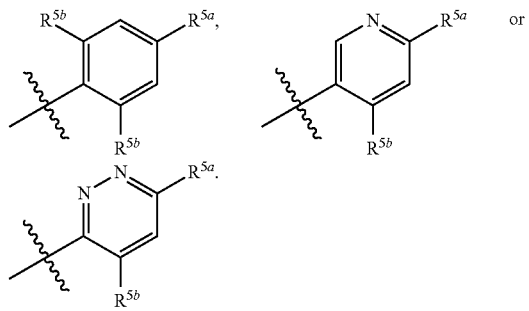

5. The compound or pharmaceutically acceptable salt thereof according to claim 1, wherein R$^{5a}$ is —CN, —SO$_2$—C$_{1-4}$ alkyl, or —CF$_3$.

6. The compound or pharmaceutically acceptable salt thereof according to claim 1, wherein R$^{5b}$ is independently selected from halo, C$_{1-4}$ alkyl, and C$_{3-7}$ cycloalkyl.

7. The compound or pharmaceutically acceptable salt thereof according to claim 1, wherein the compound is:

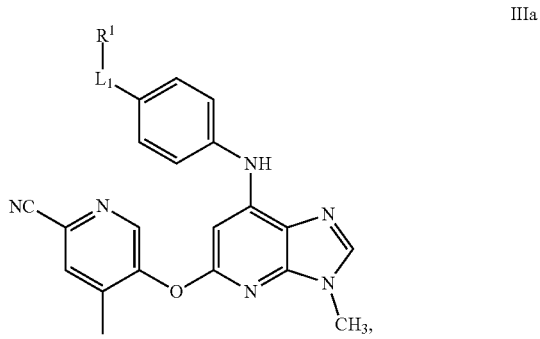

IIIa

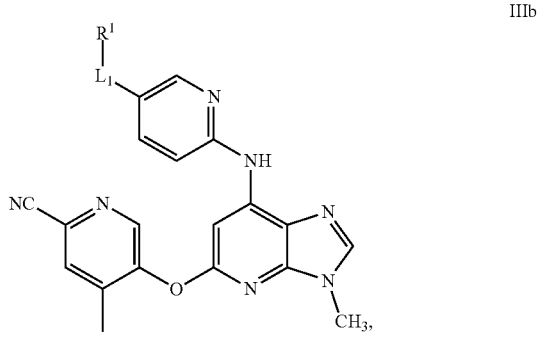

IIIb

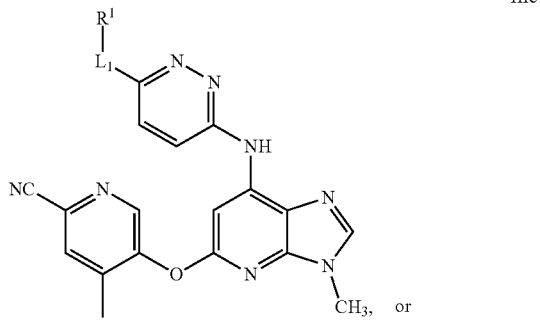

IIIc or

-continued

IIId

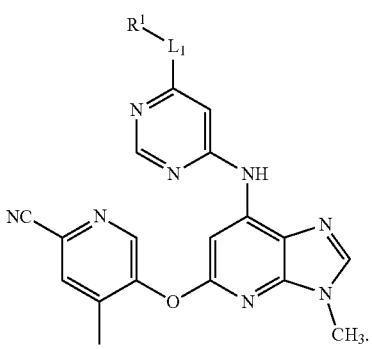

8. The compound or pharmaceutically acceptable salt thereof according to claim 1, wherein $L_1$ is a single bond or —C(=O)—.

9. The compound or pharmaceutically acceptable salt thereof according to claim 1, wherein $R^1$ is a 4-9 membered monocyclic heterocycloalkyl, spiro bicyclic heterocycloalkyl, bridged bicyclic heterocycloalkyl, or fused bicyclic heterocycloalkyl, wherein the heterocycloalkyl comprises one, two or three heteroatoms independently selected from N, S and O, and wherein the heterocycloalkyl is optionally substituted with one two or three independently selected $R^{11}$ groups.

10. The compound or pharmaceutically acceptable salt thereof according to claim 1, wherein $R^1$ is azetidinyl, oxetanyl, pyrrolidinyl, morpholinyl, octadeuteriomorpholin-4-yl, tetrahydropyranyl, piperazinyl, or dioxanyl, each of which is substituted with one, two or three independently selected $R^{11}$ groups.

11. The compound or pharmaceutically acceptable salt thereof according to claim 9, wherein $R^{11}$ is $C_{1-4}$ alkyl optionally substituted with one or more groups independently selected from halo, OH, $C_{1-4}$ alkoxy and —$NR^{9a}R^{9b}$ wherein each $R^{9a}$ and $R^{9b}$ is independently H, or $C_{1-4}$ alkyl.

12. A pharmaceutical composition comprising a pharmaceutically acceptable carrier and a pharmaceutically effective amount of a compound according to claim 1.

13. The pharmaceutical composition according to claim 12, comprising a further therapeutic agent.

14. A method for treatment of inflammatory diseases, autoinflammatory diseases, autoimmune diseases, and/or diseases associated with hypersecretion of IFNα, IL12 and/or IL23, comprising administering an effective amount of the compound, or pharmaceutically acceptable salt thereof, according to claim 1, to a subject in need thereof.

15. A method for treatment of inflammatory diseases, autoinflammatory diseases, autoimmune diseases, and/or diseases associated with hypersecretion of IFNα, IL12 and/or IL23, comprising administering the pharmaceutical composition according to claim 12, to a subject in need thereof.

16. The compound of claim 1, wherein the compound is
4- {[7-(6-Amino-pyrimidin-4-ylamino)-3-methyl-3H-imidazo[4,5-b]pyridin-5-yl]-methyl-amino}-3-ethyl-5-fluoro-benzonitrile,
5- {[7-(6-Amino-pyrimidin-4-ylamino)-3-methyl-3H-imidazo[4,5-b]pyridin-5-yl]-methyl-amino}-4-methyl-pyridine-2-carbonitrile,
4- {[7-(6-Amino-pyrimidin-4-ylamino)-3-methyl-3H-imidazo[4,5-b]pyridin-5-yl]-methyl-amino}-cyclohexanecarbonitrile,
N7-(6-Amino-pyrimidin-4-yl)-N5-(3,3-dimethyl-tetrahydro-pyran-4-yl)-3,N5-dimethyl-3H-imidazo [4,5-b]pyridine-5,7-diamine,
N7-(6-aminopyrimidin-4-yl)-N5,3-dimethyl-N5- [(1S)-1,2,2-trimethylpropyl]imidazo [4,5-b] pyridine-5,7-diamine,
(±)-(1R,3R)-3- {[7-(6-Amino-pyrimidin-4-ylamino)-3-methyl-3H-imidazo [4,5-b]pyridin-5-yl]-methyl-amino}-cyclohexanecarbonitrile,
4- {[7-(6-Amino-pyrimidin-4-ylamino)-3-methyl-3H-imidazo[4,5-b]pyridin-5-yl]-methyl-amino}-3-cyclopropyl-5-fluoro-benzonitrile,
5- {[7-(6-Amino-pyrimidin-4-ylamino)-3-methyl-3H-imidazo[4,5-b]pyridin-5-yl]-methyl-amino}-4-ethyl-pyridine-2-carbonitrile,
N7-(6-aminopyrimidin-4-yl)-N5- [(1R)-1-cyclopropyl-ethyl]-N5,3-dimethyl-imidazo [4,5-b] pyridine-5,7-diamine,
N7-(6-Amino-pyrimidin-4-yl)-3,N5-dimethyl-N5-((3R,4S)-3-methyl-tetrahydro-pyran-4-yl)-3H-imidazo [4,5-b]pyridine-5,7-diamine,
N7- (6-Amino-pyrimidin-4-yl)-N5-bicyclo [1.1.1] pent-1-yl-3,N5-dimethyl-3H-imidazo [4,5-b]pyridine-5,7-diamine,
N7-(6-Amino-pyrimidin-4-yl)-3,N5-dimethyl-N5-(3-methyl-tetrahydro-pyran-4-yl)-3H-imidazo [4,5-b]pyridine-5,7-diamine,
N7-(6-Amino-pyrimidin-4-yl)-N5-(1-cyclopropyl-2,2,2-trifluoro-ethyl)-3,N5-dimethyl-3H-imidazo [4,5-b]pyridine-5,7-diamine,
N7-(6-Amino-pyrimidin-4-yl)-3,N5-dimethyl-N5-(5-oxa-spiro [3.5]non-8-yl)-3H-imidazo [4,5-b]pyridine-5,7-diamine,
5- (1-cyclopropyl-2,2,2-trifluoro-ethoxy)-3-methyl-N-(5-methylsulfonyl-2-pyridyl)imidazo [4,S-b]pyridin-7-amine,
6-[5-(6-Cyano-4-methyl-pyridin-3-yloxy)-3-methyl-3H-imidazo [4,5-b]pyridin-7-ylamino]-pyridazine-3-carboxylic acid ethylamide,
6-[5-(6-Cyano-4-methyl-pyridin-3-yloxy)-3-methyl-3H-imidazo [4,5-b]pyridin-7-ylamino]-N-(2-hydroxy-propyl)-nicotinamide,
6-[5-(6-Cyano-4-methyl-pyridin-3-yloxy)-3-methyl-3H-imidazo [4,5-b]pyridin-7-ylamino]-pyridazine-3-carboxylic acid (2-hydroxy-propyl)-amide,
5-[5-(6-Cyano-4-methyl-pyridin-3-yloxy)-3-methyl-3H-imidazo [4,5-b]pyridin-7-ylamino]-pyridine-2-carboxylic acid ethylamide,
2-{4-[5-(6-Cyano-4-methyl-pyridin-3-yloxy)-3-methyl-3H-imidazo [4,5-b]pyridin-7-ylamino]-phenyl}-N-ethyl-acetamide,
4-Methyl-5- {3-methyl-7-[6-(morpholine-4-carbonyl)-pyridin-3-ylamino]-3H-imidazo [4,5-b]pyridin-5-yloxy}-pyridine-2-carbonitrile,
5-[5-(6-Cyano-4-methyl-pyridin-3-yloxy)-3-methyl-3H-imidazo [4,5-b]pyridin-7-ylamino]-pyridine-2-carboxylic acid methylamide,
5-[5-(6-Cyano-4-methyl-pyridin-3-yloxy)-3-methyl-3H-imidazo [4,5-b]pyridin-7-ylamino]-pyridine-2-carboxylic acid (2-hydroxy-propyl)-amide,
5- {7- [6- (2-Methoxy-ethylamino)-pyrimidin-4-ylamino]-3-methyl-3H-imidazo [4,5-b]pyridin-5-yloxy}-4-methyl-pyridine-2-carbonitrile,
5- {7- [6- (3-Methoxy-propylamino)-pyrimidin-4-ylamino]-3-methyl-3H-imidazo [4,5-b]pyridin-5-yloxy}-4-methyl-pyridine-2-carbonitrile,
5-{7-[6-(3-Hydroxy-3-methyl-butylamino)-pyrimidin-4-ylamino]-3-methyl-3H-imidazo [4,5-b]pyridin-5-yloxy}-4-methyl-pyridine-2-carbonitrile, 5-{7-[6-(3-Hydroxy-propylamino)-pyrimidin-4-ylamino]-3-methyl-3H-imidazo [4,5-b]pyridin-5-yloxy}-4-methyl-pyridine-2-carbonitrile,
5- (7- {6- [([1,4]Dioxan-2-ylmethyl)-amino]-pyrimidin-4-ylamino}-3-methyl-3H-imidazo [4,5-b]pyridin-5-yloxy)-4-methyl-pyridine-2-carbonitrile,
5-{7-[6-(3-Methoxy-cyclobutylamino)-pyrimidin-4-ylamino]-3-methyl-3H-imidazo [4,5-b]pyridin-5-yloxy}-4-methyl-pyridine-2-carbonitrile,
5-{7-[6-(3-Methoxy-butylamino)-pyrimidin-4-ylamino]-3-methyl-3H-imidazo [4,5-b]pyridin-5-yloxy}-4-methyl-pyridine-2-carbonitrile,
4-Methyl-5-[3-methyl-7-(6-morpholin-4-yl-pyridazin-3-ylamino)-3H-imidazo [4,5-b]pyridin-5-yloxy]-pyridine-2-carbonitrile,
4-Methyl-5- {3-methyl-7-[6-(4-methyl-piperazin-1-yl)-pyridazin-3-ylamino]-3H-imidazo [4,5-b]pyridin-5-yloxy}-pyridine-2-carbonitrile,
5-{7-[6-(3-Dimethylaminomethyl-azetidin-1-yl)-pyridazin-3-ylamino]-3-methyl-3H-imidazo [4,5-b]pyridin-5-yloxy}-4-methyl-pyridine-2-carbonitrile,
(±)-4-Methyl-5-{3-methyl-7- [6- ((3R,5S)-3,4,5-trimethyl-piperazin-1-yl)-pyridazin-3-ylamino]-3H-imidazo [4,5-b]pyridin-5-yloxy}-pyridine-2-carbonitrile,
4-Methyl-5-(3-methyl-7-{6-[4-(2,2,2-trifluoro-ethyl)-piperazin-1-yl]-pyridazin-3-ylamino}-3H-imidazo [4,5-b]pyridin-5-yloxy)-pyridine-2-carbonitrile,
(±)-5- {7- [6- ((2R,6S)-2,6-Dimethyl-morpholin-4-yl)-pyridazin-3-ylamino]-3-methyl-3H-imidazo [4,5-b]pyridin-5-yloxy}-4-methyl-pyridine-2-carbonitrile,
4-Methyl-5- {3-methyl-7- [6- ((S)-2-methyl-morpholin-4-yl)-pyridazin-3-ylamino]-3H-imidazo [4,5-b]pyridin-5-yloxy}-pyridine-2-carbonitrile,
5-{7-[6-(4-Cyano-piperidin-1-yl)-pyridazin-3-ylamino]-3-methyl-3H-imidazo [4,5-b]pyridin-5-yloxy}-4-methyl-pyridine-2-carbonitrile,
4-methyl-5-[3-methyl-7- [[5-(4-propan-2-ylpiperazine-1-carbonyl)pyridin-2-yl]amino]imidazo [4,5-b]pyridin-5-yl] oxypyridine-2-carbonitrile,
5- [7- [[5- (4-cyclobutylpiperazine-1-carbonyl)pyridin-2-yl] amino]-3-methylimidazo [4,5-b]pyridin-5-yl] oxy-4-methylpyridine-2-carbonitrile,
5- [7- [[5-(4-cyclopropylpiperazine-1-carbonyl)pyridin-2-yflamino]-3-methylimidazo [4,5-b]pyridin-5-yl]oxy-4-methylpyridine-2-carbonitrile,
4-methyl-5-[3-methyl-7-[(5-morpholin-4-ylpyridin-2-yl) amino]imidazo [4,5-b]pyridin-5-yl] oxypyridine-2-carbonitrile,
4-methyl-5-[3-methyl-7- [[5-(4-methylpiperazin-1-yl)pyridin-2-yl]amino]imidazo [4,5-b]pyridin-5-yl] oxypyridine-2-carbonitrile,
4-methyl-5- [7- [[5- (4-methylpiperazine-1-carbonyl) pyridin-2-yl]amino]-3-(trideuteriomethyl)imidazo [4,5-b] pyridin-5-yl] oxypyridine-2-carbonitrile,
5- [7-[(6-aminopyrimidin-4-yl) amino]-3-methyl-imidazo [4,5-b]pyridin-5-yl]oxy-4-methyl-pyridine-2-carbonitrile,
4- [[5-[(6-cyano-4-methyl-3-pyridyl)oxy]-3-methyl-imidazo [4,5-b]pyridin-7-yl] amino]-N-ethyl-benzenesulfonamide,
N4-[5-(1-cyclopropyl-2,2,2-trifluoro-ethoxy)-3-methyl-imidazo [4,5-b]pyridin-7-yl]pyrimidine-4,6-diamine,
5- [[7-[(6-aminopyrimidin-4-yl)amino]-3-methyl-imidazo [4,5-b]pyridin-5-yl]amino]-4-methyl-pyridine-2-carbonitrile,
5- [7- [4- (aminomethyl)anilino]-3-methyl-imidazo [4,5-b] pyridin-5-yl] oxy-4-methyl-pyridine-2-carbonitrile formate salt,
4-methyl-5-[3-methyl-7-[(5-methylsulfonyl-2-pyridyl) amino] imidazo [4,5-b]pyridin-5-yl]oxy-pyridine-2-carbonitrile,
4-methyl-5-[3-methyl-7- [[5- (trifluoromethyl)-2-pyridyl] amino] imidazo [4,5-b] pyridin-5-yl] oxy-pyridine-2-carbonitrile,
4-methyl-5-[3-methyl-7-(4-methylsulfonylanilino)imidazo [4,5-b]pyridin-5-yl]oxy-pyridine-2-carbonitrile,
4-methyl-5-[3-methyl-7-[(1-methylpyrazol-4-yl)amino]imidazo [4,5-b]pyridin-5-yl]oxy-pyridine-2-carbonitrile,
4- [[5-[(6-cyano-4-methyl-3-pyridyl)oxy]-3-methyl-imidazo [4,5-b]pyridin-7-yl] amino]-N,N-dimethyl-benzamide,
4-methyl-5-[3-methyl-7-(4-morpholinosulfonylanilino)imidazo [4,5-b]pyridin-5-yl]oxy-pyridine-2-carbonitrile,
6- [[5-[(6-cyano-4-methyl-3-pyridyl)oxy]-3-methyl-imidazo [4,5-b]pyridin-7-yl] amino]-N-ethyl-4-methyl-pyridine-3-carboxamide,
3-methyl-N7-(5-methylsulfonyl-2-pyridyl)-N5-[2-methyl-1-(trifluoromethyl)propyl]imidazo [4,5-b]pyridine-5,7-diamine,
4- [[5-[(6-cyano-4-methyl-3-pyridyl)amino]-3-methyl-imidazo [4,5-1)] pyridin-7-yl]amino]-N,N-dimethyl-benzamide,
6- [[5-[(6-cyano-4-methyl-3-pyridyl)amino]-3-methyl-imidazo [4,5-1)] pyridin-7-yl]amino]-N,N-dimethyl-pyridine-3-carboxamide,
5- [7- [4- (difluoromethylsulfonyl)anilino]-3-methyl-imidazo [4,5-b]pyridin-5-yl]oxy-4-methyl-pyridine-2-carbonitrile,
5- [7- (4-cyclopropylsulfonylanilino)-3-methyl-imidazo [4,5-b] pyridin-5-yl] oxy-4-methyl-pyridine-2-carbonitrile,
5- [7-[(1,1-dimethyl-3-oxo-isoindolin-5-yl) amino]-3-methyl-imidazo [4,5-b]pyridin-5-yl] oxy-4-methyl-pyridine-2-carbonitrile,
5- [7- [4- (3-methoxypropylsulfonyl)anilino]-3-methyl-imidazo [4,5-b] pyridin-5-yl] oxy-4-methyl-pyridine-2-carbonitrile,
N4- [5-(1-cyclopropylethoxy)-3-methyl-imidazo [4,5-b] pyridin-7-yl] pyrimidine-4,6-diamine,
6- [[5-[(6-cyano-4-methyl-3-pyridyl)oxy]-3-methyl-imidazo [4,5-b]pyridin-7-yl] amino]-N,N-dimethyl-pyridazine-3-carboxamide,
6- [[5-[(6-cyano-4-methyl-3-pyridyl)oxy]-3-methyl-imidazo [4,5-b]pyridin-7-yl] amino]-N,N-dimethyl-pyridine-3-carboxamide,
4-methyl-5-[3-methyl-7- [[5- (morpholine-4-carbonyl)-2-pyridyl] amino] imidazo [4,5-b]pyridin-5-yl]oxy-pyridine-2-carbonitrile,
6- [[5-[(6-cyano-4-methyl-3-pyridyl)amino]-3-methyl-imidazo [4,5-b] pyridin-7-yl]amino]-N,N-dimethyl-pyridazine-3-carboxamide,
6- [[5-[(6-cyano-4-methyl-3-pyridyl)oxy]-3-methyl-imidazo [4,5-b]pyridin-7-yl] amino]-N,N,2-trimethyl-pyridine-3-carboxamide,
6- [[5-[(6-cyano-4-methyl-3-pyridyl)oxy]-3-methyl-imidazo [4,5-b]pyridin-7-yl] amino]-N-ethyl-2-methyl-pyridine-3-carb oxamide,
5- [7- [[5- [(dimethylamino)methyl] pyridin-2-yl] amino]-3-methylimidazo [4,5-b] pyridin-5-yl] oxy-4-methylpyridine-2-carbonitrile formate salt,
4-methyl-5-[3-methyl-7- [[5- (morpholin-4-ylmethyl) pyridin-2-yl] amino] imidazo [4,5-b]pyridin-5-yl] oxypyridine-2-carbonitrile formate salt,
5- [7- [[5- [[2-(dimethylamino)ethyl-methylamino]methyl] pyridin-2-yl]amino]-3-methylimidazo [4,5-b]pyridin-5-yl] oxy-4-methylpyridine-2-carbonitrile formate salt, 5- [7-[(5-methoxypyridin-2-yl) amino]-3-methylimidazo [4,5-b]pyridin-5-yl]oxy-4-methylpyridine-2-carbonitrile,
4-methyl-5-[3-methyl-7- [[5- [(3S)-3-methylmorpholin-4-yl]pyridin-2-yl] amino] imidazo [4,5-b]pyridin-5-yl]oxypyridine-2-carbonitrile,
4-methyl-5-[3-methyl-7- [[5-(1-methylpiperidin-4-yl) oxypyridin-2-yl] amino] imidazo [4,5-b]pyridin-5-yl] oxypyridine-2-carbonitrile,
4-methyl-5-[3-methyl-7- [[5-(oxan-4-yl)pyridin-2-yl] amino]imidazo [4,5-b]pyridin-5-yl]oxypyridine-2-carbonitrile,
5- [[7-[(6-aminopyrimidin-4-yl)amino]-3-methyl-imidazo [4,5-b]pyridin-5-yl]-cyclopropyl-amino]-4-methyl-pyridine-2-carbonitrile,
5-[7-[4-(3-hydroxyoxetan-3-yl)anilino]-3-methylimidazo [4,5-b]pyridin-5-yl] oxy-4-methylpyridine-2-carbonitrile,
4-methyl-5-[3-methyl-7- [[6- (1-methylazetidin-3-yl) oxypyridazin-3-yl]amino]imidazo [4,5-b]pyridin-5-yl] oxypyridine-2-carbonitrile,
5- [[5-[(1-cyclopropyl-2,2,2-trifluoro-ethyl)amino]-3-methyl-imidazo [4,5-b]pyridin-7-yl]amino]-N-ethyl-pyridine-2-carboxamide,
N5- (1-cyclopropyl-2,2,2-trifluoro-ethyl)-3-methyl-N7-(5-methylsulfonyl-2-pyridyl) imidazo [4,5-b]pyridine-5,7-diamine,
N7-(6-aminopyrimidin-4-yl)-3-methyl-N5-[2-methyl-1-(trifluoromethyl)propyl]imidazo [4,5-b]pyridine-5,7-diamine,
N7-(6-aminopyrimidin-4-yl)-N 5- (1-cyclobutylethyl)-3-methyl-imidazo [4,5-b]pyridine-5,7-diamine,
N7-(6-aminopyrimidin-4-yl)-N 5- (dicyclopropylmethyl)-3-methyl-imidazo [4,5-b]pyridine-5,7-diamine,
5- [7- [[5- (3-hydroxyazetidine-1-carbonyl)-2-pyridyl] amino]-3-methyl-imidazo [4,5-b]pyridin-5-yl] oxy-4-methyl-pyridine-2-carbonitrile,
N,N-dimethyl-6- [[3-methyl-5-[[(1R)-2-methyl-1- (trifluoromethyl) propyl] amino] imidazo [4,5-b]pyridin-7-yl] amino]pyridine-3-carboxamide,
N7-(6-aminopyrimidin-4-yl)-3-methyl-N5- [(1R)-2-methyl-1-(trifluoromethyl)propyl]imidazo [4,5-b]pyridine-5,7-diamine,
6- [[5-[(6-cyano-4-methyl-3-pyridyl)oxy]-3-methyl-imidazo [4,5-b]pyridin-7-yl] amino]-N-(2-dimethylaminoethyl) pyridine-3-carb oxamide,
6- [[5-[(6-cyano-4-methyl-3-pyridyl)oxy]-3-methyl-imidazo [4,5-b]pyridin-7-yl] amino]-N-(3-methoxypropyl) pyridine-3-carboxamide,
6- [[5-[(6-cyano-4-methyl-3-pyridyl)oxy]-3-methyl-imidazo [4,5-b]pyridin-7-yl] amino]-N-(3-hydroxypropyl) pyridine-3-carboxamide,
5- [7- [[5-[3-(1-hydroxy-1-methyl-ethyl) azetidine-1-carbonyl]-2-pyridyl] amino]-3-methyl-imidazo [4,5-b]pyridin-5-yl] oxy-4-methyl-pyridine-2-carbonitrile,
5- [7- [[5-(3-methoxyazetidine-1-carbonyl)-2-pyridyl] amino]-3-methyl-imidazo [4,5-b]pyridin-5-yl] oxy-4-methyl-pyridine-2-carbonitrile,
5- [7- [[5- [3- (methoxymethyl)azetidine-1-carbonyl]-2-pyridyl]amino]-3-methyl-imidazo [4,5-b]pyridin-5-yl]oxy-4-methyl-pyridine-2-carbonitrile,
4-methyl-5-[3-methyl-7- [[5-(4-methylpiperazine-1-carbonyl)-2-pyridyl] amino] imidazo [4,5-b]pyridin-5-yl]oxypyridine-2-carbonitrile,
5- [7- [[5- [3- (dimethylamino) azetidine-1-carbonyl]-2-pyridyl] amino]-3-methyl-imidazo [4,5-b]pyridin-5-yl] oxy-4-methyl-pyridine-2-carbonitrile,
5- [7- [[5- [(3R)-3-(dimethylamino)pyrrolidine-1-carbonyl] pyridin-2-yl] amino]-3-methylimidazo [4,5-b]pyridin-5-yl] oxy-4-methyl pyridine-2-carbonitrile,
4-methyl-5-[3-methyl-7- [[6-(morpholine-4-carbonyl) pyridazin-3-yl]amino]imidazo [4,5-b]pyridin-5-yl] oxypyridine-2-carbonitrile,
4-methyl-5-[3-methyl-7-(4-morpholinoanilino)imidazo [4,5-b]pyridin-5-yl] oxy-pyridine-2-carbonitrile,
4-methyl-5-[3-methyl-7-[4-(4-methylpiperazin-1-yl)anilino]imidazo [4,5-b]pyridin-5-yl] oxy-pyridine-2-carbonitrile,
5- [7- [[6-[3-(1-hydroxy-1-methyl-ethyl) azetidine-1-carbonyl] pyridazin-3-yl] amino]-3-methyl-imidazo [4,5-b]pyridin-5-yl] oxy-4-methyl-pyridine-2-carbonitrile,
5- [7- [[5- [(3S)-3-hydroxypyrrolidine-1-carbonyl]-2-pyridyl]amino]-3-methyl-imidazo [4,5-b]pyridin-5-yl] oxy-4-methyl-pyridine-2-carbonitrile,
5- [7- [[5-(3-cyclopropyl-3-hydroxy-azetidine-1-carbonyl)-2-pyridyl] amino]-3-methyl-imidazo [4,5-b]pyridin-5-yl] oxy-4-methyl-pyridine-2-carbonitrile,
4-methyl-5-[3-methyl-7- [[5-(8-oxa-3-azaspiro [4.4] nonane-3-carbonyl)-2-pyridyl] amino]imidazo [4,5-b]pyridin-5-yl] oxy-pyridine-2-carbonitrile,
5- [7- [[6-(3-hydroxyazetidine-1-carbonyl)pyridazin-3-yl] amino]-3-methyl-imidazo [4,5-b]pyridin-5-yl]oxy-4-methyl-pyridine-2-carbonitrile,
5- [7- [[6-(3-methoxyazetidine-1-carbonyl)pyridazin-3-yl] amino]-3-methyl-imidazo [4,5-b]pyridin-5-yl] oxy-4-methyl-pyridine-2-carbonitrile,
5- [7- [[6-[3-(methoxymethyl)azetidine-1-carbonyl] pyridazin-3-yl] amino]-3-methyl-imidazo [4,5-b]pyridin-5-yl] oxy-4-methyl-pyridine-2-carbonitrile,
5- [7- [[5- [3- (hydroxymethyl)azetidine-1-carbonyl]-2-pyridyl] amino]-3-methyl-imidazo [4,5-b]pyridin-5-yl] oxy-4-methyl-pyridine-2-carbonitrile,
5- [7- [[5-(3-hydroxy-3-methyl-azetidine-1-carbonyl)-2-pyridyl] amino]-3-methyl-imidazo [4,5-b]pyridin-5-yl]oxy-4-methyl-pyridine-2-carbonitrile,
4-methyl-5-[3-methyl-7- [[5-(3-oxa-6-azaspiro [3.3] heptane-6-carbonyl)-2-pyridyl] amino] imidazo [4,5-b]pyridin-5-yl] oxy-pyridine-2-carbonitrile,
5- [7- [[5-(3-methoxy-3-methyl-azetidine-1-carbonyl)-2-pyridyl]amino]-3-methyl-imidazo [4,5-b]pyridin-5-yl] oxy-4-methyl-pyridine-2-carbonitrile,
tert-butyl 1- [6- [[5-[(6-cyano-4-methyl-3-pyridyl) oxy]-3-methyl-imidazo [4,5-b] pyridin-7-yl] amino] pyridine-3-carbonyl]azetidine-3-carboxylate,
4-methyl-5-[3-methyl-7- [[5-(6-methyl-2,6-diazaspiro [3.3] heptane-2-carbonyl)-2-pyridyl]amino]imidazo [4,5-b]pyridin-5-yl]oxy-pyridine-2-carbonitrile,
5- [7- [[5-(4-hydroxypiperidine-1-carbonyl)pyridin-2-yl] amino]-3-methylimidazo [4,5-b]pyridin-5-yl] oxy-4-methylpyridine-2-carbonitrile,
5- [7- [[5-(4-methoxypiperidine-1-carbonyl) pyridin-2-yl] amino]-3-methylimidazo [4,5-b]pyridin-5-yl] oxy-4-methylpyridine-2-carbonitrile,
5- [7- [[5- [4- (dimethylamino) piperidine-1-carbonyl]pyridin-2-yl] amino]-3-methylimidazo [4,5-b]pyridin-5-yl]oxy-4-methyl pyridine-2-carbonitrile,
5- [7- [[5- [(3R)-3-hydroxypyrrolidine-1-carbonyl]pyridin-2-yl]amino]-3-methylimidazo [4,5-b]pyridin-5-yl] oxy-4-methylpyridine-2-carbonitrile,
4-{6-[5-(6-Cyano-4-methyl-pyridin-3-yloxy)-3-methyl-3H-imidazo [4,5-b]pyridin-7-ylamino]-pyridine-3-carbonyl}-piperazine-1-carboxylic acid tert-butyl ester,
5- [7- [[5- [(3R)-3- (2-methoxyethoxy) pyrrolidine-1-carbonyl]pyridin-2-yl]amino]-3-methylimidazo [4,5-b]pyridin-5-yl] oxy-4-methyl pyridine-2-carbonitrile, (1- {6- [5- (6-Cyano-4-methyl-pyridin-3-yloxy)-3-methyl-3H-imidazo [4,5-b]pyridin-7-ylamino]-pyridine-3-carbonyl 1-pyrrolidin-3-yl)-methyl-carbamic acid tert-butyl ester, 4-methyl-5-[3-methyl-7- [[5-(2-oxa-7-azaspiro [3.4] octane-7-carbonyl) pyridin-2-yl] amino] imidazo [4,5-b]pyridin-5-yl] oxypyridine-2-carbonitrile, 5- [7- [[5-[3-[(dimethylamino) methyl] azetidine-1-carbonyl] pyridin-2-yl] amino]-3-methylimidazo [4,5-b]pyridin-5-yl]oxy-4-methyl pyridine-2-carbonitrile, 5- [7- [[5- [(3S)-3- (dimethylamino) pyrrolidine-1-carbonyl] pyridin-2-yl] amino]-3-methylimidazo [4,5-b]pyridin-5-yl] oxy-4-methyl pyridine-2-carbonitrile, 4-methyl-5-[3-methyl-7- [[5-(2-oxa-6-azaspiro [3.3]heptane-6-carbonyl)pyridin-2-yl]amino]imidazo [4,5-b]pyridin-5-yl]oxypyridine-2-carbonitrile, 5- [7- [[5-[3,3-bis (hydroxymethyl) azetidine-1- carbonyl] pyridin-2-yl] amino]-3-methylimidazo [4,5-b]pyridin-5-yl] oxy-4-methyl pyridine-2-carbonitrile, 6- [[5-(6-cyano-4-methylpyridin-3-yl)oxy-3-methylimidazo [4,5-b]pyridin-7-yl]amino]-N-(2-hydroxyethyl)-N-methyl pyridine-3-carboxamide, 4-methyl-5-[3-methyl-7- [[5- (3-propan-2-yloxyazetidine-1-carbonyl) pyridin-2-yl] amino] imidazo [4,5-b]pyridin-5-yl] oxypyridine-2-carbonitrile, 5- [7- [[5-(4-hydroxy-4-methylpiperidine-1-carbonyl) pyridin-2-yl] amino]-3-methylimidazo [4,5-b]pyridin-5-yl]oxy-4-methyl pyridine-2-carbonitrile, 6- [[5-(6-cyano-4-methylpyridin-3-yl)oxy-3-methylimidazo [4,5-b]pyridin-7-yl]amino]-N-[rac-(1R,3R)-3-hydroxycyclopentyl]pyridine-3-carboxamide, 4-methyl-5-[3-methyl-7-[[5-[rac-(3R,4R)-3-fluoro-4-hydroxypyrrolidine-1-carbonyl]pyridin-2-yl]amino]imidazo [4,5-b]pyridin-5-yl]oxypyridine-2-carbonitrile, 4-methyl-5-[3-methyl-7-[[5-[rac-(3R,4R)-3,4-dihydroxypiperidine-1-carbonyl]pyridin-2-yl]amino]imidazo [4,5-b] pyridin-5-yl]oxypyridine-2-carbonitrile, 4-methyl-5-[3-methyl-7-[[5-[rac-(3R,4R)-3-fluoro-4-methoxypyrrolidine-1-carbonyl]pyridin-2-yl]amino]imidazo [4,5-b]pyridin-5-yl]oxypyridine-2-carbonitrile, 5- [7- [[6-[3-(dimethylamino)azetidin-1-yl]pyridazin-3-yl] amino]-3-methylimidazo [4,5-b]pyridin-5-yl] oxy-4-methylpyridine-2-carbonitrile, 4-methyl-5-[3-methyl-7- [[5- [(2S)-2-methylmorpholine-4-carbonyl] pyridin-2-yl] amino] imidazo [4,5-b]pyridin-5-yl] oxypyridine-2-carbonitrile, 4-methyl-5-[3-methyl-7- [[5- [(2R)-2-methylmorpholine-4-carbonyl]pyridin-2-yl] amino] imidazo [4,5-b]pyridin-5-yl] oxypyridine-2-carbonitrile, 4-methyl-5-[3-methyl-7- [[5- [(3R)-3-methylmorpholine-4-carbonyl]pyridin-2-yl] amino] imidazo [4,5-b]pyridin-5-yl] oxypyridine-2-carbonitrile, 4-methyl-5-[3-methyl-7- [[5- [(3S)-3-methylmorpholine-4-carbonyl] pyridin-2-yl] amino] imidazo [4,5-b]pyridin-5-yl] oxypyridine-2-carbonitrile, 4-methyl-5-[3-methyl-7- [[5- [rac-(2R,6S)-2,6-dimethylmorpholine-4-carbonyl]pyridin-2-yl] amino] imidazo [4,5-b]pyridin-5-yl]oxypyridine-2-carbonitrile, 4-methyl-5-[3-methyl-7- [[5- [rac-(2R,6R)-2,6-dimethylmorpholine-4-carbonyl]pyridin-2-yl] amino] imidazo [4,5-b]pyridin-5-yl]oxypyridine-2-carbonitrile, 4-methyl-5-[3-methyl-7- [[6- (4-methylpiperazine-1-carbonyl) pyridazin-3-yl] amino]imidazo [4,5-b]pyridin-5-yl] oxypyridine-2-carbonitrile, 3,5-difluoro-4-[3-methyl-7- [[5-(4-methylpiperazine-1-carbonyl)pyridin-2-yl]amino]imidazo [4,5-b]pyridin-5-yl] oxybenzonitrile, 4-methyl-5-[3-methyl-7- [[6- [(1R,4R)-5-methyl-2,5-diazabicyclo [2.2.1] heptan-2-yl]pyridazin-3-yl] amino] imidazo [4,5-b]pyridin-5-yl] oxypyridine-2-carbonitrile, 5- {7- [5- ((3R,4R)-3-Dimethylamino-4-hydroxy-pyrrolidine-1-carbonyl)-pyridin-2-ylamino]-3-methyl-3H-imidazo [4,5-b]pyridin-5-yloxy}-4-methyl-pyridine-2-carbonitrile, 5- {7- [5- ((3S,4S)-3-Hydroxy-4-morpholin-4-yl-pyrrolidine-1-carbonyl)-pyridin-2-ylamino]-3-methyl-3H-imidazo [4,5-b]pyridin-5-yloxy}-4-methyl-pyridine-2-carbonitrile, 4-methyl-5-[3-methyl-7- [[5- [2- (trifluoromethyl)morpholine-4-carbonyl] pyridin-2-yl] amino] imidazo [4,5-b]pyridin-5-yl]oxypyridine-2-carbonitrile, 5- [7- [[5-(2-cyclopropylmorpholine-4-carbonyl)pyridin-2-yl]amino]-3-methylimidazo [4,5-b]pyridin-5-yl]oxy-4-methyl pyridine-2-carbonitrile, 4-methyl-5-[3-methyl-7- [[5- [(3R)-3-propan-2-ylmorpholine-4-carbonyl] pyridin-2-yl] amino] imidazo [4,5-b]pyridin-5-yl]oxypyridine-2-carbonitrile, 4-methyl-5-[3-methyl-7- [[5-(2-oxa-5-azabicyclo [2.2.1] heptane-5-carbonyl) pyridin-2-yl] amino] imidazo [4,5-b] pyridin-5-yl]oxypyridine-2-carbonitrile, 5- [7- [[5-(3-cyclopropylmorpholine-4-carbonyl)pyridin-2-yl]amino]-3-methylimidazo [4,5-b]pyridin-5-yl]oxy-4-methyl pyridine-2-carbonitrile, 4- [6- [[5-(6-cyano-4-methylpyridin-3-yl)oxy-3-methylimidazo [4,5-b]pyridin-7-yl]amino] pyridine-3-carbonyl]morpholine-2-carbonitrile, 4-Methyl-5- {3-methyl-7- [5- ((3aS,6aS)-1-methyl-hexahydro-pyrrolo [3,4-b]pyrrole-5-carbonyl)-pyridin-2-ylamino]-3H-imidazo [4,5-b]pyridin-5-yloxy}-pyridine-2-carbonitrile, 4- [6- [[5-(6-cyano-4-methylpyridin-3-yl)oxy-3-methylimidazo [4,5-b]pyridin-7-yl]amino] pyridine-3-carbonyl]morpholine-3-carbonitrile, 5- [7- [[6- [(2R)-2-(hydroxymethyl)morpholin-4-yl] pyridazin-3-yl]amino]-3-methylimidazo [4,5-b]pyridin-5-yl] oxy-4-methyl pyridine-2-carbonitrile, 4-methyl-5-[3-methyl-7- [[6- (2,2,3,3,5,5,6,6-octadeuteriomorpholin-4-yl) pyridazin-3-yl] amino] imidazo [4,5-b] pyridin-5-yl]oxy-pyridine-2-carbonitrile, 5- [7- [[6- [(2S)-2-(hydroxymethyl)morpholin-4-yl] pyridazin-3-yl]amino]-3-methylimidazo [4,5-b]pyridin-5-yl] oxy-4-methyl pyridine-2-carbonitrile, 5- [7- [[6- [(2S,6S)-2,6-dimethylmorpholin-4-yl]pyridazin-3-yl] amino]-3-methylimidazo [4,5-b]pyridin-5-yl] oxy-4-methylpyridine-2-carbonitrile, 4-methyl-5-[3-methyl-7- [[6- (1,4-oxazepan-4-yl) pyridazin-3-yl] amino] imidazo [4,5-b]pyridin-5-yl]oxypyridine-2-carbonitrile, 5- [7- [[6- [(2R,6R)-2,6-dimethylmorpholin-4-yl] pyridazin-3-yl] amino]-3-methylimidazo [4,5-b]pyridin-5-yl]oxy-4-methyl pyridine-2-carbonitrile, 5- [7- [[6-[2-(hydroxymethyl)morpholin-4-yl]pyridazin-3-yl]amino]-3-methylimidazo [4,5-b]pyridin-5-yl]oxy-4-methylpyridine-2-carbonitrile, 4-methyl-5-[3-methyl-7- [[6-(8-oxa-3-azabicyclo [3.2.1] octan-3-yl)pyridazin-3-yl]amino]imidazo [4,5-b]pyridin-5-yl] oxypyridine-2-carbonitrile, 4- [6- [[5-(6-cyano-4-methylpyridin-3-yl)oxy-3-methylimidazo [4,5-b]pyridin-7-yl]amino]pyridazin-3-yl]morpholine-2-carbonitrile, 4-methyl-5-[3-methyl-7- [[6- [(2R)-2-methylmorpholin-4-yl] pyridazin-3-yl] amino]imidazo [4,5-b]pyridin-5-yl] oxypyridine-2-carbonitrile, 4-methyl-5-[3-methyl-7- [[6- [(2R)-2-propan-2-ylmorpholin-4-yl]pyridazin-3-yl]amino]imidazo [4,5-b]pyridin-5-yl] oxypyridine-2-carbonitrile, 4-methyl-5-[3-methyl-7-[[6-[(1S,4S)-2-oxa-5-azabicyclo[2.2.1]heptan-5-yl]pyridazin-3-yl]amino]imidazo[4,5-b]pyridin-5-yl]oxypyridine-2-carbonitrile, 5-[7-[[6-(2,2-dimethylmorpholin-4-yl)pyridazin-3-yl]amino]-3-methylimidazo[4,5-b]pyridin-5-yl]oxy-4-methylpyridine-2-carbonitrile, 4-methyl-5-[3-methyl-7-[[6-[rac-(2R,6R)-2,6-dimethylmorpholin-4-yl]pyridazin-3-yl]amino]imidazo[4,5-b]pyridin-5-yl]oxypyridine-2-carbonitrile, 4-methyl-5-[3-methyl-7-[[6-[(2S)-2-propan-2-ylmorpholin-4-yl]pyridazin-3-yl]amino]imidazo[4,S-b]pyridin-5-yl]oxypyridine-2-carbonitrile, 4-methyl-5-[3-methyl-7-[[5-(piperazine-1-carbonyl)pyridin-2-yl]amino]imidazo[4,5-b]pyridin-5-yl]oxypyridine-2-carbonitrile, N7-(6-aminopyrimidin-4-yl)-N5-(1-cyclopropyl-2,2,2-trifluoro-ethyl)-3-methyl-imidazo[4,5-b]pyridine-5,7-diamine, 4-methyl-5-[3-methyl-7-[(5-piperazin-1-yl-2-pyridyl)amino]imidazo[4,5-b]pyridin-5-yl]oxy-pyridine-2-carbonitrile, 5-[7-[[5-[4-(dimethylamino)-1-piperidyl]-2-pyridyl]amino]-3-methyl-imidazo[4,5-b]pyridin-5-yl]oxy-4-methyl-pyridine-2-carbonitrile, 5-[7-[[5-[3-(dimethylamino)pyrrolidin-1-yl]-2-pyridy amino]-3-methyl-imidazo[4,5-b]pyridin-5-yl]oxy-4-methyl-pyridine-2-carbonitrile, 5-[7-[[5-[2-methoxyethyl(methyl)amino]-2-pyridyl]amino]-3-methyl-imidazo[4,5-b]pyridin-5-yl]oxy-4-methyl-pyridine-2-carbonitrile, 5-[7-[[5-[4-(hydroxymethyl)-1-piperidyl]-2-pyridyl]amino]-3-methyl-imidazo[4,5-b]pyridin-5-yl]oxy-4-methyl-pyridine-2-carbonitrile, 5-[7-[[5-(dimethylamino)-2-pyridyl]amino]-3-methyl-imidazo[4,5-b]pyridin-5-yl]oxy-4-methyl-pyridine-2-carbonitrile, 4-methyl-5-[3-methyl-7-[[1-(2-morpholinoethyl)pyrazol-4-yl]amino]imidazo[4,5-b]pyridin-5-yl]oxy-pyridine-2-carbonitrile, 5-[[7-[(6-aminopyrimidin-4-yl)amino]-3-methyl-imidazo[4,5-b]pyridin-5-yl]-(2-hydroxypropyl)amino]-4-methyl-pyridine-2-carbonitrile, 4-methyl-5-[3-methyl-7-[[5-(2,2,3,3,5,5,6,6-octadeuterio-4-methyl-piperazine-1-carbonyl)-2-pyridyl]amino]imidazo[4,5-b]pyridin-5-yl]oxy-pyridine-2-carbonitrile, 4-methyl-5-[3-methyl-7-[[5-(2,2,6,6-tetradeuterio-4-methyl-piperazine-1-carbonyl)-2-fpyridyl]amino]imidazo[4,5-b]pyridin-5-yl]oxy-pyridine-2-carbonitrile, or 4-methyl-5-[3-methyl-7-[[5-[2,2,3,3,5,5,6,6-octadeuterio-4-(trideuteriomethyl)piperazine-1-carbonyl]-2-pyridyl]amino]imidazo[4,5-b]pyridin-5-yl]oxy-pyridine-2-carbonitrile.

17. A pharmaceutical composition comprising a pharmaceutically acceptable carrier and a pharmaceutically effective amount of a compound according to claim 16.

18. A method for treatment of inflammatory diseases, autoinflammatory diseases, autoimmune diseases, and/or diseases associated with hypersecretion of IFNα, IL12 and/or IL23, comprising administering an effective amount of the compound, or pharmaceutically acceptable salt thereof, according to claim 16, to a subject in need thereof.

19. A method for treatment of inflammatory diseases, autoinflammatory diseases, autoimmune diseases, and/or diseases associated with hypersecretion of IFNα, IL12 and/or IL23, comprising administering the pharmaceutical composition according to claim 18, to a subject in need thereof.

\* \* \* \* \*